US010301320B2

(12) United States Patent
Markowitz et al.

(10) Patent No.: US 10,301,320 B2
(45) Date of Patent: *May 28, 2019

(54) COMPOSITIONS AND METHODS OF MODULATING 15-PGDH ACTIVITY

(71) Applicants: CASE WESTERN RESERVE UNIVERSITY, Cleveland, OH (US); Board of Regents of the University of Texas System, Austin, TX (US); University of Kentucky Research Foundation, Lexington, KY (US)

(72) Inventors: Sanford Markowitz, Pepper Pike, OH (US); James K. V. Willson, Dallas, TX (US); Bruce Posner, Richardson, TX (US); Joseph Ready, Carrolton, TX (US); Youngyou Zhang, Cleveland, OH (US); Hsin-Hsiung Tai, Lexington, KY (US); Monika Antczak, Ft. Worth, TX (US); Stanton Gerson, Hunting Valley, OH (US); KiBeom Bae, Buk-gu (KR); Sung Yeun Yang, Yeonje-Gu (KR); Amar Desai, Cleveland, OH (US)

(73) Assignees: University of Kentucky Research Foundation, Lexington, KY (US); Case Western Reserve University, Cleveland, OH (US); Board of Regents of the University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/359,330

(22) Filed: Nov. 22, 2016

(65) Prior Publication Data
US 2017/0165241 A1  Jun. 15, 2017

Related U.S. Application Data

(63) Continuation of application No. 14/395,021, filed as application No. PCT/US2013/036790 on Apr. 16, 2013.

(60) Provisional application No. 61/624,670, filed on Apr. 16, 2012.

(51) Int. Cl.
| A61K 31/4365 | (2006.01) |
| C07D 495/04 | (2006.01) |
| C07D 213/71 | (2006.01) |
| C07D 213/73 | (2006.01) |
| C07D 213/75 | (2006.01) |
| C07D 213/76 | (2006.01) |
| C07D 215/08 | (2006.01) |
| C07D 237/20 | (2006.01) |
| C07D 405/12 | (2006.01) |
| C07D 239/42 | (2006.01) |
| C07D 241/20 | (2006.01) |
| C07D 261/14 | (2006.01) |
| C07D 207/263 | (2006.01) |
| C07D 275/03 | (2006.01) |
| C07D 209/08 | (2006.01) |
| C07D 277/46 | (2006.01) |
| C07D 295/185 | (2006.01) |
| C07C 311/21 | (2006.01) |
| A61K 31/519 | (2006.01) |

(52) U.S. Cl.
CPC ........ *C07D 495/04* (2013.01); *A61K 31/4365* (2013.01); *A61K 31/519* (2013.01); *C07C 311/21* (2013.01); *C07D 207/263* (2013.01); *C07D 209/08* (2013.01); *C07D 213/71* (2013.01); *C07D 213/73* (2013.01); *C07D 213/75* (2013.01); *C07D 213/76* (2013.01); *C07D 215/08* (2013.01); *C07D 237/20* (2013.01); *C07D 239/42* (2013.01); *C07D 241/20* (2013.01); *C07D 261/14* (2013.01); *C07D 275/03* (2013.01); *C07D 277/46* (2013.01); *C07D 295/185* (2013.01); *C07D 405/12* (2013.01); *C07C 2601/14* (2017.05)

(58) Field of Classification Search
CPC .................................................. A61K 31/4365
See application file for complete search history.

(56) References Cited

U.S. PATENT DOCUMENTS

| 4,966,974 | A | 10/1990 | Klausener et al. |
| 7,091,216 | B2* | 8/2006 | Toupence ............. C07D 491/04 514/302 |
| 7,320,967 | B2 | 1/2008 | Michelet et al. |
| 7,396,525 | B2 | 7/2008 | Rozot et al. |
| 2004/0087593 | A1 | 5/2004 | Clark et al. |
| 2006/0034786 | A1 | 2/2006 | Michelet et al. |
| 2007/0071699 | A1 | 3/2007 | Boulle |
| 2007/0078175 | A1 | 4/2007 | Boulle et al. |
| 2008/0206320 | A1 | 8/2008 | Michelet et al. |

(Continued)

FOREIGN PATENT DOCUMENTS

| FR | 2838641 A1 | 4/2002 |
| JP | 2007527850 A | 10/2007 |

(Continued)

OTHER PUBLICATIONS

"A Guide to the Graphic Representation and Nomenclature of Chemical Formulae in the European Pharmacopoeia" European Pharmacopoeia 2011 2nd Edition.*

(Continued)

*Primary Examiner* — David K O'Dell
(74) *Attorney, Agent, or Firm* — Tarolli, Sundheim, Covell & Tummino LLP

(57) ABSTRACT

Compounds and methods of modulating 15-PGDH activity, modulating tissue prostaglandin levels, treating disease, diseases disorders, or conditions in which it is desired to modulate 15-PGDH activity and/or prostaglandin levels include 15-PGDH inhibitors and 15-PGDH activators described herein.

15 Claims, 87 Drawing Sheets

(56) References Cited

U.S. PATENT DOCUMENTS

| | | |
|---|---|---|
| 2008/0249117 A1 | 10/2008 | Michelet et al. |
| 2010/0022521 A1 | 1/2010 | Nogradi et al. |
| 2011/0014250 A1 | 1/2011 | Michelet et al. |
| 2011/0142816 A1 | 6/2011 | Landry et al. |
| 2011/0269954 A1 | 11/2011 | Cho et al. |

FOREIGN PATENT DOCUMENTS

| | | |
|---|---|---|
| KR | 2010137090 A | 12/2010 |
| KR | 2013103945 A | 9/2013 |
| WO | 2007/038519 A1 | 4/2007 |
| WO | 2007/127183 A1 | 11/2007 |
| WO | 2011/042860 A2 | 4/2011 |
| WO | 2013/158649 A1 | 10/2013 |
| WO | 2013/180336 A1 | 12/2013 |
| WO | 2014/160947 A1 | 10/2014 |
| WO | 2015/065716 A1 | 5/2015 |
| WO | 2016/124939 A1 | 8/2016 |
| WO | 2016/144958 D2 | 9/2016 |
| WO | 2016/168472 A1 | 10/2016 |

OTHER PUBLICATIONS

Mayo Clinic Staff "Diseases and Conditions Chronic kidney disease" Jan. 30, 2015 Online "http://www.mayoclinic.org/diseasesconditions/kidneydisease/basics/causes/con2002677" accessed Dec. 11, 2015.*

Galie et. al. "Guidelines for the diagnosis and treatment of pulmonary hypertension" European Heart Journal (2009) 30, 2493-2537.*

Healthline Online "http://www.healthline.com/health/inflammatory-bowel-disease", accessed Sep. 9, 2015.*

Breyer "Prostanoid Receptors: Subtypes and Signaling" Annu. Rev. Pharmacol. Toxicol. 2001. 41:661-90.*

Randhawa Korean Journal of Physiology & Pharmacology (2014), 18(4), 279-288.*

Solomon "The dextran sulphate sodium (DSS) model of colitis: an overview" Comp Clin Pathol (2010) 19:235-239.*

Tatsuwaki, Hiroshi, et al., Reduction of 15-hydroxyprostaglandin dehydrogenase expression is an independent dehydrogenase expression is an independent predictor of poor survival associated with enhanced cell proliferation in gastric adenocarcinoma, Cancer Science, Feb. 2010, vol. 100, No. 2, p. 550-558.

Hoggati, Jonathan, et al., "Recovery from hematopoietic injury by modulating prostaglandin E2 signaling post-rradiation", Blood Cells, Molecules and Diseases 50 (2013) 147-153.

Pelus, Louis, M., et al., Pleiotropic effects of prostaglandin E2 in hematopoiesis; prostaglandin E2 and other eicosanoids regulate hematopoietic stem and progenitor cell function, Prostaglandins & other Lipid Mediators 96 (2011) 3-9.

Pelus, L.M., et al., "Pulse exposure of haematopoietic grafts to prostaglandin E2 in vitro facilitates engraftment and recovery", Cell Prolif., 2011, 44 {Suppl. 1), 22-29.

Hoggati, Jonathan, et al., "Differential stem- and progenitor-cell trafficking by prostaglandin E2", Nature, 2011.

Sasaki, S., et al., "Prostaglandin E2 Inhibits Lesion Formation in Dextran Sodium Sulphate-Induced Colitis in Rats and Reduces the Levels of Mucosal Inflammatory Cytokines", Scand. J. Immunol. 51, 23-28, 2000.

Tessner, Teresa, G., et al., "Prostaglandins Prevent Decreased Epithelial Cell Proliferation Associated With Dextran Sodium Sulfate Injury in Mice", Gastroenterology 1998;115:874-882.

Cutler, Corey, et al., "Prostaglandin-modulated umbilical cord blood hematopoietic stem cell transplantation" Blood, 2013.

Baker, Michael E., Licorice and enzymes other than 1 I β-hydroxysteroid dehydrogenase: An evolutionary perspective,Department of Medicine, University of California, Steroids, Feb. 1994. vol. 59, p. 136-141.

Hagedorn, Elliott J., et al., "Getting more for your marrow: Boosting hematopoietic stem cell numbers with PGE2", BoostinghematopoieticstemcellnumberswithPGE2, Exp Cell Res {2014), http://dx.doi.org/10.1016/j.yexcr.2014.07.030.

Karna, Sandeep,et al., "Novel Potent 15-Hydroxyprostaglandin Dehydrogenase Inhibitors", J. of Advanced Engineering and Technology, vol. 3, No. 3 (2010) pp. 301-304.

Niesen, Frank H., et al.,"High-Affinity Inhibitors of Human NAD+-Dependent 15-Hydroxyprostaglandin Dehydrogenase: Mechanisms of Inhibition and Structure-Activity Relationships", PLOS ONE, vol. 5, No. 11, Nov. 2, 2010 (Nov. 2, 2010), p. e13719.

A. Archelas, et al., "Absolute Configuration of [alpha]-Methylstyrene Oxide: The Correct Absolute Configuration/Optical Rotation Correlation", The Journal of Organic Chemistry, vol . 64, No. 16, Aug. 1, 1999 (Aug. 1, 1999), pp. 6112-6114.

Supplementary European Search Report for Application No. 14859042. 5-1462 / 3057973.

Speth, Jennifer, et al., "Pharmacologic increase in HIF1 a enhances hematopoietic stem and progenitor homing and engraftment", Blood 2014 123: 203-207.

Zhang, Youngyou, et al. "Inhibition of the Prostaglandin Degrading Enzyme 15-PGDH Potentiates Tissue Regeneration" Science. Jun. 12, 2015; 348(6240): aaa2340. doi:10.1126/science.aaa2340.

Castellone, Maria, et al. "Prostaglandin E2 Promotes Colon Cancer Cell Growth Through a Gs-AXIN- -Catenin Signaling AXIS", Dec. 2, 2005, vol. 310, Science.

Goessling, Wolfram, et al., "Genetic interaction of PGE2 and Wnt signaling regulates developmental specification of stem cells and regeneration", Cell. Mar. 20, 2009; 136(6): 1136-1147. doi: 10.1016/j. cell.2009.01.015.

Frisch, Benjamin, et al., "In vivo prostaglandin E2 treatment alters the bone marrow microenvironment and preferentially expands short-term hematopoietic stem cells", Blood, Nov. 5, 2009 z vol. 114, No. 19,pp. 4054-4063.

Hoggati, Jonathan, et al., "Prostaglandin E2 enhances long-term repopulation but does not permanently alter inherent stem cell competitiveness", Blood, Oct. 24, 2013 x vol. 122, No. 17, pp. 2997-3000.

Jung, Peter, et al., "Isolation and in vitro expansion of human colonic stem cells", Nature Medicine 17, 1225-1227 (2011).

Brown, Jr, et al., "COX-2: a molecular target for colorectal cancer prevention", J. Clin Oncol. Apr. 20, 2005;23(12):2840-55.

Kalugin "Functionalized sulfurcontaining compounds. 13.* Synthesis of substituted 3amino2(organylsulfinyl)and (organylsulfonyl)thieno[2,3b]pyridines." Russian Chemical Bulletin, International Edition, vol. 55, No. 3, pp. 529-534, Mar. 2006.

Pubchem Database compound CI D 3337991, 2-butylsulfonyl-4-phenyl-6-thiophen-2-ylthieno[2,3-b]pyridin-3-amine, entered into the database on Sep. 7, 2005, Online "http://pubchem.ncbi.nlm.nih.gov/compound/3337991#section=Top" accessed Oct. 10, 2015.

Online "http://web.archive.org/web/20071219115313/http://www.akosgmbh.de/AKosSamples/index.html "2011, accessed.

Online: "http ://web.archive.org/web/200706301 71 813/http://www. enam ine. net/index. php ?option=com content&task=view &id=22&menuid=51 &PHPSESSID=64a4f248f69d671 a413f487bb62c4d90" dated Jun. 30, 2007, accessed Apr. 1, 2015.

Online "http://web.archive.org/web/20031225052253/http://www.specs.net/", accessed Apr. 1, 2015.

Online "http://web.archive.org/web/20130122020518/http://www.chembridge.com/screening_libraries/" 2011, accessed Oct. 10, 2015.

Zhang "Inhibition of the prostaglandin-degrading enzyme 15-PGDH potentiates tissue regeneration" Science Jun. 12, 2015 • vol. 348 Issue 6240 1223.

Obeid, J., et al., "Tyr-179 and Lys-183 are essential for enzymatic activity of 11 beta-hydroxysteroid dehydroxysteroid dehydrogenase", Biochem Biophys Res Commun. Oct. 15, 1992;188(1):222-7.

Ensor, CM, et al., "Site-directed mutagenesis of the conversed tyrosine 151 of human placental NAO(+)-dependent 15-hydroxyprostaglandin dehydrogenase yields a catalytically inactive enzyme", Biochem Biophys Res Commun. Apr. 30, 1991; 176(2):840-5.

(56) References Cited

OTHER PUBLICATIONS

Tanaka, N., et al., "Crystal Structures of the binary and ternary complexes of 7 alpha-hydroxysteroid dehydrogenase from *Escherichia coli*.", Biochemistry Jun. 18, 1996;35(24):7715-30.
Duveau, DY, et al., "Structure-activity relationship studies and biological characterization of human NAO(+)-dependent 15 hydroxyprostaglandin dehydrogenase", Bioorg Med Chem Lett. Jan. 15, 2014;24(2):630-5.
Piao, Yu Lan, et al., Wound healing effects of new 15-hydroxyprostaglandin dehydrogenase inhibitors, Prostaglandins, Leukotrienes and Essential Fatty Acids 91 (2014)325-332.
Bray, James E., et al. "The human short-chain dehydrogenase/reductase (SOR) superfamily: A bioinformatics Summary", Chemico-Biological Interactions 178(2009) 99-109.
Markowitz, Sanford, et al., "Molecular Basis of Colorectal Cancer", N Engl J Med 2009;361 :2449-60.
Yan, Min, et al., "15-Hydroxyprostaglandin dehydrogenase, a COX-2 oncogene antagonist, is a TGF-~-induced suppressor of human gastrointestinal cancers", PNAS, Dec. 14, 2004, vol. 101, No. 50, 17468-17473.
Ensor, Charles Mark, et al., "Bacterial expression and site-directed mutagenesis of two critical residues ( tyrosine-151 and lysine-155) of human placental NAO +-dependent 15-hydroxyprostaglandin dehydrogenase", Biochimica et Biophysica Acta 1208 (1994) 151-156.
Yan, Min, et al, "15-Hydroxyprostaglandin dehydrogenase inactivation as a mechanism of resistance to celecoxib chemoprevention of colon tumors", PNAS, Jun. 9, 2009, vol. 106, No. 23, 9409-9413.
Tai, Hsin-Hsiung, et al., "Prostaglandin catabolizing enzymes", Prostaglandins & other Lipid Mediators 68-69 (2002) 483-493.
Choi, Dubok, et al., "Control of the intracellular levels of prostaglandin E2 through inhibition of the 15-hydroxyprostaglandin dehydrogenase for wound healing", Choi, D.; et al. Bioorg. Med. Chem. (2013), http:f/dx.doi.org/10.1016/j.bmc.2013.05.049.
Myung, Seung-Jae, et al., "15-Hydroxyprostaglandin dehydrogenase is an in vivo suppressor of colon tumorigenesis" PNAS, Aug. 8, 2006, vol. 103, No. 32, 12098-12102.
Otani, Taisuke, et al., "Levels of NAD+-dependent 15-hydroxyprostaglandin dehydrogenase are reduced in inflammatory bowel disease: evidence for involvement of TNF-a", Am J Physiol Gastrointest Liver Physiol 290: G361-G368, 2006.
Cho, Hoon, et al., "Role of glutamine 148 of human 15-hydroxyprostaglandin dehydrogenase in catalytic oxidation of prostaglandin E2", Bioorganic & Medicinal Chemistry 14 {2006) 6486-6491.
Clifford, P.C., et al., "Treatment of Vasospastic disease with prostaglandin E1", British Medical Journal vol. 281, Oct. 18, 1980, pp. 1031-1034.
Jadhav, Ajit, et al., "Potent and Selective Inhibitors of NAD+-dependent 15-hydroxyprostaglandin dehydrogenase (HPGD)", Probe Report 2011.
Markowitz, Sanford, et al., "Aspirin and Colon Cancer—Targeting Prevention", N Engl J med 256;21, May 27, 2007.
North, Trista E., "PGE2-regulated wnt signaling and N-acetylcysteine are synergistically hepatoprotective in zebrafish acetaminophen injury", PNAS, Oct. 5, 2010, vol. 107, No. 40, pp. 17315-17320.
Wu, Ying, et al., "Synthesis and Biological Evaluation of Novel Thiazolidinedione Analogues as 15-Hydroxyprostaglandin Dehydrogenase Inhibitors", J Med Chem, Apr. 5, 2011, 54, 5260-5264.
Cho, et al., "Inhibition of NAD+-dependent 15-hydroxyprostaglandin dehydrogenase (15-PGDH) by cyclooxygenase inhibitors and chemopreventive agents", Prostaglandins, Leukotrienes and Essential FattyAcids {2002) 67(6), 461-465.
Hamza, Adel, et al., "Understanding human 15-hydroxyprostaglandin dehydrogenase binding with NAO+ and PGE2 by homology modeling, docking and molecular dynamics simulation", Bioorganic & Medicinal Chemistry 13 (2005) 4544-4551.
Berg, Daniel J., et al. "Rapid Development of Colitis in NSAID-Treated IL-10-Deficient Mice", Gastroenterology 2002; 123: 1527-1542.
Kabashima, Kenji, et al., "The prostaglandin receptor EP4 suppresses colitis, mucosal damage and CD4 cell activation in the gut", J. Clin. Invest. 109:883-893 (2002).
Berk, L.B., et al., "16,16-Dimethyl Prostaglandin E2 and/or Syngeneic Bone Marrow Transplantation Increase Mouse Survival After Supra-Lethal Total Body Irradiation", Int. J Radiation Oncology Biol. Phys. vol. 18. pp. 1387-1392.
Goessling, Wolfram, et al., "Prostaglandin E2 Enhances Human Cord Blood Stem Cell Xenotransplants and Shows Long-Term Safety in Preclinical Nonhuman Primate Transplant Models", Cell Stem Cell 8, 445-458, Apr. 8, 2011.
Porter, Rebecca L., et al., "Prostaglandin E2 Increases Hematopoietic Stem Cell Survival and Accelerates Hematopoietic Recovery After Radiation Injury", Stem Cells 2013;31 :372-383.
Kurland, JI, et al., "prostaglandin E in the positive and negative feedback control of myeloid Role for monocyte-macrophage-derived colony-stimulating factor and stem cell proliferation" Blood 1978 52: 388-407.
Hoffman, Corey M., et al., "Minireview: Complexity of Hematopoietic Stem Cell Regulation in the Bone Marrow Microenvironment", Mol Endocrinol, 2014.
Frisch, Benjamin J., et al., "In vivo prostaglandin E2 treatment alters the bone marrow stem cells microenvironment and preferentially expands short-term hematopoietic", Blood 2009 114: 4054-4063.
Gentile, P., et al., "In vivo modulation of murine myelopoiesis following intravenous administration of prostaglandin E2", Blood 1983 62: 1100-1107.
Office Action for Japanese Patent Application No. 2015-507115, dated Jan. 1, 2017.
Blake et al., "Studies with Deuterated Drugs", Journal of Pharmaceutical Sciences, vol. 64, 1975, pp. 367-391.
Hall, P. R. et al., "Small molecule inhibitors of hantavirus infection", Bioorganic & Medicinal Chemistry Letters, 2010, vol. 20, No. 23, pp. 7085-7091.
Partial Supplementary European Search Report for Application No. 16780752.8-1116/3283074, dated Aug. 14, 2018.
Lakatos, et al., "The Role of PPARs in Lung Fibrosis", PPAR Research, vol. 2007, pp. 1-10, Jan. 1, 2017.
Partial Supplementary European Search Report for Application No. 16762344.6/3267995, dated Oct. 22, 2018.
Examination Report for Australian Application No. 2018200368, dated Jul. 31, 2018.

\* cited by examiner

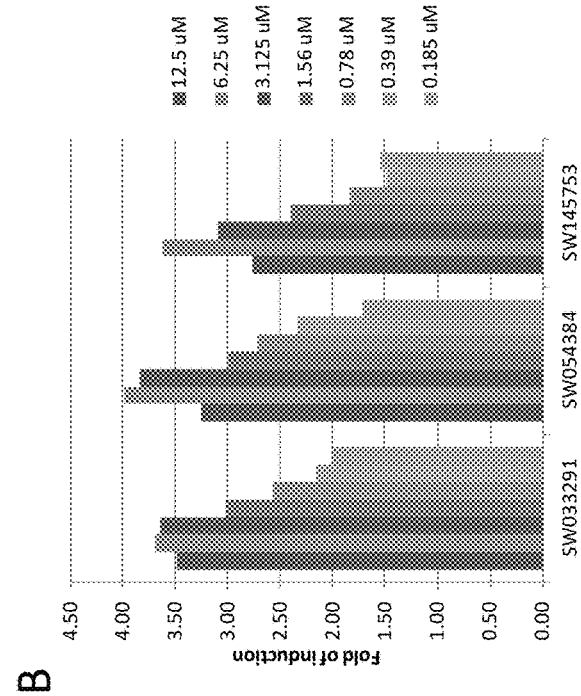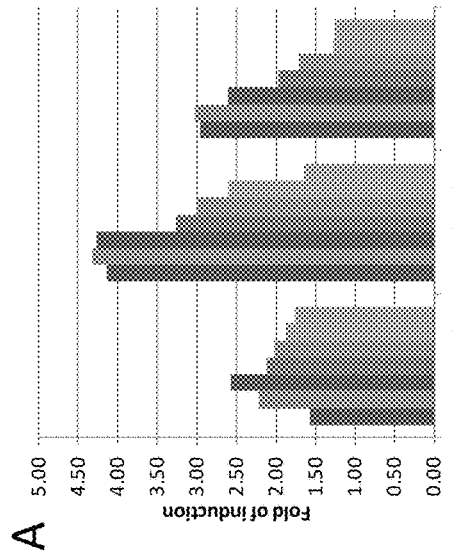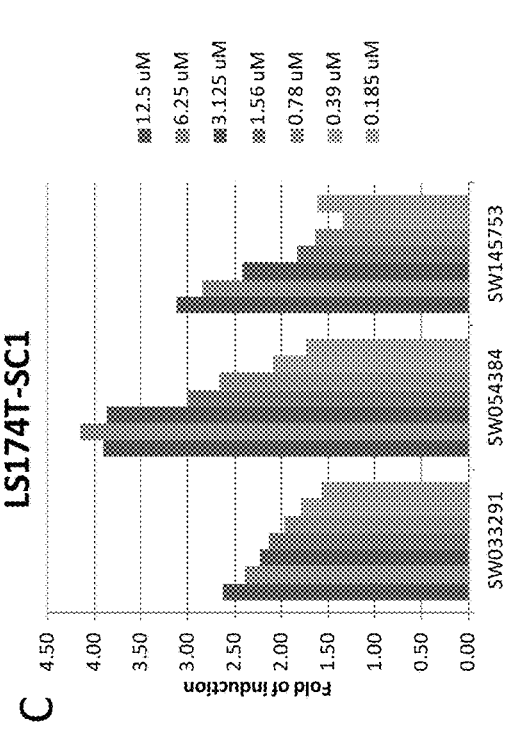
Figs. 1A-C

SW124531:
1) Stabilized WT/MU 15-PGDH
2) didn't change the HSD17B4 protein level Mutant PGDH: (Y151L and K155E): lacks enzyme activity

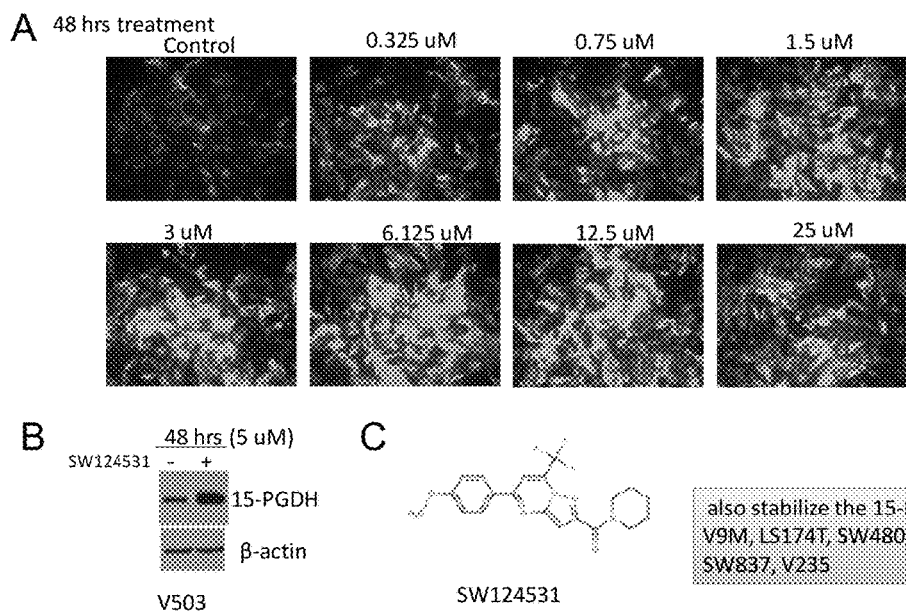
Figs. 5A-C

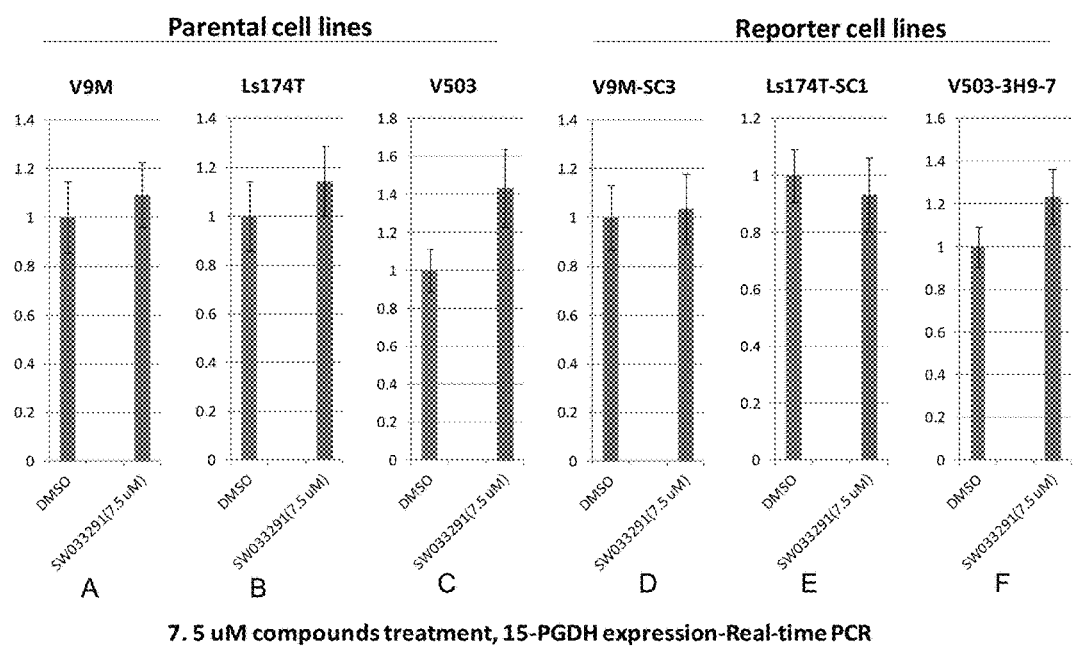
Figs. 6A-F

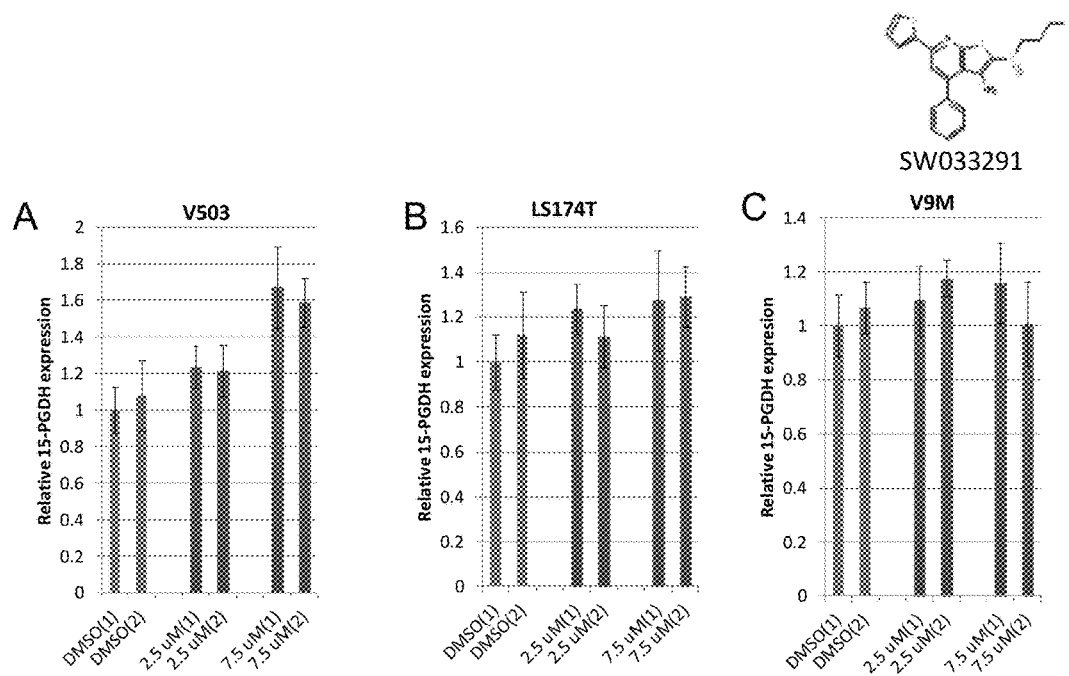
Figs. 7A-C

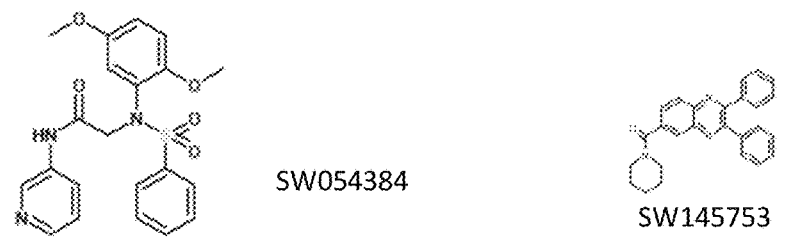
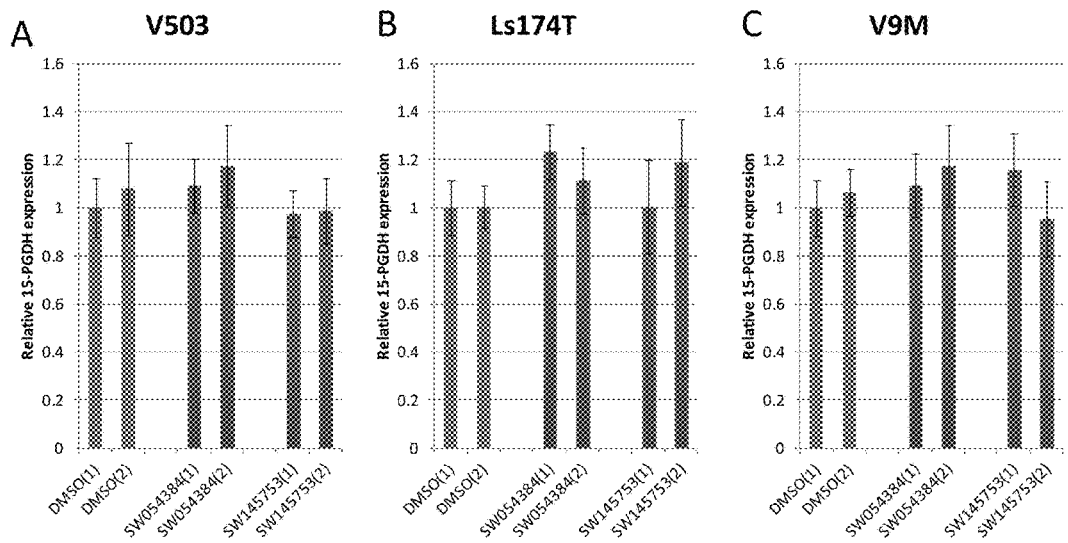
Figs. 8A-C

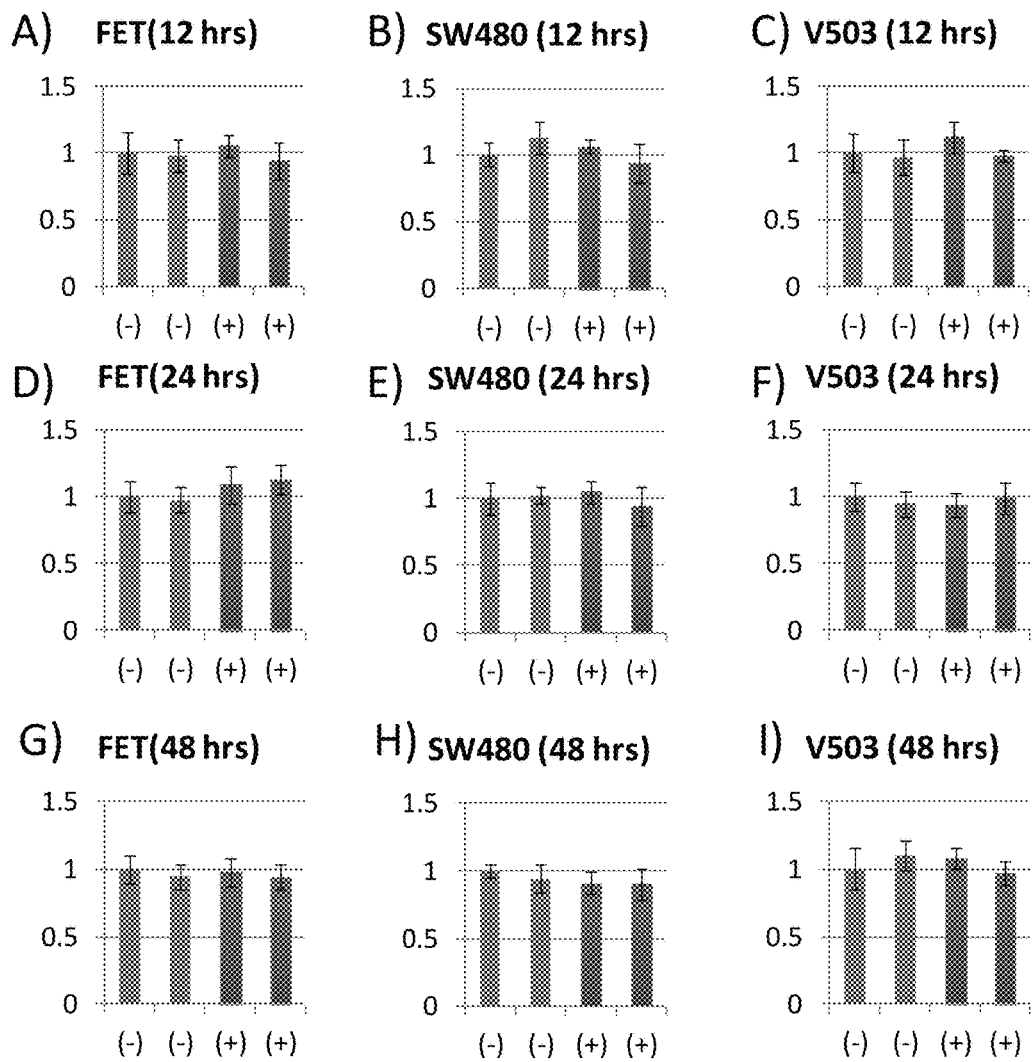
Figs. 9A-I

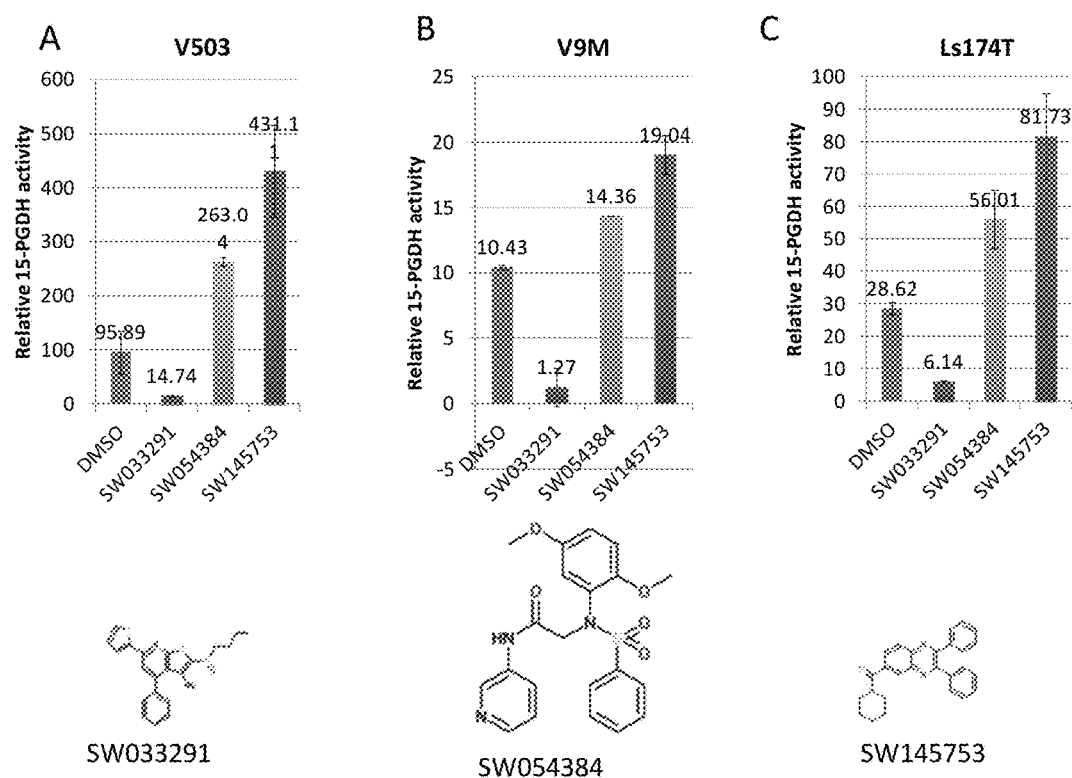
Figs. 10A-C

In Vitro activity assay of recombinant 15- PGDH when treated with compounds (04/28/2011)
| [drug] nM | 50000 | 5000 | 2500 | 1250 | 500 | 250 | 125 | 50 | 25 | 12.5 | 6.25 | 5 | 1.25 | 0 | IC50 |
|---|---|---|---|---|---|---|---|---|---|---|---|---|---|---|---|
| sw0543 84 | 438 | 1767 | | 2504 | 2904 | | | 2809 | | | | 2857 | | 2869 | >5000 |
| sw1457 53 | 141 | 151 | | 125 | 145 | 217 | 291 | 441 | 798 | 1186 | 1652 | 2198 | | 2198 | <12.5 |
| Cay1 | 213 | 163 | 223 | 278 | 538 | 815 | 1272 | 1781 | 2286 | 2782 | 2870 | | | 2959 | 25 to 62.5 |
| SW033291 | 117 | 139 | 113 | 95 | 96 | 81 | 135 | 113 | 204 | 303 | 260 | 598 | | 2729 | <1nm |
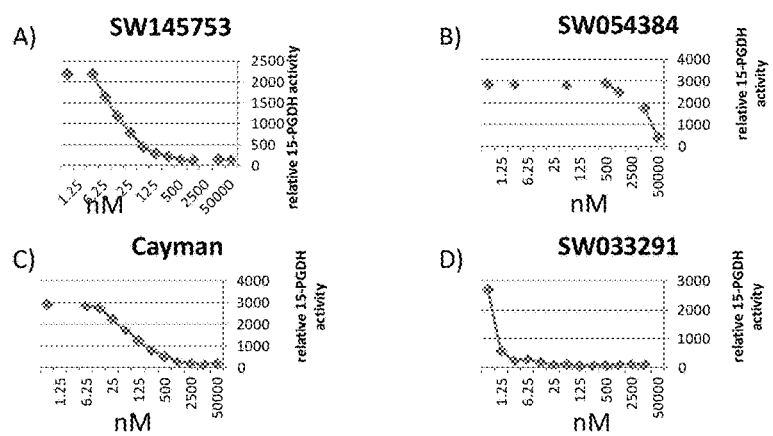
Figs. 11A-D

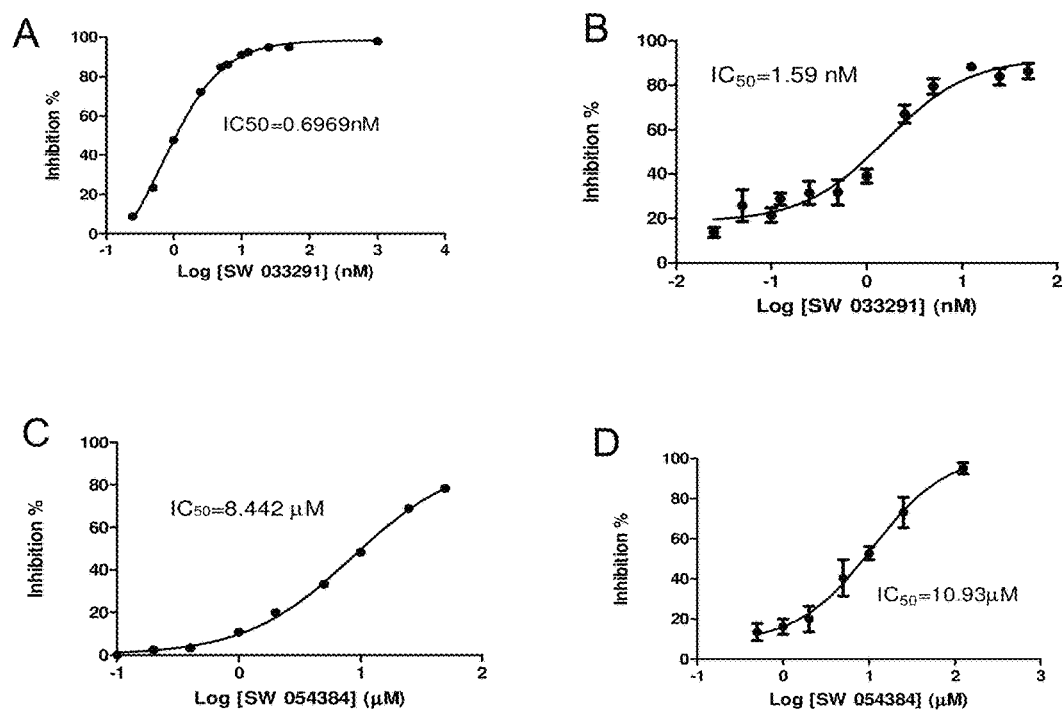
Figs. 12A-D

Increased PGDH activity in pellets of SW124531 treated cells

Table A

| Treatment<br>Activity Cell | DMSO(1) | DMSO(2) | SW124531(1) | SW124531(2) | TGFb(1) | TGFb(2) |
|---|---|---|---|---|---|---|
| SW480 | 87.5 | 139.0476 | 204.3796 | 191.0256 | | |
| V235 | 634.0336 | 691.2371 | 1049.474 | 1068.852 | 1054.327 | 854.2017 |
| V9M | 16.28788 | 9.803922 | 19.55128 | 21.69118 | | |
| V503 | 101.2987 | 105.5556 | 296.5278 | 284.8684 | | |
| V400 | 7.420925 | 5.080831 | 6.730769 | 5.865103 | | |
| V400-S2-36 | 652.2059 | 653.5354 | 1428.235 | 2004.487 | | |
| SW837 | 905.102 | 885.1351 | 1122.34 | 1180.899 | | |

SW124531 is an in vitro inhibitor of PGDH

IC50=54.68 nM

DSF for compounds at 10 uM for WT-PGDH
-------- test the binding of the compound with 15-PGDH

A

B

| CF \ Tm \ CP | DMSO | SW054384 | SW145753 | SW033291 | SW124531 | 15-PGDH inhibitor( Cayman) | Lapatinib |
|---|---|---|---|---|---|---|---|
| Water | 50 | 50.5 | 50 | 50 | 50 | 50.5 | 50.5 |
| NAD(+), 10 uM | 50 | 50 | 56.5 | 51.5, 64.5 | 53 | 51.5 | 50.5 |
| NADH, 10 uM | 50.5 | 50.5 | 57 | 51.5, 65.5 | 53.5 | 51.5 | 50.5 |
|  |  |  |  |  |  |  |  |
| NAD(+), 100 uM | 52 | 52.5 | 58, 64 | 53, 70.5 | 59.5 | 57.5 | 52.5 |
| NADH, 100 uM | 51 | 51 | 59 | 52, 68 | 54.5 | 55 | 50.5 |

Figs. 14A-B

DSF for compounds at 10 uM for Mu-PGDH

A                                    B

No obvious Tm shift, could be due to absent binding or weak binding

Mutant PGDH: (Y151L and K155E)

Figs. 15A-B

IL1β, 18 hrs -> 2.5 uM compound 5 hrs,
IL1b+SW054384(2), pretreated with 2.5 uM SW054384 24 hrs.

Figs. 16A-B

Pretreatment with compound for 24 hrs, add PGE-2 for 24 hrs

Figs. 18A-B

Scratch wound healing of HaCaT confluent monolayer treated with PGDH Inhibitor SW033291 or With TGF-beta

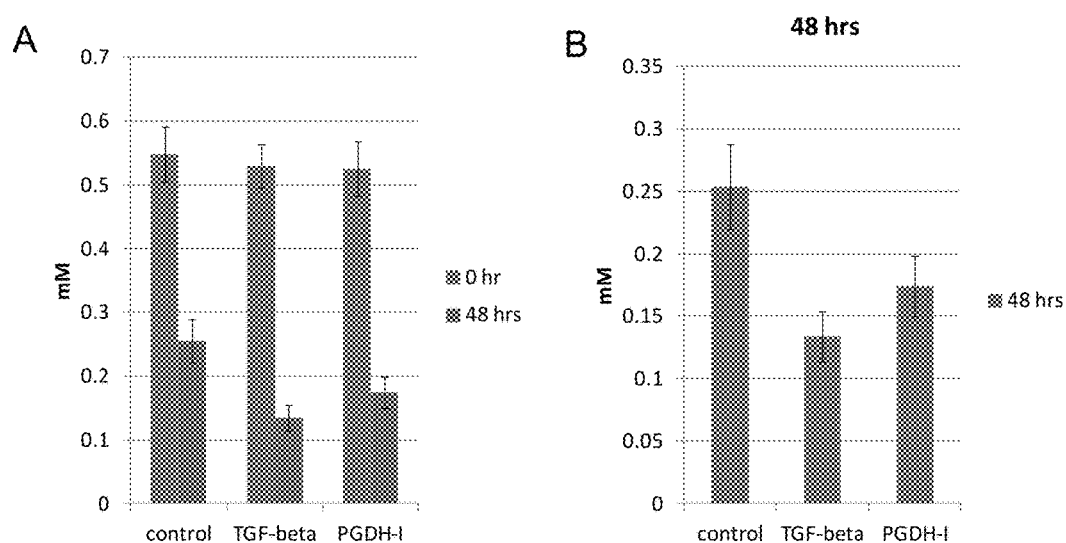
Figs. 20A-B

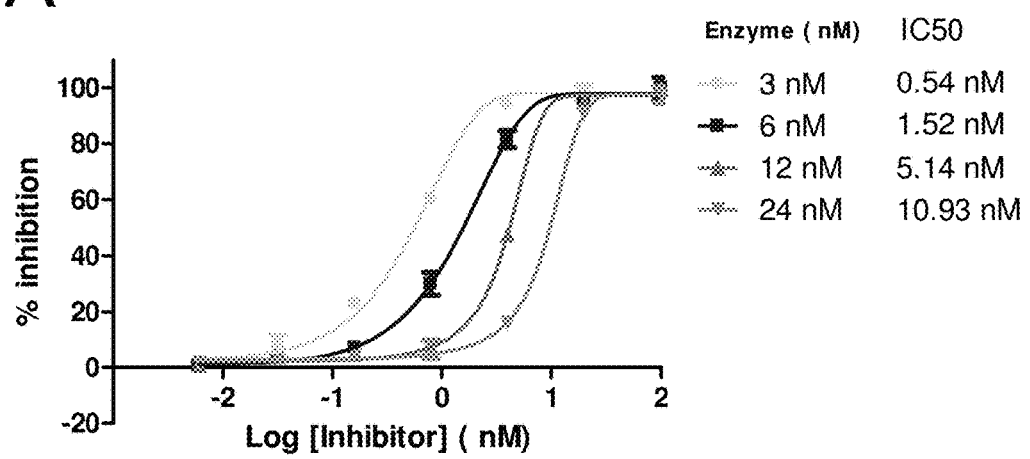
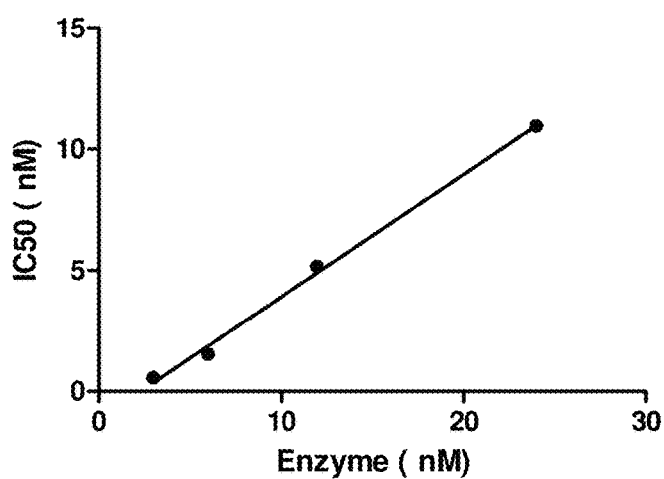
Figs. 21A-B

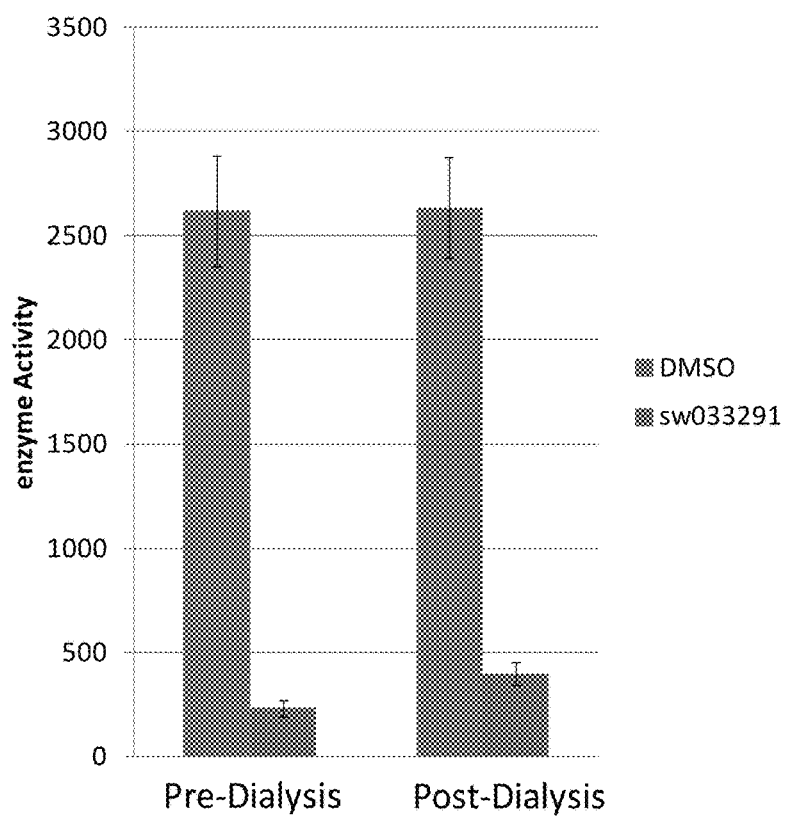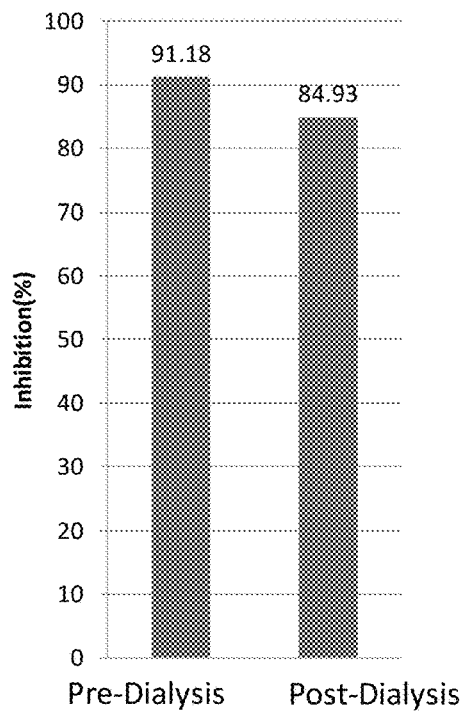
Figs. 22A-B

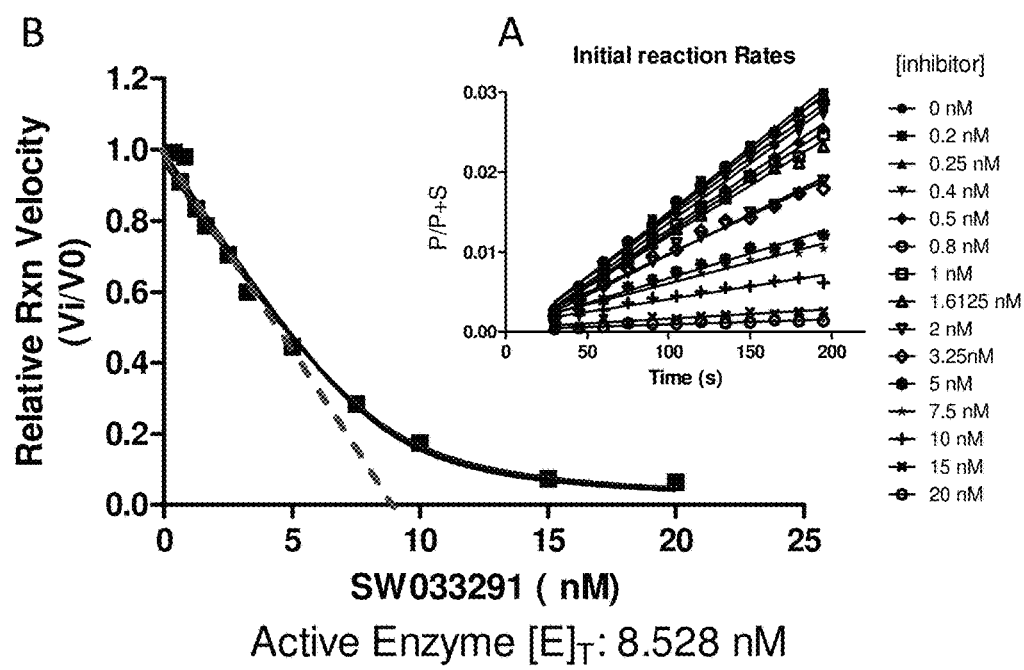
Figs. 23A-B

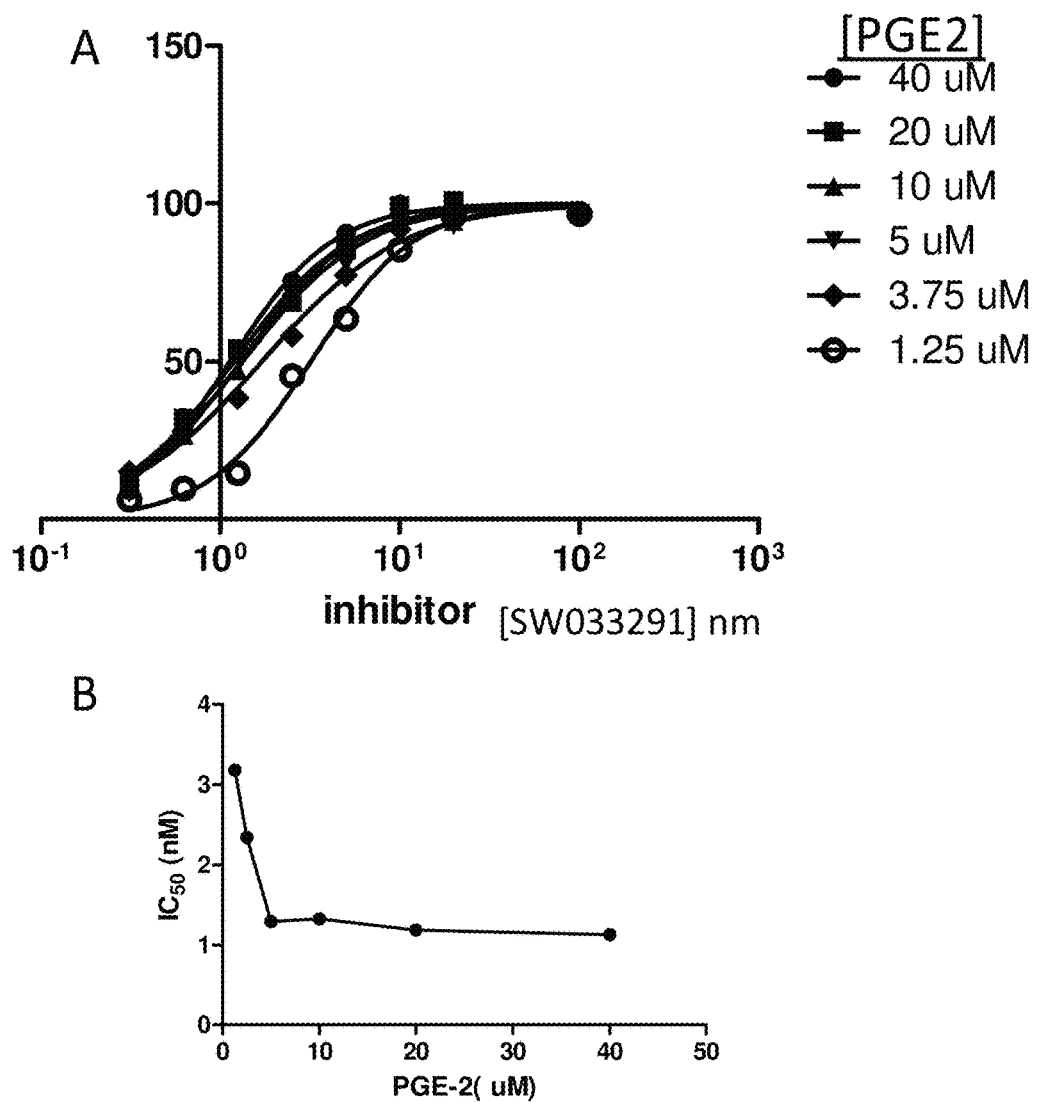
Figs. 24A-B

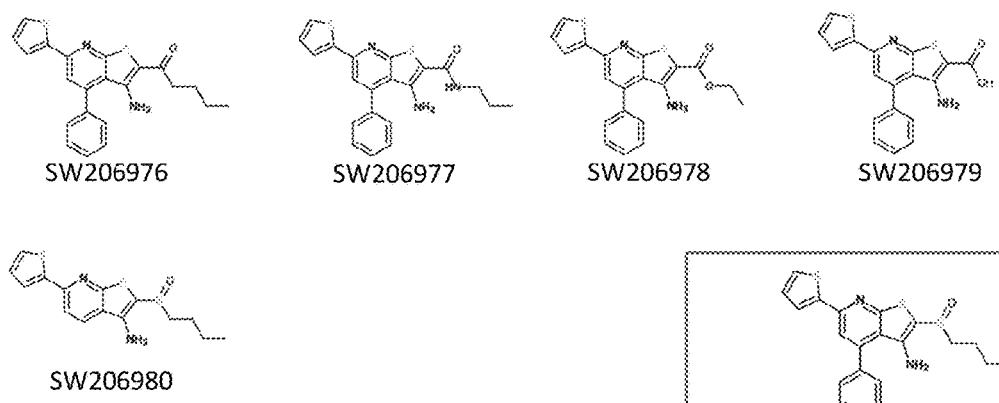
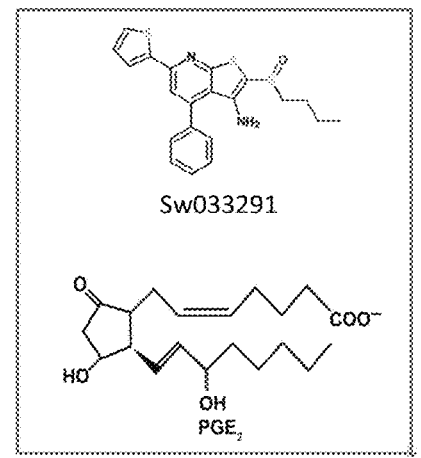
| modification from SW033291 | SW ID | M.W. |
|---|---|---|
|  | SW033291 | 412.591 |
| sulfoxide group->Ketone | SW206976 | 392.54 |
| sulfoxide group->amide | SW206977 | 393.53 |
| sulfoxide group->Ester | SW206978 | 380.48 |
| sulfoxide group->acid | SW206979 | 352.43 |
| without phenyl group | SW206980 | 336.5 |
Fig. 26

Figs. 27A-C

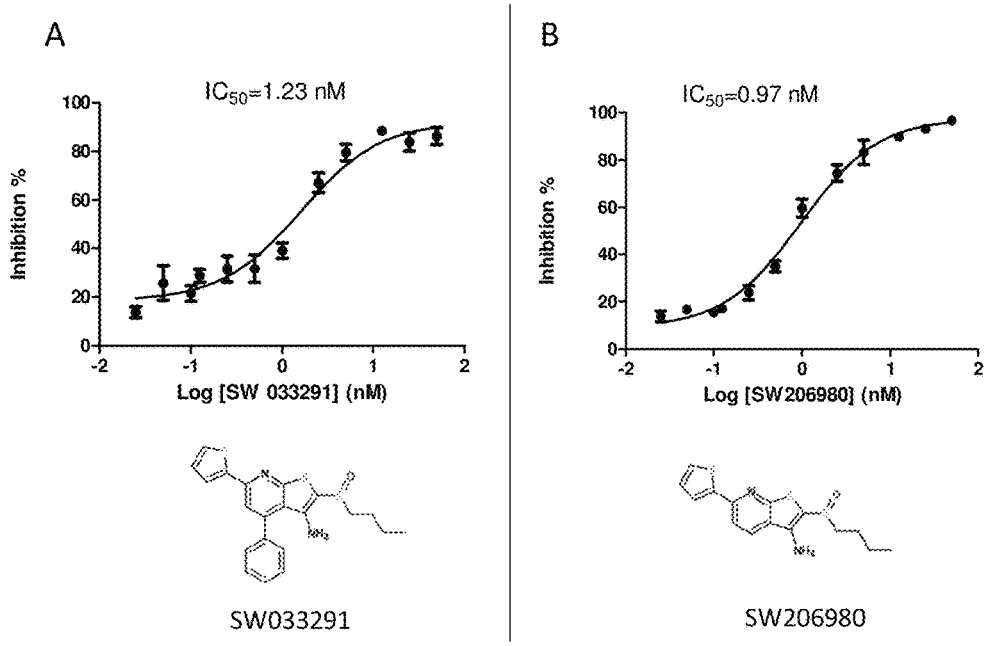
SW0206980 is a slightly more potent 15-PGDH inhibitor than is SW033291
Figs. 29A-B
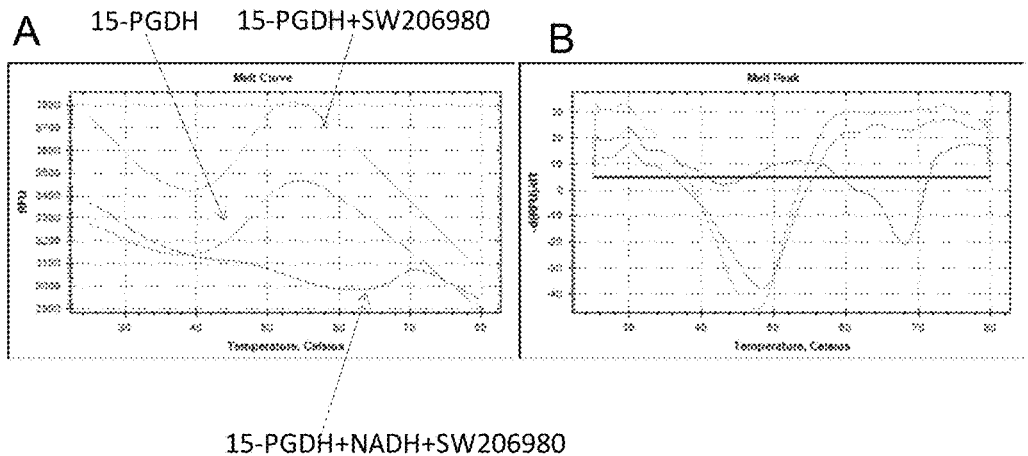
The same Melting profile as SW033291, Major peak at 68c
10 uM protein+ 125 uM NADH+10 uM Compound
Figs. 30A-B

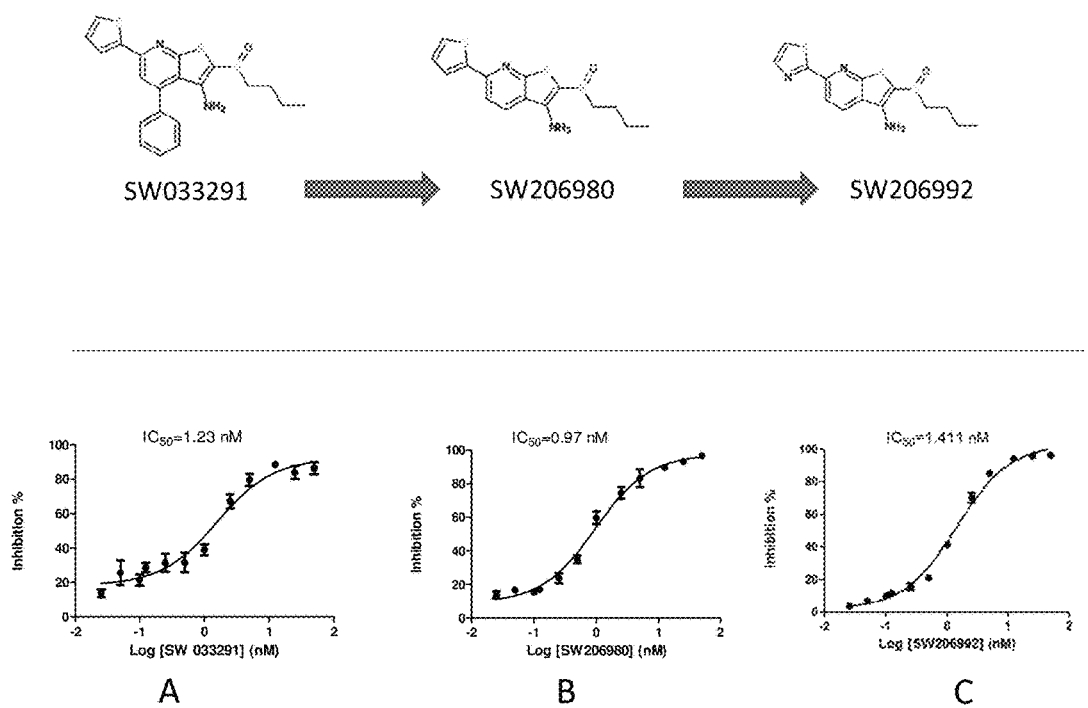
Figs. 31A-C

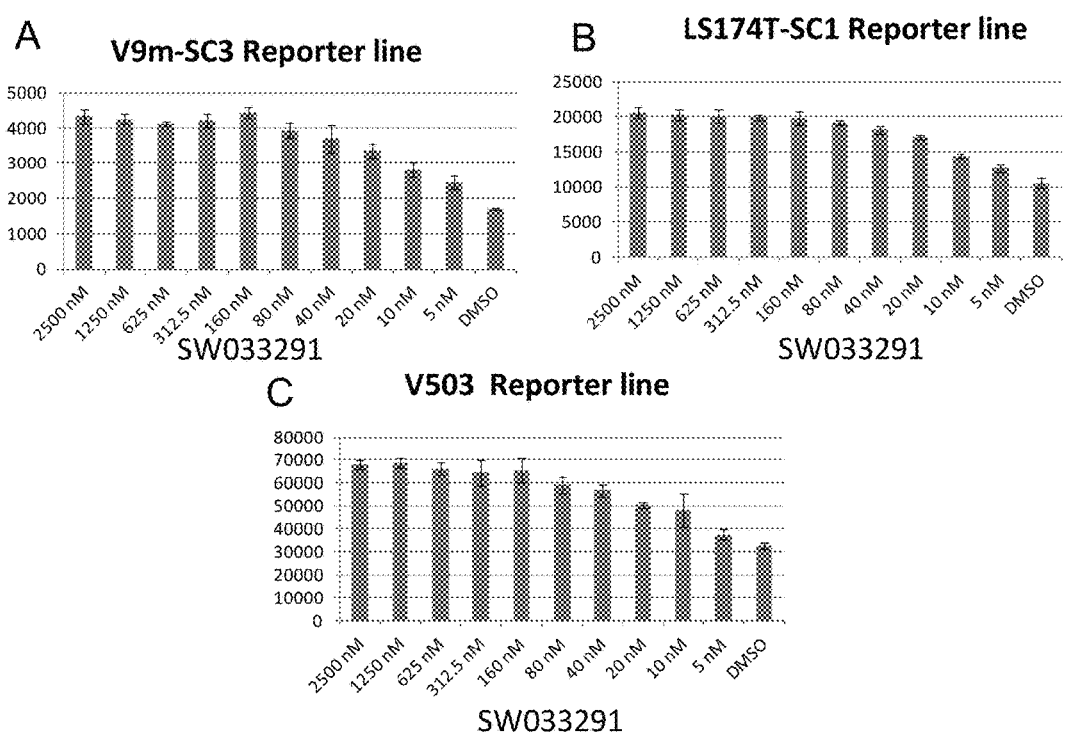
Figs. 32A-C

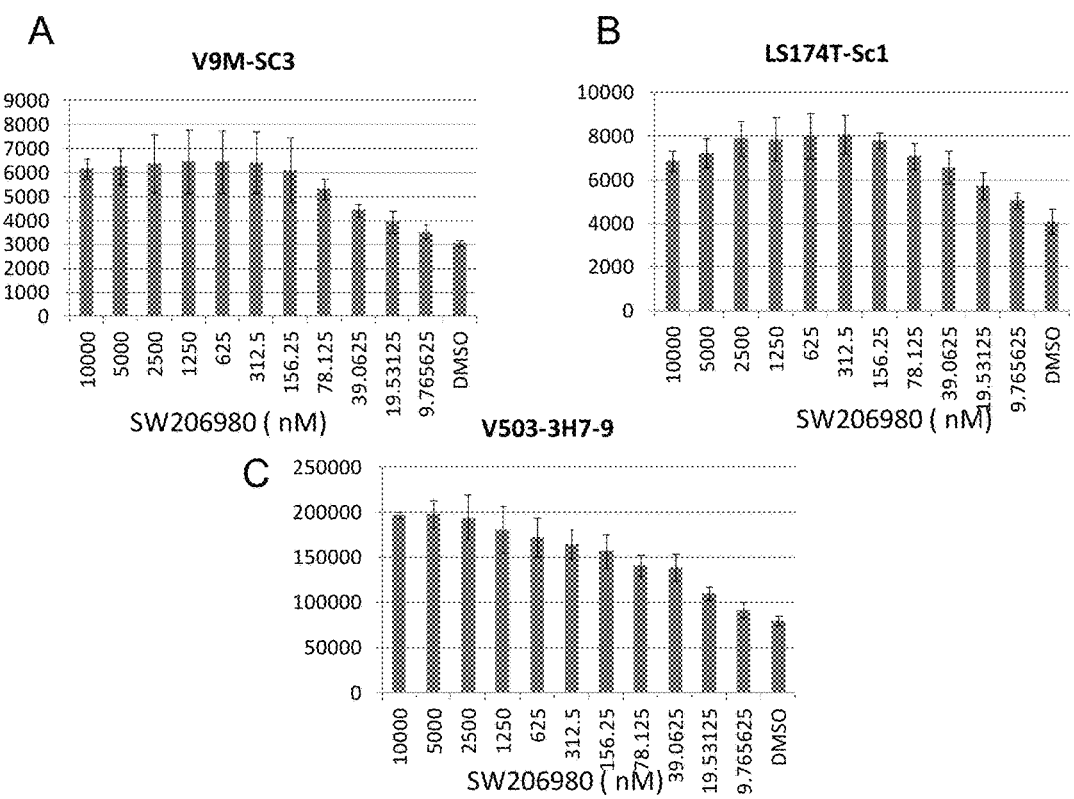
Figs. 33A-C

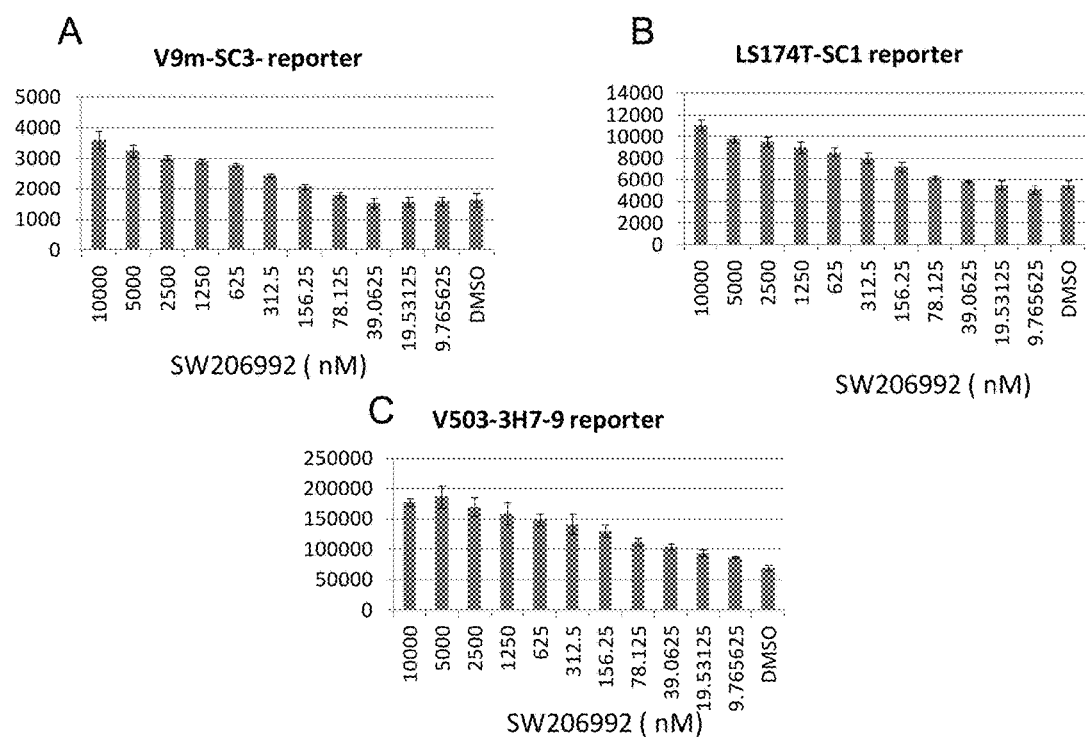
Figs. 34A-C

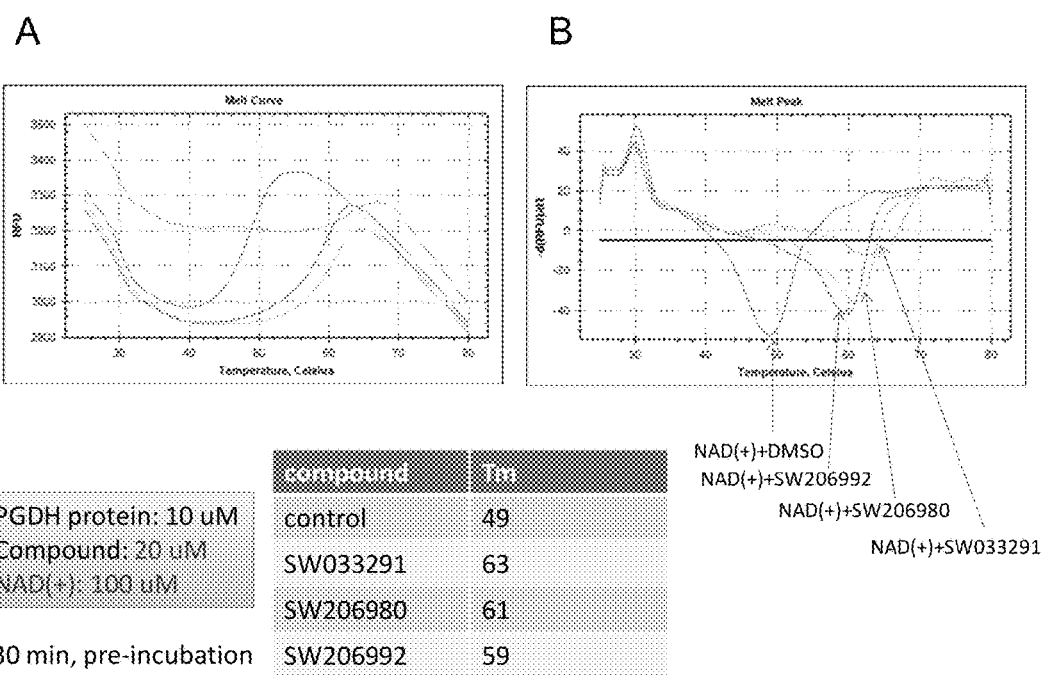
Figs. 35A-B

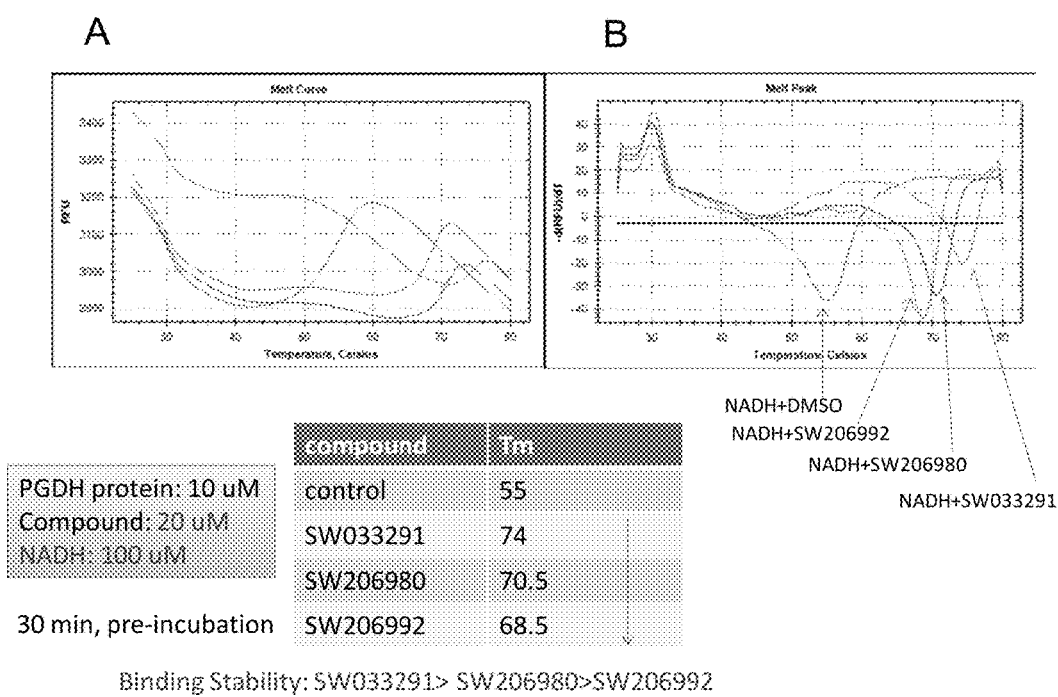
Figs. 36A-B

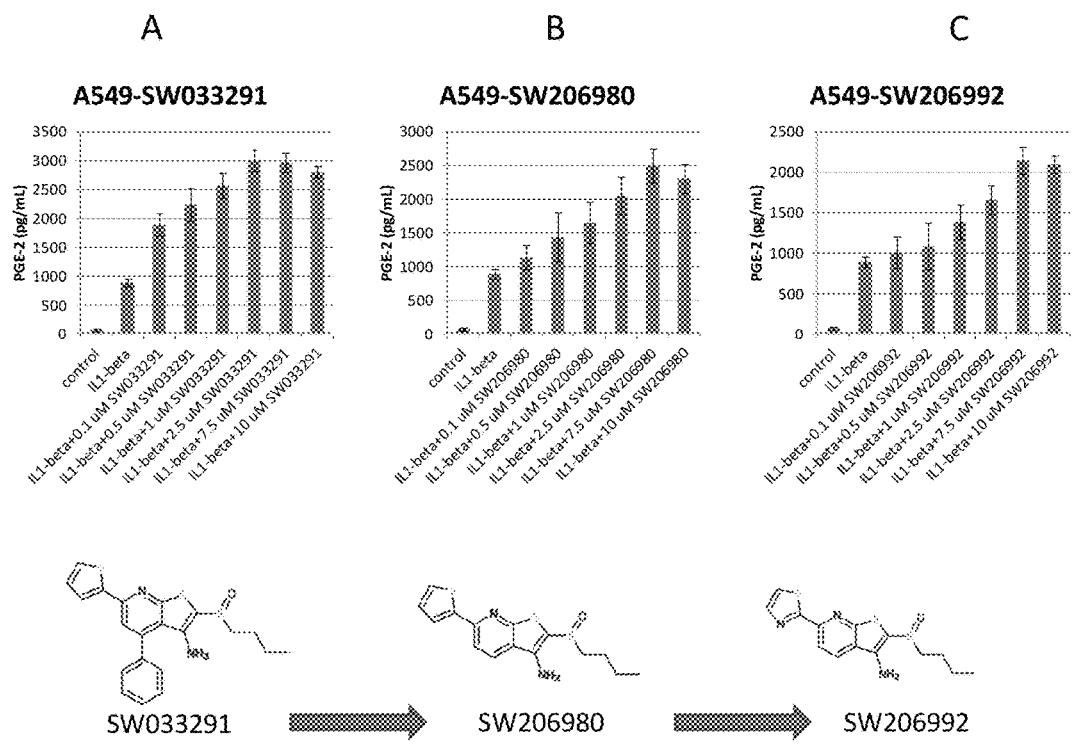
Figs. 37A-C

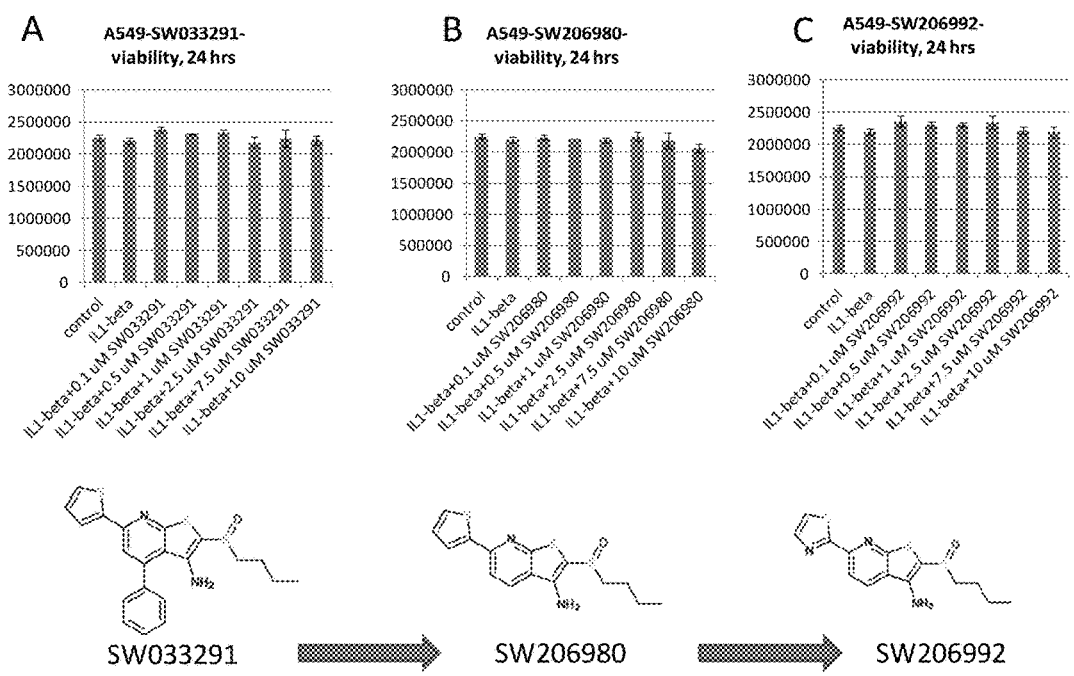
Figs. 38A-C

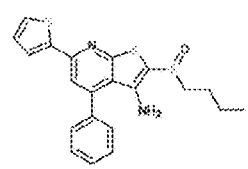
SW033291
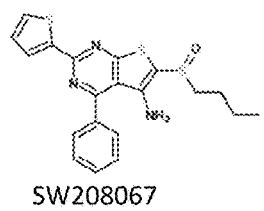 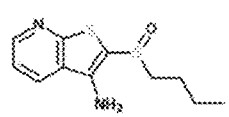 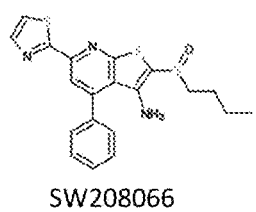
SW208067    SW208064    SW208066
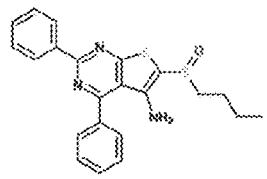 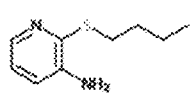 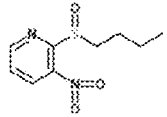 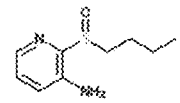
SW208065    SW208068    SW208069    SW208070
Fig. 39

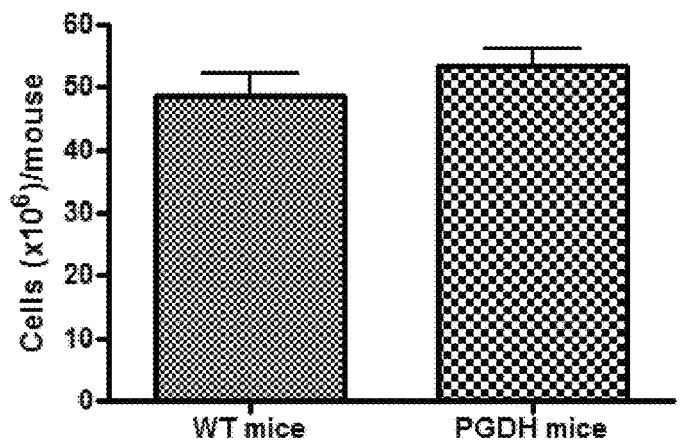
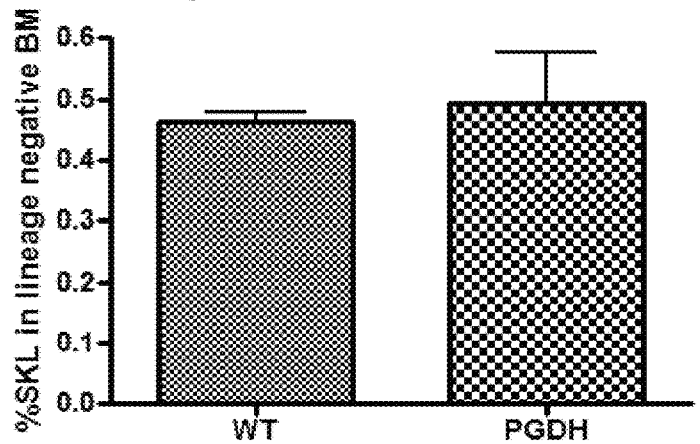
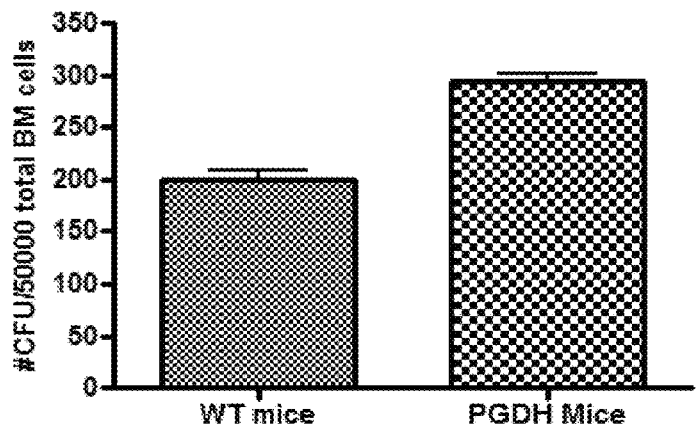
Figs. 46A-C

Figs. 48A-C

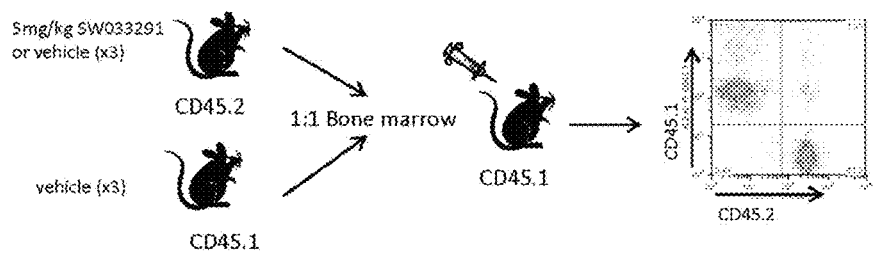
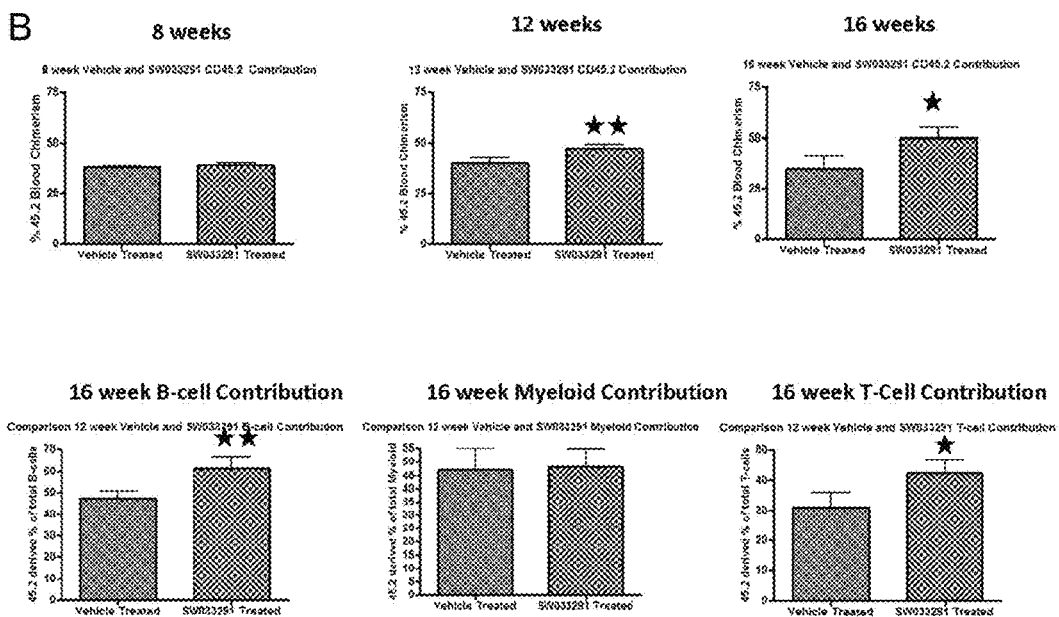
Figs. 49

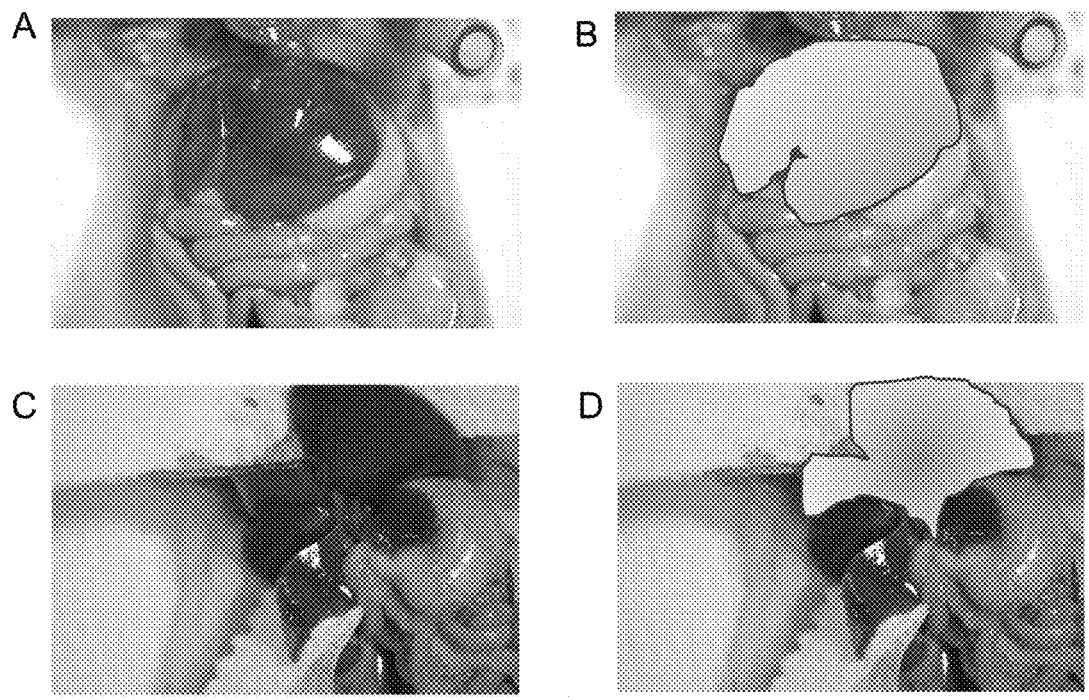
Figs. 52A-D
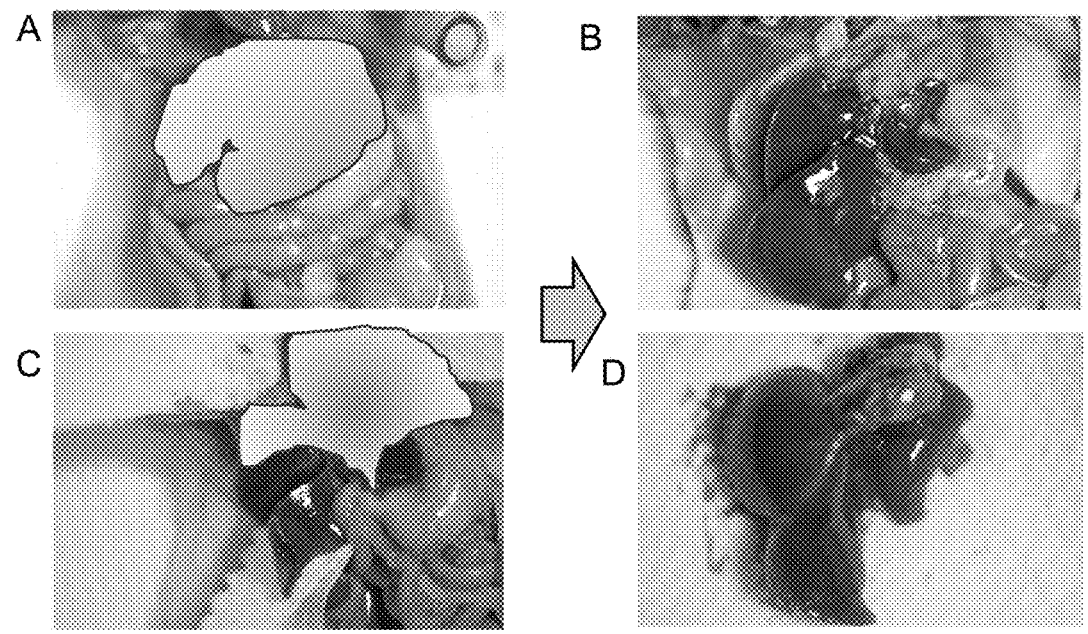
Figs. 53A-D

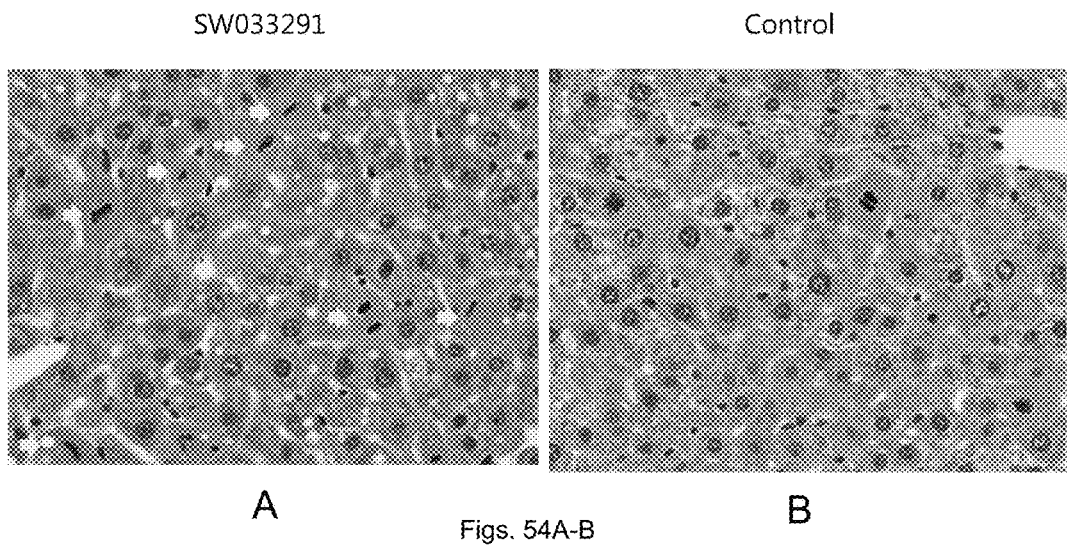
Figs. 54A-B
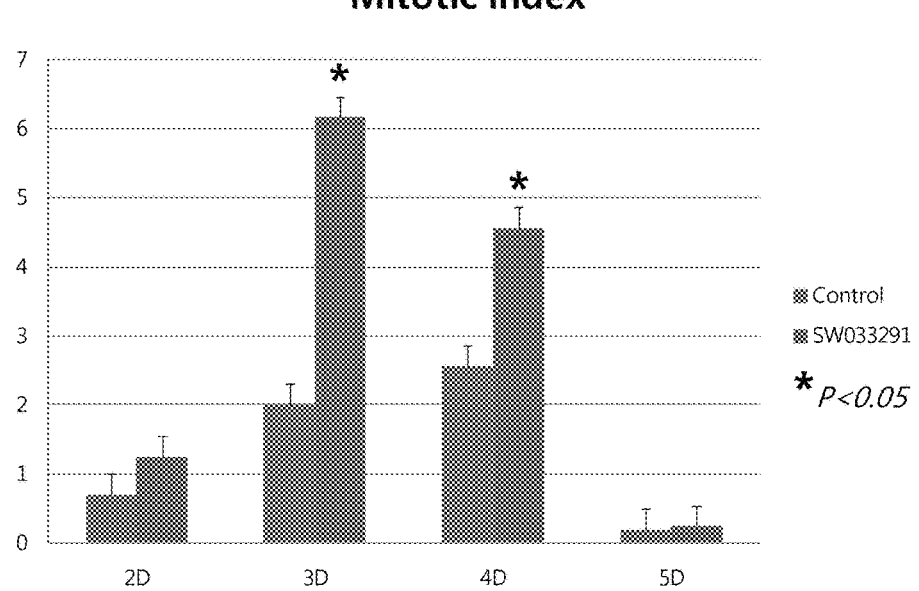
Fig. 55

Figs. 59A-B

BrdU stain on POD 2

BrdU stain on POD 2

Figs. 75A-B

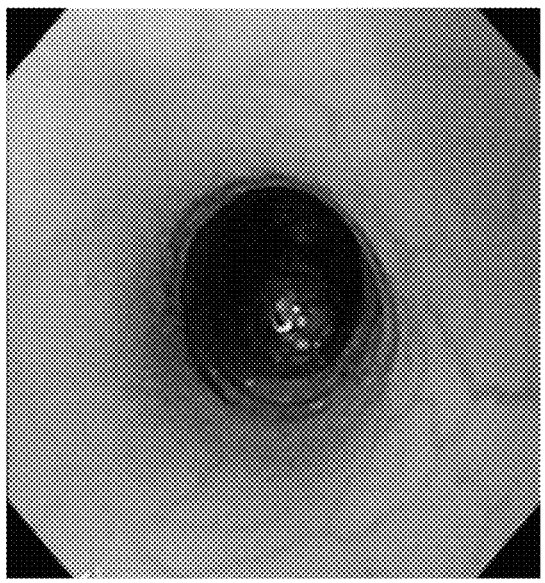
Figs. 77A-B

COMPOSITIONS AND METHODS OF MODULATING 15-PGDH ACTIVITY

RELATED APPLICATION

This application claims priority from U.S. Provisional Application No. 61/624,670, filed Apr. 16, 2012, the subject matter of which is incorporated herein by reference in its entirety.

GOVERNMENT FUNDING

This invention was made with government support under Grant No. R01CA127306, R01CA127306-0351, AND 5P50CA150964, awarded by The National Institutes of Health. The United States government may have certain rights to the invention.

BACKGROUND 15-hydroxy-prostaglandin dehydrogenase (15-PGDH) represents the key enzyme in the inactivation of a number of active prostaglandins, leukotrienes and hydroxyeicosatetraenoic acids (HETEs) (e.g., by catalyzing oxidation of $PGE_2$ to 15-keto-prostaglandin E2, 15 k-PGE). The human enzyme is encoded by the HPGD gene and consists of a homodimer with subunits of a size of 29 kDa. The enzyme belongs to the evolutionarily conserved superfamily of short-chain dehydrogenase/reductase enzymes (SDRs), and according to the recently approved nomenclature for human enzymes, it is named SDR36C1. Thus far, two forms of 15-PGDH have been identified, NAD+-dependent type I 15-PGDH and the type II NADP-dependent 15-PGDH, also known as carbonyl reductase 1 (CBR1, SDR21C1). However, the preference of CBR1 for NADP and the high Km values of CBR1 for most prostaglandin suggest that the majority of the in vivo activity can be attributed to type I 15-PGDH.

Recent studies suggest that inhibitors of 15-PGDH and activators of 15-PGDH could be therapeutically valuable. It has been shown that there is an increase in the incidence of colon tumors in 15-PGDH knockout mouse models. A more recent study implicates increased 15-PGDH expression in the protection of thrombin-mediated cell death. It is well known that 15-PGDH is responsible for the inactivation of prostaglandin E2 ($PGE_2$), which is a downstream product of COX-2 metabolism. $PGE_2$ has been found to be neurotoxic both in vitro and in vivo; thus, COX-2 specific inhibitors, which decrease $PGE_2$ release, exhibit neuroprotective effects. $PGE_2$ has also been shown to be beneficial in a variety of biological processes, such as hair density, dermal wound healing, and bone formation.

SUMMARY

Embodiments described herein relate to compounds and methods of modulating 15-PGDH activities, modulating tissue prostaglandin levels, and/or treating diseases, disorders, or conditions in which it is desired to modulate 15-PGDH activity and/or prostaglandin levels.

In some embodiments, a 15-PGDH inhibitor can be administered to a tissue of a subject at an amount effective to increase prostaglandin levels in the tissue. The 15-PGDH inhibitor can include formula (I):

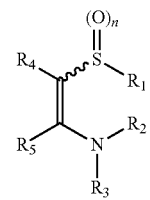

(I)

wherein n is 0-2;

$R_1$ is a $C_{1-8}$ alkyl, which is linear, branched, or cyclic and which is unsubstituted or substituted (e.g., $R_1$ can be a $C_{2-6}$ alkyl, $C_{2-4}$ alkyl, or $C_4$ alkyl, which is linear, branched, or cyclic and which is unsubstituted or substituted);

$R_2$ and $R_3$ are the same or different and are each selected from the group consisting of a H, a lower alkyl group, $(CH_2)_{n1}$ OR' (wherein n1=1, 2, or 3), $CF_3$, $CH_2$—$CH_2X$, O—$CH_2$—$CH_2X$, $CH_2$—$CH_2$—$CH_2X$, O—$CH_2$—$CH_2X$ (wherein X=F, Cl, Br, or I), CN, (C═O)—R', (C═O)N(R')$_2$, O(CO)R', COOR' (wherein R' is H or a lower alkyl group);

$R_4$ and $R_5$ are the same or different and are each selected from the group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—$NH_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—$NH_2$), carbamide (—NH—(CO)—$NH_2$), cyano (—CN), isocyano (—$N^+C^-$), cyanato (—O—CN), isocyanato (—O—$N^+$═$C^-$), isothiocyanato (—S—CN), azido (—N═$N^+$═$N^-$), formyl (—(CO)—H), thioformyl (—(CS)—H), amino (—$NH_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), imino (—CR═NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR═N(alkyl), where R═hydrogen, alkyl, aryl, alkaryl, aralkyl, etc.), arylimino (—CR═N(aryl), where R═hydrogen, alkyl, aryl, alkaryl, etc.), nitro (—$NO_2$), nitroso (—NO), sulfo (—$SO_2$—OH), sulfonato (—$SO_2$—$O^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)($O^-$)$_2$), phosphinato (—P(O)($O^-$)), phospho (—$PO_2$), phosphino (—$PH_2$), combinations thereof, and wherein $R_4$ and $R_5$ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl; and pharmaceutically acceptable salts thereof.

In other embodiments, the 15-PGDH inhibitor can i) at 2.5 µM concentration, stimulate a Vaco503 reporter cell line expressing a 15-PGDH luciferase fusion construct to a luciferase output level of greater than 70 (using a scale on which a value of 100 indicates a doubling of reporter output over baseline); ii) at 2.5 µM concentration stimulate a V9m reporter cell line expressing a 15-PGDH luciferase fusion construct to a luciferase output level of greater than 75; iii) at 7.5 µM concentration stimulate a LS174T reporter cell line expressing a 15-PGDH luciferase fusion construct to a luciferase output level of greater than 70; iv) at 7.5 µM concentration, does not activate a negative control V9m cell line expressing TK-*renilla* luciferase reporter to a level greater than 20; and v) inhibits the enzymatic activity of recombinant 15-PGDH protein at an IC50 of less than 1 µM.

In other embodiments, the 15-PGDH inhibitor can i) at 2.5 µM concentration, stimulate a Vaco503 reporter cell line expressing a 15-PGDH luciferase fusion construct to increase luciferase output; ii) at 2.5 µM concentration stimulate a V9m reporter cell line expressing a 15-PGDH luciferase fusion construct to increase luciferase output; iii) at 7.5 µM concentration stimulate a LS174T reporter cell line expressing a 15-PGDH luciferase fusion construct to increase luciferase output; iv) at 7.5 µM concentration, does not activate a negative control V9m cell line expressing TK-*renilla* luciferase reporter to a luciferase level greater than 20% above background; and v) inhibits the enzymatic activity of recombinant 15-PGDH protein at an IC50 of less than 1 µM.

In other embodiments, the 15-PGDH inhibitor can inhibit the enzymatic activity of recombinant 15-PGDH at an IC50 of less than 1 µM, or preferably at an IC50 of less than 250 nM, or more preferably at an IC50 of less than 50 nM, or more preferably at an IC50 of less than 5 nM.

In still other embodiments, the 15-PGDH inhibitor can be applied to skin of a subject to promote and/or stimulate pigmentation of the skin and/or hair growth and/or inhibit hair loss. The 15-PGDH inhibitor can also be administered to a subject to promote wound healing, regenerate tissue, and/or treat at least one of oral ulcers, ulcerative colitis, gastrointestinal ulcers, inflammatory bowel disease, vascular insufficiency, colitis, Raynaud's disease, Buerger's disease, diabetic neuropathy, pulmonary artery hypertension, cardiovascular disease, diabetic ulcers, renal disease, and erectile dysfunction. The 15-PGDH inhibitor can further be administered to a subject in combination with a prostanoid agonist for the purpose of enhancing the therapeutic effect of the agonist in prostaglandin responsive conditions.

In some embodiments, the 15-PGDH inhibitor can be administered to tissue of a subject to increase tissue stem cells. The 15-PGDH inhibitor can also be administered to a bone marrow graft donor or a hematopoietic stem cell donor to increase the fitness of a donor bone marrow graft or a donor hematopoietic stem cell graft. The 15-PGDH inhibitor can be administered to bone marrow of a subject to increase stem cells in the subject. The 15-PGDH inhibitor can further be administered to bone marrow of a subject to increase the fitness of the marrow as a donor graft.

In other embodiments the 15-PGDH inhibitor can be administered to a preparation of hematopoietic stem cells of a subject to increase the fitness of the stem cell preparation as a donor graft. The 15-PGDH inhibitor can also be administered to a preparation of peripheral blood hematopoietic stem cells of a subject to increase the fitness of the stem cell preparation as a donor graft. The 15-PGDH inhibitor can further be administered to a preparation of umbilical cord stem cells to increase the fitness of the stem cell preparation as a donor graft.

In yet other embodiments, the 15-PGDH inhibitor can be administered to a subject to mitigate bone marrow graft rejection, to enhance bone marrow graft engraftment, and/or to enhance engraftment of a hematopoietic stem cell graft, or an umbilical cord stem cell graft.

In still other embodiment, the 15-PGDH inhibitor can be administered to a subject or to a tissue graft of a subject to mitigate graft rejection or to enhance graft engraftment.

In other embodiments, the 15-PGDH inhibitor can be administered to a subject or to tissue of the subject to confer resistance to toxic or lethal effects of exposure to radiation.

In other embodiments, the 15-PGDH inhibitor can be administered to a subject for the treatment of osteoporosis, bone fractures, or promoting healing after bone injury or joint replacement.

In an alternative example, the 15-PGDH inhibitor can be administered to a subject or to the liver of a subject to promote liver regeneration following liver resection or following toxic injury to the liver. In one instance, toxic injury to the liver may be caused by overdose of acetaminophen or related hepatotoxic compounds.

In still other embodiments of the application, a 15-PGDH activator can be administered to a tissue of a subject at an amount effective to increase 15-PGDH levels and decrease prostaglandin levels in the tissue. The 15-PGDH activator can include formula (IV):

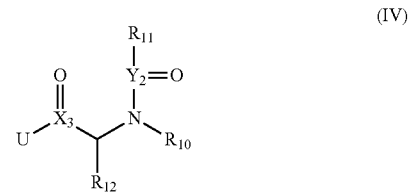

(IV)

wherein $X_3$ and $Y_2$ are independently C or SO;

U is OR" (wherein R" is H, a substituted or unsubstituted alkyl group, or substituted or unsubstituted aryl group) or

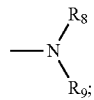

$R_8$, $R_9$, $R_{10}$, $R_{11}$, and $R_{12}$ are each selected from the group consisting of H, F, Cl, Br, I, an alkyl group, $(CH_2)_{n1}OR'$ (wherein n1=1, 2, or 3), $CF_3$, $CH_2-CH_2X$, $O-CH_2-CH_2X$, $CH_2-CH_2-CH_2X$, $O-CH_2-CH_2X$ (wherein X=F, Cl, Br, or I), CN, (C=O)—R', $N(R')_2$, $NO_2$, (C=O)N(R')$_2$, O(CO)R', OR', SR', COOR' (wherein R' is H or a lower alkyl group), a substituted or unsubstituted aryl, a substituted or unsubstituted cycloalkyl, a substituted or unsubstituted heterocyclyl, and $R_8$ and $R_9$ may be linked to form a cyclic or polycyclic ring; and pharmaceutically acceptable salts thereof.

In some embodiments, the activator can i) at 7.5 µM concentration, stimulate a Vaco503 reporter cell line expressing a 15-PGDH luciferase fusion construct to a luciferase output level of greater than 50 (using a scale on which a value of 100 indicates a doubling of reporter output over baseline); ii) at 7.5 µM concentration stimulate a V9m reporter cell line expressing a 15-PGDH luciferase fusion construct to a luciferase output level of greater than 50; iii) at 7.5 µM concentration stimulate a LS174T reporter cell line expressing a 15-PGDH luciferase fusion construct to a luciferase output level of greater than 50; iv) at 7.5 µM concentration, does not activate the negative control V9m cell line expressing TK-*renilla* luciferase reporter to a level any greater than 25; and v) against recombinant 15-PGDH protein the compound shows an $IC_{50}$ concentration for inhibiting 15-PGDH enzyme activity of greater than or equal to 2.5 µM.

In some embodiments, the activator can i) at 7.5 µM concentration, stimulate a Vaco503 reporter cell line expressing a 15-PGDH luciferase fusion construct to increase luciferase output; ii) at 7.5 µM concentration stimulate a V9m reporter cell line expressing a 15-PGDH luciferase fusion construct to increase luciferase output; iii) at 7.5 µM concentration stimulate a LS174T reporter cell line expressing a 15-PGDH luciferase fusion construct to increase luciferase output; iv) at 7.5 µM concentration, does not activate the negative control V9m cell line expressing TK-*renilla* luciferase reporter to a luciferase level any greater than 25% above; and v) against recombinant 15-PGDH protein the compound shows an $IC_{50}$ concentration for inhibiting 15-PGDH enzyme activity of greater than or equal to 2.5 µM.

In other embodiments, the 15-PGDH activator can be administered to a subject to treat a neoplasia, such as a colon neoplasia. The 15-PGDH activator can also be administered to a subject to prevent neoplasia, such as a colon neoplasia. The 15-PGDH activator can also be administered to a subject to reduce inflammation and/or pain.

BRIEF DESCRIPTION OF THE DRAWINGS

FIGS. 1(A-C) illustrate graphs showing luciferase activity of cells that express a 15-PGDH luciferase fusion construct created by targeted gene knock-in of *renilla* luciferase into the last coding exon of 15-PGDH treated with the compounds SW033291, SW054384, and SW145753 at various concentrations. The activity is demonstrated in three different colon cancer cell lines all engineered to contain the 15-PGDH-luciferase fusion. These cell lines are Vaco-9m (V9m), LS174T, Vaco503 (V503).

FIGS. 5(A-C) illustrate 15-PGDH protein levels in V503 cells treated with SW124531 as assayed by immuno-fluorescence (upper two rows) and by western blot (lower panel).

FIGS. 6(A-F) illustrate graphs showing 15-PGDH mRNA levels in colon cancer cell lines treated with SW033291.

FIGS. 7(A-C) illustrate graphs showing 15-PGDH mRNA levels in colon cancer cell lines treated with SW033291.

FIGS. 8(A-C) illustrate graphs showing 15-PGDH mRNA levels in colon cancer cell lines treated with SW054384 and SW145753.

FIGS. 9(A-I) illustrate graphs showing 15-PGDH mRNA levels in colon cancer cell lines treated with 5 µM SW124531.

FIGS. 10(A-C) illustrate graphs showing 15-PGDH activity in cell lines treated with SW033291, SW054384, and SW145753. Activity is measured as pmol $PGE_2$/min/million cells.

FIGS. 11(A-D) illustrates a table and plots showing activity of recombinant 15-PGDH protein (a 15-PGDH-GST fusion protein) incubated with varying concentrations of the test compounds.

FIGS. 12(A-D) illustrate plots showing the activity of recombinant 15-PGDH protein treated with SW033291 and SW054384, with panels 12A and C measuring transfer of tritium from a radiolabeled PGE2 substrate and panels 12 B and D measuring generation of NADH by fluorescence.

FIGS. 20(A-B) illustrate graphs showing the quantitation of scratch width at 0 and 48 hours in the control, SW033291 (2.5 µM) treated cells, and the TGF-beta (1 ng/ml) treated cells.

FIGS. 21(A-B) illustrate plots showing: (A) percent inhibition of PGDH using titrations of 15-PGDH inhibitor SW033291 run at different 15-PGDH concentrations; and (B) the IC50 of 15-PGDH inhibitor SW033291 versus 15-PGDH concentration.

FIGS. 22(A-B) illustrate graphs showing: (A) 15-PGDH enzyme inhibiting activity and (B) percent inhibition of activity due to of SW033291 as measured before and after dialysis of the 15-PGDH and SW033291 mixture.

FIGS. 23(A-B) illustrate a plot showing reaction rates and relative reaction velocity of 15-PGDH at varying concentrations of SW033291.

FIGS. 24(A-B) illustrate plots showing: (A) inhibition of 15-PGDH by SW033291 in the presence of PGE-2; and (B) IC50 of SW033291 against 15-PGDH versus PGE2 concentration.

FIG. 26 illustrates a schematic diagram showing additional analogues of SW033291.

FIGS. 29(A-B) illustrate plots showing the IC50 against 15-PGDH of SW033291 and SW0206980.

FIGS. 30(A-B) illustrate plots showing melting profiles of SW0206890 and SW033291 binding to 15-PGDH.

FIGS. 31(A-C) illustrate plots showing percent inhibition of 15-PGDH activity by SW033291, SW206980, and SW206992.

FIGS. 32(A-C) illustrate graphs showing luciferase activity of colon cancer cell lines V503, LS174T, and V503 treated with various concentrations of SW033291.

FIG. 33(A-C) illustrate graphs showing luciferase activity of colon cancer cell lines V503, LS174T, and V503 treated with various concentrations of SW0206980.

FIG. 34(A-C) illustrate graphs showing luciferase activity of colon cancer cell lines V503, LS174T, and V503 treated with various concentrations of SW0206992.

FIGS. 35(A-B) illustrate plots showing melting profiles of SW206992, SW0206890 and SW033291 binding to 15-PGDH.

FIGS. 36(A-B) illustrate plots showing melting profiles of SW206992, SW0206890 and SW033291 binding to 15-PGDH.

FIGS. 37(A-C) illustrate graphs showing the effect of SW206992, SW0206890 and SW033291 on the regulation of PGE-2 in A549 cells stimulated with IL1-Beta.

FIGS. 38(A-C) illustrate graphs showing the effect of SW206992, SW0206890 and SW033291 on cell numbers in A549 cells after stimulated with IL1-Beta.

FIG. 39 illustrates a schematic diagram of additional analogues of SW033291.

FIGS. 46(A-C) illustrate graphs showing: (A) total bone marrow cellularity; (B) SKL population of wild type versus PGDH−/− mice; and (C) average CFU counts in wild type versus PGDH−/− mice (designated as either PGDH−/− or as PGDH).

FIGS. 49(A-B) illustrate: (A) a schematic diagram following CD45.2 antigen marked cells in lethally irradiated C57BL/6J mice rescued with a bone marrow transplant from donor mice treated with SW033291 or with vehicle; and (B) graphs showing chimerism, of donor B-Cells, myeloid cells, and T-Cells after such treatment.

FIGS. 52(A-D) illustrate photographs showing preoperative and post-operative view of mouse liver.

FIGS. 53(A-D) illustrate photographs showing post-hepatectomy views of the mouse liver (at left) and regeneration of mouse liver on post-operative day 7 (at right).

FIGS. 54(A-B) illustrate micrographs of post-hepatectomy mouse livers of mouse administered SW033291 and control vehicle, with arrows designating mitotic figures.

FIG. 55 illustrates a graph showing mitosis in liver of SW033291 treated mouse versus the control mouse.

FIGS. 77(A-B) illustrate photographs showing colonoscopic findings and mouse endoscopic index of colitis severity (MEICs) for a DSS treated mouse receiving a control vehicle or SW033291.

DETAILED DESCRIPTION

Figure 2:
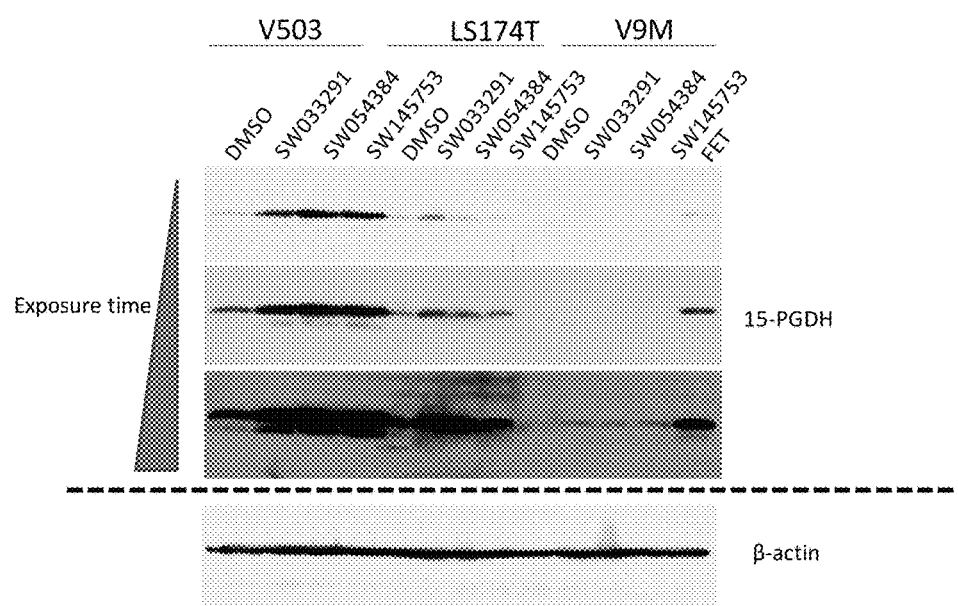
FIG. 2 illustrates western blots demonstrating the levels of 15-PGDH protein in cell lines V9M, LS174T, and V503 treated with 7.5 µM of SW033291, SW054384, and SW145753 for 48 hours. Untreated FET cells provide a positive control for 15-PGDH expression.

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

It will be noted that the structure of some of the compounds of the application include asymmetric (chiral) carbon atoms. It is to be understood accordingly that the isomers arising from such asymmetry are included herein, unless indicated otherwise. Such isomers can be obtained in substantially pure form by classical separation techniques and by stereochemically controlled synthesis. The compounds of this application may exist in stereoisomeric form, therefore can be produced as individual stereoisomers or as mixtures.

The term "isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

The term "chiral isomer" means a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has 2n−1 enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Alternatively, when one or more chiral centers are present, a stereoisomer may be characterized as (+) or (−). Absolute configuration refers to the arrangement in space of the substituents attached to the chiral center. The substituents attached to the chiral center under consideration are ranked in accordance with the Sequence Rule of Cahn, Ingold and Prelog. (Cahn et al, Angew. Chem. Inter. Edit. 1966, 5, 385; errata 511; Cahn et al., Angew. Chem. 1966, 78, 413; Cahn and Ingold, J Chem. Soc. 1951 (London), 612; Cahn et al., Experientia 1956, 12, 81; Cahn, J., Chem. Educ. 1964, 41, 116).

The term "geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules. Further, the structures and other compounds discussed in this application include all atropic isomers thereof.

The term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The term "derivative" refers to compounds that have a common core structure, and are substituted with various groups as described herein.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physico-chemically or topologically based. Examples of carboxylic acid bioisosteres include acyl sulfonimides, tetrazoles, sulfonates, and phosphonates. See, e.g., Patani and LaVoie, Chem. Rev. 96, 3147-3176 (1996).

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

The term "treating" is art-recognized and includes inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" is art-recognized and includes stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

The term "pharmaceutical composition" refers to a formulation containing the disclosed compounds in a form suitable for administration to a subject. In a preferred embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, inhalational, and the like. Dosage forms for the topical or transdermal administration of a compound described herein includes powders, sprays, ointments, pastes, creams, lotions, gels, solutions, patches, nebulized compounds, and inhalants. In a preferred embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" is defined as a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the application are capable of further forming salts. All of these forms are also contemplated herein.

"Pharmaceutically acceptable salt" of a compound means a salt that is pharmaceutically acceptable and that possesses the desired pharmacological activity of the parent compound. For example, the salt can be an acid addition salt. One embodiment of an acid addition salt is a hydrochloride salt. The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile being preferred. Lists of salts are found in Remington's Pharmaceutical Sciences, 18th ed. (Mack Publishing Company, 1990).

The compounds described herein can also be prepared as esters, for example pharmaceutically acceptable esters. For example, a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds described herein can also be prepared as prodrugs, for example pharmaceutically acceptable prodrugs. The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds can be delivered in prodrug form. Thus, the compounds described herein are intended to cover prodrugs of the presently claimed compounds, methods of delivering the same and compositions containing the same. "Prodrugs" are intended to include any covalently bonded carriers that release an active parent drug in vivo when such prodrug is administered to a subject. Prodrugs are prepared by modifying functional groups present in the compound in such a way that the modifications are cleaved, either in routine manipulation or in vivo, to the parent compound. Prodrugs include compounds wherein a hydroxy, amino, sulfhydryl, carboxy, or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, ester groups (e.g., ethyl esters, morpholinoethanol esters) of carboxyl functional groups, N-acyl derivatives (e.g., N-acetyl)N-Mannich bases, Schiff bases and enaminones of amino functional groups, oximes, acetals, ketals and enol esters of ketone and aldehyde functional groups in compounds of Formula I, and the like, See Bundegaard, H. "Design of Prodrugs" p 1-92, Elesevier, New York-Oxford (1985).

The term "protecting group" refers to a grouping of atoms that when attached to a reactive group in a molecule masks, reduces or prevents that reactivity. Examples of protecting groups can be found in Green and Wuts, Protective Groups in Organic Chemistry, (Wiley, 2.sup.nd ed. 1991); Harrison and Harrison et al., Compendium of Synthetic Organic Methods, Vols. 1-8 (John Wiley and Sons, 1971-1996); and Kocienski, Protecting Groups, (Verlag, $3^{rd}$ ed. 2003).

The term "amine protecting group" is intended to mean a functional group that converts an amine, amide, or other nitrogen-containing moiety into a different chemical group that is substantially inert to the conditions of a particular chemical reaction. Amine protecting groups are preferably removed easily and selectively in good yield under conditions that do not affect other functional groups of the molecule. Examples of amine protecting groups include, but are not limited to, formyl, acetyl, benzyl, t-butyldimethylsilyl, t-butyldiphenylsilyl, t-butyloxycarbonyl (Boc), p-methoxybenzyl, methoxymethyl, tosyl, trifluoroacetyl, trimethylsilyl (TMS), fluorenyl-methyloxycarbonyl, 2-trimethylsilyl-ethyoxycarbonyl, 1-methyl-1-(4-biphenylyl)ethoxycarbonyl, allyloxycarbonyl, benzyloxycarbonyl (CBZ), 2-trimethylsilyl-ethanesulfonyl (SES), trityl and substituted trityl groups, 9-fluorenylmethyloxycarbonyl (FMOC), nitro-veratryloxycarbonyl (NVOC), and the like. Those of skill in the art can identify other suitable amine protecting groups.

Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

Additionally, the salts of the compounds described herein, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

The term "solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The compounds, salts and prodrugs described herein can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs.

Tautomerizations can be catalyzed by: Base: 1. deprotonation; 2. formation of a delocalized anion (e.g., an enolate); 3. protonation at a different position of the anion; Acid: 1. protonation; 2. formation of a delocalized cation; 3. deprotonation at a different position adjacent to the cation.

The term "analogue" refers to a chemical compound that is structurally similar to another but differs slightly in composition (as in the replacement of one atom by an atom of a different element or in the presence of a particular functional group, or the replacement of one functional group by another functional group). Thus, an analogue is a compound that is similar or comparable in function and appearance, but not in structure or origin to the reference compound.

A "patient," "subject," or "host" to be treated by the subject method may mean either a human or non-human animal, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder.

The terms "prophylactic" or "therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" are art-recognized and include molecules and other agents that are biologically, physiologically, or pharmacologically active substances that act locally or systemically in a patient or subject to treat a disease or condition. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" or "pharmaceutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

The term "ED50" is art-recognized. In certain embodiments, ED50 means the dose of a drug, which produces 50% of its maximum response or effect, or alternatively, the dose, which produces a pre-determined response in 50% of test subjects or preparations. The term "LD50" is art-recognized. In certain embodiments, LD50 means the dose of a drug, which is lethal in 50% of test subjects. The term "therapeutic index" is an art-recognized term, which refers to the therapeutic index of a drug, defined as LD50/ED50.

The terms "$IC_{50}$," or "half maximal inhibitory concentration" is intended to refer to the concentration of a substance (e.g., a compound or a drug) that is required for 50% inhibition of a biological process, or component of a process, including a protein, subunit, organelle, ribonucleoprotein, etc.

With respect to any chemical compounds, the present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

When a bond to a substituent is shown to cross a bond connecting two atoms in a ring, then such substituent can be bonded to any atom in the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

When an atom or a chemical moiety is followed by a subscripted numeric range (e.g., $C_{1-6}$), it is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

The term "alkyl" is intended to include both branched (e.g., isopropyl, tert-butyl, isobutyl), straight-chain e.g., methyl, ethyl, propyl, butyl, pentyl, hexyl, heptyl, octyl, nonyl, decyl), and cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. Such aliphatic hydrocarbon groups have a specified number of carbon atoms. For example, $C_{1-6}$ alkyl is intended to include $C_1$, $C_2$, $C_3$, $C_4$, $C_5$, and $C_6$ alkyl groups. As used herein, "lower alkyl" refers to alkyl groups having from 1 to 6 carbon atoms in the backbone of the carbon chain. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), for example four or fewer. Likewise, certain cycloalkyls have from three to eight carbon atoms in their ring structure, such as five or six carbons in the ring structure.

The term "substituted alkyls" refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)). If not otherwise indicated, the terms "alkyl" and "lower alkyl" include linear, branched, cyclic, unsubstituted, substituted, and/or heteroatom-containing alkyl or lower alkyl, respectively.

The term "alkenyl" refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, cyclopentenyl, cyclohexenyl, cyclooctenyl, and the like. Generally, although again not necessarily, alkenyl groups can contain 2 to about 18 carbon atoms, and more particularly 2 to 12 carbon atoms. The term "lower alkenyl" refers to an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl or heterocycloalkenyl (e.g., heterocylcohexenyl) in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" refers to a linear or branched hydrocarbon group of 2 to 24 carbon atoms containing at least one triple bond, such as ethynyl, n-propynyl, and the like. Generally, although again not necessarily, alkynyl groups can contain 2 to about 18 carbon atoms, and more particularly can contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The terms "alkyl", "alkenyl", and "alkynyl" are intended to include moieties which are diradicals, i.e., having two points of attachment. A nonlimiting example of such an alkyl moiety that is a diradical is —$CH_2CH_2$—, i.e., a $C_2$ alkyl group that is covalently bonded via each terminal carbon atom to the remainder of the molecule.

The term "alkoxy" refers to an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$-$C_6$ alkoxy" or "lower alkoxy" herein contain 1 to 3 carbon atoms, and particularly preferred such substituents contain 1 or 2 carbon atoms (i.e., methoxy and ethoxy).

The term "aryl" refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 20 carbon atoms, and particularly preferred aryl groups can contain 5 to 14 carbon atoms. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diaryl amino, and alkylaryl amino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl). If not otherwise indicated, the term "aryl" includes unsubstituted, substituted, and/or heteroatom-containing aromatic substituents.

The term "alkaryl" refers to an aryl group with an alkyl substituent, and the term "aralkyl" refers to an alkyl group with an aryl substituent, wherein "aryl" and "alkyl" are as defined above. Exemplary aralkyl groups contain 6 to 24 carbon atoms, and particularly preferred aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethylnaphthyl, 7-cyclooctyl-naphthyl, 3-ethyl-cyclopenta-1,4-diene, and the like.

The terms "heterocyclyl" or "heterocyclic group" include closed ring structures, e.g., 3- to 10-, or 4- to 7-membered rings, which include one or more heteroatoms. "Heteroatom" includes atoms of any element other than carbon or hydrogen. Examples of heteroatoms include nitrogen, oxygen, sulfur and phosphorus.

Heterocyclyl groups can be saturated or unsaturated and include pyrrolidine, oxolane, thiolane, piperidine, piperazine, morpholine, lactones, lactams, such as azetidinones and pyrrolidinones, sultams, and sultones. Heterocyclic groups such as pyrrole and furan can have aromatic character. They include fused ring structures, such as quinoline and isoquinoline. Other examples of heterocyclic groups include pyridine and purine. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Heterocyclic groups can also be substituted at one or more constituent atoms with, for example, a lower alkyl, a lower alkenyl, a lower alkoxy, a lower alkylthio, a lower alkylamino, a lower alkylcarboxyl, a nitro, a hydroxyl, —$CF_3$, or —CN, or the like.

The term "halo" or "halogen" refers to fluoro, chloro, bromo, and iodo. "Counterion" is used to represent a small, negatively charged species such as fluoride, chloride, bromide, iodide, hydroxide, acetate, and sulfate.

The terms "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, silyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—$NH_2$), mono-($C_1$-$C_{24}$ alkyl)-substituted carbamoyl (—(CO)—NH($C_1$-$C_{24}$ alkyl)), di-($C_1$-$C_4$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano (—CN), isocyano (—$N^+C^-$), cyanato (—O—CN), isocyanato (—$ON^+C^-$), isothiocyanato (—S—CN), azido (—N=$N^+$=$N^-$), formyl (—(CO)—H), thioformyl (—(CS)—H), amino (—$NH_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, etc.), arylimino (—CR=N (aryl), where R=hydrogen, alkyl, aryl, alkaryl, etc.), nitro (—$NO_2$), nitroso (—NO), sulfo (—$SO_2$—OH), sulfonato (—$SO_2$—$O^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)($O^-$)$_2$), phosphinato (—P(O)($O^-$)), phospho (—$PO_2$), and phosphino (—$PH_2$); and the hydrocarbyl moieties $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, and $C_6$-$C_{24}$ aralkyl.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The terms "stable compound" and "stable structure" are meant to indicate a compound that is sufficiently robust to survive isolation, and as appropriate, purification from a reaction mixture, and formulation into an efficacious therapeutic agent.

The terms "free compound" is used herein to describe a compound in the unbound state.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

The term "small molecule" is an art-recognized term. In certain embodiments, this term refers to a molecule, which has a molecular weight of less than about 2000 amu, or less than about 1000 amu, and even less than about 500 amu.

All percentages and ratios used herein, unless otherwise indicated, are by weight.

The term "neoplasm" refers to any abnormal mass of cells or tissue as a result of neoplasia. The neoplasm may be benign, potentially malignant (precancerous), or malignant (cancerous). An adenoma is an example of a neoplasm.

The terms "adenoma", "colon adenoma" and "polyp" are used herein to describe any precancerous neoplasm of the colon.

The term "colon" as used herein is intended to encompass the right colon (including the cecum), the transverse colon, the left colon and the rectum.

The terms "colorectal cancer" and "colon cancer" are used interchangeably herein to refer to any cancerous neoplasia of the colon (including the rectum, as defined above).

The terms "gene expression" or "protein expression" includes any information pertaining to the amount of gene transcript or protein present in a sample, as well as information about the rate at which genes or proteins are produced or are accumulating or being degraded (e.g., reporter gene data, data from nuclear runoff experiments, pulse-chase data etc.). Certain kinds of data might be viewed as relating to both gene and protein expression. For example, protein levels in a cell are reflective of the level of protein as well as the level of transcription, and such data is intended to be included by the phrase "gene or protein expression information". Such information may be given in the form of amounts per cell, amounts relative to a control gene or protein, in unitless measures, etc.; the term "information" is not to be limited to any particular means of representation and is intended to mean any representation that provides relevant information. The term "expression levels" refers to a quantity reflected in or derivable from the gene or protein expression data, whether the data is directed to gene transcript accumulation or protein accumulation or protein synthesis rates, etc.

The terms "healthy" and "normal" are used interchangeably herein to refer to a subject or particular cell or tissue that is devoid (at least to the limit of detection) of a disease condition.

The term "nucleic acid" refers to polynucleotides such as deoxyribonucleic acid (DNA), and, where appropriate, ribonucleic acid (RNA). The term should also be understood to include analogues of either RNA or DNA made from nucleotide analogues, and, as applicable to the embodiment being described, single-stranded (such as sense or antisense) and double-stranded polynucleotides. In some embodiments, "nucleic acid" refers to inhibitory nucleic acids. Some categories of inhibitory nucleic acid compounds include antisense nucleic acids, RNAi constructs, and catalytic nucleic acid constructs. Such categories of nucleic acids are well-known in the art.

Embodiments described herein relate to compounds and methods of modulating 15-PGDH activity, modulating tissue prostaglandin levels, and/or treating diseases, disorders, or conditions in which it is desired to modulate 15-PGDH activity and/or prostaglandin levels. "Inhibitors," "activators," and "modulators" of 15-PGDH expression or of 15-PGDH activity are used to refer to inhibitory, activating, or modulating molecules, respectively, identified using in vitro and in vivo assays for 15-PGDH expression or 15-PGDH activity, e.g., ligands, agonists, antagonists, and their homologs and mimetics. The term "modulator" includes inhibitors and activators. Inhibitors are agents that, e.g., inhibit expression of 15-PGDH or bind to, partially or totally block stimulation, decrease, prevent, delay activation, inactivate, desensitize, or down regulate the activity of 15-PGDH, e.g., antagonists. Activators are agents that, e.g., induce or activate the expression of a 15-PGDH or bind to, stimulate, stabilize, increase, open, activate, facilitate, or enhance activation, sensitize or up regulate the activity of 15-PGDH, e.g., agonists. Modulators include naturally occurring and synthetic ligands, small chemical molecules, and the like.

15-PGDH inhibitors described herein can provide a pharmacologic method for elevating prostaglandin levels in tissue. Known activities of prostaglandins include promoting hair growth, promoting skin pigmentation, and promoting skin darkening or the appearance of skin tanning. Known activities of prostaglandins also include ameliorating pulmonary artery hypertension. 15-PGDH inhibitors described herein may also be utilized to increase tissue stem cell numbers for purposes that would include increasing resistance to tissue damage by radiation, increasing resistance to environmental exposures to radiation, increasing stem cell numbers to increase fitness of bone marrow or other types of transplantation (through either in vivo exposure to 15-PGDH inhibitors described herein to increase stem cell numbers prior to harvest of a transplanted tissue, or through ex vivo exposure of a harvested tissue prior to transplant into a recipient host). 15-PGDH inhibitors described herein may also be utilized for purposes that would include promoting liver regeneration, including liver regeneration after liver resection, and liver regeneration after toxic insults, which for example may be the toxic insult of acetaminophen overdose. Prostaglandin signaling is also known to promote wound healing, protect the stomach from ulceration, and promote healing of ulcers of stomach and intestines. Additionally, 15-PGDH inhibitors described herein can promote activity of human keratinocytes in "healing" scratches across cultures of keratinocyte cells. Hence, 15-PGDH inhibitors described herein may be utilized to also heal ulcers of other tissues, including, but not limited to skin, and including but not limited to diabetic ulcers. Further, 15-PGDH inhibitors described herein may be utilized for the treatment of erectile dysfunction.

15-PGDH activators described herein can increase levels of 15-PGDH protein in cells and in increase levels of 15-PGDH enzymatic activity in cells. Increasing tissue levels of 15-PGDH can decrease tissue levels of prostaglandins. Activities associated with compounds that decrease tissue prostaglandins include decreasing development of human tumors, particularly decreasing development of human colon tumors. Accordingly, compounds that increase tissue 15-PGDH activity can lower risk of development of colon and other tumors. Compounds that increase 15-PDGH activity can also be used to treat colon and other tumors. Compounds that increase 15-PDGH may be used to treat or to prevent tumors when given singly, or when given in combination with inhibitors of cyclooxygenase-1 and/or cyclooxygenase-2 enzymes, or when given in combination with other therapeutic agents.

15-PGDH inhibitors and activators described herein can be identified using assays in which putative modulator compounds are applied to cells expressing 15-PGDH and then the functional effects on 15-PGDH activity are determined. Samples or assays comprising 15-PGDH that are treated with a potential activator, inhibitor, or modulator are compared to control samples without the inhibitor, activator, or modulator to examine the extent of effect. Control samples (untreated with modulators) are assigned a relative 15-PGDH activity value of 100%. Inhibition of 15-PGDH is achieved when the 15-PGDH activity value relative to the control is about 80%, optionally 50% or 25%, 10%, 5% or 1%. Activation of 15-PGDH is achieved when the 15-PGDH activity or expression value relative to the control is 105%, optionally 110%, optionally 125%, optionally 150%, optionally 200%, 300%, 400%, 500%, or 1000-3000% or more higher.

Agents tested as modulators of 15-PGDH can be any small chemical molecule or compound. Typically, test compounds will be small chemical molecules, natural products, or peptides. The assays are designed to screen large chemical libraries by automating the assay steps and providing compounds from any convenient source to assays, which are typically run in parallel (e.g., in microtiter formats on microtiter plates in robotic assays). Modulators also include agents designed to increase the level of 15-PGDH mRNA or the level of translation from an mRNA.

In some embodiments, the modulator of 15-PGDH can be a 15-PGDH inhibitor that includes a compound having the following formula (I):

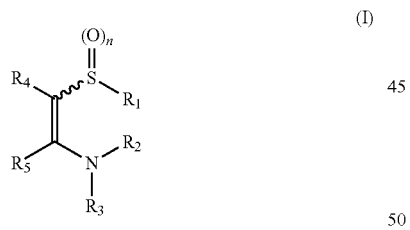

(I)

wherein n is 0-2;
$R_1$ is a $C_{1-8}$ alkyl, which is linear, branched, or cyclic and which is unsubstituted or substituted (e.g., $R_1$ can be $C_{2-6}$ alkyl, $C_{2-4}$ alkyl, or $C_4$ alkyl, which is linear, branched, or cyclic and which is unsubstituted or substituted);
$R_2$ and $R_3$ are the same or different and are each selected from the group consisting of a H, a lower alkyl group, $(CH_2)_{n1}$ OR' (wherein n1=1, 2, or 3), $CF_3$, $CH_2$—$CH_2X$, O—$CH_2$—$CH_2X$, $CH_2$—$CH_2$—$CH_2X$, O—$CH_2$—$CH_2X$ (wherein X=F, Cl, Br, or I), CN, (C=O)—R', (C=O)N(R')$_2$, O(CO)R', COOR' (wherein R' is H or a lower alkyl group);
$R_4$ and $R_5$ are the same or different and are each selected from the group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamide (—NH—(CO)—NH$_2$), cyano (—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), phosphino (—PH$_2$), combinations thereof, and wherein $R_4$ and $R_5$ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl; and pharmaceutically acceptable salts thereof.

In other embodiments, the 15-PGDH inhibitor can include a compound having the following formula (II):

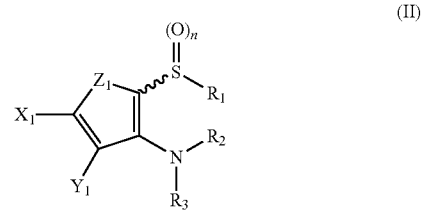

(II)

wherein n is 0-2;
$R_1$ is a $C_{1-8}$ alkyl, which is linear, branched, or cyclic, and which is unsubstituted or substituted;
$R_2$ and $R_3$ are the same or different and are each selected from the group consisting of a H, a lower alkyl group, $(CH_2)_{n1}$ OR' (wherein n1=1, 2, or 3), $CF_3$, $CH_2$—$CH_2X$, O—$CH_2$—$CH_2X$, $CH_2$—$CH_2$—$CH_2X$, O—$CH_2$—$CH_2X$ (wherein X=F, Cl, Br, or I), CN, (C=O)—R', (C=O)N(R')$_2$, O(CO)R', COOR' (wherein R' is H or a lower alkyl group);
$Z_1$ is NR', O or S (wherein R' is H or a lower alkyl group);
$X_1$ and $Y_1$ are the same or different and are each selected from the group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano (—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), phosphino (—PH$_2$), combinations thereof, and wherein X$_1$ and Y$_1$ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl; and pharmaceutically acceptable salts thereof.

Examples of 15-PGDH inhibitors having formulas (I) or (II) include the following compounds:

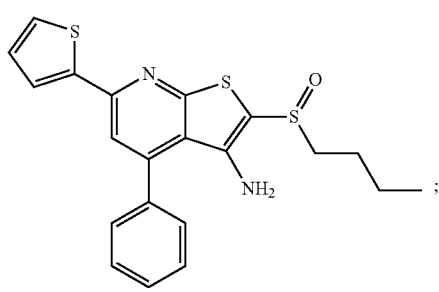

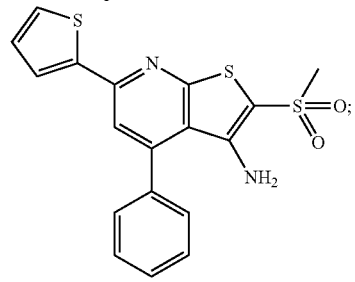

-continued

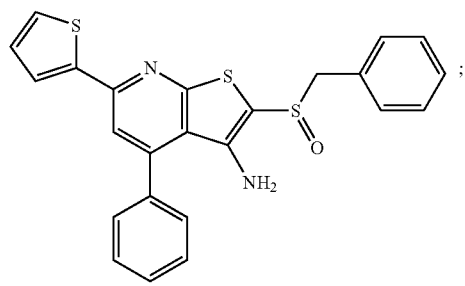

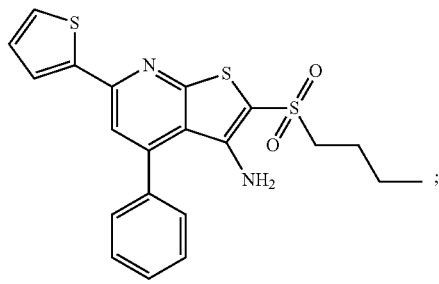

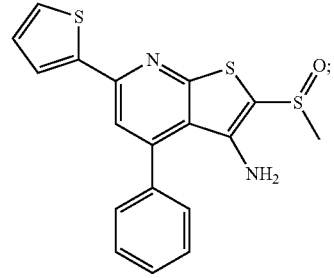

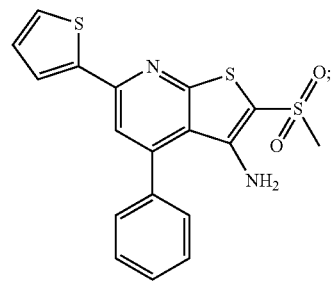

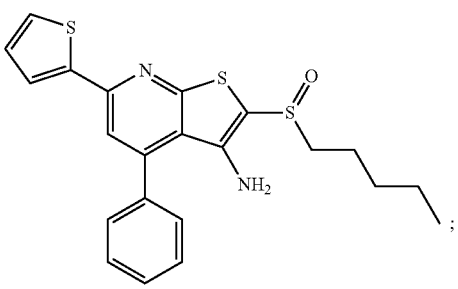

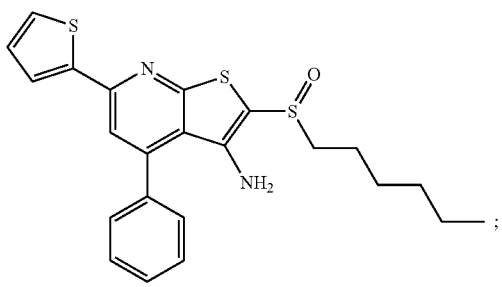

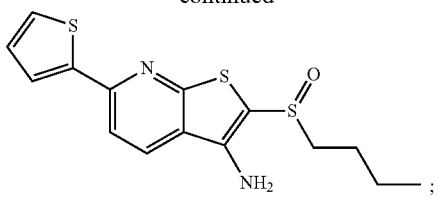

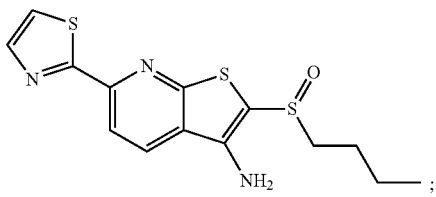

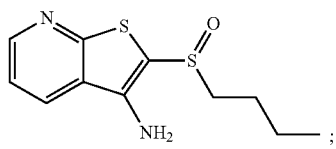

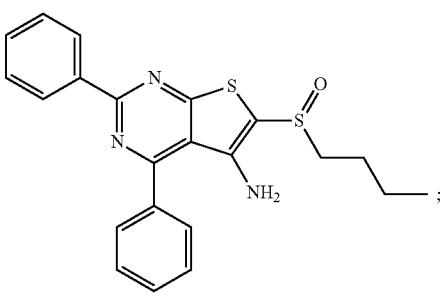

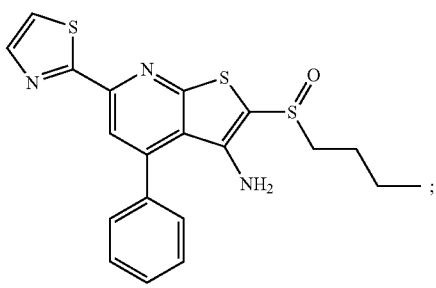

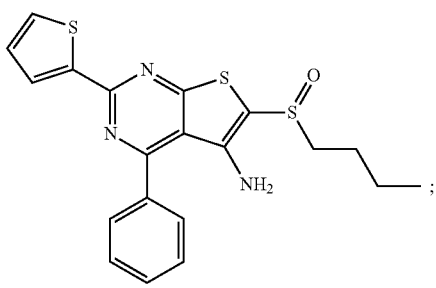

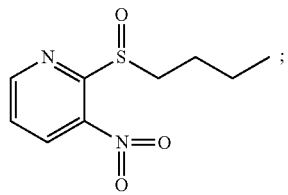

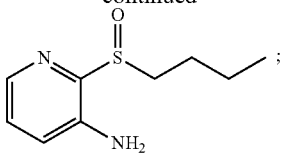

and pharmaceutically acceptable salts thereof.

In certain embodiments, the 15-PGDH inhibitor having formula (I) or (II) can be selected that can ia) at 2.5 μM concentration, stimulate a Vaco503 reporter cell line expressing a 15-PGDH luciferase fusion construct to a luciferase output level of greater than 70 (using a scale on which a value of 100 indicates a doubling of reporter output over baseline); iia) at 2.5 μM concentration stimulate a V9m reporter cell line expressing a 15-PGDH luciferase fusion construct to a luciferase output level of greater than 75; iiia) at 7.5 μM concentration stimulate a LS174T reporter cell line expressing a 15-PGDH luciferase fusion construct to a luciferase output level of greater than 70; and iva) at 7.5 μM concentration, does not activate a negative control V9m cell line expressing TK-*renilla* luciferase reporter to a level greater than 20; and va) inhibits the enzymatic activity of recombinant 15-PGDH protein at an IC50 of less than 1 μM In other embodiments, the 15-PGDH inhibitor can ib) at 2.5 μM concentration, stimulate a Vaco503 reporter cell line expressing a 15-PGDH luciferase fusion construct to increase luciferase output; iib) at 2.5 μM concentration stimulate a V9m reporter cell line expressing a 15-PGDH luciferase fusion construct to increase luciferase output; iiib) at 7.5 μM concentration stimulate a LS174T reporter cell line expressing a 15-PGDH luciferase fusion construct to increase luciferase output; ivb) at 7.5 μM concentration, does not activate a negative control V9m cell line expressing TK-*renilla* luciferase reporter to a luciferase level greater than 20% above background; and vb) inhibits the enzymatic activity of recombinant 15-PGDH protein at an IC50 of less than 1 μM.

In other embodiments, the 15-PGDH inhibitor can inhibit the enzymatic activity of recombinant 15-PGDH at: ic) an IC50 of less than 1 uM, or preferably iic) at an IC50 of less than 250 nM, or more preferably iiic) at an IC50 of less than 50 nM, or more preferably iv) at an IC50 of less than 5 nM.

An example of a 15-PGDH inhibitor having formula (I) that meets the above noted criteria (ia-va) includes a compound having the formula (III): An example of a 15-PGDH inhibitor having formula (I) that meets the above noted criteria (ib-vb) includes a compound having the formula (III): An example of a 15-PGDH inhibitor having formula (I) that meets the above noted criteria ic, and/or iic, and or iiic, and or ivc, includes a compound having the formula (III): In still other embodiments, the 15-PGDH inhibitor can include a compound having the following formula (III):

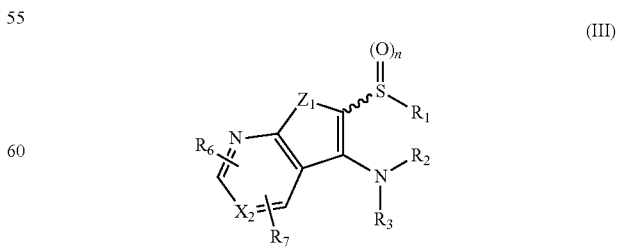

(III)

wherein n is 0-2;

$R_1$ is a $C_{1-8}$ alkyl, which is linear, branched, or cyclic and which is unsubstituted or substituted;

R$_2$ and R$_3$ are the same or different and are each selected from the group consisting of a H, a lower alkyl group, (CH$_2$)$_{n1}$ OR' (wherein n1=1, 2, or 3), CF$_3$, CH$_2$—CH$_2$X, O—CH$_2$—CH$_2$X, CH$_2$—CH$_2$—CH$_2$X, O—CH$_2$—CH$_2$X (wherein X=F, Cl, Br, or I), CN, (C=O)—R', (C=O)N(R')$_2$, O(CO)R', COOR' (wherein R' is H or a lower alkyl group);

Z$_1$ is NR', O or S (wherein R' is H or a lower alkyl group);

X$_2$ is N or C;

R$_6$ and R$_7$ are optional and if present are the same or different and are each selected from the group consisting of a H, F, Cl, Br, I, a lower alkyl group, (CH$_2$)$_{n1}$OR' (wherein n1=1, 2, or 3), CF$_3$, CH$_2$—CH$_2$X, O—CH$_2$—CH$_2$X, CH$_2$—CH$_2$—CH$_2$X, O—CH$_2$—CH$_2$X (wherein X=F, Cl, Br, or I), CN, (C=O)—R', N(R')$_2$, NO$_2$, (C=O)N(R')$_2$, O(CO)R', OR', SR', COOR' (wherein R' is H or a lower alkyl group); substituted or unsubstituted aryl, a substituted or unsubstituted cycloalkyl, and a substituted or unsubstituted heterocyclyl; and pharmaceutically acceptable salts thereof.

15-PGDH inhibitors having formula (III) can be synthesized as shown:

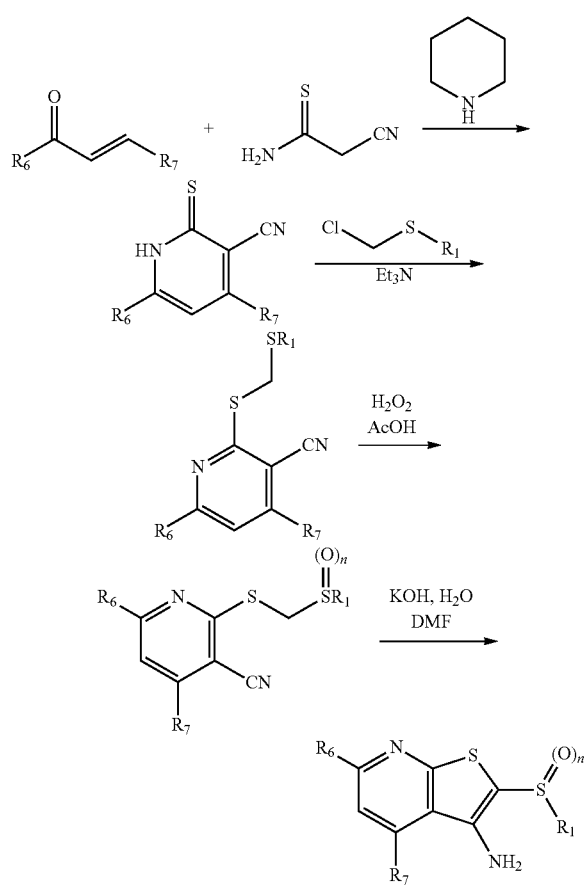

Any reaction solvent can be used in the above preparation process as long as it is not involved in the reaction. For example, the reaction solvent includes ethers such as diethyl ether, tetrahydrofuran and dioxane; halogenized hydrocarbons, such as dichloromethane and chloroform; amines such as pyridine, piperidine and triethylamine; alkylketones, such as acetone, methylethylketone and methylisobutyl; alcohols, such as methanol, ethanol and propanol; non-protonic polar solvent, such as N,N-dimethylformamide, N,N-dimethylacetamide, acetonitrile, dimethylsulfoxide and hexamethyl phosphoric acid triamide. Among non-reactive organic solvents that are ordinarily used in the organic synthesis, preferable solvents are those from which water generated in the reaction can be removed by a Dean-Stark trap. The examples of such solvents include, but are not limited to benzene, toluene, xylene and the like. The reaction product thus obtained may be isolated and purified by condensation, extraction and the like, which is ordinarily conducted in the field of the organic synthesis, if desired, by silica gel column chromatography. The individual enantiomers of PGDH inhibitors having the formula III can be separated by a preparative HPLC using chromatography columns containing chiral stationary phases.

Further, embodiments of this application include any modifications for the preparation method of the 15-PGDH inhibitors described above. In this connection, any intermediate product obtainable from any step of the preparation method can be used as a starting material in the other steps. Such starting material can be formed in situ under certain reaction conditions. Reaction reagents can also be used in the form of their salts or optical isomers.

Depending on the kinds of the substituents to be used in the preparation of the 15-PGDH inhibitors, and the intermediate product and the preparation method selected, novel 15-PGDH inhibitors can be in the form of any possible isomers such as substantially pure geometrical (cis or trans) isomers, optical isomers (enantiomers) and racemates.

In some embodiments, a 15-PGDH inhibitor having formula (III) can include a compound with the following formula:

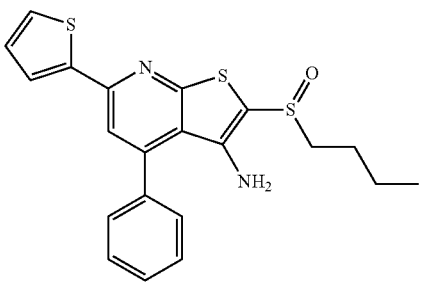 [SMILES: CCCCS(=O)c1sc2nc(-c3cccs3)cc(-c3ccccc3)c2c1N]

and pharmaceutically acceptable salts thereof.

Advantageously, the 15-PDGH inhibitor having formula (III) was found to: i) inhibit recombinant 15-PGDH at 1 nM concentration; ii) inhibit 15-PGDH in cell lines at 100 nM concentration, iii) increase PGE$_2$ production by cell lines; iv) is chemically stable in aqueous solutions over broad pH range; v) is chemically stable when incubated with hepatocyte extracts, vi) is chemically stable when incubated with hepatocyte cell lines; vii) shows 253 minutes plasma half-life when injected IP into mice; and viii) shows no immediate toxicity over 24 hours when injected IP into mice at 0.6 μmole/per mouse and at 1.2 μmole/per mouse and also no toxicity when injected IP into mice at 0.3 μmole/per mouse twice daily for 21 days.

In other embodiments, a 15-PGDH inhibitor having formula (III) can include a compound with the following formula:

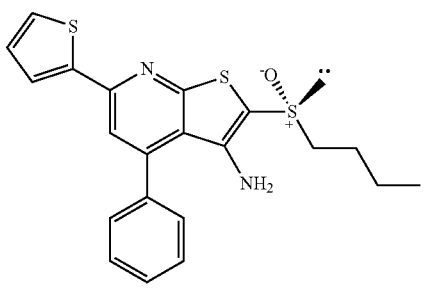

and pharmaceutically acceptable salts thereof.

In still other embodiments, a 15-PGDH inhibitor having formula (III) can include a compound with the following formula:

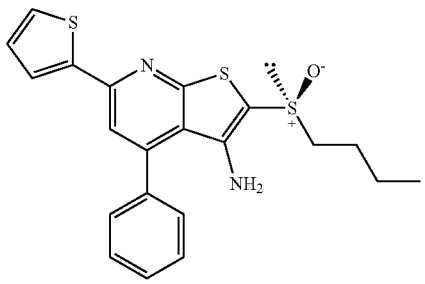

and pharmaceutically acceptable salts thereof.

In other embodiments, the 15-PDHG inhibitor can comprise a (+) or (−) optical isomer of a 15-PGDH inhibitor having formula (III). In still other embodiments, the 15-PDHG inhibitor can comprise a mixture at least one of a (+) or (−) optical isomer of a 15-PGDH inhibitor having formula (III). For example, the 15-PGDH inhibitor can comprise a mixture of: less than about 50% by weight of the (−) optical isomer of a 15-PGDH inhibitor having formula (III) and greater than about 50% by weight of the (+) optical isomer of a 15-PGDH inhibitor having formula (III), less than about 25% by weight of the (−) optical isomer of a 15-PGDH inhibitor having formula (III) and greater than about 75% by weight of the (+) optical isomer of a 15-PGDH inhibitor having formula (III), less than about 10% by weight of the (−) optical isomer of a 15-PGDH inhibitor having formula (III) and greater than about 90% by weight of the (+) optical isomer of a 15-PGDH inhibitor having formula (III), less than about 1% by weight of the (−) optical isomer of a 15-PGDH inhibitor having formula (III) and greater than about 99% by weight of the (+) optical isomer of a 15-PGDH inhibitor having formula (III), greater than about 50% by weight of the (−) optical isomer of a 15-PGDH inhibitor having formula (III) and less than about 50% by weight of the (+) optical isomer of a 15-PGDH inhibitor having formula (III), greater than about 75% by weight of the (−) optical isomer of a 15-PGDH inhibitor having formula (III) and less than about 25% by weight of the (+) optical isomer of a 15-PGDH inhibitor having formula (III), greater than about 90% by weight of the (−) optical isomer of a 15-PGDH inhibitor having formula (III) and less than about 10% by weight of the (+) optical isomer of a 15-PGDH inhibitor having formula (III), or greater than about 99% by weight of the (−) optical isomer of a 15-PGDH inhibitor having formula (III) and less than about 1% by weight of the (+) optical isomer of a 15-PGDH inhibitor having formula (III).

In a still further embodiment, the 15-PDGH inhibitor can consist essentially of or consist of the (+) optical isomer of a 15-PGDH inhibitor having formula (III). In yet another embodiment, the PDGH inhibitor can consist essentially of or consist of the (−) optical isomer of a 15-PGDH inhibitor having formula (III).

The 15-PGDH inhibitors described herein can be used for the prevention or the treatment of diseases that are associated with 15-PGDH and/or decreased prostaglandin levels and/or where it desirable to increase prostaglandin levels in the subject. For example, as discussed above, it is known that prostaglandins play an important role in hair growth. Specifically, internal storage of various types ($A_2$, $F_{2\alpha}$, $E_2$) of prostaglandins in the various compartments of hair follicles or their adjacent skin environments has been shown to be essential in maintaining and increasing hair density (Colombe L et. al, 2007, Exp. Dermatol, 16(9), 762-9). It has been reported that 15-PGDH, which is involved in the degradation of prostaglandins is present in the hair follicle dermal papillae, inactivates prostaglandins, especially, $PGF_{2\alpha}$ and $PGE_2$, to cause scalp damage and alopecia (Michelet J F et. al., 2008, Exp. Dermatol, 17(10), 821-8). Thus, the compounds described herein, which have a suppressive or inhibitory activity against 15-PGDH that degrades prostaglandins, can improve scalp damage, prevent alopecia and promote hair growth and be used in a pharmaceutical composition for the prevention of alopecia and the promotion of hair growth.

In other embodiments, the 15-PGDH inhibitors described herein can be used in a pharmaceutical composition for promoting and/or inducing and/or stimulating pigmentation of the skin and/or skin appendages, and/or as an agent for preventing and/or limiting depigmentation and/or whitening of the skin and/or skin appendages, in particular as an agent for preventing and/or limiting canities.

In still other embodiments, the 15-PGDH inhibitors described herein can be used in a pharmaceutical composition for the prevention or the treatment of cardiovascular disease and/or diseases of vascular insufficiency, such as Raynaud's disease, Buerger's disease, diabetic neuropathy, and pulmonary artery hypertension. Prostaglandins including prostaglandin homologues produced in the body have been known to maintain the proper action of the blood vessel wall, especially to contribute to vasodilation for blood flow, preventing platelet aggregation and modulating the proliferation of smooth muscle that surrounds blood vessel walls (Yan. Cheng et. al., 2006, J. Clin., Invest). In addition, the inhibition of prostaglandins production or the loss of their activity causes the degeneration of the endothelium in the blood vessel walls, platelet aggregation and the dysfunction of cellular mechanism in the smooth muscle. Among others, the production of prostaglandins in blood vessels was shown to be decreased in hypertension patients, including pulmonary artery hypertension.

In other embodiments, the 15-PGDH inhibitors described herein can be used in a pharmaceutical composition for the prevention or the treatment of oral and/or gastrointestinal diseases, such as oral ulcers, gum disease, gastritis, colitis, ulcerative colitis, and gastric ulcers. Gastritis and gastric ulcer, representatives of the gastrointestinal diseases, are defined as the conditions where gastrointestinal mucus membrane is digested by gastric acid to form ulcer. In the stomach walls generally consisting of mucosa, submucosa, muscle layer and serosa, gastric ulcer even damages submucosa and muscle layer, while gastritis damages mucosa only. Although the morbidity rates of gastritis and gastric ulcer are relatively high, the causes thereof have not been clarified yet. Until now, they are known to be caused by an imbalance between aggressive factors and defensive factors, that is, the increase in aggressive factors such as the increase in gastric acid or pepsin secretion, or the decrease in defensive factors such as structural or morphological deficit of the gastric mucus membrane, the decrease in mucus and bicarbonate ion secretion, the decrease in prostaglandin production, or the like.

Currently available therapeutic agents for gastritis and gastric ulcer comprise various drugs for strengthening the defensive factors such as an antacid, which does not affect, gastric acid secretion but neutralizes gastric acid that has been already produced, an inhibitor of gastric acid secretion, a promoter of prostaglandin secretion, and a coating agent for stomach walls. Especially, prostaglandins are known to be essential in maintaining the mechanism for protecting and defending gastric mucus membrane (Wallace J L., 2008, Physiol Rev., 88(4), 1547-65, S. J. Konturek et al., 2005, Journal of Physiology and Pharmacology, 56(5)). In view of the above, since the 15-PGDH inhibitors described herein show a suppressive or inhibitory activity against 15-PGDH, which degrades prostaglandins that protect gastric mucus membrane, they can be effective for the prevention or the treatment of gastrointestinal diseases, inter alia, gastritis and gastric ulcer.

In the kidney, prostaglandins modulate renal blood flow and may serve to regulate urine formation by both renovascular and tubular effects. In clinical studies, $PGE_1$ has been used to improve creatinine clearance in patients with chronic renal disease, to prevent graft rejection and cyclosporine toxicity in renal transplant patients, to reduce the urinary albumin excretion rate and N-acetyl-beta-D-glucosaminidase levels in patients with diabetic nephropathy (see Porter, Am., 1989, J. Cardiol., 64: 22E-26E). In addition, U.S. Pat. No. 5,807,895 discloses a method of preventing renal dysfunction by intravenous administration of prostaglandins such as $PGE_1$, $PGE_2$ and $PGI_2$. Furthermore, it has been reported that prostaglandins serve as vasodilators in the kidney, and, thus, the inhibition of prostaglandin production in the kidney results in renal dysfunction (Hao. C M, 2008, Annu Rev Physiol, 70, 357.about.77).

Thus, the 15-PGDH inhibitors described herein, which have a suppressive or inhibitory activity against 15-PGDH that degrades prostaglandins, may be effective in the prevention or the treatment of renal diseases that are associated with renal dysfunction.

The term "renal dysfunction" as used herein includes such manifestations as follows: lower than normal creatinine clearance, lower than normal free water clearance, higher than normal blood urea, nitrogen, potassium and/or creatinine levels, altered activity of kidney enzymes such as gamma glutamyl synthetase, alanine phosphatidase, N-acetyl-beta-D-glucosaminidase, or beta-w-microglobulin; and increase over normal levels of macroalbuminuria.

Prostaglandins including $PGE_1$, $PGE_2$ and $PGF_{2\alpha}$ have also been shown to stimulate bone resorption and bone formation to increase the volume and the strength of the bone (H. Kawaguchi et. al., Clinical Orthop. Rel. Res., 313, 1995; J. Keller et al., Eur. Jr. Exp. Musculoskeletal Res., 1, 1992, 8692). Considering that 15-PGDH inhibits the activities of prostaglandins as mentioned in the above, the inhibition of 15-PGDH activity may lead to the promotion of bone resorption and bone formation that are inhibited by 15-PGDH. Thus, the 15-PGDH inhibitors described herein can be effective for the promotion of bone resorption and bone formation by inhibiting 15-PGDH activity. 15-PGDH inhibitors can also be used to increase bone density, treat osteoporosis, promote healing of fractures, or promote healing after bone surgery or joint replacement.

In yet other embodiments, the 15-PGDH inhibitors described herein can effective for treating 15-PGDH expressing cancers. Inhibition of 15-PGDH can inhibit the growth, proliferation, and metastasis of 15-PGDH expressing cancers.

In still other embodiments, the 15-PGDH inhibitors described herein can be effective for wound healing. Among various prostaglandins, $PGE_2$ is known to serve as a mediator for wound healing. Therefore, when skin is injured by wounds or burns, the inhibition of 15-PGDH activity can produce the treatment effect of the wounds or the burns by $PGE_2$.

Additionally, as discussed above, increased prostaglandin levels have been shown to stimulate signaling through the Wnt signaling pathway via increased beta-catenin mediated transcriptional activity. Wnt signaling is known to be a key pathway employed by tissue stem cells, and increasing $PGE_2$ signaling has in model organisms been shown to increase numbers of hematopoietic stem cells. Hence, 15-PGDH inhibitors described herein may be utilized to increase tissue stem cell numbers for purposes that would include increasing resistance to tissue damage by radiation, increasing resistance to environmental exposures to radiation, increasing stem cell numbers to increase fitness of bone marrow or other types of transplantation (through either in vivo exposure to 15-PGDH inhibitors described herein to increase stem cell numbers prior to harvest of a transplanted tissue, or through ex vivo exposure of a harvested tissue prior to transplant into a recipient host, or through treatment of the recipient host either before, during, or after receipt of the transplant).

In some embodiments, the 15-PGDH inhibitor can be administered to a bone marrow graft donor or a hematopoietic stem cell donor to increase the fitness of a donor bone marrow graft or a donor hematopoietic stem cell graft.

In other embodiments, the 15-PGDH inhibitor can also be administered to bone marrow of a subject to increase stem cells in the subject or to increase the fitness of the marrow as a donor graft.

In still other embodiments, the 15-PGDH inhibitor can be administered to a preparation of hematopoietic stem cells, peripheral blood hematopoietic stem cells, or umbilical cord stem cells of the subject to increase the fitness of the stem cell preparation as a donor graft or to decrease the number of units of umbilical cord blood required for transplantation.

In yet other embodiments, the 15-PGDH inhibitor can be administered to a subject to mitigate bone marrow graft rejection, to enhance bone marrow graft engraftment, to enhance engraftment of a hematopoietic stem cell graft, or an umbilical cord stem cell graft, to enhance engraftment of a hematopoietic stem cell graft, or an umbilical cord stem cell graft, and/or to decrease the number of units of umbilical cord blood required for transplantation into the subject. The administration can be, for example, following treatment of the subject or the marrow of the subject with radiation therapy, chemotherapy, or immunosuppressive therapy.

In other embodiments, the 15-PGDH inhibitor can be administered to a recipient of a bone marrow transplant, of a hematopoietic stem cell transplant, or of an umbilical cord stem cell transplant, in order to decrease the administration of other treatments or growth factors.

In further embodiments, the 15-PGDH inhibitor can be administered to a subject or to a tissue graft of a subject to mitigate graft rejection, to enhance graft engraftment, to enhance graft engraftment following treatment of the subject or the marrow of the subject with radiation therapy, chemotherapy, or immunosuppressive therapy, to confer resistance to toxic or lethal effects of exposure to radiation, confer resistance to the toxic effect of Cytoxan, the toxic effect of fludarabine, the toxic effect of chemotherapy, or the toxic effect of immunosuppressive therapy, to decrease infection, and/or to decrease pulmonary toxicity from radiation.

Additionally, in model organism $PGE_2$ signaling stimulates liver regeneration and increase survival after exposure to hepatoxic agents, such as acetaminophen. Hence, 15-PGDH inhibitors described herein may be utilized to increase liver regeneration after liver resection, or to increase liver regeneration and increase survival after exposures to hepatoxic agents, including but not limited to acetaminophen and similar compounds.

PGE1 analogues have also been used in the treatment of erectile dysfunction. Accordingly, in some embodiments, 15-PGDH inhibitors described herein can used either alone or combination with a prostaglandin for the treatment of erectile dysfunction.

The 15-PGDH inhibitors described herein can be provided in a pharmaceutical composition or cosmetic composition depending on the pathological or cosmetic condition or disorder being treated. A pharmaceutical composition containing the 15-PGDH inhibitors described herein as an active ingredient may be manufactured by mixing the derivative with a pharmaceutically acceptable carrier(s) or an excipient(s) or diluting the 15-PGDH inhibitors with a diluent(s) in accordance with conventional methods. The pharmaceutical composition may further contain fillers, anticohesives, lubricants, wetting agents, flavoring agents, emulsifying agents, preservatives and the like. The pharmaceutical composition may be formulated into a suitable formulation in accordance with the methods known to those skilled in the art so that it can provide an immediate, controlled or sustained release of the 15-PGDH inhibitors after being administered into a mammal.

In some embodiments, the pharmaceutical composition may be formulated into a parenteral or oral dosage form. The solid dosage form for oral administration may be manufactured by adding excipient, if necessary, together with binder, disintegrants, lubricants, coloring agents, and/or flavoring agents, to the 15-PGDH inhibitors and shaping the resulting mixture into the form of tablets, sugar-coated pills, granules, powder or capsules. The additives that can be added in the composition may be ordinary ones in the art. For example, examples of the excipient include lactose, sucrose, sodium chloride, glucose, starch, calcium carbonate, kaolin, microcrystalline cellulose, silicate and the like. Exemplary binders include water, ethanol, propanol, sweet syrup, sucrose solution, starch solution, gelatin solution, carboxymethylcellulose, hydroxypropyl cellulose, hydroxypropyl starch, methylcellulose, ethylcellulose, shellac, calcium phosphonate and polypyrrolidone. Examples of the disintegrant include dry starch, sodium arginate, agar powder, sodium bicarbonate, calcium carbonate, sodium lauryl sulfate, stearic monoglyceride and lactose. Further, purified talc, stearates, sodium borate, and polyethylene glycol may be used as a lubricant; and sucrose, bitter orange peel, citric acid, tartaric acid, may be used as a flavoring agent. In some embodiments, the pharmaceutical composition can be made into aerosol formulations (e.g., they can be nebulized) to be administered via inhalation.

The 15-PGDH inhibitors described herein may be combined with flavoring agents, buffers, stabilizing agents, and the like and incorporated into oral liquid dosage forms such as solutions, syrups or elixirs in accordance with conventional methods. One example of the buffers may be sodium citrate. Examples of the stabilizing agents include tragacanth, acacia and gelatin.

In some embodiments, the 15-PGDH inhibitors described herein may be incorporated into an injection dosage form, for example, for a subcutaneous, intramuscular or intravenous route by adding thereto pH adjusters, buffers, stabilizing agents, relaxants, topical anesthetics. Examples of the pH adjusters and the buffers include sodium citrate, sodium acetate and sodium phosphate. Examples of the stabilizing agents include sodium pyrosulfite, EDTA, thioglycolic acid and thiolactic acid. The topical anesthetics may be procaine HCl, lidocaine HCl and the like. The relaxants may be sodium chloride, glucose and the like.

In other embodiments, the 15-PGDH inhibitors described herein may be incorporated into suppositories in accordance with conventional methods by adding thereto pharmaceutically acceptable carriers that are known in the art, for example, polyethylene glycol, lanolin, cacao butter or fatty acid triglycerides, if necessary, together with surfactants such as Tween.

The pharmaceutical composition may be formulated into various dosage forms as discussed above and then administered through various routes including an oral, inhalational, transdermal, subcutaneous, intravenous or intramuscular route. The dosage can be a pharmaceutically effective amount. The pharmaceutically effective amount can be an amount of the 15-PGDH inhibitor to treat or improve alopecia, cardiovascular disease, gastrointestinal disease, wounds, and renal disease. The pharmaceutically effective amount of the compound will be appropriately determined depending on the kind and the severity of the disease to be treated, age, sex, body weight and the physical condition of the patients to be treated, administration route, duration of therapy and the like. Generally, the effective amount of the compound may be in the range of about 1 to 1,000 mg in the oral administration, about 0.1 to 500 mg in the intravenous administration, about 5 to 1,000 mg in the rectal administration. Generally, the daily dosage for adults is in the range of about 0.1 to 5,000 mg, preferably about to 1,000 mg but cannot be determined uniformly because it depends on age, sex, body weight and the physical condition of the patients to be treated. The formulation may be administered once a day or several times a day with a divided dose.

Cosmetic compositions containing the 15-PGDH inhibitor can include any substance or preparation intended to be brought into contact with the various superficial parts of the human body (epidermis, body hair and hair system, nails, lips and external genital organs) or with the teeth or the buccal mucous membranes for the purpose, exclusively or mainly, of cleansing them, of giving them a fragrance, of modifying their appearance and/or of correcting body odors and/or protecting them or of maintaining them in good condition.

The cosmetic composition can comprise a cosmetically acceptable medium that may be water or a mixture of water and at least one solvent selected from among hydrophilic organic solvents, lipophilic organic solvents, amphiphilic organic solvents, and mixtures thereof.

For topical application, the cosmetic composition can be administered in the form of aqueous, alcoholic, aqueous-alcoholic or oily solutions or suspensions, or of a dispersion of the lotion or serum type, of emulsions that have a liquid or semi-liquid consistency or are pasty, obtained by dispersion of a fatty phase in an aqueous phase (O/W) or vice versa (W/O) or multiple emulsions, of a free or compacted powder to be used as it is or to be incorporated into a physiologically acceptable medium, or else of microcapsules or microparticles, or of vesicular dispersions of ionic and/or nonionic type. It may thus be in the form of a salve, a tincture, milks, a cream, an ointment, a powder, a patch, an impregnated pad, a solution, an emulsion or a vesicular dispersion, a lotion, aqueous or anhydrous gels, a spray, a suspension, a shampoo, an aerosol or a foam. It may be anhydrous or aqueous. It may also comprise solid preparations constituting soaps or cleansing cakes.

The cosmetic compositions may in particular comprise a hair care composition, and in particular a shampoo, a setting lotion, a treating lotion, a styling cream or gel, restructuring lotions for the hair, a mask, etc. The cosmetic compositions can be a cream, a hair lotion, a shampoo or a conditioner. These can be used in particular in treatments using an application that may or may not be followed by rinsing, or else in the form of a shampoo. A composition in the form of a foam, or else in the form of spray or an aerosol, then comprising propellant under pressure, is also intended. It can thus be in the form of a lotion, serum, milk, cream, gel, salve, ointment, powder, balm, patch, impregnated pad, cake or foam.

In particular, the compositions for application to the scalp or the hair can be in the form of a hair care lotion, for example for daily or twice-weekly application, of a shampoo or of a hair conditioner, in particular for twice-weekly or weekly application, of a liquid or solid soap for cleansing the scalp, for daily application, of a hairstyle shaping product (lacquer, hair setting product or styling gel), of a treatment mask, or of a foaming gel or cream for cleansing the hair. These may also be in the form of a hair dye or mascara to be applied with a brush or a comb.

Moreover, for topical application to the eyelashes or body hair, the compositions may be in the form of a pigmented or unpigmented mascara, to be applied with a brush to the eyelashes or alternatively to beard or moustache hair. For a composition administration by injection, the composition may be in the form of an aqueous lotion or an oily suspension. For oral use, the composition may be in the form of capsules, granules, oral syrups or tablets. According to a particular embodiment, the composition is in the form of a hair cream or hair lotion, a shampoo, a hair conditioner or a mascara for the hair or for the eyelashes.

In a known manner, the cosmetic compositions may also contain adjuvants that are normal in the cosmetics field, such as hydrophilic or lipophilic gelling agents, hydrophilic or lipophilic additives, preservatives, antioxidants, solvents, fragrances, fillers, UV-screening agents, odor absorbers and dyestuffs. The amounts of these various adjuvants are those conventionally used in the cosmetics field, and are for example from 0.1% to 20%, in particular less than or equal to 10%, of the total weight of the composition. According to their nature, these adjuvants can be introduced into the fatty phase, into the aqueous phase and/or into the lipid spherules.

In some embodiments, the 15-PGDH inhibitor can be administered in a combinatorial therapy or combination therapy that includes administration of a 15-PGDH inhibitor with one or more additional active agents. The phrase "combinatorial therapy" or "combination therapy" embraces the administration of the 15-PGDH inhibitor, and one or more therapeutic agents as part of a specific treatment regimen intended to provide beneficial effect from the co-action of these therapeutic agents. Administration of these therapeutic agents in combination typically is carried out over a defined period (usually minutes, hours, days or weeks depending upon the combination selected). "Combinatorial therapy" or "combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example by administering to the subject an individual dose having a fixed ratio of each therapeutic agent or in multiple, individual doses for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissue. The therapeutic agents can be administered by the same route or by different routes. The sequence in which the therapeutic agents are administered is not narrowly critical.

In some embodiments, the additional active agent can be chosen in particular from lipoxygenase inhibitors as described in EP 648488, the bradykinin inhibitors described in particular in EP 845700, prostaglandins and their derivatives, in particular those described in WO 98/33497, WO 95/11003, JP 97-100091, JP 96-134242, the agonists or antagonists of the receptors for prostaglandins, and the nonprostanoic analogues of prostaglandins as described in EP 1175891 and EP 1175890, WO 01/74307, WO 01/74313, WO 01/74314, WO 01/74315 or WO 01/72268.

In other embodiments, the 15-PGDH inhibitors can be administered in combination with active agents, such as vasodilators, prostanoid agonists, antiandrogens, cyclosporins and their analogues, antimicrobials, triterpenes, alone or as a mixture. The vasodilators can include potassium channel agonists including minoxidil and its derivatives, aminexil and the compounds described in U.S. Pat. Nos. 3,382,247, 5,756,092, 5,772,990, 5,760,043, 5,466,694, 5,438,058, 4,973,474, chromakalin and diazoxide. The antiandrogens can include 5.alpha.-reductase inhibitors such as finasteride and the compounds described in U.S. Pat. No. 5,516,779, cyproterone acetate, azelaic acid, its salts and its derivatives, and the compounds described in U.S. Pat. No. 5,480,913, flutamide and the compounds described in U.S. Pat. Nos. 5,411,981, 5,565,467 and 4,910,226. The antimicrobial compounds can include selenium derivatives, ketoconazole, triclocarban, triclosan, zinc pyrithione, itraconazole, asiatic acid, hinokitiol, mipirocine, and the compounds described in EP 680745, clinycine hydrochloride, benzoyl or benzyl peroxide and minocycline. The anti-inflammatory agents can include inhibitors specific for Cox-2 such as for example NS-398 and DuP-697 (B. Batistini et al., DN&P 1994; 7(8):501-511) and/or inhibitors of lipoxygenases, in particular 5-lipoxygenase, such as for example zileuton (F. J. Alvarez & R. T. Slade, Pharmaceutical Res. 1992; 9(11):1465-1473).

Other active compounds, which can be present in pharmaceutical and/or cosmetic compositions can include aminexil and its derivatives, 6O-[(9Z,12Z)octadec-9,12-dienoyl]hexapyranose, benzalkonium chloride, benzethonium chloride, phenol, oestradiol, chlorpheniramine maleate, chlorophyllin derivatives, cholesterol, cysteine, methionine, benzyl nicotinate, menthol, peppermint oil, calcium pantotenate, panthenol, resorcinol, protein kinase C inhibitors, prostaglandin H synthase 1 or COX-1 activators, or COX-2 activators, glycosidase inhibitors, glycosaminoglycanase inhibitors, pyroglutamic acid esters, hexosaccharidic or acylhexosaccharidic acids, substituted ethylenearyls, N-acylated amino acids, flavonoids, derivatives and analogues of ascomycin, histamine antagonists, triterpenes, such as ursolic acid and the compounds described in U.S. Pat. Nos. 5,529,769, 5,468,888, 5,631,282, saponins, proteoglycanase inhibitors, agonists and antagonists of oestrogens, pseudopterins, cytokines and growth factor promoters, IL-1 or IL-6 inhibitors, IL-10 promoters, TNF inhibitors, vitamins, such as vitamin D, analogues of vitamin B12 and panthotenol, hydroxy acids, benzophenones, esterified fatty acids, and hydantoin.

Pharmaceutical and/or cosmetic compositions including the 15-PGDH inhibitor described herein can additionally contain, for example, at least one compound chosen from prostaglandins, in particular prostaglandin $PGE_1$, $PGE_2$, their salts, their esters, their analogues and their derivatives, in particular those described in WO 98/33497, WO 95/11003, JP 97-100091, JP 96-134242, in particular agonists of the prostaglandin receptors. It may in particular contain at least one compound such as the agonists (in acid form or in the form of a precursor, in particular in ester form) of the prostaglandin $F_2\alpha$ receptor, such as for example latanoprost, fluprostenol, cloprostenol, bimatoprost, unoprostone, the agonists (and their precursors, in particular the esters such as travoprost) of the prostaglandin $E_2$ receptors such as 17-phenyl $PGE_2$, viprostol, butaprost, misoprostol, sulprostone, 16,16-dimethyl $PGE_2$, 11-deoxy $PGE_1$, 1-deoxy $PGE_1$, the agonists and their precursors, in particular esters, of the prostacycline (IP) receptor such as cicaprost, iloprost, isocarbacycline, beraprost, eprostenol, treprostinil, the agonists and their precursors, in particular the esters, of the prostaglandin $D_2$ receptor such as BW245C ((4S)-(3-[(3R,S)-3-cyclohexyl-3-isopropyl]-2,5-dioxo)-4-imidazolidineheptanoic acid), BW246C ((4R)-(3-[(3R,S)-3-cyclohexyl-3-isopropyl]-2,5-dioxo)-4-imidazolidineheptanoic acid), the agonists and their precursors, in particular the esters, of the receptor for the thromboxanes A2 (TP) such as I-BOP ([1S-[1a,2a(Z), 3b(1E,3S),4a]]-7-[3-[3-hydroxy-4-[4-(iodophenoxy)-1-butenyl]-7-oxabicyclo-[2.2.1]hept-2-yl]-5-heptenoic acid).

Advantageously, the composition can include at least one 15-PGDH inhibitor as defined above and at least one prostaglandin or one prostaglandin derivative such as for example the prostaglandins of series 2 including in particular $PGF_{2\alpha}$ and $PGE_2$ in saline form or in the form of precursors, in particular of the esters (example isopropyl esters), their derivatives such as 16,16-dimethyl $PGE_2$, 17-phenyl $PGE_2$ and 16,16-dimethyl 17-phenyl $PGF_{2\alpha}$, prostaglandins of series 1 such as 11-deoxyprostaglandin E1, 1-deoxyprostaglandin E1 in saline or ester form, is their analogues, in particular latanoprost, travoprost, fluprostenol, unoprostone, bimatoprost, cloprostenol, viprostol, butaprost, misoprostol, their salts or their esters.

In accordance with another aspect of the application, the modulator of 15-PGDH can be a 15-PGDH activator that can promote or stimulate the activity of 15-PGDH. In certain embodiments, the 15-PDGH activator can include a compound having the formula (IV):

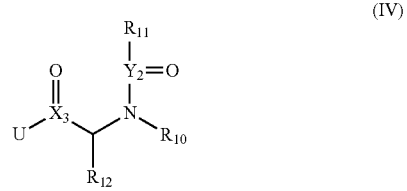

(IV)

wherein $X_3$ and $Y_2$ are independently C or SO;

U is OR" (wherein R" is H, a substituted or unsubstituted alkyl group, or substituted or unsubstituted aryl group) or

$R_8$, $R_9$, $R_{10}$, $R_{11}$, and $R_{12}$ are each selected from the group consisting of H, F, Cl, Br, I, an alkyl group, $(CH_2)_{n1}OR'$ (wherein n1=1, 2, or 3), $CF_3$, $CH_2$—$CH_2X$, O—$CH_2$—$CH_2X$, $CH_2$—$CH_2$—$CH_2X$, O—$CH_2$—$CH_2X$ (wherein X=F, Cl, Br, or I), CN, (C=O)—R', $N(R')_2$, $NO_2$, (C=O)N(R')$_2$, O(CO)R', OR', SR', COOR' (wherein R' is H or a lower alkyl group), a substituted or unsubstituted aryl, a substituted or unsubstituted cycloalkyl, a substituted or unsubstituted heterocyclyl, and $R_8$ and $R_9$ may be linked to form a cyclic or polycyclic ring; and pharmaceutically acceptable salts thereof.

In other embodiments, the 15-PDGH activator can include a compound having the formula (V):

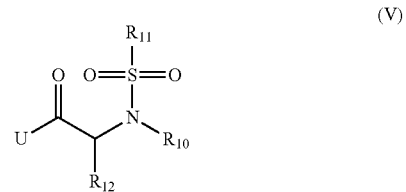

(V)

wherein U is OR" (wherein R" is H, a substituted or unsubstituted alkyl group, or substituted or unsubstituted aryl group) or

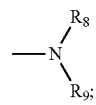

$R_8$, $R_9$, $R_{10}$, $R_{11}$, and $R_{12}$ are each selected from the group consisting of H, F, Cl, Br, I, an alkyl group, $(CH_2)_{n1}OR'$ (wherein n1=1, 2, or 3), $CF_3$, $CH_2$—$CH_2X$, O—$CH_2$—$CH_2X$, $CH_2$—$CH_2$—$CH_2X$, O—$CH_2$—$CH_2X$ (wherein X=F, Cl, Br, or I), CN, (C=O)—R', $N(R')_2$, $NO_2$, (C=O)N(R')$_2$, O(CO)R', OR', SR', COOR' (wherein R' is H or a lower alkyl group), a substituted or unsubstituted aryl, a substituted or unsubstituted cycloalkyl, a substituted or unsubstituted heterocyclyl, and $R_8$ and $R_9$ may be linked to form a cyclic or polycyclic ring; and pharmaceutically acceptable salts thereof.

In certain embodiments, a 15-PGDH activator having formula (IV) or (V) can be selected that can: ia) at 7.5 μM concentration, stimulate a Vaco503 reporter cell line expressing a 15-PGDH luciferase fusion construct to a luciferase output level of greater than 50 (using a scale on which a value of 100 indicates a doubling of reporter output over baseline); iia) at 7.5 μM concentration stimulate a V9m reporter cell line expressing a 15-PGDH luciferase fusion construct to a luciferase output level of greater than 50; iiia)

at 7.5 µM concentration stimulate a LS174T reporter cell line expressing a 15-PGDH luciferase fusion construct to a luciferase output level of greater than 50; iva) at 7.5 µM concentration, does not activate the negative control V9m cell line expressing TK-*renilla* luciferase reporter to a level any greater than 25; and va) against recombinant 15-PGDH protein the compound shows an IC50 concentration for inhibiting 15-PGDH enzyme activity of greater than 2.5 µM.

In certain embodiments, a 15-PGDH activator having formula (IV) or (V) can be selected that can: ib) at 7.5 µM concentration, stimulate a Vaco503 reporter cell line expressing a 15-PGDH luciferase fusion construct to increase luciferase output; iib) at 7.5 µM concentration stimulate a V9m reporter cell line expressing a 15-PGDH luciferase fusion construct to increase luciferase output; iiib) at 7.5 µM concentration stimulate a LS174T reporter cell line expressing a 15-PGDH luciferase fusion construct to increase luciferase output; ivb) at 7.5 µM concentration, does not activate the negative control V9m cell line expressing TK-*renilla* luciferase reporter to a luciferase level any greater than 25% above; and vb) against recombinant 15-PGDH protein the compound shows an $IC_{50}$ concentration for inhibiting 15-PGDH enzyme activity of greater than or equal to 2.5 µM.

In other embodiments, a 15-PGDH activator having formula (IV) or (V) that meets the above noted criteria (ia-va) and/or that meet the above noted criteria (ib-vb) includes a compound having the formula (VI):

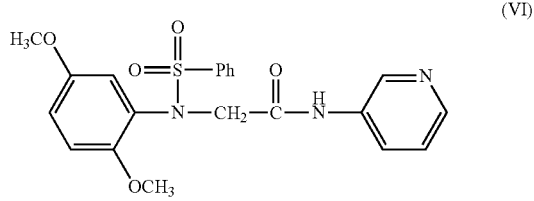 [SMILES: COc1ccc(OC)c(N(CC(=O)Nc2cccnc2)S(=O)(=O)c2ccccc2)c1]

(VI)

and pharmaceutically acceptable salts thereof.

In other embodiments, the 15-PGDH activator can be an analogue of a compound having the formula (VI). Such analogues can have the following formula (VII):

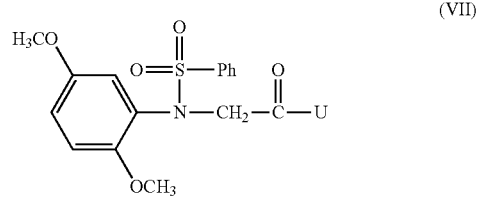

(VII)

wherein U is OR" (wherein R" is H, a substituted or unsubstituted alkyl group, or substituted or unsubstituted aryl group) or

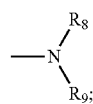

$R_8$ and $R_9$ are each selected from the group consisting of H, F, Cl, Br, I, an alkyl group, $(CH_2)_{n1}OR'$ (wherein n1=1, 2, or 3), $CF_3$, $CH_2—CH_2X$, $O—CH_2—CH_2X$, $CH_2—CH_2—CH_2X$, $O—CH_2—CH_2—CH_2X$ (wherein X=F, Cl, Br, or I), CN, (C=O)—R', N(R')$_2$, NO$_2$, (C=O)N(R')$_2$, O(CO)R', OR', SR', COOR' (wherein R' is H or a lower alkyl group), a substituted or unsubstituted aryl, a substituted or unsubstituted cycloalkyl, a substituted or unsubstituted heterocyclyl, and $R_8$ and $R_9$ may be linked to form a cyclic or polycyclic ring; and pharmaceutically acceptable salts thereof.

Examples of 15-PGDH activators having the formula (VII) include:

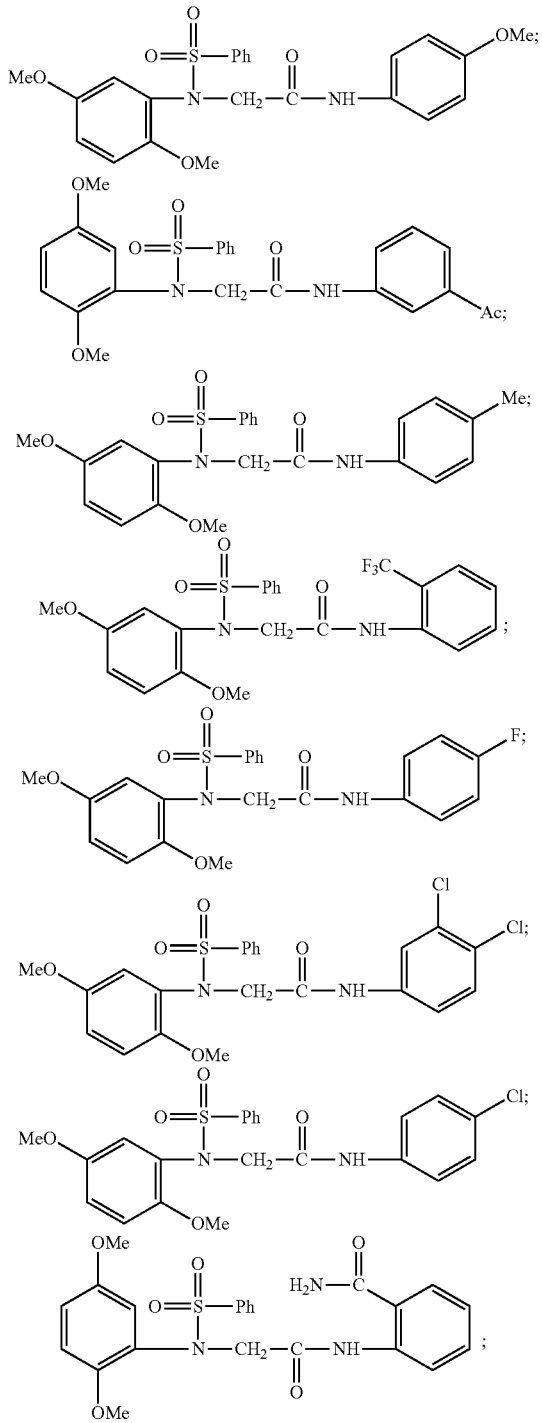

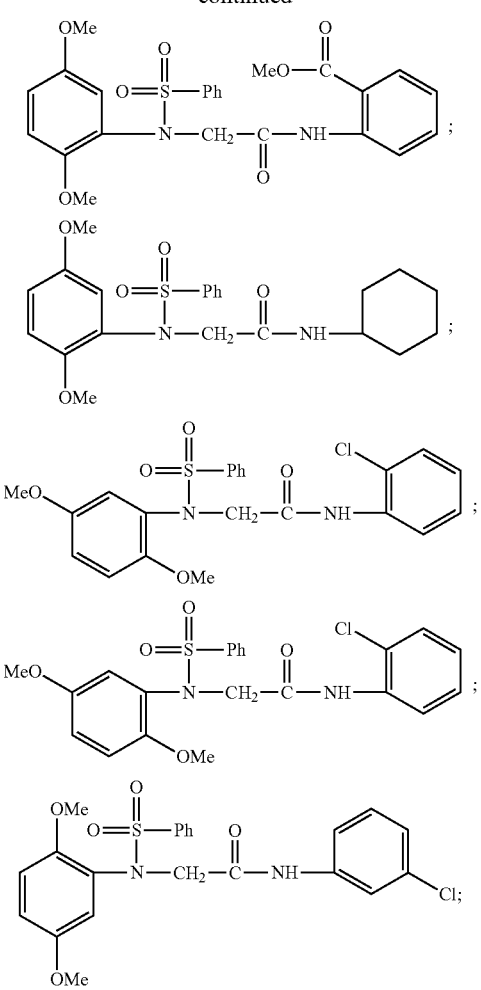
and pharmaceutically acceptable salts thereof.
Other examples of compounds having formula (VII) include:
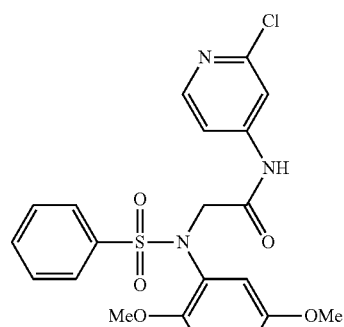
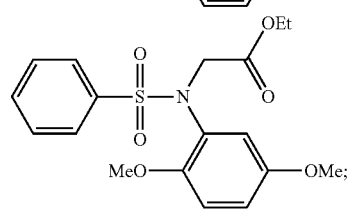
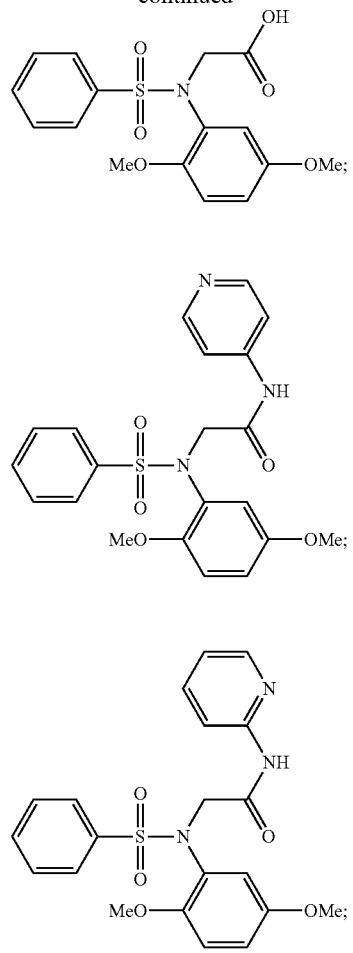
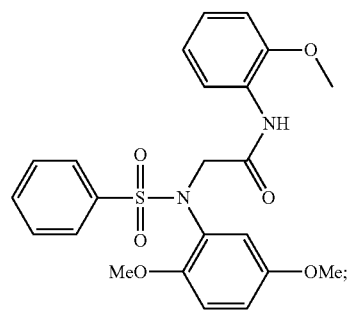
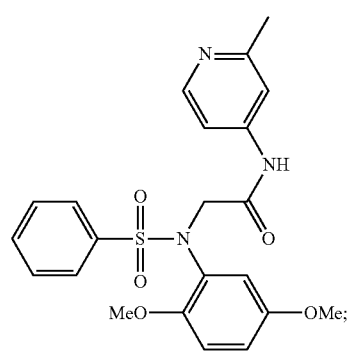

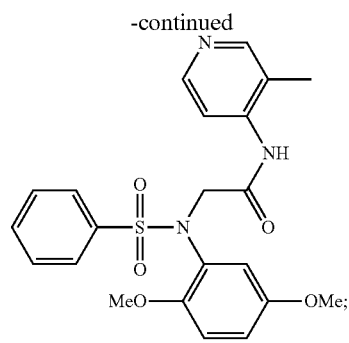
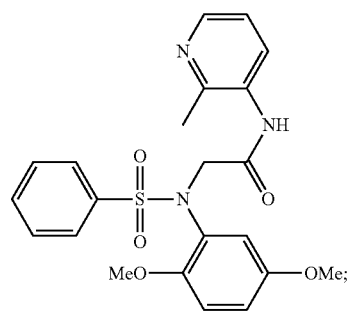
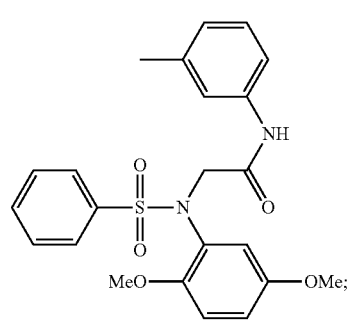
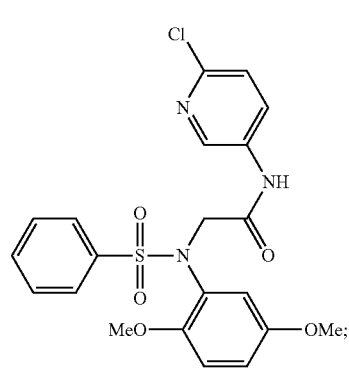
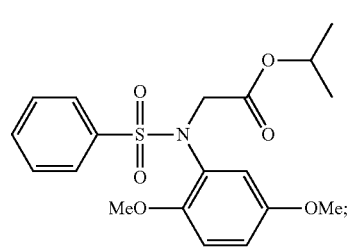
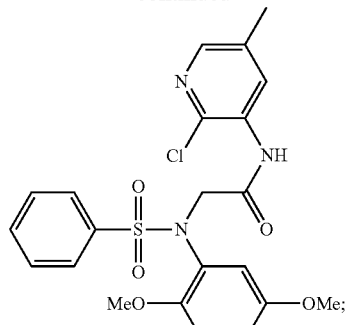
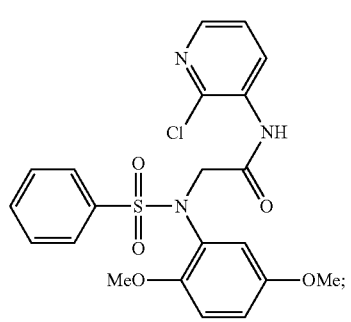
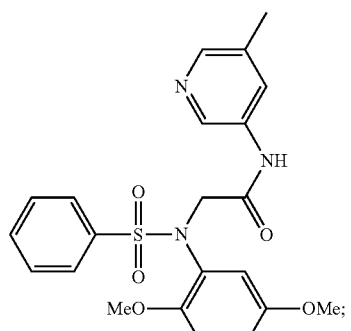
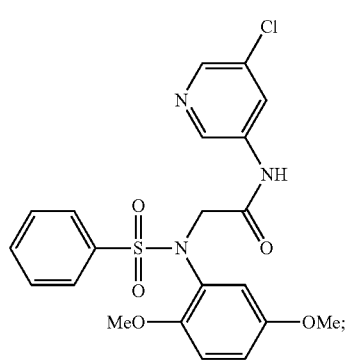
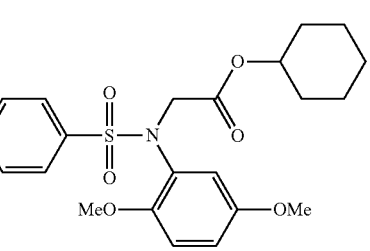

-continued
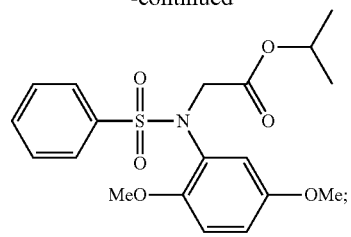
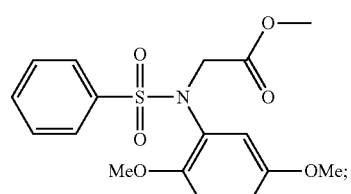
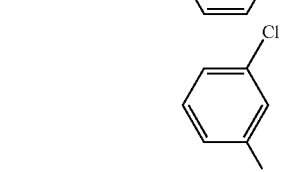
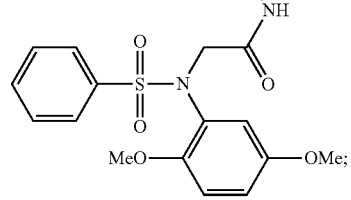
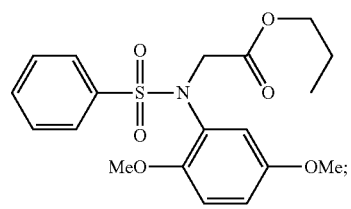
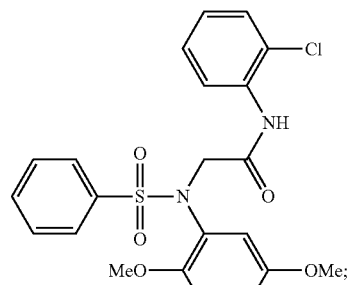
-continued
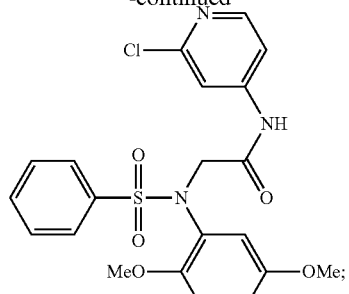
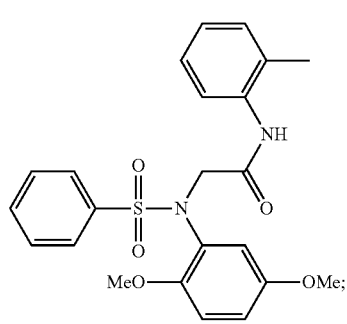
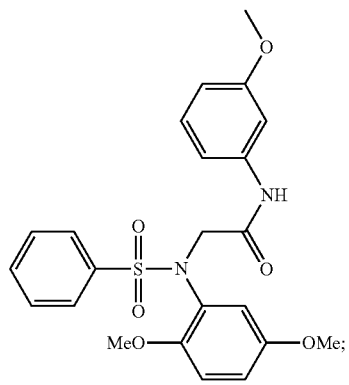
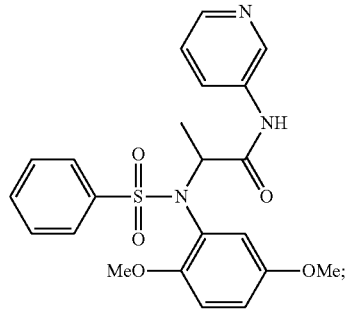
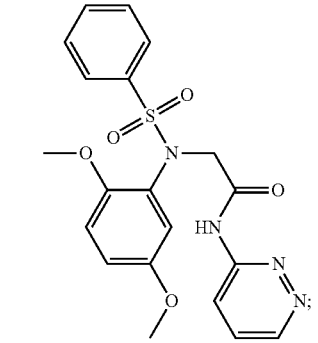

49
-continued
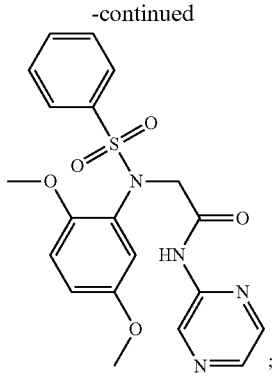
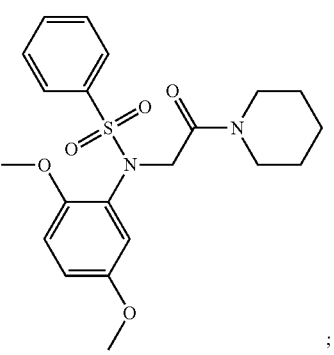
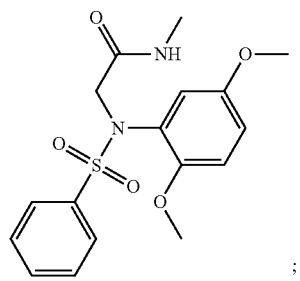
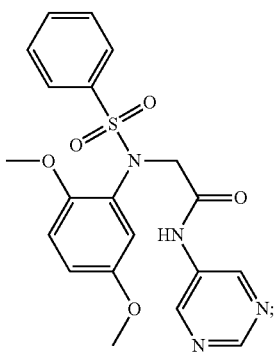
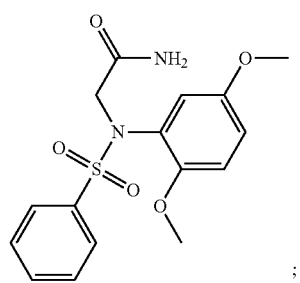
50
-continued
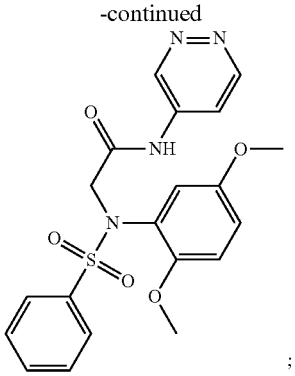
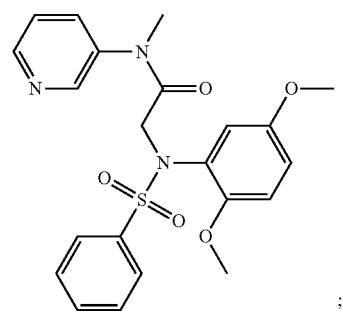
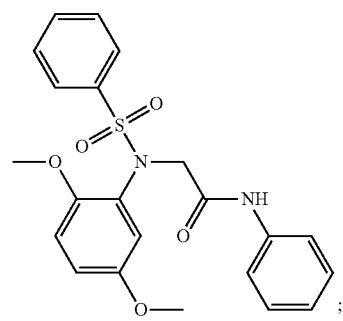
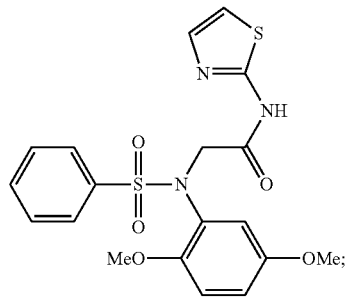
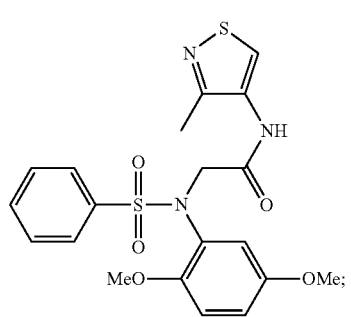

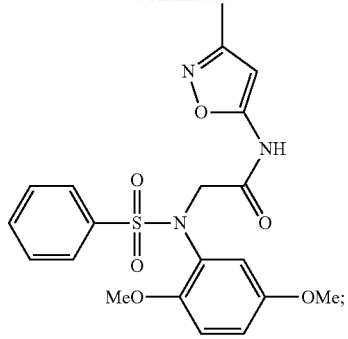
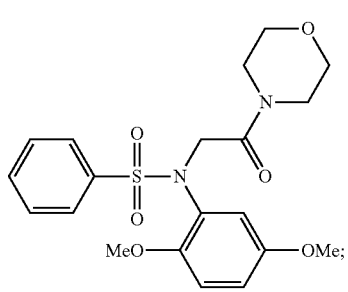
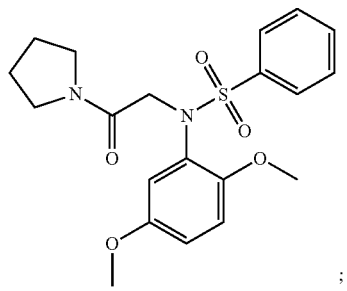
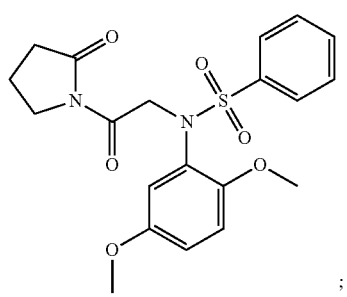
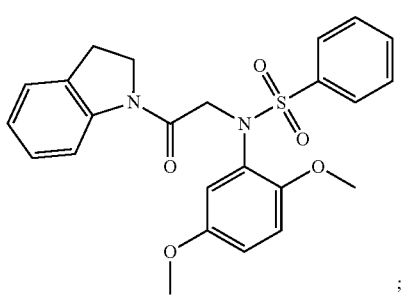
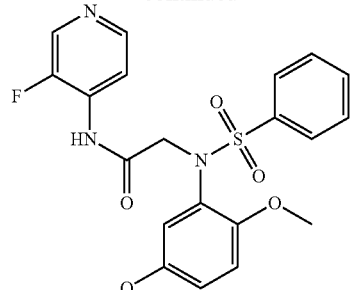
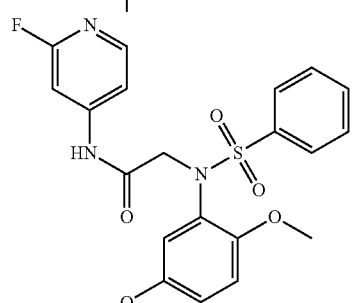
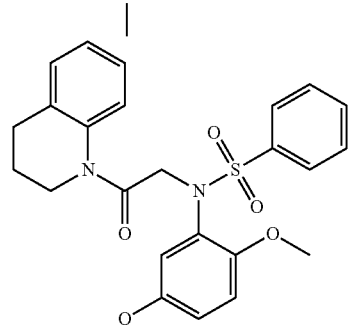
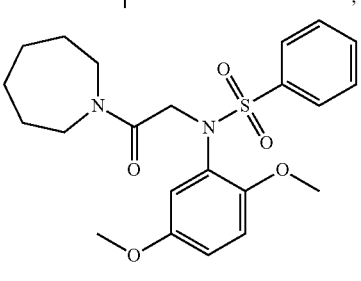
and pharmaceutically acceptable salts thereof.
In other embodiments, the 15-PGDH activator can be an analogue of compound (VI) having the following formula (VIII):
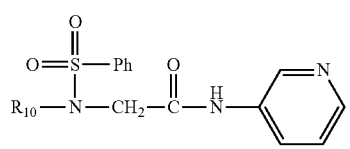
(VIII)
wherein $R_{10}$ is selected from the group consisting of a substituted or unsubstituted aryl, a substituted or unsubstituted cycloalkyl, and a substituted or unsubstituted heterocyclyl; and pharmaceutically acceptable salts thereof.
Examples of 15-PGDH activators having the formula (VIII) include:
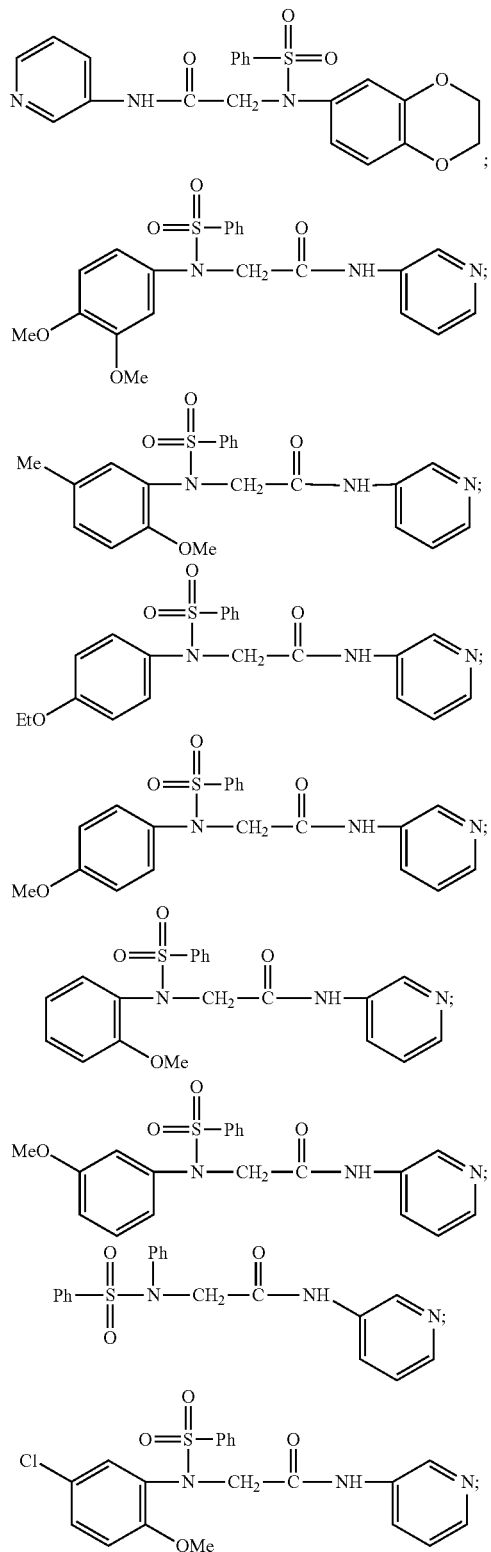
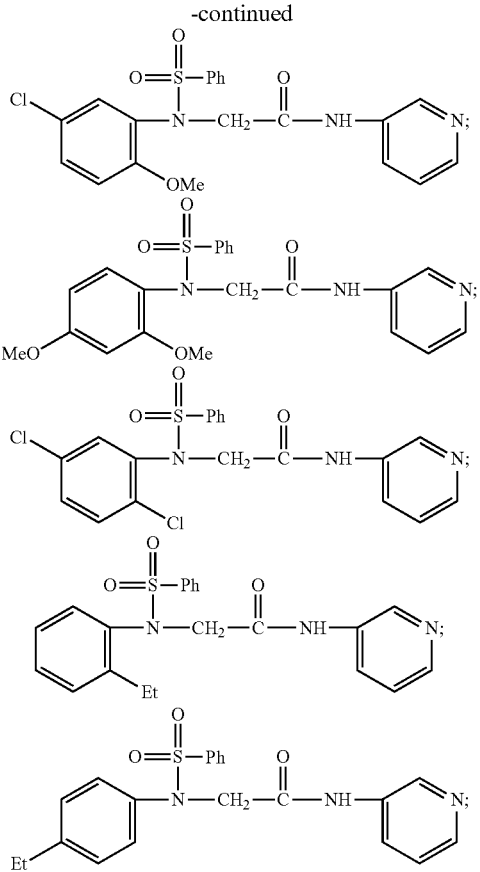
and pharmaceutically acceptable salts thereof.
Still other examples of compounds having the formula (VIII) include:
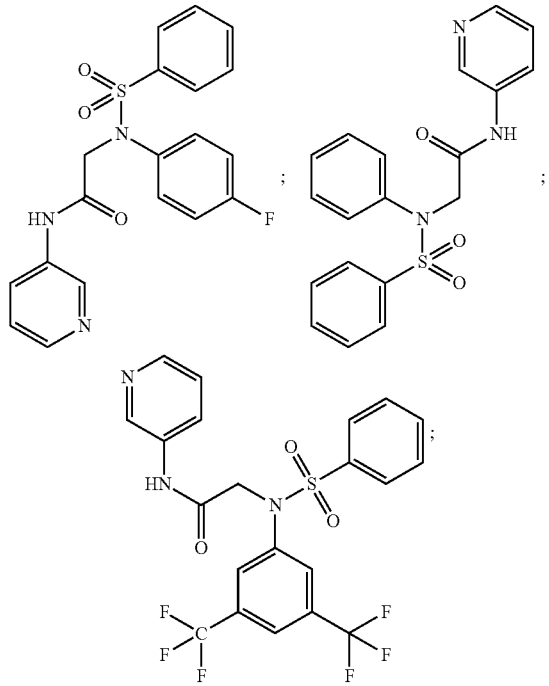
and pharmaceutically acceptable salts thereof.

In still other embodiments, the 15-PGDH activator can be an analogue of compound (VI) having the formula (IX):

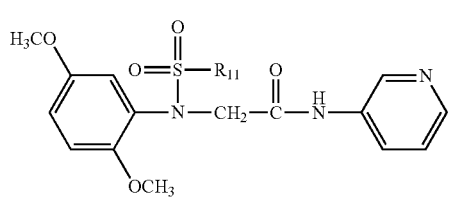
(IX)

wherein $R_{11}$ is H, F, Cl, Br, I, a lower alkyl group, $(CH_2)_{n1}OR'$ (wherein n1=1, 2, or 3), $CF_3$, $CH_2$—$CH_2X$, O—$CH_2$—$CH_2X$, $CH_2$—$CH_2$—$CH_2X$, O—$CH_2$—$CH_2X$ (wherein X=F, Cl, Br, or I), CN, (C=O)—R', $N(R')_2$, $NO_2$, (C=O)$N(R')_2$, O(CO)R', OR', SR', COOR' (wherein R' is H or a lower alkyl group), a substituted or unsubstituted aryl, a substituted or unsubstituted cycloalkyl, and a substituted or unsubstituted heterocyclyl; and pharmaceutically acceptable salts thereof.

Examples of 15-PGDH activators having the formula (IX) include:

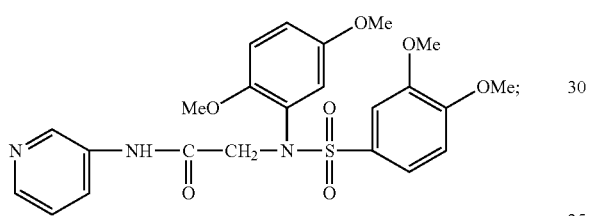

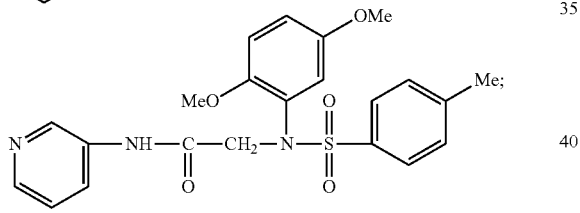

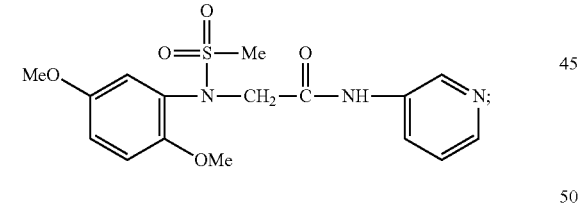

and pharmaceutically acceptable salts thereof.

Still other examples of compounds having formula (IX) include:

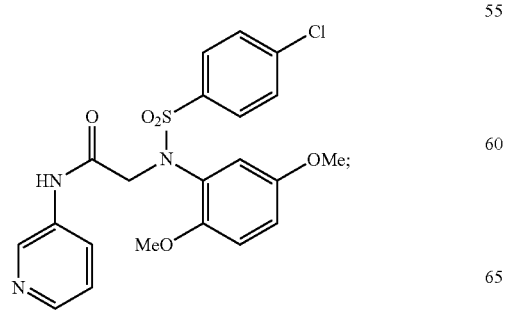

-continued

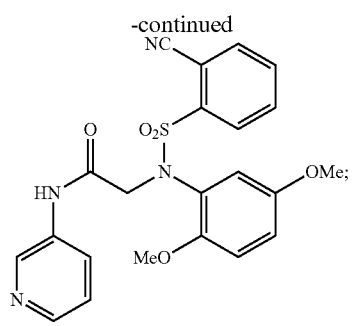

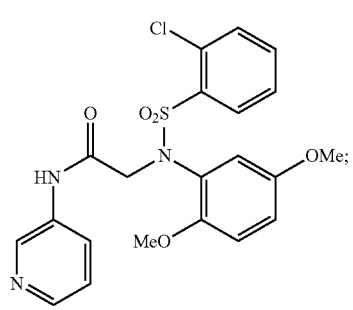

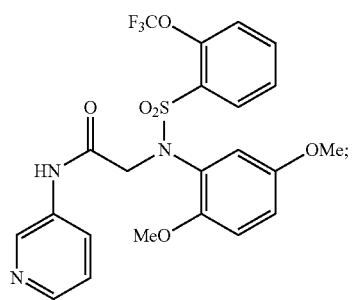

-continued
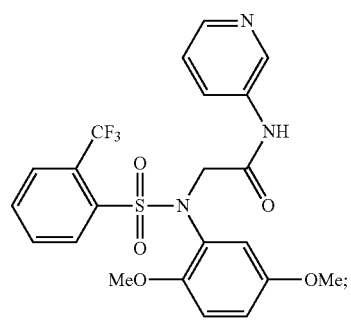
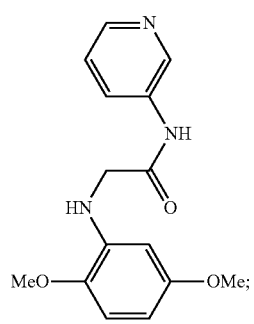
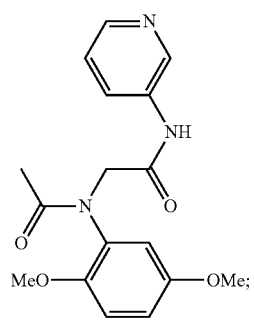
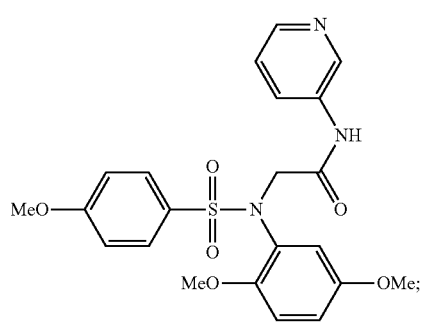
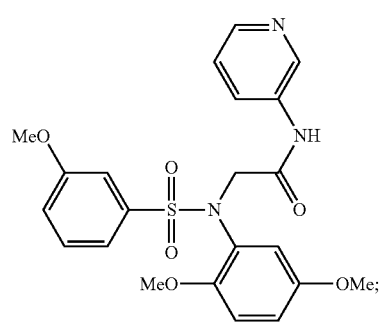
-continued
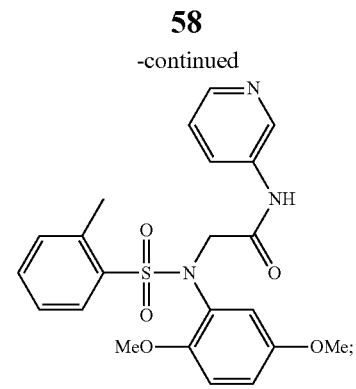
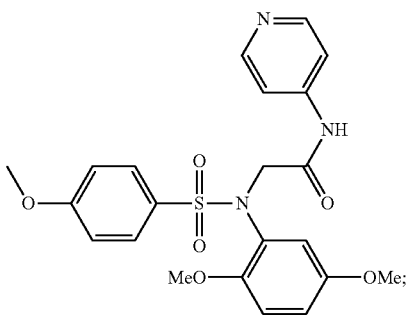
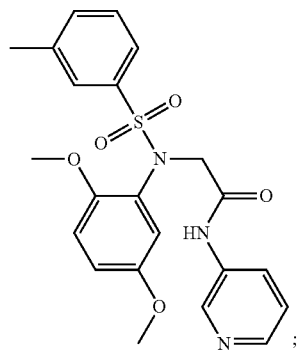
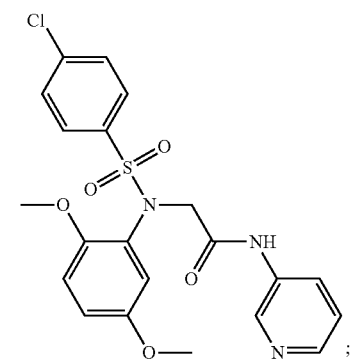
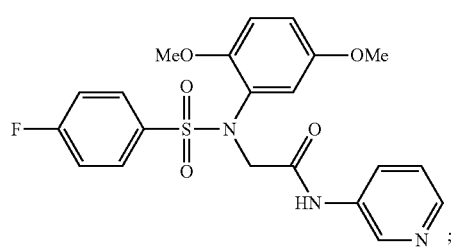

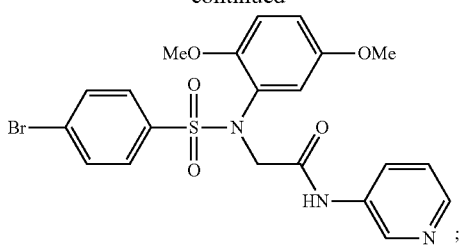
and pharmaceutically acceptable salts thereof.
In other embodiments, the 15-PGDH activator can be an analogue of compound (IV) having the following formulas:
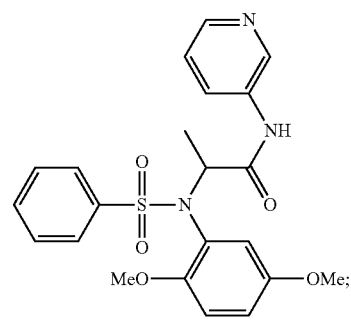
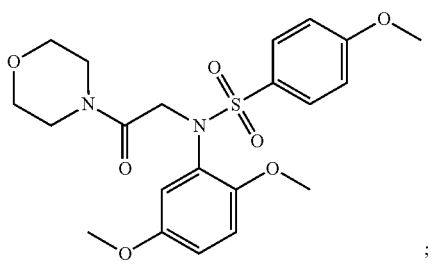
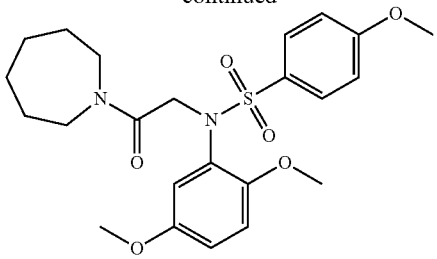

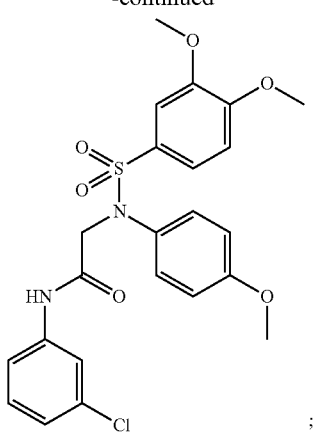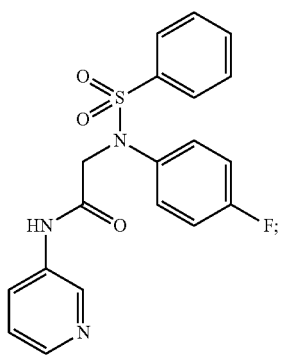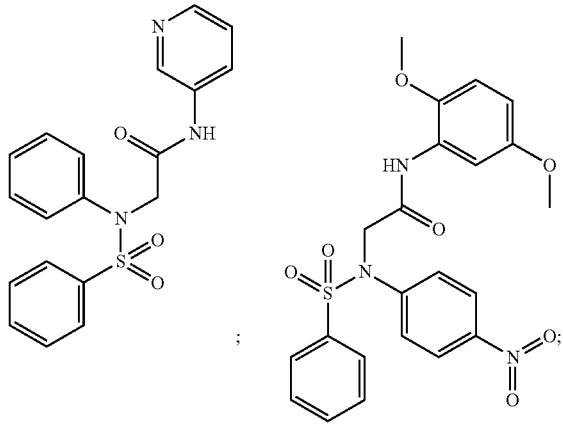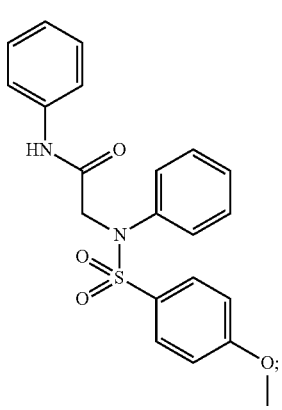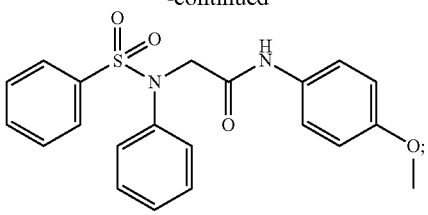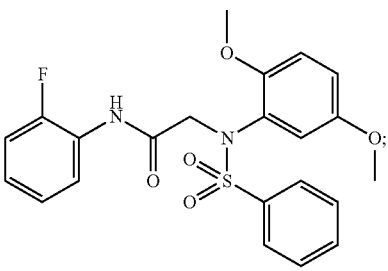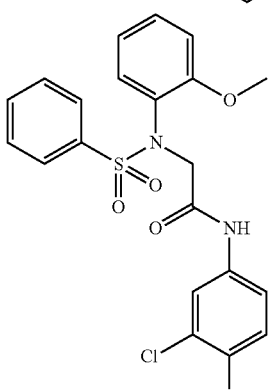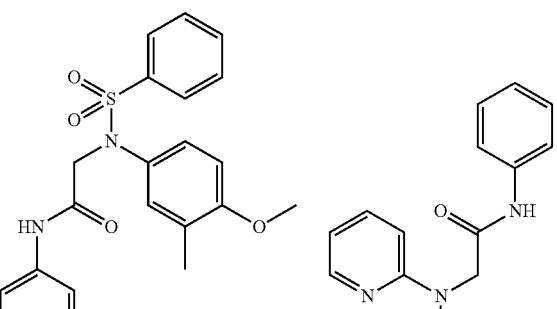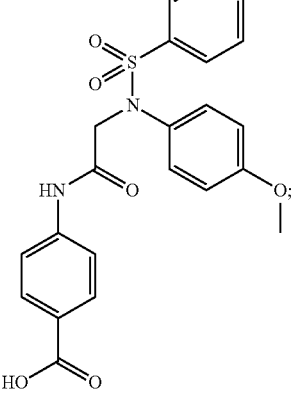

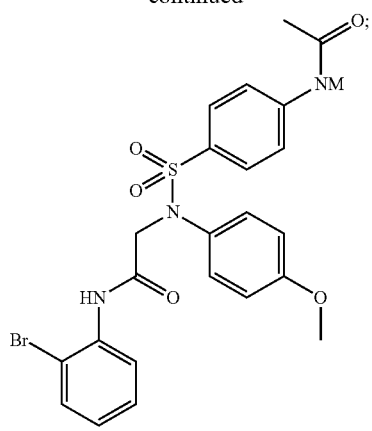
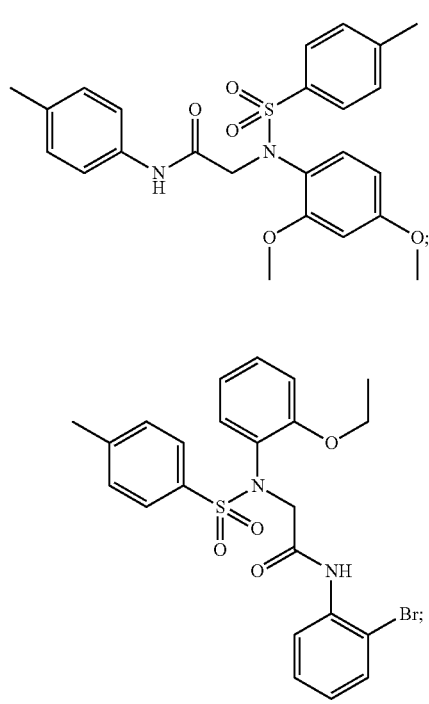
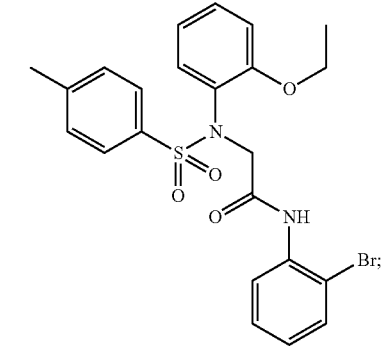
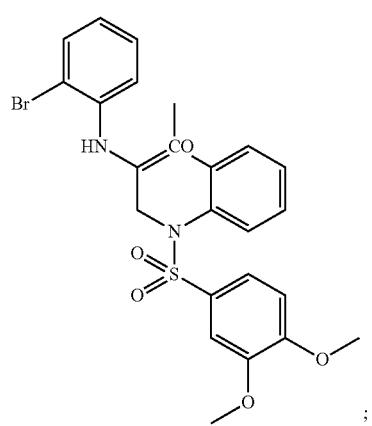
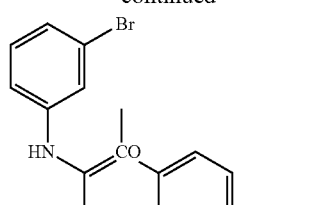
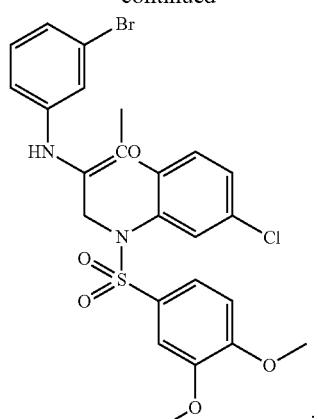
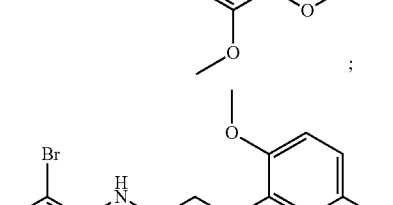
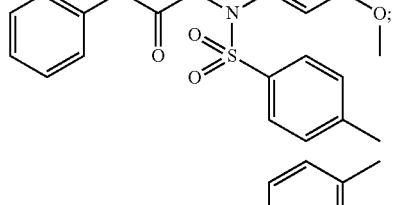
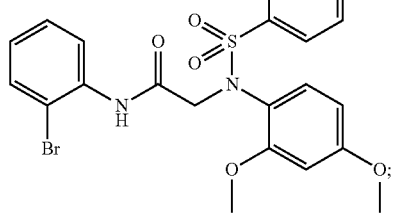
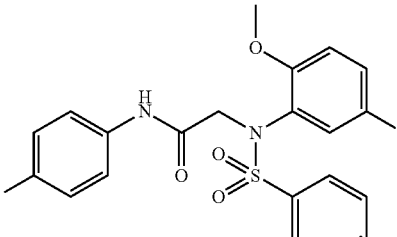
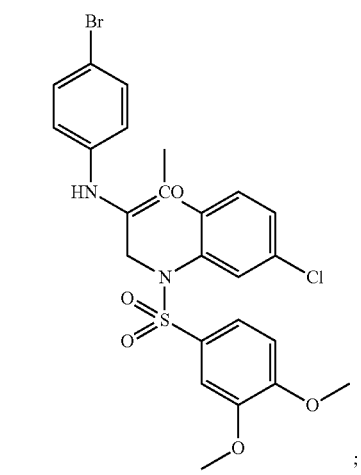

65
-continued
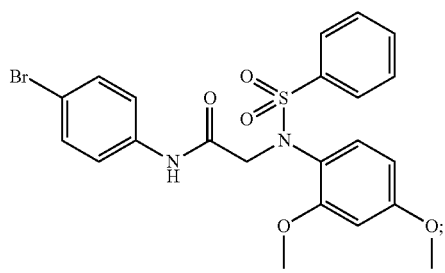
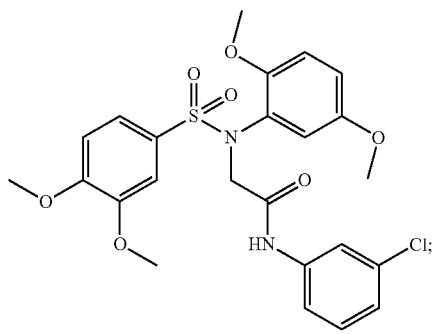
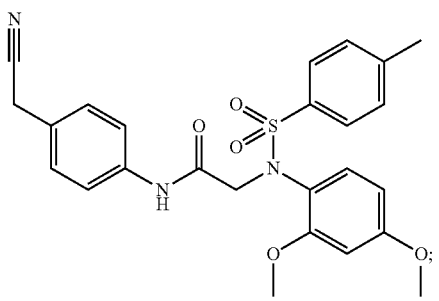
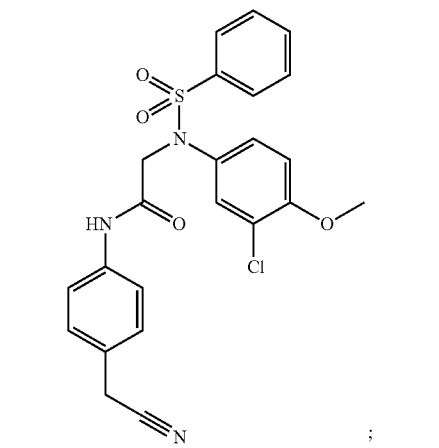
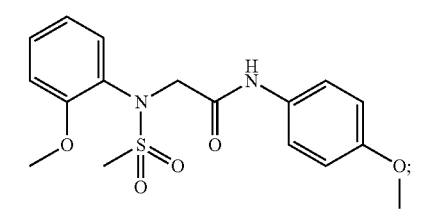
66
-continued
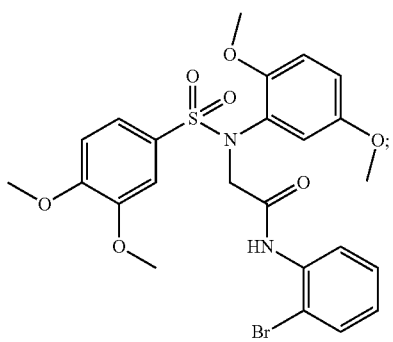
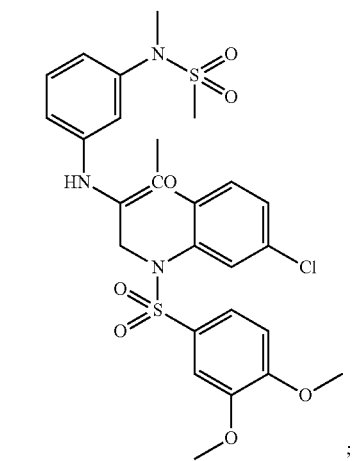
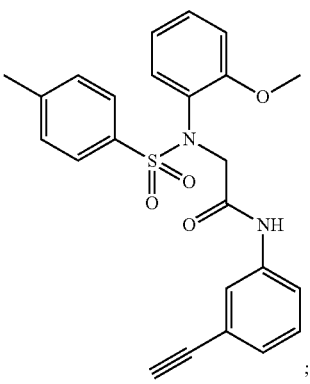
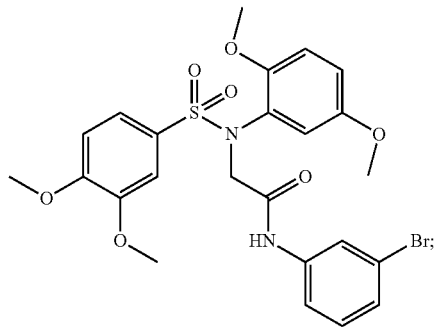

67
-continued
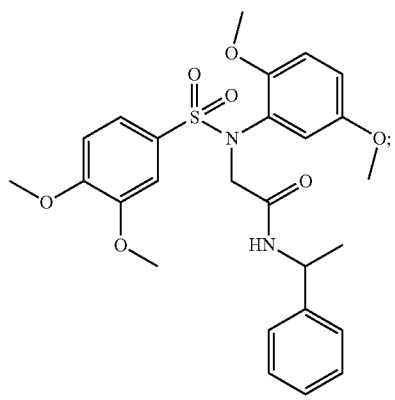
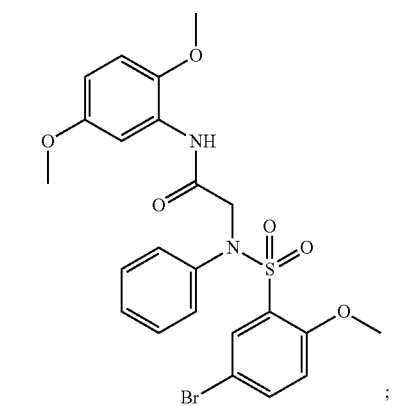
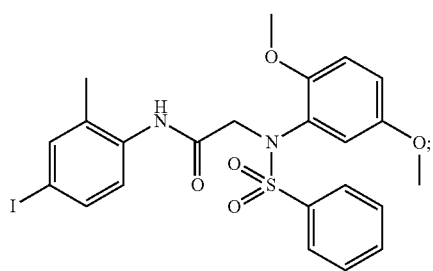
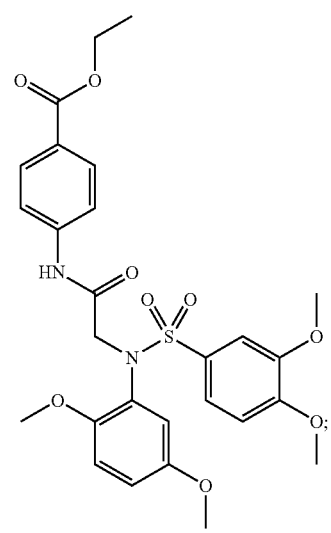
68
-continued
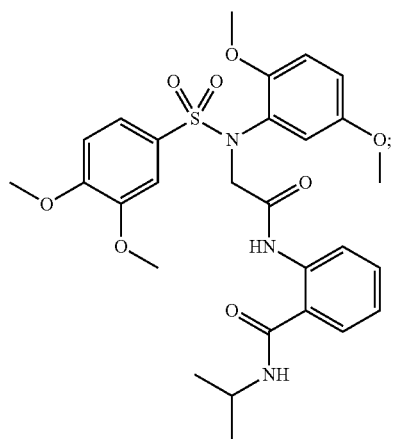
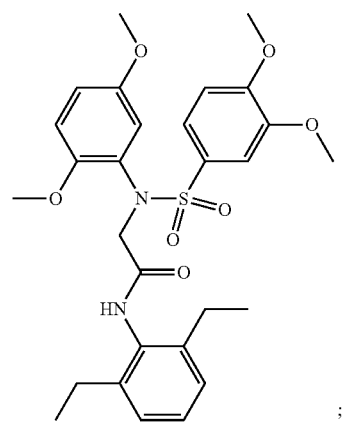
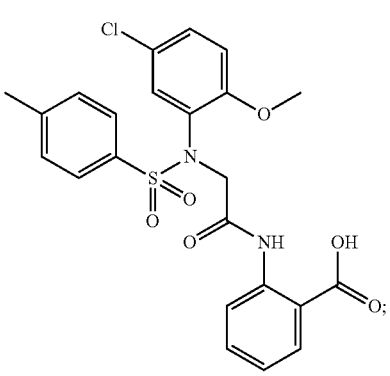
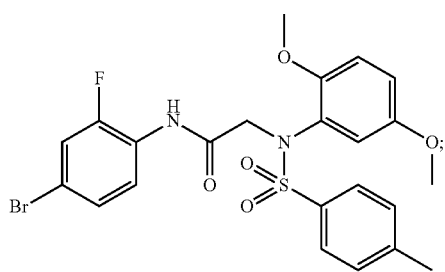

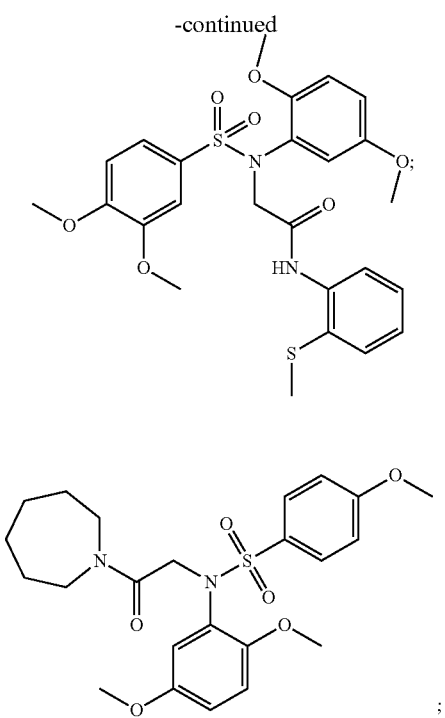

and pharmaceutically acceptable salts thereof.

The 15-PGDH activators described herein can be used for the prevention or the treatment of diseases that are associated with decreased 15-PGDH levels and/or increased prostaglandin levels. Increasing tissue levels of 15-PGDH should decrease tissue levels of prostaglandins. Activities associated with compounds that decrease tissue prostaglandins include decreasing development of human tumors. For example, administration of 15-PGDH activators can be used to treat patients with colon neoplasia, e.g., colon cancer or colon adenoma, or to treat and prevent new disease in patients with a history of colon neoplasia, or to reverse resistance to NSAID therapy for neoplasia therapy or neoplasia preventive therapy. Further, administration of 15-PGDH activators described herein can be used to treat subjects having an NSAID-responsive condition. In certain embodiments, 15-PGDH activators enhance NSAID-responsiveness in subjects who are relatively unresponsive to NSAID treatment.

The 15-PGDH activators described herein can be also be used in a method of treating any NSAID-responsive condition. The NSAID-responsive condition applies to a subject who is NSAID-resistant or a subject who was determined to be resistant to NSAID therapy. In the method, a therapeutically effective amount of 15-PGDH activators can be administered alone or in combination with an effective an effective amount of 15-PGDH protein, cDNA, or an active fragment thereof. The patient may be a subject at risk of developing colon neoplasia (e.g., based on family history), or a subject at risk of colon adenoma relapse, but is suspected of being resistant to NSAID therapy. Further, the patient may be any subject who is undergoing or about to undergo NSAID therapy for any NSAID-responsive condition, but who experiences NSAID resistance.

The 15-PGDH activators described herein can be provided in a pharmaceutical composition that includes pharmaceutically acceptable carrier. In some embodiments, the 15-PGDH activator can be provided alone or in combination with other components (e.g., an NSAID), can be made into aerosol formulations (i.e., they can be "nebulized") to be administered via inhalation. The 15-PGDH activator can also be provided alone or in combination with other components in aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. Compositions including the 15-PGDH activator can be administered, for example, orally, nasally, topically, intravenously, intraperitoneally, or intrathecally. The formulations can be presented in unit-dose or multi-dose sealed containers, such as ampoules and vials. Solutions and suspensions can be prepared from sterile powders, granules, and tablets of the kind previously described. The modulators can also be administered as part of a prepared food or drug.

The dose administered to a patient should be sufficient to induce a beneficial response in the subject over time. The optimal dose level for any patient will depend on a variety of factors including the efficacy of the specific modulator employed, the age, body weight, physical activity, and diet of the patient, on a possible combination with other drugs, and on the severity of the case of diabetes. It is recommended that the daily dosage of the 15-PGDH activator can be determined for each individual patient by those skilled in the art. The size of the dose also will be determined by the existence, nature, and extent of any adverse side-effects that accompany the administration of a particular compound in a particular subject.

In some embodiments, the 15-PGDH activator can be administered in a combination therapy includes administration of a single pharmaceutical dosage formulation that contains a 15-PGDH activator and one or more additional active agents, as well as administration of a 15-PGDH activator and each active agent in its own separate pharmaceutical dosage formulation. For example, a 15-PGDH activator and celecoxib can be administered to the human subject together in a single oral dosage composition, such as a tablet or capsule, or each agent can be administered in separate oral dosage formulations. In other embodiments, an NSAID, e.g., celecoxib or aspirin, may be administered with an effective amount of the 15-PGDH activator. Where separate dosage formulations are used, a 15-PGDH activator and one or more additional active agents can be administered at essentially the same time (i.e., concurrently), or at separately staggered times (i.e., sequentially). Combination therapy is understood to include all these regimens.

The invention is further illustrated by the following example, which is not intended to limit the scope of the claims.

Example 1

This Example describes the activities of four compounds with respect to the enzyme 15-Prostaglandin Dehydrogenase (15-PGDH) (encoded by the gene HPGD). The compounds are SW033291, SW054384, SW124531, SW145753 and have the following formulas:

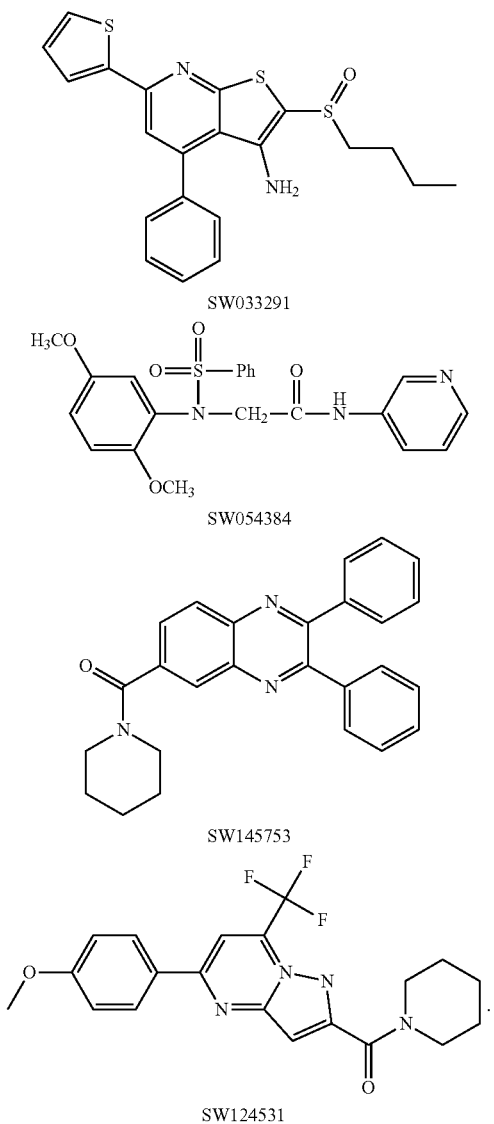

SW033291

SW054384

SW145753

SW124531

FIG. 1 shows that SW033291, SW054384, and SW145753 all increase luciferase activity of cells the express a 15-PGDH luciferase fusion construct created by targeted gene knock-in of *renilla* luciferase into the last coding exon of 15-PGDH. The activity is demonstrated in three different colon cancer cell lines all engineered to contain the 15-PGDH-luciferase fusion. These cell lines are Vaco-9m (V9m), LS174T, Vaco503 (V503). SW054384 is in general the best inducer, and shows maximum activity at 6.25 μM. Value of 1.0 on the Y-axis is the basal level of reporter activity in cells treated with drug free DMSO vehicle.

FIG. 2 shows western blots demonstrating that SW033291, SW054384, and SW145753 all increase levels of 15-PGDH protein in cell lines V503, LS174T, and V503 treated with 7.5 μM compound for 48 hours. Untreated FET cells provide a positive control for 15-PGDH expression.

Figure 3:
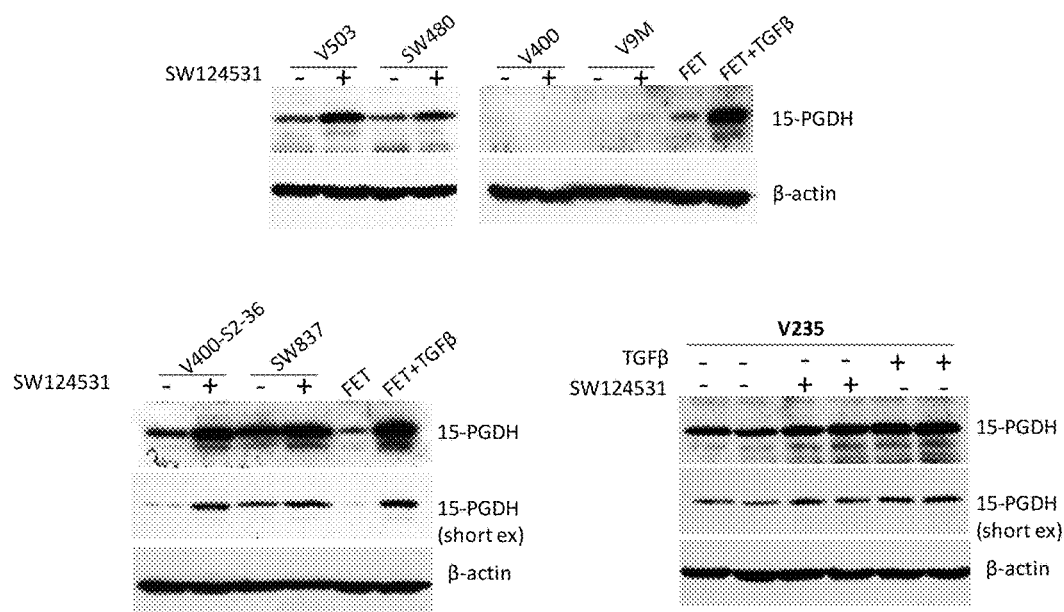
FIG. 3 illustrates western blots demonstrating 15-PGDH protein levels in colon cell lines treated with SW124531 (FET cells treated with TGF-ß (10 ng/ml for 48 hours) are used as a positive control for 15-PGDH expression in certain panels).

FIG. 3 shows western blot demonstrating SW124531 also increases 15-PGDH protein levels in colon cell lines (FET cells treated with TGF-ß (10 ng/ml) for 48 hours are used as a positive control for 15-PGDH expression in certain panels).

Figure 4:
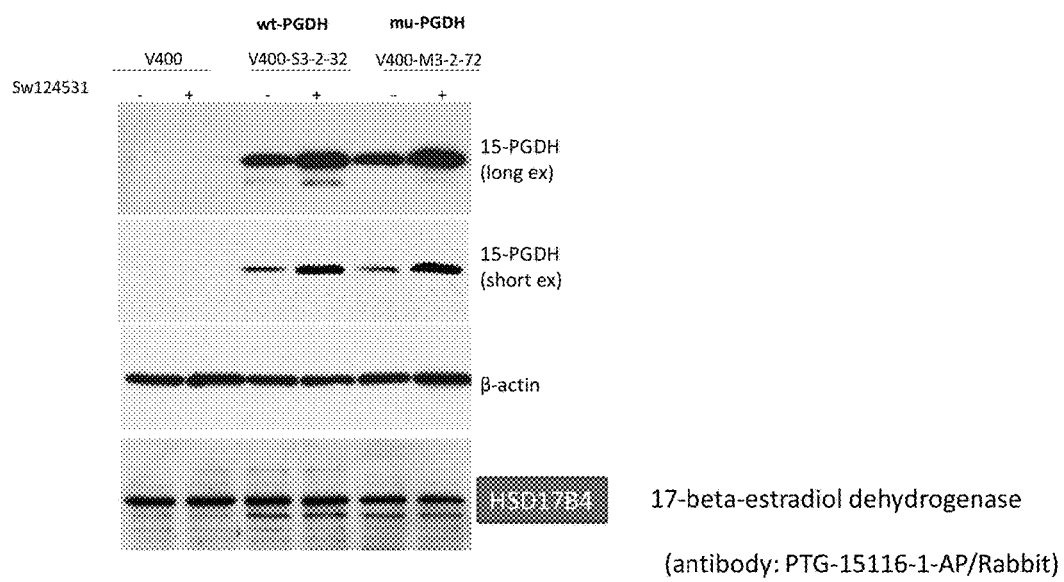
FIG. 4 illustrates western blots demonstrating the levels of 15-PGDH protein (wt-PGDH) expressed from a cDNA expression vector in V400-S3-2-32 cells treated with 5 µM SW124531, and protein levels of a catalytically dead mutant 15-PGDH (mu-PGDH) also expressed from a cDNA expression vector in V400-M3-2-72 cells treated with SW124531.

FIG. 4 shows western blot demonstrating 5 μM SW124531 increases levels of 15-PGDH protein (wt-PGDH) expressed from a cDNA expression vector in V400-S3-2-32 cells, and also increases protein levels of a catalytically dead mutant 15-PGDH (mu-PGDH) also expressed from a cDNA expression vector in V400-M3-2-72 cells. As these proteins are expressed from a heterologous CMV promoter, the findings suggest that the compounds work directly on stabilizing the 15-PGDH protein. The compounds show no effects on levels of a related enzyme, 17-beta-estradiol-dehydrogenase.

FIG. 5 shows increase in 15-PGDH protein levels in V503 cells treated with SW124531 as assayed by immuno-fluorescence (upper two rows) and by western blot (lower panel).

FIGS. 6-9 show that SW033291, SW054384, SW145753, and SW124531 do not in general alter 15-PGDH mRNA levels in treated colon cancer cell lines as assessed by real-time PCR. The only exception is the slight increase in 15-PGDH mRNA in SW033291 treated V503 cells, which is less than the induction of 15-PGDH protein as well as 15-PGDH-luciferase reporter levels seen in SW033291 treated V503 cells. In these studies parental cell lines (not containing the 15-PGDH-luciferase reporter) are employed.

FIG. 10 shows the effects of three compounds on total 15-PGDH activity in cell lines treated with the compounds. Cell lines were treated with compounds at 7.5 μM for 48 hours, and then pelleted. Pellets were lysed and total 15-PGDH activity measured and normalized to 1,000,000 input cells per pellet. 15-PGDH activity was assayed by measuring the transfer of tritium from 15(S)-[15-3H] $PGE_2$ to glutamate by coupling 15-PGDH with glutamate dehydrogenase as described in (Chi X, Freeman B M, Tong M, Zhao Y, Tai H H. 15-Hydroxyprostaglandin dehydrogenase (15-PGDH) is up-regulated by flurbiprofen and other non-steroidal anti-inflammatory drugs in human colon cancer HT29 cells. Arch Biochem Biophys. 2009; 487(2):139-45.). Activity is measured as pmol $PGE_2$/min/million cells. As shown, SW033291 markedly inhibits 15-PGDH activity in all three of the cell lines tested. We conclude that although SW033291 increases total 15-PGDH protein levels in cells, it also inactivates 15-PGDH enzyme activity.

In contrast, 15-PGDH enzyme activity is increased in cells treated with SW054384 and in cells treated with SW145753.

FIG. 11 shows the effect on activity of recombinant 15-PGDH protein (a 15-PGDH-GST fusion protein) incubated with varying concentrations of the test compounds, with 15-PGDH activity across a range of compound concentrations recorded on the table and displayed on the corresponding graphs. As shown, SW033291 is a potent inhibitor of 15-PGDH activity, with an IC50 of <1.25 nM. This contrasts with the IC50 of between 25 nM-62.5 nM measured for the commercial 15-PGDH inhibitor available from Cayman Chemical (Cayman catalogue item 10638, Cayman Chemical number 13695).

FIG. 11 also shows that at very high concentration SW054384 can inhibit recombinant 15-PGDH activity, with an IC50 of between 5 μM-50 μM. We conclude that SW054384 increases total 15-PGDH level and activity in cells treated with 7.5 μM compound, but can inhibit in vitro recombinant 15-PGDH protein in vitro assays using 5 μM-50 μM compound.

FIG. 11 also shows that SW145753 can inhibit activity of recombinant 15-PGDH enzyme in an in vitro assay at an IC50 between 12-6.25 nM. This suggests the activity of SW145753 in increasing versus in inhibiting 15-PGDH activity may be discordant in cells versus in the in vitro assay (perhaps due to washout of drugs when washing the cells), or may be concentration dependent.

FIG. 12 shows repeat testing of the effects of SW033291 and SW054384 on activity of recombinant 15-PGDH protein tested in vitro. Assays were done by measuring the transfer of tritium from 15(S)-[15-3H] $PGE_2$ to glutamate (at 1 μM $PGE_2$ substrate) shown at left (panels A, C), or by direct fluorescence monitoring of NADH generation by 15-PGDH (done at 20 μM $PGE_2$ substrate) shown at right (panels B, D). SW033291 is again confirmed as a highly potent 15-PGDH inhibitor with an IC50 of 0.7 nM as measured in the tritium assay and an IC50 of 1.6 nM as measured in the fluorescence assay. The relative insensitivity of the IC50 to substrate concentration suggests that SW033291 is a non-competitive inhibitor of 15-PGDH.

SW054384 shows very weak inhibitory activity, with IC50s that are 10,000 fold higher than that of SW033291 (8.4 μM and 11 μM in the tritium and fluorescent based assays respectively). This is consistent with the activity of SW054384 being on balance to increase 15-PGDH protein level and enzyme activity in cells.

Figure 13:
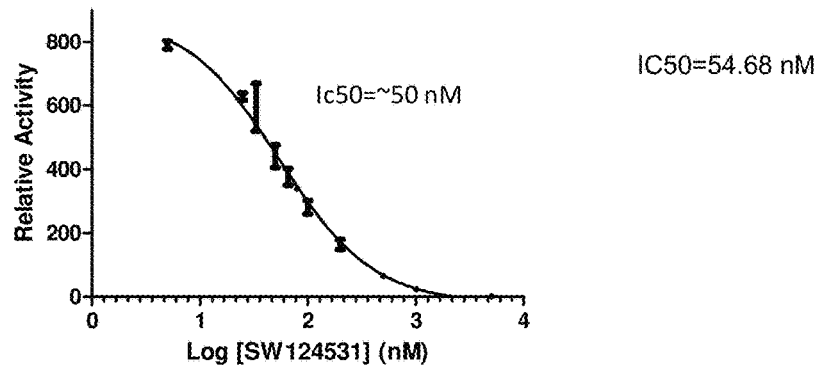
FIG. 13 illustrates a table and plot showing 15-PGDH activity measured by following transfer of tritium from a radiolabeled PGE2 substrate in cells treated with SW124531 (upper panel) and in recombinant 15-PGDH protein treated with SW124531 (lower panel).

FIG. 13 shows results of assays of 15-PGDH activity using the tritium method in cells treated with SW124531 (upper panel) and in recombinant 15-PGDH protein treated with SW124531 (lower panel). SW124531 shows activity in increasing 15-PGDH activity in most cell lines, though this activity is best in cell lines in which basal 15-PGDH activity is >10 units. SW124531 also inhibits activity of 15-PGDH recombinant protein at an IC50 of 50 nM.

Figure 14:
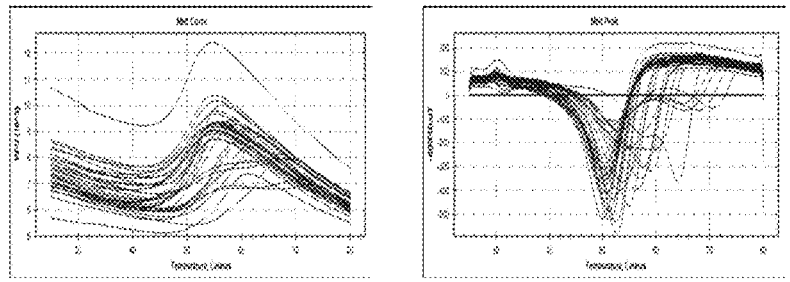
FIGS. 14(A-B) illustrate melt curves and a table showing different compound's ability to directly bind to recombinant 15-PGDH protein as measured by shifting the melting temperature of the protein.

FIG. 14 shows assay of different compounds for ability to directly bind to recombinant 15-PGDH protein as measured by shifting the melting temperature of the protein. The melting of the protein is followed by measurement of the fluorescence of SYPRO Orange dye (Sigma #S5692) that increases as the dye binds to hydrophobic residues exposed as the protein melt. The graph at upper left shows the melt curves of 15-PGDH with all of the assays done in the presence of the different compounds superimposed on each other. The graph at upper right plots the negative derivative of fluorescence versus temperature for each of the curves shown at left, with the melting point measured as the temperature of the negative peak (i.e., the point of most rapid change in the fluorescence versus temperature plot). The results are shown in tabular form on the table below. Lapatinib is used as a negative control. There is no binding of any drug in the absence of enzyme co-factor (either NAD or NADH). In the presence of either NAD or NADH, SW033291 creates two peaks in the melting curve, with one of these peaks displaced by 15 degrees Celsius, consistent with SW033291 binding directly to 15-PGDH. SW124531 and SW145753 also show evidence of direct binding to 15-PGDH. In this assay, SW054384 cannot be demonstrated to bind 15-PGDH. It is possible that SW054384 does bind to 15-PGDH, but that the binding is weak and is melted off at a temperature below the melting temperature of the 15-PGDH protein. Assays were done at both 10 μM and 100 μM cofactor (testing both NAD and NADH), which compares well with the published Km of NAD of 15.8 μM.

Figure 15:
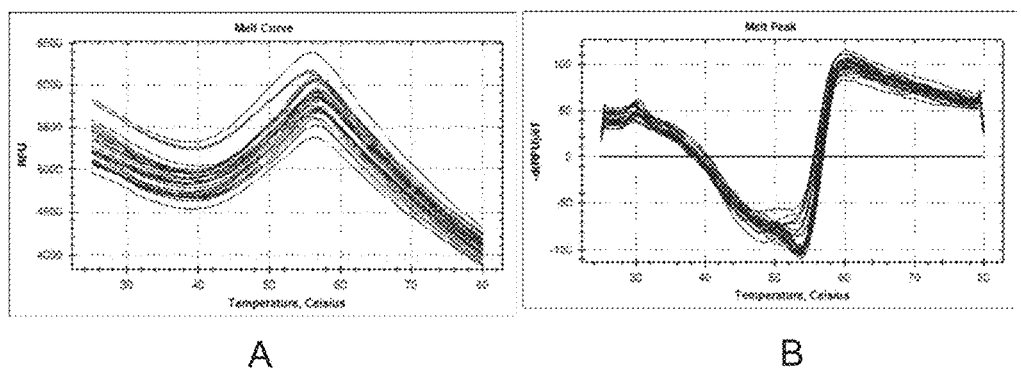
FIGS. 15(A-B) illustrate melt curves temperature of catalytically inactive mutant 15-PGDH protein treated with the test compounds.

FIG. 15 shows that none of the four compounds tested induce a shift in the melting temperature of catalytically inactive mutant 15-PGDH protein. We interpret the induction of 15-PGDH mutant protein by SW124531 as suggesting that SW124531 likely has weak binding to mutant 15-PGDH that is able to stabilize protein at 37° C., but with the drug melted off at a temperature below 50° C., that is the melting temperature of the protein.

Figure 16:
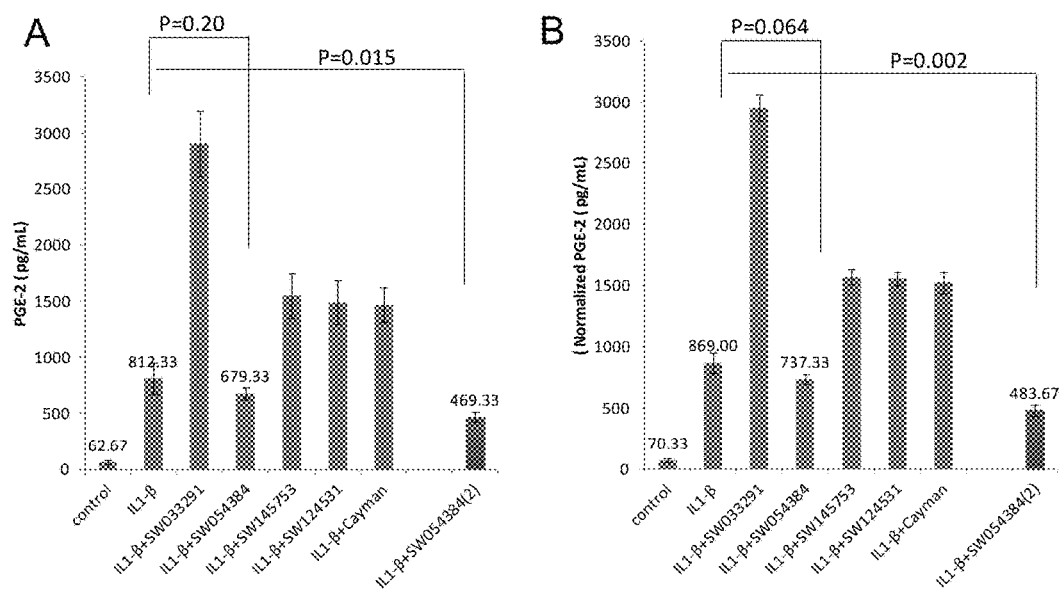
FIGS. 16(A-B) illustrates graphs showing $PGE_2$ levels that are assayed in the medium of A549 cells that have been stimulated by IL1-beta for 23 hours, with the test compounds.

FIG. 16 shows the in vivo modulation by compounds of 15-PGDH activity as reflected in $PGE_2$ levels that are assayed in the medium of A549 cells that have been stimulated by IL1-beta for 23 hours, with compound added for the last 5 hours (blue bars). The increment in $PGE_2$ level shows the clear inhibition of 15-PGDH activity in the cells by addition of SW033291 (as well as SW145753, SW124531, and a commercial 15-PGDH inhibitor from Cayman Chemical. In an additional iteration (red bars) (2), SW054384 was added commencing 24 hours before addition of IL1-beta, and then maintained for the next 26 hours in the presence of IL1-beta. The lower level of $PGE_2$ produced supports that in these cells SW054384 increased the 15-PGDH activity. Panel at left shows raw data; whereas, panel at right shows data normalized for cell numbers present at end of the experiment. $PGE_2$ levels are assayed by ELISA.

Figure 17:
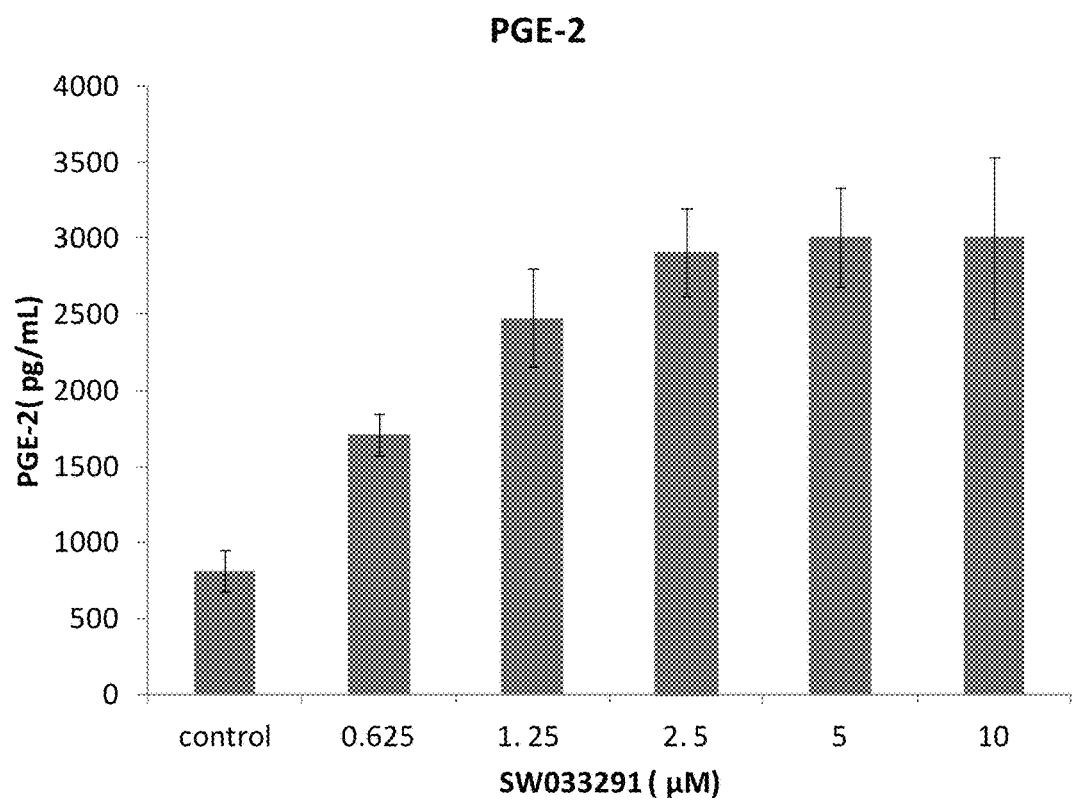
FIG. 17 illustrates a graph showing the dose response effect of SW033291 on $PGE_2$ production from IL1-beta treated A549 cells.

FIG. 17 shows the dose response of effect on SW033291 on $PGE_2$ production from IL1-beta treated A549 cells, as reflected in $PGE_2$ levels that are assayed in the medium of A549 cells that have been stimulated by IL1-beta for 24 hours, with SW033291 added for the last 8 hours.

Figure 18:
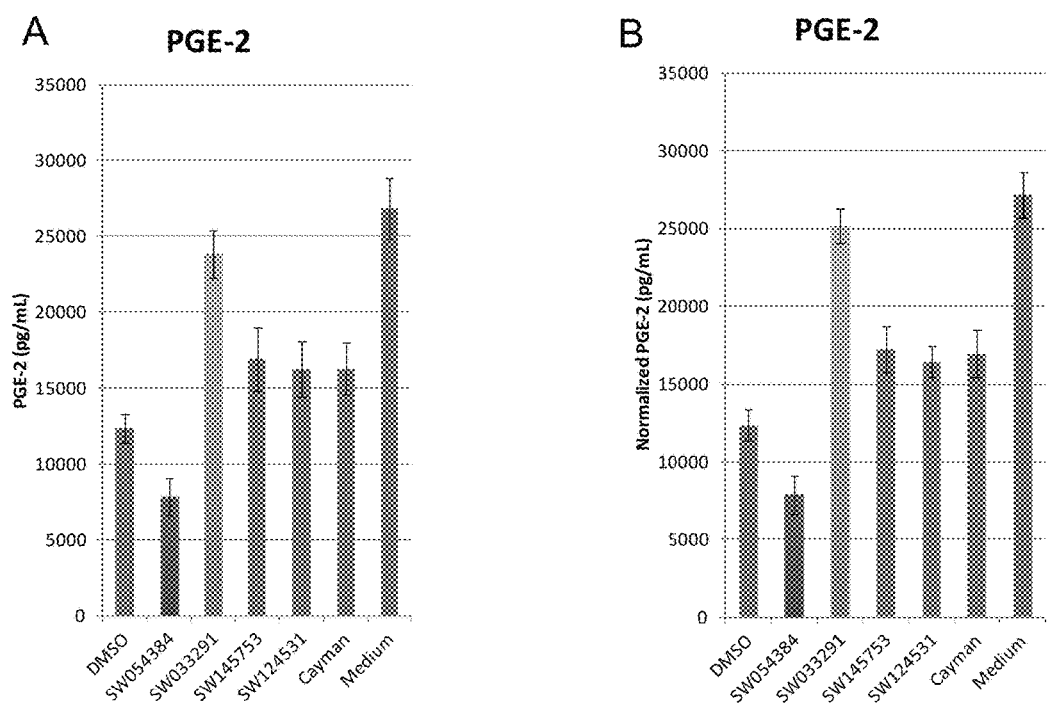
FIGS. 18(A-B) illustrate graphs showing the in vivo modulations by compounds (2.5 µM) of PGDH activity as reflected in $PGE_2$ levels following addition of $PGE_2$ into the medium of Vaco-503 cells.

FIG. 18 shows the in vivo modulations by 2.5 μM compounds of 15-PGDH activity as reflected in $PGE_2$ levels following addition of $PGE_2$ into the medium of Vaco-503 cells. In this study cells are treated with compound for 24 hours after which $PGE_2$ is added into the medium. After an added 24 hours $PGE_2$ levels remaining in the medium are assayed by Elisa. Data labeled "medium" is a control lane with $PGE_2$ added to medium alone, in the absence of cells. Data labeled DMSO is a control in which cells are treated with DMSO only (the diluent for the compounds). The difference between the "medium" and the "DMSO" lanes represents the cell dependent degradation of $PGE_2$ by 15-PGDH. Again demonstrated, is the near complete blockade of 15-PGDH activity by addition of 2.5 uM SW033291, as reflected by the blockade in $PGE_2$ degradation. Additionally demonstrated is the stimulation of 15-PGDH activity by SW054384, as reflected by the increased degradation of $PGE_2$.

Figure 19:
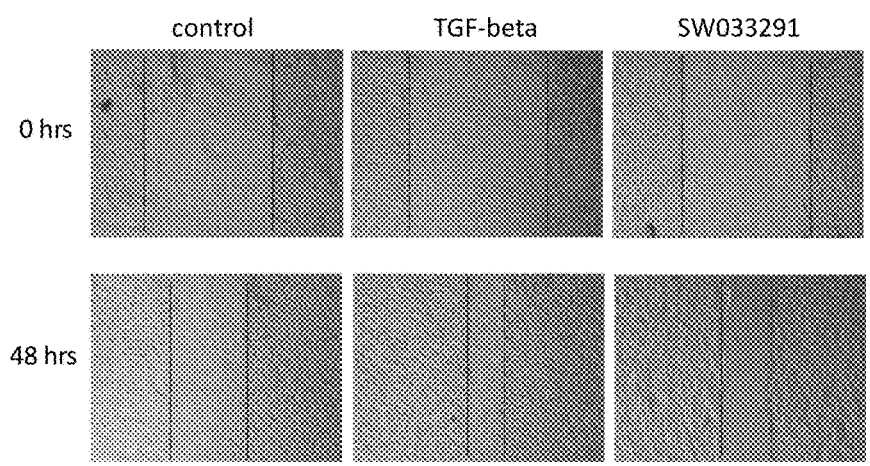
FIG. 19 illustrates images showing the activity of SW033291 in speeding the healing of a model wound consisting of a scratch in a monolayer of HaCaT cells observed over 48 hours of treatment.

FIG. 19 shows the activity of 2.5 μM SW033291 in speeding the healing of a model wound consisting of a scratch in a monolayer of HaCaT cells observed over 48 hours of treatment. TGF-beta serves as the positive control in the assay.

FIG. 20 shows the quantitation of the width of the scratch at 0 and 48 hours in the control, 2.5 μM SW033291 treated cells, and the TGF-beta (1 ng/ml) treated cells.

Example 2

Analysis of Analogues of Lead Compounds SW033291, a 15-PGDH Inhibitor

This Example provides data on a group of structural analogues of SW033291. Data provided includes level of induction of a 15-PGDH-luciferase fusion gene reporter, recorded as % increased luciferase activity over basal level, in three colon cancer cell lines, V9m, V503, and LS174T, engineered to contain the reporter, and treated with either 2.5 uM or 7.5 uM compound (i.e., Values are recorded on a scale where 100 indicates of doubling of luciferase activity over baseline level). Also recorded is the IC50 of each compound for inhibiting enzymatic activity of recombinant 15-PGDH in an in vitro assay.

TABLE 2

| Structures | ID | Enzyme inhibition (IC$_{50}$, nM) | V9M reporter activity (2.5 uM) | V9M reporter activity (7.5 uM) | LS174T reporter activity (2.5 uM) | LS174T reporter activity (7.5 uM) | V503 reporter activity (2.5 uM) | V503 reporter activity (7.5 uM) |
|---|---|---|---|---|---|---|---|---|
| 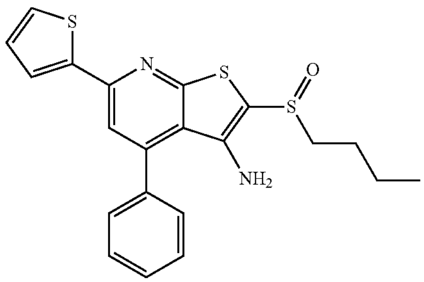 [SMILES: CCCCS(=O)c1sc2nc(-c3cccs3)cc(-c3ccccc3)c2c1N] | SW033291 | 1.23 nM | 98.24 | 93.16 | 123.46 | 106.73 | 126.32 | 99.34 |
| 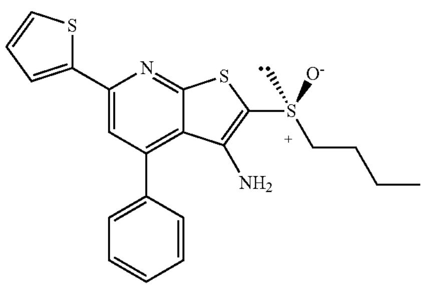 [SMILES: CCCC[S@](C)([O-])c1sc2nc(-c3cccs3)cc(-c3ccccc3)c2c1N] | SW033291 isomer B | 0.76 nM | colspan="6" Note: Structures shown are for illustrative purposes. We don'd know which structure corresponds to Isomer A or B. Residual activity of isomer A may be due to small amounts of Isomer B present in the preparation. | | | | | |
| 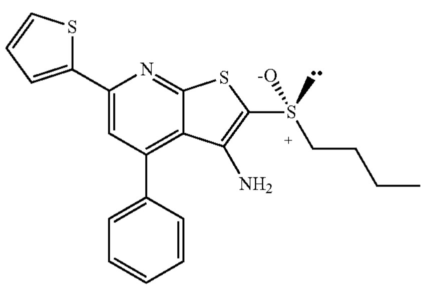 | SW033291 isomer A | 56.56 nM | colspan="6" Note: Structures shown are for illustrative purposes. We don't know which structure corresponds to Isomer A or B. Residual activity of isomer A may be due to small amounts of Isomer B present in the preparation. | | | | | |
| 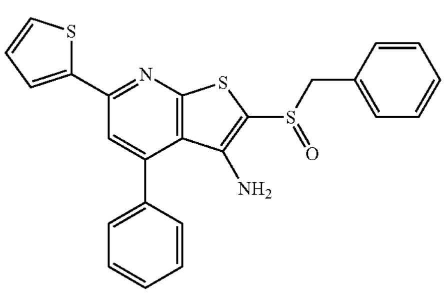 [SMILES: Nc1c(S(=O)Cc2ccccc2)sc2nc(-c3cccs3)cc(-c3ccccc3)c12] | SW033292 | | 1.51 | | | | | |
| 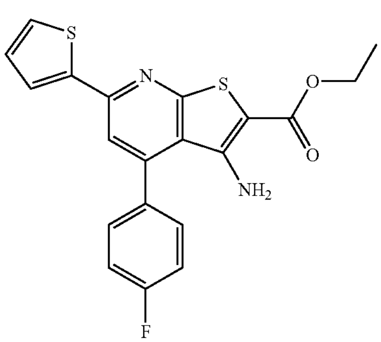 [SMILES: CCOC(=O)c1sc2nc(-c3cccs3)cc(-c3ccc(F)cc3)c2c1N] | 413423 | | −5.65 | −8.76 | 3.41 | 3.91 | 7.89 | 3.13 |

TABLE 2-continued
| Structures | ID | Enzyme inhibition (IC$_{50}$, nM) | V9M reporter activity (2.5 uM) | V9M reporter activity (7.5 uM) | LS174T reporter activity (2.5 uM) | LS174T reporter activity (7.5 uM) | V503 reporter activity (2.5 uM) | V503 reporter activity (7.5 uM) |
|---|---|---|---|---|---|---|---|---|
| 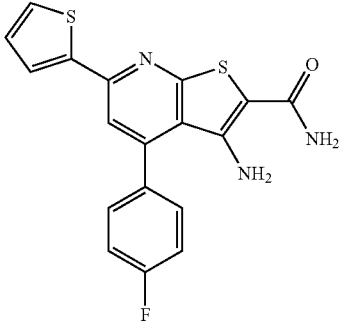 [SMILES: NC(=O)c1sc2nc(-c3cccs3)cc(-c3ccc(F)cc3)c2c1N] | 980653 | | 8.83 | 11.96 | 5.76 | 10.99 | −10.47 | −15.21 |
| 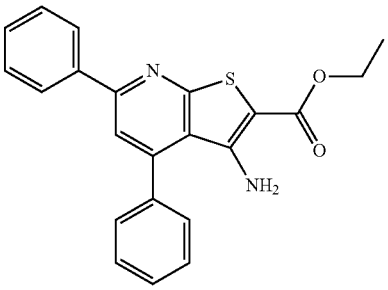 [SMILES: CCOC(=O)c1sc2nc(-c3ccccc3)cc(-c3ccccc3)c2c1N] | 405320 | | 8.77 | −15.45 | 9.95 | −2.57 | −7.73 | −33.68 |
| 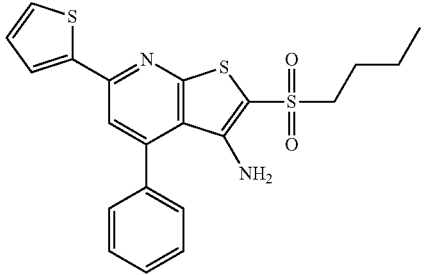 [SMILES: CCCCS(=O)(=O)c1sc2nc(-c3cccs3)cc(-c3ccccc3)c2c1N] | SW208078 | 25 nM | 36.16 | 34.90 | 72.71 | 40.01 | 87.73 | 83.77 |
| 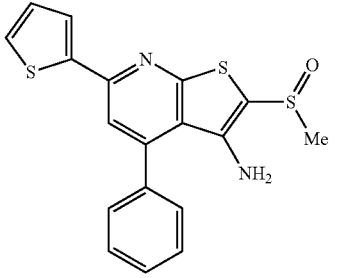 | SW208079 | 125 nM | 36.01 | 32.75 | 53.42 | 43.83 | 85.29 | 61.82 |
| 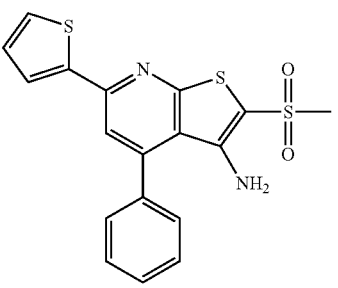 [SMILES: CS(=O)(=O)c1sc2nc(-c3cccs3)cc(-c3ccccc3)c2c1N] | SW033290 | 525 nM | −34.33 | −25.45 | −0.24 | −6.58 | 30.93 | 17.71 |

TABLE 2-continued

| Structures | ID | Enzyme inhibition (IC$_{50}$, nM) | V9M reporter activity (2.5 uM) | V9M reporter activity (7.5 uM) | LS174T reporter activity (2.5 uM) | LS174T reporter activity (7.5 uM) | V503 reporter activity (2.5 uM) | V503 reporter activity (7.5 uM) |
|---|---|---|---|---|---|---|---|---|
| 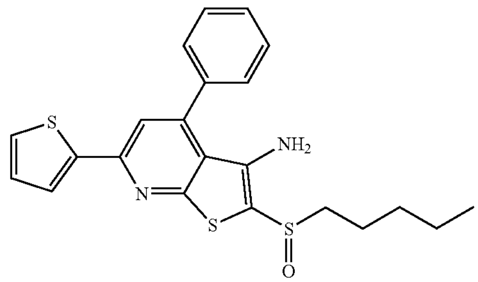 [SMILES: CCCCCS(=O)c1sc2nc(-c3cccs3)cc(-c3ccccc3)c2c1N] | SW208080 | 2.64 nM | 102.08 | 98.65 | 117.81 | 116.64 | 103.70 | 127.19 |
| 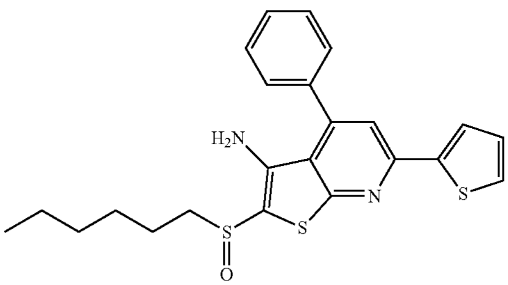 [SMILES: CCCCCCS(=O)c1sc2nc(-c3cccs3)cc(-c3ccccc3)c2c1N] | SW208081 | 18 nM | 37.79 | 63.56 | 64.53 | 95.14 | 90.46 | 105.37 |
| 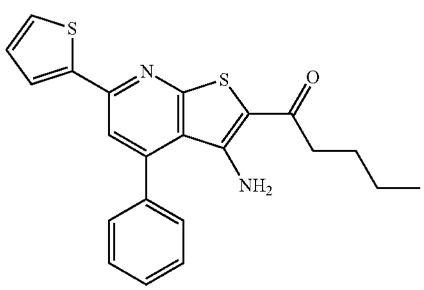 [SMILES: CCCCC(=O)c1sc2nc(-c3cccs3)cc(-c3ccccc3)c2c1N] | SW206976 | >7.5 uM | 11.80 | 17.51 | 42.38 | 20.56 | 16.79 | 49.53 |
| 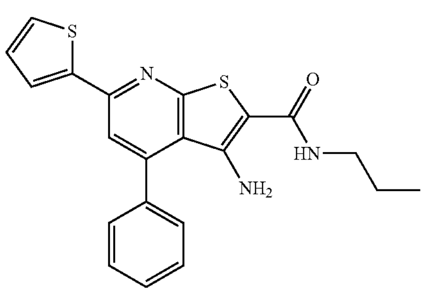 [SMILES: CCCNC(=O)c1sc2nc(-c3cccs3)cc(-c3ccccc3)c2c1N] | SW206977 | >7.5 uM | 3.5028 | 0.45 | 34.88 | 29.35 | 33.00 | 37.62 |
| 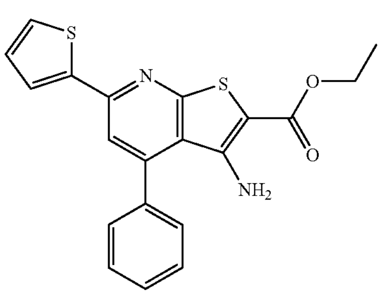 [SMILES: CCOC(=O)c1sc2nc(-c3cccs3)cc(-c3ccccc3)c2c1N] | SW206978 | >7.5 uM | 7.5141 | 8.02 | 31.44 | 26.19 | 38.84 | 35.75 |

TABLE 2-continued

| Structures | ID | Enzyme inhibition (IC$_{50}$, nM) | V9M reporter activity (2.5 uM) | V9M reporter activity (7.5 uM) | LS174T reporter activity (2.5 uM) | LS174T reporter activity (7.5 uM) | V503 reporter activity (2.5 uM) | V503 reporter activity (7.5 uM) |
|---|---|---|---|---|---|---|---|---|
| 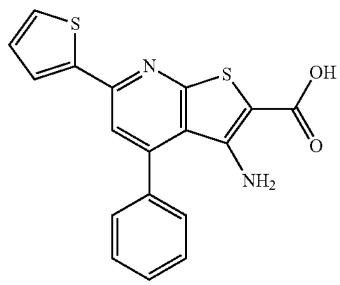 [SMILES: Nc1c(C(=O)O)sc2nc(-c3cccs3)cc(-c3ccccc3)c12] | SW206979 | >7.5 uM | −12.59 | −20.62 | 34.26 | 32.79 | 21.66 | 42.92 |
| 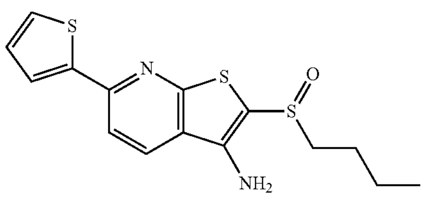 [SMILES: CCCCS(=O)c1sc2nc(-c3cccs3)ccc2c1N] | SW206980 | 0.97 nM | 99.37 | 92.71 | 117.24 | 92.15 | 129.57 | 108.51 |
| 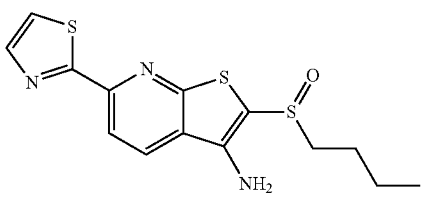 [SMILES: CCCCS(=O)c1sc2nc(-c3nccs3)ccc2c1N] | SW206992 | 1.411 nM | 86.44 | 121.75 | 85.81 | 72.03 | 161.20 | 145.39 |
| 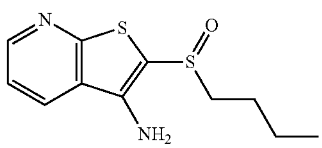 [SMILES: CCCCS(=O)c1sc2ncccc2c1N] | SW208064 | 151.4 nM | 82.58 | 50.11 | 126.18 | 96.23 | 126.18 | 96.23 |
| 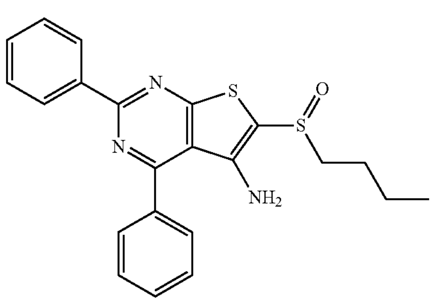 [SMILES: CCCCS(=O)c1sc2nc(-c3ccccc3)nc(-c3ccccc3)c2c1N] | SW208065 | 4.865 nM | 120.19 | 118.92 | 73.50 | 87.74 | 73.50 | 87.74 |
| 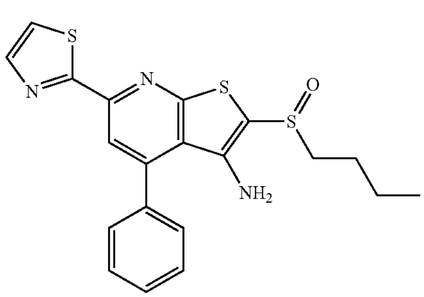 [SMILES: CCCCS(=O)c1sc2nc(-c3nccs3)cc(-c3ccccc3)c2c1N] | SW208066 | 1.368 nM | 122.72 | 111.63 | 123.89 | 93.74 | 123.89 | 93.74 |

TABLE 2-continued

| Structures | ID | Enzyme inhibition (IC$_{50}$, nM) | V9M reporter activity (2.5 uM) | V9M reporter activity (7.5 uM) | LS174T reporter activity (2.5 uM) | LS174T reporter activity (7.5 uM) | V503 reporter activity (2.5 uM) | V503 reporter activity (7.5 uM) |
|---|---|---|---|---|---|---|---|---|
| 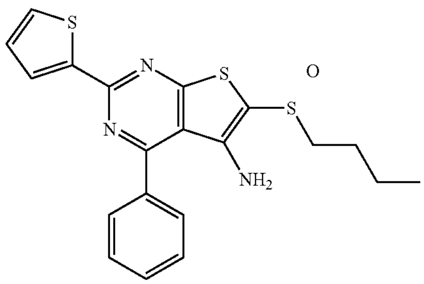 | SW208067 | 2.395 nM | 121.69 | 108.47 | 94.30 | 79.63 | 94.30 | 79.63 |
| 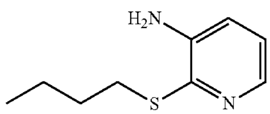 | SW208068 | >7.5 uM | 12.90 | 12.35 | 14.90 | 15.00 | 14.90 | 15.00 |
| 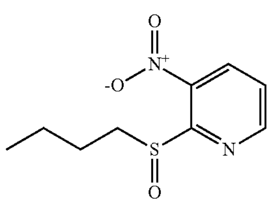 | SW208069 | >7.5 uM | −14.48 | 0.23 | 19.47 | 15.13 | 19.47 | 15.13 |
| 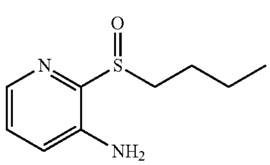 | SW208070 | >7.5 uM | 22.56 | 12.11 | 19.69 | 15.43 | 19.69 | 15.43 |

We first note that the 15-PGDH inhibitory activity of SW033291 is at least 98% due to the activity of one of the two optical isomers of this compound, designated isomer A and B. The structural assignment of isomer A versus isomer B is not yet established.

There is an important effect on the length of the carbon side chain of SW033291 on the IC50 for inhibiting recombinant 15-PGDH in vitro. Compared to SW033291 (4 carbons): SW208080 (5 carbons) has IC50 1.5 times higher, SW208081 (6 carbons) has IC50 10 times higher, and SW208079 (1 carbon) has IC50 over 60-fold higher, with marked loss of activity in inducing the cell line reporters.

The sulfoxide group appears to be a critical substituent, as inactive substitutions of the sulfoxide include the corresponding: ketone (SW206976), amide (SW206977), ester (SW206978), and carboxylic acid (SW206979). However, inhibitory activity is observed for the sulfone analogs.

Deletion of the phenyl group on SW033291 (SW206980) lowers the IC50 by half. SW206980 continues to be a highly active compound in reporter induction when applied to reporter cell lines at 2.5 uM concentration.

Example 3

The following Example describes the synthesis of SW033291 and analogues thereof as well as provides mass spectrometry NMR confirmation of the structures.

Scheme 1

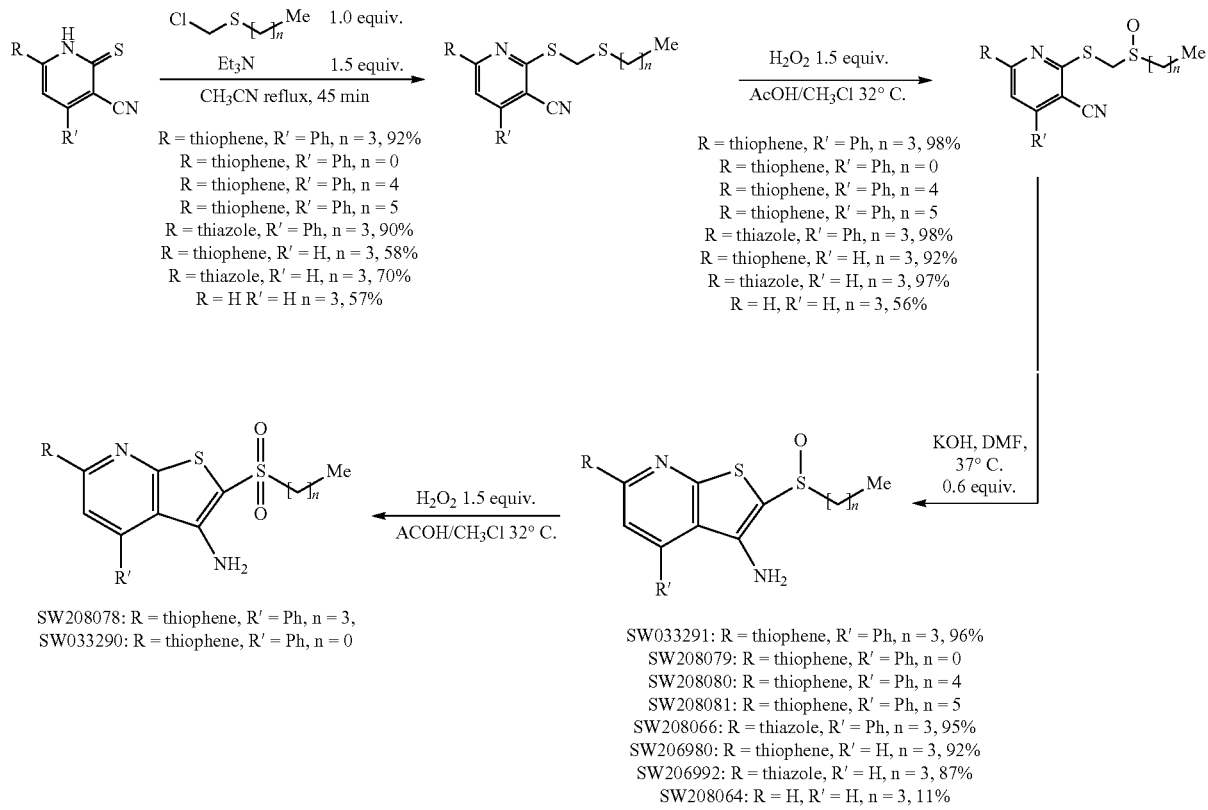

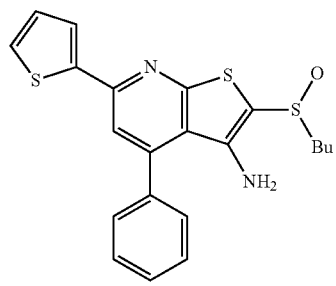

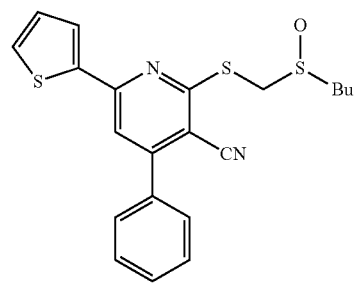

SW033291 2-(butylsulfinyl)-4-phenyl-6-(thiophen-2-yl)thieno[2,3-b]pyridin-3-amine was prepared using procedure describe by Kalugin. To the solution of 4-(((butylthio)methyl)sulfinyl)-2,6-diphenylpyrimidine-5-carbonitrile (0.53 mmol, 220 mg) in DMF (0.25 M)/EtOH (0.5 M) was added KOH (0.32 mmol, 18 mg, 0.6 equiv., 0.1 M in water). The reaction mixture was stirred at 35° C. for 40 min. Once complete, the reaction was diluted with EtOAc and washed with 10% aq. solution of acidic acid, the organic phase was separated and aqueous layer was extracted twice with EtOAc, dried over magnesium sulfate, filtered and concentrated under reduced pressure to give 211 mg of SW033291 2-(butylsulfinyl)-4-phenyl-6-(thiophen-2-yl)thieno[2,3-b]pyridin-3-amine (96%). $^1$H NMR (400 MHz, CDCl$_3$) δ 7.67-7.60 (m, 1H), 7.57-7.35 (m, 7H), 7.10 (dd, J=5.0, 3.7 Hz, 1H), 4.54 (s, 2H), 3.26 (ddd, J=12.8, 9.1, 6.0 Hz, 1H), 3.09 (ddd, J=12.8, 9.1, 6.6 Hz, 1H), 1.83-1.61 (m, 2H), 1.53-1.38 (m, 2H), 0.93 (t, J=7.3 Hz, 3H). ESI-MS (m/z): 413 [M+H]$^+$.

2-(((butylthio)methyl)sulfinyl)-4-phenyl-6-(thiophen-2-yl)nicotinonitrile. Acetic Acid (900 μL) and hydrogen peroxide (0.57 mmol, 1.5 equiv., 30% solution in water) were added to the solution of 2-(((butylthio)methyl)sulfinyl)-4-phenyl-6-(thiophen-2-yl)nicotinonitrile (0.38 mmol, 150 mg) in chloroform (900 μL). The reaction mixture was stirring at 32° C. for 45 min. The reaction was then diluted with EtOAc and washed with saturated NaHCO$_3$ solution, dried over magnesium sulfate, filtered and concentrated under reduced pressure to give 153 mg of designed product (98%). $^1$H NMR (400 MHz, CDCl$_3$) δ 7.75 (dd, J=3.8, 1.1 Hz, 1H), 7.66-7.57 (m, 2H), 7.58-7.51 (m, 4H), 7.47 (s, 1H), 7.16 (dd, J=5.0, 3.8 Hz, 1H), 4.74 (d, J=13.0 Hz, 1H), 4.41 (d, J=13.0 Hz, 1H), 2.97 (dt, J=13.0, 8.2 Hz, 1H), 2.81 (dt, J=12.9, 7.3 Hz, 1H), 1.94-1.76 (m, 2H), 1.53-1.38 (m, 2H), 0.94 (t, J=7.4 Hz, 3H). ESI-MS (m/z): 413 [M+H]$^+$

87

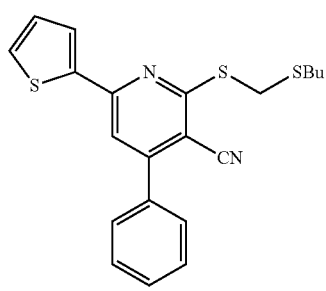

2-(((butylthio)methyl)thio)-4-phenyl-6-(thiophen-2-yl)nicotinonitrile. A mixture of 4-phenyl-6-(thiophen-2-yl)-2-thioxo-1,2-dihydropyridine-3-carbonitrile (0.34 mmol, 101 mg), butyl(chloromethyl)sulfane (0.34 mmol, 48 mg, 1.0 equiv.) and Et$_3$N (0.51 mmol, 72 µL, 1.5 equiv.) was refluxed in dry CH$_3$CN (350 µL) for 20 min. The reaction mixture was then diluted with EtOAc and water. The organic phase was separated and aqueous layer was extracted twice with EtOAc. The combined extractions were washed with saturated NaCl solution, dried over magnesium sulfate, filtered and concentrated under reduced pressure. The residue was purified by flash chromatography to give 124 mg of designed product (92%). $^1$H NMR (400 MHz, CDCl$_3$) δ 7.70 (dd, J=3.8, 1.1 Hz, 1H), 7.64-7.56 (m, 1H), 7.55-7.47 (m, 5H), 7.40 (d, J=1.1 Hz, 1H), 7.14 (dd, J=5.0, 3.8 Hz, 1H), 4.53 (s, 2H), 2.74 (t, J=8.0 Hz, 2H), 1.72-1.57 (m, 2H), 1.49-1.34 (m, 2H), 0.90 (t, J=7.4 Hz, 3H). ESI-MS (m/z): 397 [M+H]$^+$.

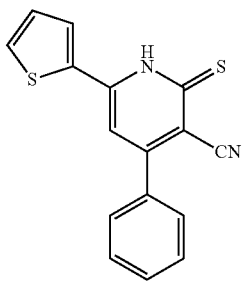 [SMILES: N#Cc1c(-c2ccccc2)cc(-c2cccs2)[nH]c1=S]

4-phenyl-6-(thiophen-2-yl)-2-thioxo-1,2-dihydropyridine-3-carbonitrile. To a solution of 3-phenyl-1-(thiophen-2-yl)prop-2-en-1-one (2.34 mmol, 500 mg) and cyanothioacetamide (7.0 mmol, 717 mg, 3.0 equiv.) in ethanol (7 mL), a few drops of piperidine were added. The reaction was refluxed for 3 h. The solid that formed was collected and recrystallized from acetic acid to give designed product in 46% isolated yield. $^1$H NMR (400 MHz, DMSO-d$_6$) δ 8.17 (d, J=3.8 Hz, 1H), 7.96 (d, J=5.0 Hz, 1H), 7.74-7.62 (m, 2H), 7.54 (dd, J=5.1, 2.0 Hz, 3H), 7.31-7.19 (m, 1H), 7.01 (s, 1H). ESI-MS (m/z): 295 [M+H]$^+$.

Scheme 2

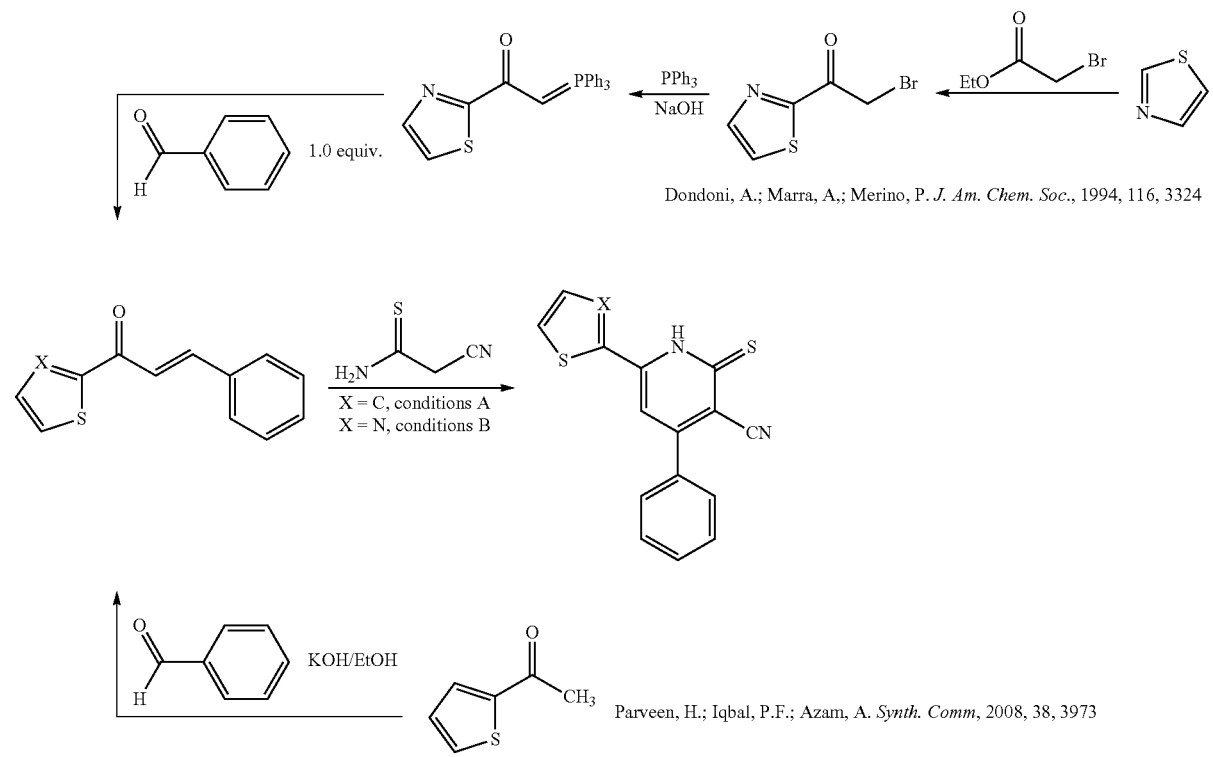

A: X = C, cyanothioacetamide 3 equiv.; piperidine 0.5 equiv.; EtOH reflux, 3 h, 46%
B: X = N, cyanothioacetamide 1.1 euiv.; DABCO 0.5 equiv.; EtOH, reflux, 12 h, 40%

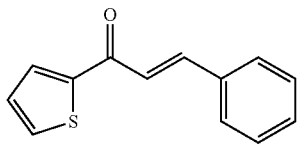 [SMILES: O=C(/C=C/c1ccccc1)c1cccs1]

3-phenyl-1-(thiophen-2-yl)prop-2-en-1-one was prepared from benzaldehyde and 1-(thiophen-2-yl)ethanone via aldol condensation using procedure described by Azam showed in Scheme 2. $^1$H NMR (400 MHz, CDCl$_3$) δ 7.88-7.80 (m, 2H), 7.67 (dd, J=4.9, 1.1 Hz, 1H), 7.66-7.59 (m, 2H), 7.47-7.34 (m, 4H), 7.18 (dd, J=5.0, 3.8 Hz, 1H). ESI-MS (m/z): 215 [M+H]$^+$.

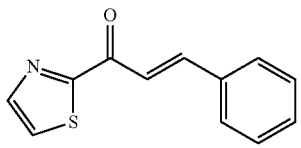 [SMILES: O=C(/C=C/c1ccccc1)c1nccs1]

3-phenyl-1-(thiazol-2-yl)prop-2-en-1-one was prepared from via Wittig reaction using procedure described by Merino showed in Scheme 2. $^1$H NMR (400 MHz, Chloroform-d) δ 8.06 (d, J=3.0 Hz, 1H), 7.99 (s, 1H), 7.96 (s, 1H), 7.75-7.67 (m, 3H), 7.44-7.38 (m, 3H). ESI-MS (m/z): 216 [M+H]$^+$.

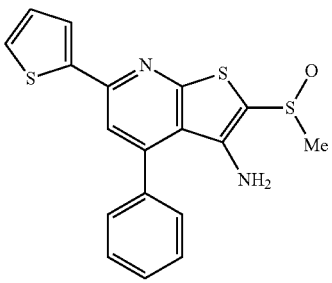

SW208079-1-A 2-(methylsulfinyl)-4-phenyl-6-(thiophen-2-yl)thieno[2,3-b]pyridin-3-amine was prepared by using synthetic procedures described for the preparation of analog SW033291 and showed in Scheme 1 and 2. $^1$H NMR (500 MHz, CDCl$_3$) δ 7.67-7.50 (m, 5H), 7.50-7.36 (m, 3H), 7.16-7.09 (m, 1H), 4.58 (s, 2H), 2.99 (s, 3H). ESI-MS (m/z): 371 [M+H]$^+$.

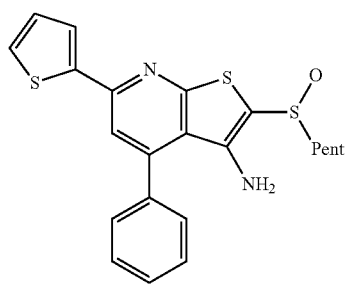

SW208080-1-A 2-(pentylsulfinyl)-4-phenyl-6-(thiophen-2-yl)thieno[2,3-b]pyridin-3-amine was prepared by using synthetic procedures described for the preparation of analog SW033291 and showed in Scheme 1 and 2. $^1$H NMR (500 MHz, CD$_2$Cl$_2$) δ 7.98-7.36 (m, 8H), 7.33-6.85 (m, 1H), 4.47 (s, 2H), 3.28-3.15 (m, 1H), 3.09-2.99 (m, 1H), 1.81-1.59 (m, 2H), 1.50-1.25 (m, 4H), 0.88 (t, J=7.2 Hz, 3H). ESI-MS (m/z): 427 [M+H]$^+$.

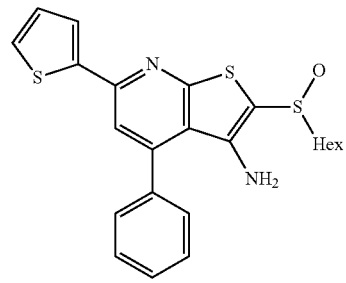

SW208081-1-A 2-(hexylsulfinyl)-4-phenyl-6-(thiophen-2-yl)thieno[2,3-b]pyridin-3-amine was prepared by using synthetic procedures described for the preparation of analog SW033291 and showed in Scheme 1 and 2. $^1$H NMR (500 MHz, CD$_2$Cl$_2$) δ 7.78-7.66 (m, 1H), 7.63-7.46 (m, 7H), 7.27-7.02 (m, 1H), 4.11 (s, 2H), 3.43-3.20 (m, 1H), 3.11 (ddd, J=13.8, 9.4, 6.4 Hz, 1H), 1.89-1.63 (m, 2H), 1.58-1.39 (m, 4H), 1.40-1.21 (m, 2H), 0.91 (d, J=6.8 Hz, 3H). ESI-MS (m/z): 441 [M+H]$^+$.

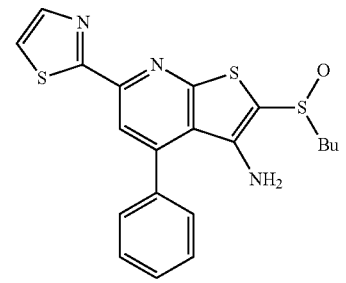

SW208066, 2-(butylsulfinyl)-4-phenyl-6-(thiazol-2-yl)thieno[2,3-b]pyridin-3-amine was prepared by using synthetic procedures described for the preparation of analog SW033291 and showed in Scheme 1 and 2. $^1$H NMR (400 MHz, CDCl$_3$) δ 8.06 (s, 1H), 7.92 (d, J=3.2 Hz, 1H), 7.65-7.39 (m, 6H), 4.63 (s, 2H), 3.28 (ddd, J=12.8, 9.0, 6.2 Hz, 1H), 3.11 (ddd, J=12.8, 9.0, 6.8 Hz, 1H), 1.85-1.63 (m, 2H), 1.56-1.42 (m, 2H), 0.94 (t, J=7.3 Hz, 3H). ESI-MS (m/z): 414 [M+H]$^+$.

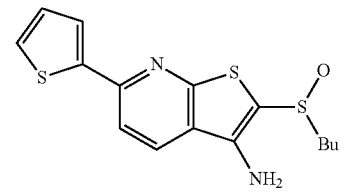

SW206980, 2-(butylsulfinyl)-6-(thiophen-2-yl)thieno[2,3-b]pyridin-3-amine was prepared by using synthetic procedures described for the preparation of analog SW033291 and showed in Scheme 1 and 2. $^1$H NMR (400 MHz, CDCl$_3$) δ 7.79 (d, J=8.5, 1H), 7.65-7.49 (m, 2H), 7.39 (dt, J=5.1, 0.7 Hz, 1H), 7.06 (dd, J=5.0, 3.7, Hz, 1H), 5.20 (s, 2H), 3.26 (ddd, J=12.8, 9.0, 6.2 Hz, 1H), 3.10 (ddd, J=12.8, 9.1, 6.6 Hz, 1H), 1.78-1.60 (m, 2H), 1.55-1.39 (m, 2H), 0.92 (t, J=7.3 Hz, 3H). ESI-MS (m/z): 337 [M+H]$^+$

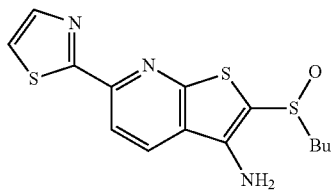

SW206992, 2-(butylsulfinyl)-6-(thiazol-2-yl)thieno[2,3-b]pyridin-3-amine was prepared by using synthetic procedures described for the preparation of analog SW033291 and showed in Scheme 1 and 2. $^1$H NMR (400 MHz, CDCl$_3$) δ 8.15 (d, J=8.5 Hz, 1H), 7.95 (d, J=8.5 Hz, 1H), 7.90 (d, J=3.2 Hz, 1H), 7.44 (d, J=3.2 Hz, 1H), 3.29 (ddd, J=12.7, 9.0, 6.2 Hz, 1H), 3.13 (ddd, J=12.8, 9.0, 6.7 Hz, 1H), 1.83-1.61 (m, 2H), 1.59-1.38 (m, 2H), 0.92 (t, J=7.3 Hz, 3H). ESI-MS (m/z): 338 [M+H]$^+$.

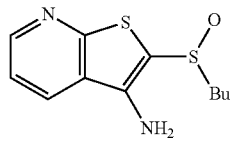

SW208064, 2-(butylsulfinyl)thieno[2,3-b]pyridin-3-amine was prepared by using synthetic procedures described for the preparation of analog SW033291 and showed in Scheme 1. $^1$H NMR (400 MHz, CDCl$_3$) δ 8.61 (dd, J=4.7, 1.6 Hz, 1H), 7.89 (dd, J=8.1, 1.6 Hz, 1H), 7.33 (dd, J=8.1, 4.6 Hz, 1H), 3.39-3.18 (m, 1H), 3.20-3.03 (m, 1H), 1.74 (p, J=7.6 Hz, 2H), 1.63-1.38 (m, 2H), 0.94 (t, J=7.3 Hz, 3H). ESI-MS (m/z): 255 [M+H]$^+$.

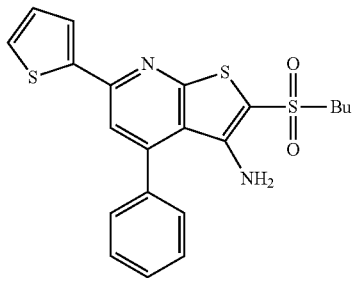

SW208078-1-A 2-(butylsulfonyl)-4-phenyl-6-(thiophen-2-yl)thieno[2,3-b]pyridin-3-amine. Acetic Acid (50 μL) and hydrogen peroxide (0.036 mmol, 1.5 equiv., 30% solution in water) were added to the solution of SW033291 2-(butylsulfinyl)-4-phenyl-6-(thiophen-2-yl)thieno[2,3-b]pyridin-3-amine (0.024 mmol, 10 mg) in chloroform (50 μL). The reaction mixture was stirring at 32° C. for 4 h. The reaction was diluted with EtOAc and washed with saturated NaHCO$_3$ solution, dried over magnesium sulfate, filtered and concentrated under reduced pressure to give crude 2-(butylsulfonyl)-4-phenyl-6-(thiophen-2-yl)thieno[2,3-b]pyridin-3-amine, which was purified by flash chromatography in 8% isolated yield. $^1$H NMR (400 MHz, CDCl$_3$) δ 7.71 (d, J=3.8 Hz, 1H), 7.64-7.54 (m, 3H), 7.53-7.42 (m, 4H), 7.15 (dd, J=5.0, 3.7 Hz, 1H), 5.09 (s, 2H), 3.38-3.02 (m, 2H), 1.92-1.67 (m, 2H), 1.52-1.28 (m, 2H), 0.92 (t, J=7.4 Hz, 3H). ESI-MS (m/z): 429 [M+H]$^+$.

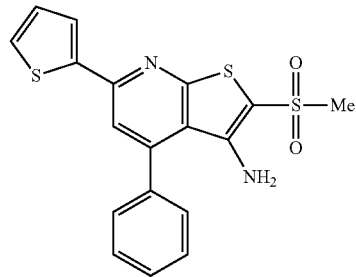 [SMILES: CS(=O)(=O)c1sc2nc(-c3cccs3)cc(-c3ccccc3)c2c1N]

SW033290-2-A 2-(methylsulfonyl)-4-phenyl-6-(thiophen-2-yl)thieno[2,3-b]pyridin-3-amine was prepared by using synthetic procedures described for the preparation of analog SW208078-1-A and showed in Scheme 1 and 2. $^1$H NMR (500 MHz, CDCl$_3$) δ 7.78-7.68 (m, 1H), 7.64-7.54 (m, 3H), 7.53-7.45 (m, 4H), 7.18-7.10 (m, 1H), 5.08 (s, 2H), 3.14 (s, 3H). ESI-MS (m/z): 387 [M+H]$^+$.

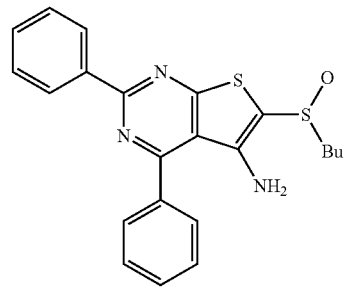

SW208065, 6-(butylsulfinyl)-2,4-diphenylthieno[2,3-d]pyrimidin-5-amine. To the solution of 4-(((butylthio)methyl)sulfinyl)-2,6-diphenylpyrimidine-5-carbonitrile (0.07 mmol, 30 mg) in DMF (0.25 M) was added KOH (0.035 mmol, 2 mg, 0.5 equiv., 0.1 M in water). The reaction mixture was stirred at room temperature for 20 min. Once complete, the reaction was diluted with EtOAc and washed with 5% aq. solution of acidic acid. The organic phase was separated and aqueous layer was extracted twice with EtOAc, dried over magnesium sulfate, filtered and concentrated under reduced pressure to give crude product, which was purified by flash chromatography in 70% isolated yield. ¹H NMR (400 MHz, CDCl₃) δ 8.73-8.37 (m, 2H), 7.78-7.68 (m, 2H), 7.66-7.55 (m, 3H), 7.53-7.40 (m, 3H), 4.83 (s, 2H), 3.30 (ddd, J=12.7, 8.9, 6.3 Hz, 1H), 3.21-3.01 (m, 1H), 1.87-1.66 (m, 2H), 1.57-1.41 (m, 2H), 0.95 (t, J=7.3 Hz, 3H). ESI-MS (m/z): 408 [M+H]⁺ were washed with saturated NaCl solution, dried over magnesium sulfate, filtered and concentrated under reduced pressure. The residue obtained was then purified by flash chromatography to give 59 mg of designed product (75%). ¹H NMR (400 MHz, CDCl₃) δ 8.75-8.36 (m, 2H), 8.35-7.91 (m, 2H), 7.71-7.41 (m, 6H), 4.59 (s, 2H), 2.74 (t, J=7.5 Hz, 2H), 1.75-1.58 (m, 2H), 1.49-1.34 (m, 2H), 0.91 (t, J=7.3 Hz, 3H). ESI-MS (m/z): 392 [M+H]⁺.

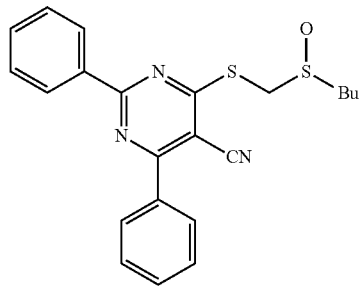

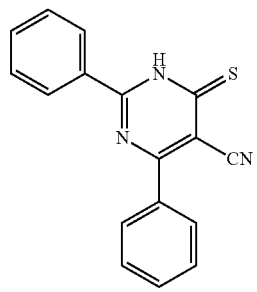

4-(((butylthio)methyl)sulfinyl)-2,6-diphenylpyrimidine-5-carbonitrile. Acetic Acid (600 μL) and hydrogen peroxide (0.37 mmol, 1.5 equiv., 30% solution in water) were added to the solution of 4-(((butylthio)methyl)thio)-2,6-diphenylpyrimidine-5-carbonitrile (0.25 mmol, 98 mg) in chloroform (900 μL). The reaction mixture was stirring at 32° C. for 45 min. Once complete, the reaction was diluted with EtOAc and washed with saturated NaHCO₃ solution, dried over magnesium sulfate, filtered and concentrated under reduced pressure to give 88 mg of designed product (98%). ¹H NMR (400 MHz, CDCl₃) δ 8.57 (dt, J=7.7, 1.2 Hz, 2H), 8.28-8.05 (m, 2H), 7.80-7.40 (m, 6H), 4.82 (d, J=13.2 Hz, 1H), 4.49 (d, J=13.3 Hz, 1H), 2.95 (dt, J=13.0, 8.1 Hz, 1H), 2.84 (dt, J=13.0, 7.3 Hz, 1H), 1.91-1.74 (m, 2H), 1.56-1.40 (m, 2H), 0.95 (t, J=7.4 Hz, 3H). ESI-MS (m/z): 408 [M+H]⁺

4,6-diphenyl-2-thioxo-1,2-dihydropyridine-3-carbonitrile was prepared according procedure described by Soto. A mixture of NaOiPr (1.5 mmol, 1.0 equiv., prepared in situ from sodium and dry iPrOH), benzothioamide (1.5 mmol, 205 mg, 1.0 equiv.) and 2-(ethoxy(phenyl)methylene)malononitrile (1.5 mmol, 297 mg, 1.5 equiv.) in iPrOH (75 mL) was stirred for 5 h at room temperature. The reaction was then acidified with con. HCl and stirred overnight, evaporated and obtained solid was recrystallized from acetic acid to give 265 mg of 4,6-diphenyl-2-thioxo-1,2-dihydropyridine-3-carbonitrile (61%). ¹H NMR (400 MHz, DMSO-d₆) δ 8.23-8.12 (m, 2H), 8.07-7.91 (m, 2H), 7.74-7.49 (m, 6H). ESI-MS (m/z): 290 [M+H]⁺

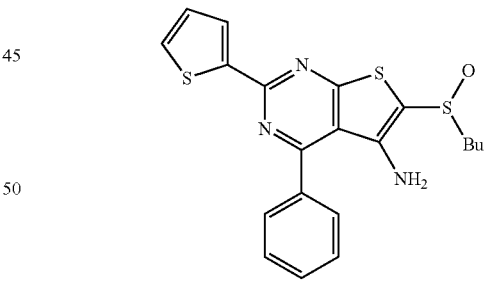

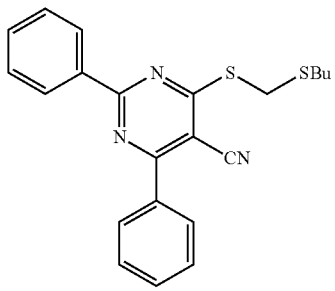

4-(((butylthio)methyl)thio)-2,6-diphenylpyrimidine-5-carbonitrile. A mixture of 4,6-diphenyl-2-thioxo-1,2-dihydropyridine-3-carbonitrile (0.35 mmol, 101 mg), butyl(chloromethyl)sulfane (0.35 mmol, 48 mg, 1.0 equiv.) and Et₃N (0.87 mmol, 2.5 equiv.) was refluxed in dry CH₃CN (200 μL) for 20 min. The reaction was diluted with EtOAc and water. The organic phase was separated and aqueous layer was extracted twice with EtOAc. The combined extractions SW208067, 6-(butylsulfinyl)-4-phenyl-2-(thiophen-2-yl)thieno[2,3-d]pyrimidin-5-amine was prepared by using synthetic procedures described for the preparation of analog SW208065 and showed in Scheme 3. ¹H NMR (400 MHz, CDCl₃) δ 8.10 (dd, J=3.7, 1.3 Hz, 1H), 7.74-7.65 (m, 2H), 7.62-7.53 (m, 3H), 7.50 (dd, J=5.0, 1.2 Hz, 1H), 7.14 (dd, J=5.0, 3.7 Hz, 1H), 4.79 (s, 2H), 3.28 (ddd, J=12.8, 9.0, 6.2 Hz, 1H), 3.11 (ddd, J=12.8, 9.0, 6.7 Hz, 1H), 1.84-1.63 (m, 2H), 1.54-1.41 (m, 2H), 0.94 (t, J=7.3 Hz, 3H). ESI-MS (m/z): 414 [M+H]⁺.

Scheme 3
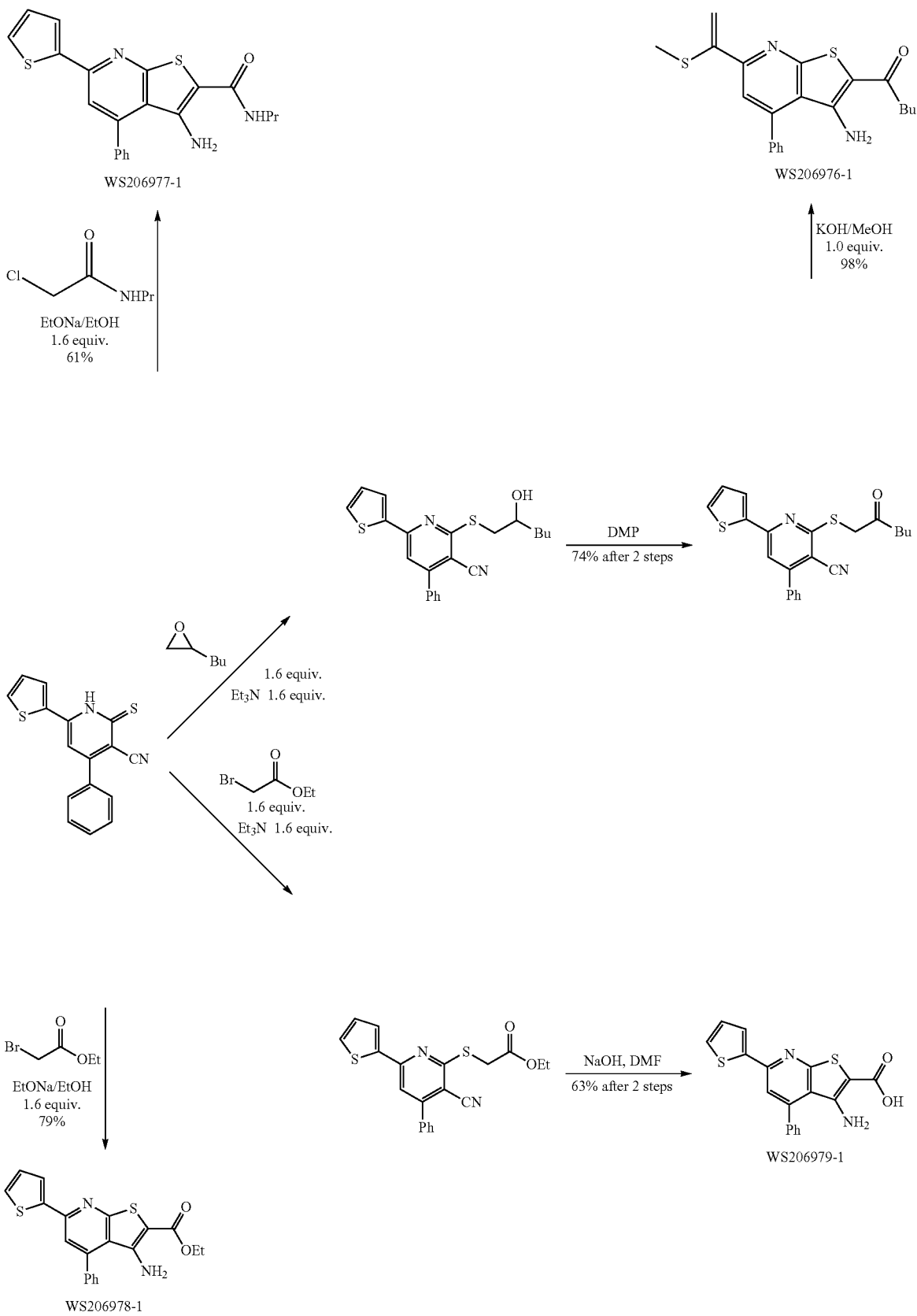

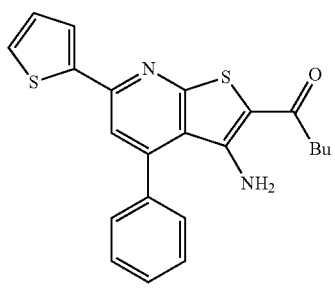

SW206976-1, 1-(3-amino-4-phenyl-6-(thiophen-2-yl)thieno[2,3-b]pyridin-2-yl)pentan-1-one. To the solution of 2-((2-oxohexyl)thio)-4-phenyl-6-(thiophen-2-yl)nicotinonitrile (0.13 mmol, 50 mg) in ethanol (500 μL) was added KOH (0.13 mmol, 2 mg, 1.0 equiv.). The reaction mixture was stirred at 50° C. for 30 min. Once complete, the reaction was diluted with EtOAc and washed with 10% aq. HCl. The organic phase was separated and aqueous layer was extracted twice with EtOAc, dried over magnesium sulfate, filtered and concentrated under reduced pressure to afford designed product in 98% yield.

$^1$H NMR (400 MHz, CDCl$_3$) δ 7.65 (dd, J=3.8, 1.1 Hz, 1H), 7.62-7.56 (m, 2H), 7.55-7.48 (m, 4H), 7.40 (s, 1H), 7.13 (dd, J=5.0, 3.8 Hz, 1H), 4.13 (s, 2H), 2.72 (t, J=7.4 Hz, 2H), 1.72-1.56 (m, 2H), 1.42-1.25 (m, 2H), 0.88 (t, J=7.3 Hz, 3H). ESI-MS (m/z): 393 [M+H]$^+$.

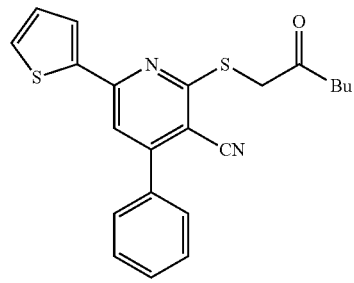

2-((2-oxohexyl)thio)-4-phenyl-6-(thiophen-2-yl)nicotinonitrile. A mixture of 4-phenyl-6-(thiophen-2-yl)-2-thioxo-1,2-dihydropyridine-3-carbonitrile (0.068 mmol, 20 mg), Et$_3$N (0.11 mmol, 15 μL, 1.6 equiv.) and 2-butyloxirane (0.11 mmol, 11 mg, 1.6 equiv.) in MeOH (500 μL) was stirred at room temperature. When the reaction was complete as judged by TLC, the reaction mixture was evaporated; the crud product dissolved in DCM and DMP (0.10 mmol, 1.5 equiv.) was added at 0° C. The reaction mixture was stirred at room temperature for 2 h and then was quenched by addition of 1:1 mixture of 20% Na$_2$S$_2$O$_3$/NaHCO$_3$ solution. The organic layer was separated, dried over magnesium sulfate and the solvent was removed under reduced pressure. The crude product was purified by flash chromatography to afford designed product in 72% yield. $^1$H NMR (400 MHz, CDCl$_3$) δ 8.02 (s, 1H), 7.97 (d, J=3.1 Hz, 1H), 7.71-7.59 (m, 2H), 7.55 (d, J=3.2 Hz, 1H), 7.55-7.46 (m, 4H), 4.52 (s, 2H), 2.75 (t, J=7.8 Hz, 2H), 1.73-1.54 (m, 2H), 1.51-1.26 (m, 2H), 0.91 (t, J=7.3 Hz, 3H). ESI-MS (m/z): 393 [M+H]$^+$.

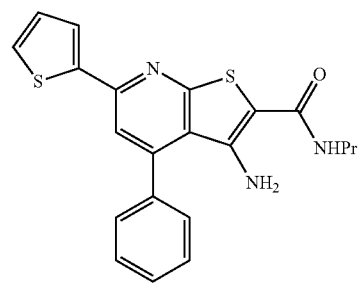

SW206977, 3-amino-4-phenyl-N-propyl-6-(thiophen-2-yl)thieno[2,3-b]pyridine-2-carboxamide. A mixture of 4-phenyl-6-(thiophen-2-yl)-2-thioxo-1,2-dihydropyridine-3-carbonitrile (0.12 mmol, 35 mg), 2-chloro-N-propylacetamide (0.12 mmol, 16 mg, 1.0 equiv.) and EtONa (0.19 mmol, 1.6 equiv.) in ethanol (1 mL) was stirred at 50° C. When the reaction was complete as judged by TLC, the reaction was diluted with EtOAc and washed with 10% aq. HCl. The organic phase was separated and aqueous layer was extracted twice with EtOAc, dried over magnesium sulfate, filtered and concentrated under reduced pressure to afford designed product in 61% yield. $^1$H NMR (400 MHz, CDCl$_3$) δ 7.65 (d, J=3.7, 1H), 7.58-7.49 (m, 3H), 7.49-7.38 (m, 4H), 7.10 (dd J=4.9, 3.7 Hz, 1H), 5.75 (s, 2H), 5.59-5.38 (m, 1H), 3.35 (td J=7.0, 5.9 Hz, 1H), 1.64-1.58 (m, 2H), 0.96 (t, J=7.4 Hz, 3H). ESI-MS (m/z): 394 [M+H]$^+$.

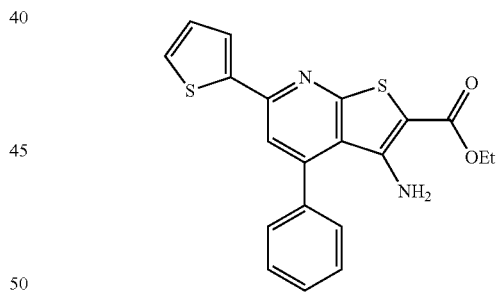

SW206978, Ethyl 3-amino-4-phenyl-6-(thiophen-2-yl)thieno[2,3-b]pyridine-2-carboxylate. A mixture of 4-phenyl-6-(thiophen-2-yl)-2-thioxo-1,2-dihydropyridine-3-carbonitrile (0.34 mmol, 100 mg), ethyl 2-chloroacetate (0.54 mmol, 1.6 equiv.) and EtONa (0.54 mmol, 1.6 equiv.) in ethanol (1 mL) was stirred at reflux. When the reaction was complete as judged by TLC, the reaction was diluted with EtOAc and washed with 10% aq. HCl. The organic phase was separated and aqueous layer was extracted twice with EtOAc, dried over magnesium sulfate, filtered and concentrated under reduced pressure to afford designed product in 79% yield. $^1$H NMR (400 MHz, DMSO-d$_6$) δ 8.01 (d, J=3.7 Hz, 1H), 7.87-7.67 (m, 2H), 7.56 (d, J=6.5 Hz, 5H), 7.36-

6.90 (m, 1H), 5.73 (s, 2H), 4.23 (q, J=7.1 Hz, 2H), 1.25 (t, J=7.0 Hz, 3H). ESI-MS (m/z): 381 [M+H]+.

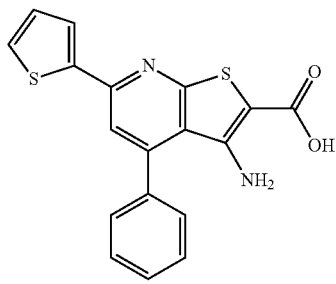 [SMILES: Nc1c(C(=O)O)sc2nc(-c3cccs3)cc(-c3ccccc3)c12]

SW206979, 3-Amino-4-phenyl-6-(thiophen-2-yl)thieno[2,3-b]pyridine-2-carboxylic acid. To a solution of -phenyl-6-(thiophen-2-yl)-2-thioxo-1,2-dihydropyridine-3-carbonitrile (0.34 mmol, 100 mg) and ethyl 2-chloroacetate (0.54 mmol, 1.6 equiv.) in ethanol (1 mL), Et₃N (0.54 mmol, 1.6 equiv.) was added. The reaction was refluxed for 20 min. The reaction was then diluted with EtOAc and water. The organic phase was separated and aqueous layer was extracted twice with EtOAc. The combined extractions were washed with saturated NaCl solution, dried over magnesium sulfate, filtered and concentrated under reduced pressure to afford designed product. Ethyl 2-((3-cyano-4-phenyl-6-(thiophen-2-yl)pyridin-2-yl)thio)acetate was then dissolved in DMF and treated with 1M aq. NaOH at 50° C. to give SW206979, 3-amino-4-phenyl-6-(thiophen-2-yl)thieno[2,3-b]pyridine-2-carboxylic acid in 63% yield. ¹H NMR (400 MHz, DMSO-d₆) δ 8.00 (dd, J=3.7, 1.1 Hz, 1H), 7.79-7.64 (m, 2H), 7.55 (dt, J=7.6, 3.2 Hz, 5H), 7.16 (dd, J=5.0, 3.7 Hz, 1H), 5.72 (s, 2H). ESI-MS (m/z): 353 [M+H]+.

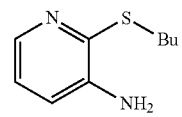

SW208068, 2-(butylthio)pyridin-3-amine. To the solution of butane-1-thiol (7.0 mmol, 628 mg, 1.1 equiv.) in THF (30 mL) was added NaH (6.6 mmol, 158 mg, 1.05 equiv.) at 0° C. After the reaction mixture was stirred at room temperature for 30 min. 2-chloro-3-nitropyridine (6.33 mmol, 1.0 g) was portion wise added and left with stirring at room temperature. for 2 h. Water was then added to the reaction mixture, and the resulting mixture was extracted with ethyl acetate. The organic layer was washed with a saturated aqueous solution of sodium chloride, and dried over sodium sulfate, filtered and concentrated under reduced pressure to afford crude product. Because of difficulties with purification, impure 2-(butylthio)-3-nitropyridine was directly used for the next step. Nitropyridine (0.47 mmol, 100 mg) was dissolved in a mixed solvent of acetic acid (3.3 ml) and conc. hydrochloric acid (130 μL), and zinc (5.7 mmol, 370 mg) was added in small portions while being cooled with ice. After the mixture was stirred for 30 minutes, the reaction mixture was filtered, and the filtrate was neutralized with an aqueous solution of NaHCO₃, and extracted with DCM. The organic layer was washed with water and then with a saturated aqueous solution of sodium chloride, and dried over sodium sulfate. Subsequently, the solvent was evaporated to obtain 2-(butylthio)pyridin-3-amine as a pale yellow oil. ¹H NMR (400 MHz, CDCl₃) δ 7.94 (dd, J=4.1, 2.0 Hz, 1H), 7.05-6.51 (m, 2H), 3.84 (s, 2H), 3.51-2.95 (m, 2H), 1.72-1.60 (m, 2H), 1.56-1.36 (m, 2H), 0.91 (t, J=7.4 Hz, 3H). ESI-MS (m/z): 183 [M+H]+.

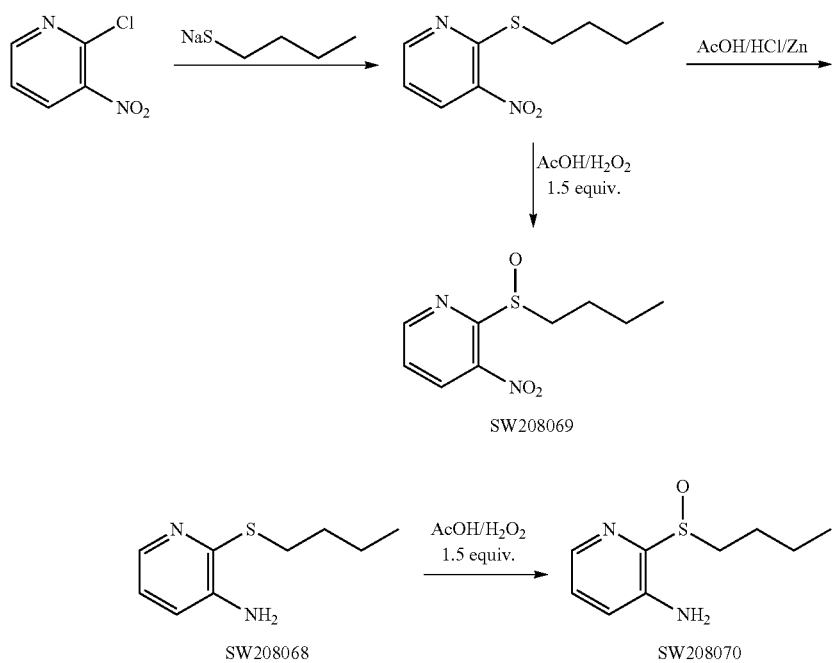

Scheme 4

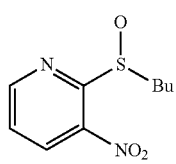

SW208069, 2-(butylsulfinyl)-3-nitropyridine. To the solution of butane-1-thiol (7.0 mmol, 628 mg, 1.1 equiv.) in THF (30 mL) was added NaH (6.6 mmol, 158 mg, 1.05 equiv.) at 0° C. After the reaction mixture was stirred at room temperature for 30 min 2-chloro-3-nitropyridine (6.33 mmol, 1.0 g) was portion wise added and left with stirring at room temperature, for 2 h. Water was then added to the reaction mixture, and the resulting mixture was extracted with ethyl acetate. The organic layer was washed with a saturated aqueous solution of sodium chloride, and dried over magnesium sulfate, filtered and concentrated under reduced pressure to afford crude product. Because of difficulties with purification, impure 2-(butylthio)-3-nitropyridine was used directly for the next step. Nitropyridine (0.47 mmol, 100 mg) was dissolved in a mixed solvent of acetic acid (1.2 ml) and chloroform (1.2 mL), and hydrogen peroxide (0.7 mmol, 1.5 equiv., 30% solution in water) was added. After the mixture was stirred for 45 minutes, at 32° C., the reaction was diluted with EtOAc and washed with saturated NaHCO$_3$ solution, dried over magnesium sulfate, filtered and concentrated under reduced pressure to 2-(butylsulfinyl)-3-nitropyridine. $^1$H NMR (400 MHz, CDCl$_3$) δ 9.14 (dd, J=4.6, 1.5 Hz, 1H), 8.54 (dd, J=8.2, 1.5 Hz, 1H), 7.67 (dd, J=8.2, 4.6 Hz, 1H), 3.18 (ddd, J=12.7, 9.3, 7.2 Hz, 1H), 3.00 (ddd, J=12.7, 9.1, 4.9 Hz, 1H), 2.17-1.92 (m, 1H), 1.91-1.70 (m, 1H), 1.68-1.35 (m, 2H), 0.96 (t, J=7.3 Hz, 3H). ESI-MS (m/z): 229 [M+H]$^+$.

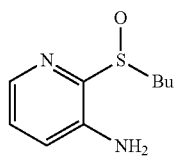

SW208070, 2-(butylsulfinyl)pyridin-3-amine was prepared by using synthetic procedure described for the preparation of analog SW208069 and showed in Scheme 4. $^1$H NMR (400 MHz, CDCl$_3$) δ 7.90 (dd, J=4.4, 1.4 Hz, 1H), 7.09 (dd, J=8.3, 4.4 Hz, 1H), 6.93 (dd, J=8.3, 1.4 Hz, 1H), 5.30 (s, 2H), 3.24 (ddd, J=13.0, 9.5, 5.4 Hz, 1H), 3.03 (ddd, J=13.0, 9.8, 6.3 Hz, 1H), 1.95-1.61 (m, 2H), 1.55-1.35 (m, 2H), 0.93 (t, J=7.3 Hz, 3H). ESI-MS (m/z): 199 [M+H]$^+$.

Example 4

Analysis of the Mechanism of 15-PGDH Inhibition by SW033291 and Related Compounds The following Example provides data relating to the mechanism of action by which SW033291 inhibits 15-PGDH.

Duplicate titrations of 15-PGDH Inhibitor (SW033291) were run at 4 different concentrations of 15-PGDH (24 nM, 12 nM, 6 nM, 3 nM). Reactions contained the indicated concentration of enzyme, 250 μM NAD(+), 25 μM PGE-2, and were assembled and incubated at room temperature for 3 minutes.

FIGS. 21 (A-B) show the shift in IC$_{50}$ value with changing enzyme concentration. The result is indicative of a tight-binding mode of inhibition with dependency on enzyme: inhibitor stoichiometry, rather than on the absolute concentration of the inhibitor. In all cases, the IC$_{50}$ values are less than the enzyme concentration, indicating that nM drug is almost fully bound by the enzyme.

FIGS. 22 (A-B) indicate that SW033291 behaves very much like an irreversible inhibitor of 15-PGDH, and cannot be efficiently dialyzed off the 15-PGDH protein.

The testing of whether SW033291 is a reversible inhibitor proceeded by:
(i) an 8 ul aliquot taken of 15-PGDH stock (8 mg/mL 15-PGDH in 500 μL of 15-PGDH assay buffer) (4 nmol 15-PGDH, 4 μM 15-PGDH), was incubated on ice with: (a) addition of 5 μL of 100 mM NAD(+)+addition of 3.2 μL of 2.5 mM SW033291 stock, then dialyzed versus 1 L buffer for 12 hours, followed by a fresh 1 L of buffer for 12 more hours; or (b) addition of 5 μL, 100 mM NAD(+)+addition of 3.2 μL DMSO then dialyzed versus 1 L buffer for 12 hours, followed by a fresh 1 L of buffer for 12 more hours.
(ii) Pre-dialysis, remove 1 μL and dilute in 200 μL assay Buffer (20 nM), then measure 15-PGDH activity.
(iii) Post-Dialysis, at 24 hrs, remove 1 μL and dilute in 200 μL assay Buffer (20 nM), then measure 15-PGDH activity.

Dialysis buffer is 50 mM Tris pH7.4, 40 mM NaCl, 0.1 mM DTT, 0.01% Tween-20.

Under the conditions of the assay SW033291 inhibited 91% of 15-PGDH pre-dialysis, and 85% of 15-PGDH activity post-dialysis—that is dialysis did not reverse the inhibition of 15-PGDH. Control 15-PGDH protein that was dialyzed in the absence of SW033291 remained fully active.

FIGS. 23(A-B) show (A) at upper right the reaction rates for 15-PGDH in the presence of a graded set of increasing concentrations of SW033291. In the graph at upper right P is the NADH concentration as a proxy for 15-keto-PGE2. (P+S) is the starting PGE2 concentration of 20 μM. The assay was carried out in the presence of 10 nM recombinant 15-PGDH. In the graph at lower left (B), Vo is the initial velocity of the reaction in the absence of SW033291, and Vi is the initial velocity of the reaction in the presence of the corresponding concentration of SW033291. The line shows the curve generated by fitting the data to the Morrison equation. The curve fitting yields a calculated a Ki$^{App}$ value of 0.1015 nM. The dashed line intersects the X axis at 8.5 nM. This represents the point at which [inhibitor]=[active enzyme] showing that the enzyme preparation contains 85% active enzyme. In the Morrison equation, Ki is the binding affinity of the inhibitor; [S] is substrate concentration; and Km is the concentration of substrate at which enzyme activity is at half maximal. Note that IC50 is the functional strength of the inhibitor. Whereas the IC$_{50}$ value for a compound may vary between experiments depending on experimental conditions, the Ki is an absolute value. Ki is the inhibition constant for a drug; the concentration of competing ligand in a competition assay which would occupy 50% of the receptors if no ligand were present.

FIGS. 24(A-B) show duplicate titrations of 15-PGDH Inhibitor (SW033291) that were run at 6 different concentrations of PGE2 (1.25 uM-40 uM). In the graph at top, Y-axis is % inhibition of the reaction by SW033291. The X-axis is the concentration of SW033291 in nM. Reactions contain 5.0 nM added 15-PGDH, 250 μM NAD(+), and indicated concentrations of PGE-2, were assembled and incubated at room temperature for 60 minutes. The Km for PGE2 is approximately 5 uM, and reactions run with PGE2 concentrations below 5 uM go very slowly making it difficult to quantitate inhibition by SW033291. However, in reactions with PGE2 at concentrations of 5 uM-40 uM, the $IC_{50}$ for SW033291 is unaffected by the increasing PGE2 concentration, showing that the inhibition is noncompetitive.

Figure 25:
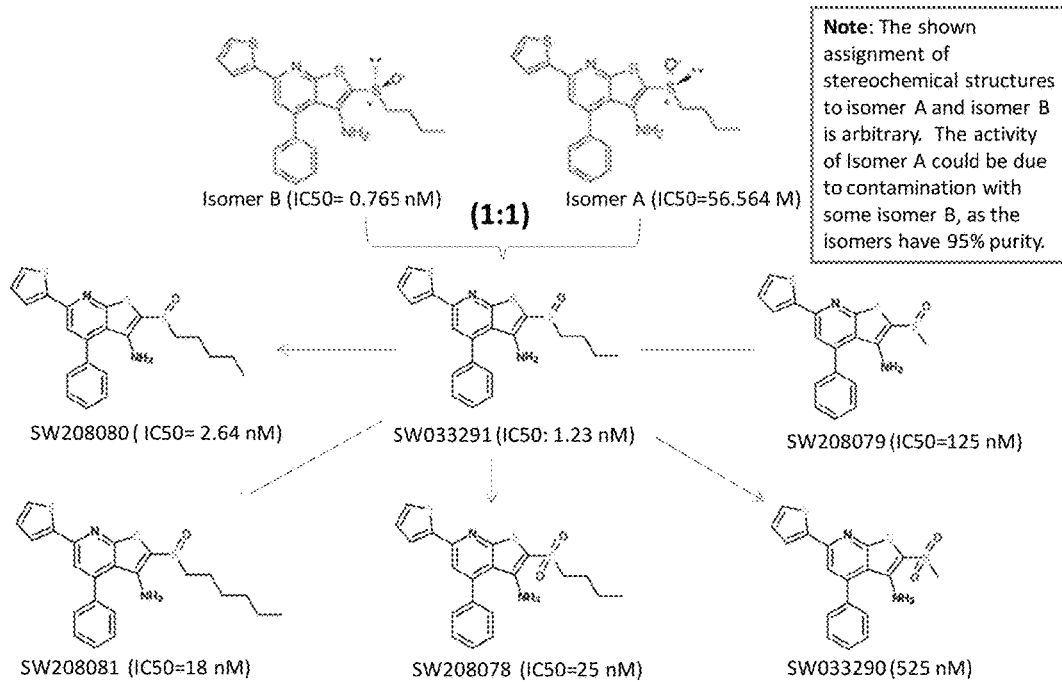
FIG. 25 illustrates a schematic diagram showing the structure activity relationships of analogues of SW033291 versus their IC50 against 15-PGDH.

FIG. 25 shows the structure activity relationships of analogues of SW033291 versus their IC50 against recombinant 15-PGDH. Assignments of structures to the two isomers, A and B, of SW033291 are arbitrary, as the structure of the active isomer (isomer B) has not been determined. The optical isomers of SW033291 were separated by preparative HPLC using a 10 mm×250 mm Chiralcel ODH column, 5% isopropanol in hexanes, 1 mL/min. The 'A' isomer is the faster eluting isomer. The 'B' isomer is the slower eluting isomer.

The analogue family shows that SW033291, with a 4 carbon side chain, is 2-fold more potent than SW208080 (5 carbon side chain), 15-fold more potent than SW208081 (6 carbon side chain), and 100-fold more potent than SW208079 (1 carbon side chain). SW033291 is also 20-fold more potent than SW208078, the analogue that converts the sulfoxide group to a sulfone.

FIG. 26 shows structures of additional SW033291 analogs that convert the sulfoxide group to a ketone, an amide, an ester, or a carboxylic acid. Also shown is structure SW206980 that deletes the phenyl ring from SW033291.

Figure 27:
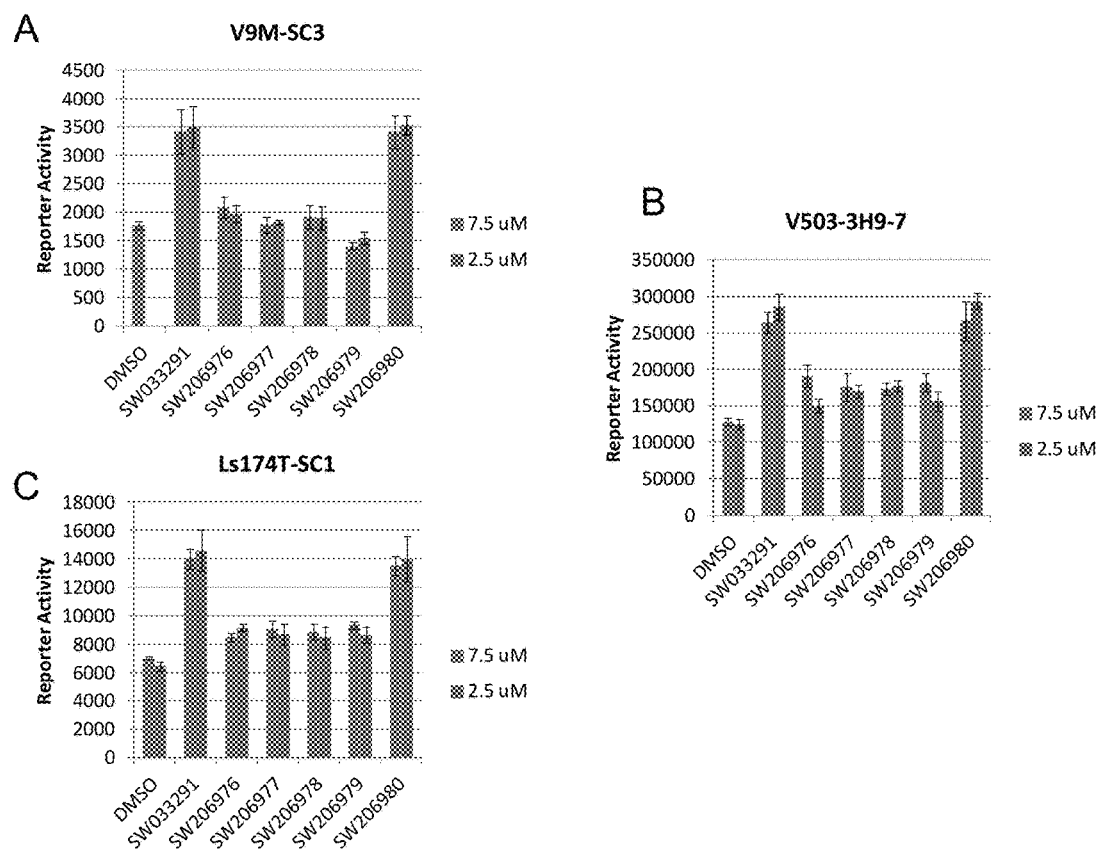
FIGS. 27(A-C) illustrate graphs showing luciferase activity of colon cancer cell lines V503, LS174T, and V503 treated with 2.5 µM and 7.5 µM the compounds of FIG. 26.

FIGS. 27(A-C) show graphs that show the level of compound's activity in inducing the 15-PGDH-luciferase fusion reporter in three different test cell line backgrounds, V9m, LS174T, and V503. Each compound was tested at two concentrations, 2.5 uM, and 7.5 uM. Y-axis is luciferase activity.

At 2.5 μM-7.5 μM, SW206980, that deletes the phenyl group of SW033291, shows activity comparable to SW033291 in all three reporter lines.

Structures that have converted the sulfoxide group to a ketone, amide, ester, or carboxylic acid show major loss of activity in inducing the reporter.

Figure 28:
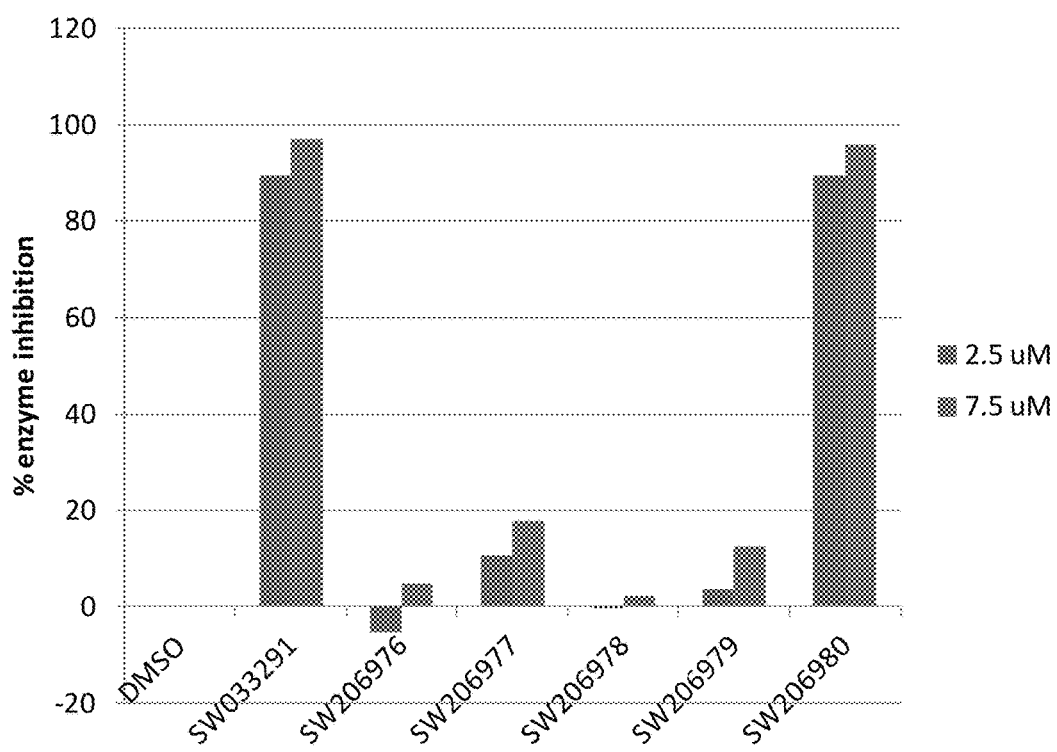
FIG. 28 illustrates a graph showing percent inhibition of 15-PGDH activity by the compounds of FIG. 26.

FIG. 28 shows graphs that show the percent of 15-PGDH enzyme activity that is inhibited at 2.5 uM and at 7.5 uM by each of the 5 test compounds. SW206980 that deletes the phenyl group of SW033291, shows at these concentrations similar potency to SW03291 in inhibiting 15-PGDH activity.

Structures that have converted the sulfoxide group to a ketone, amide, ester, or carboxylic acid show major loss of activity as 15-PGDH inhibitors.

FIGS. 29(A-B) show a titration curve that plots percent inhibition of 15-PGDH enzyme activity at different concentrations of SW033291 and SW0206980. Under identical assay conditions, SW206980 shows a slightly lower IC50.

FIGS. 30(A-B) show that SW206980 binds directly to 15-PGDH and markedly shifts its melting curve. Shown at left is the melt curve of 15-PGDH as reflected by fluorescence of the hydrophobic dye SYPRO Orange. Shown at right is the negative first derivative of the melt curve.

Three conditions are plotted, that of 10 uM 15-PGDH, that of 10 uM 15-PGDH plus 10 uM SW206980, and that of 10 uM 15-PGDH plus 125 uM NADH plus 10 μM SW206980. The melting temperature, as reflected by the inflection point of the curve at right is shifted by 20° C., from 48-degrees up to 68-degrees, in the presence of SW206980 and NADH, reflecting that SW206980 directly binds to and markedly stabilizes the tertiary structure of 15-PGDH, in a manner requiring the presence of the NADH cofactor.

FIGS. 31(A-C) show further analogues of SW033291 that build on the previous finding that removal of the SW033291 phenyl ring (SW206980) retained activity. The new analog (SW206992) adds a nitrogen to the left-hand ring.

Table 3 provides a comparison of the properties of SW033291, SW206980, and SW206992.

TABLE 3

Summary of three SW033291 analogs

|  | SW033291 | SW206980 | SW206992 |
| --- | --- | --- | --- |
| $IC_{50}$ | 1.59 nM | 0.97 nM | 1.411 nM |
| Time to inhibition (10 nM) | ~5 mins | ~2 mins | ~2 mins |
| Δ Tm (NADH) | 19° C. | 15.5° C. | 19° C. |
| Concentration for Full Cell Line Reporter Induction | ~100 nM | >300 nM | >1 uM |
| Hepatocyte stability | Stable > couple hrs | T½ = 80 mins |  |
| Toxicity | >10 μM | >7.5 μM | >7.5 μM |

Time to inhibition refers to the time needed to inhibit the generation of NADH by 15-PGDH from the moment with drug is added into the reaction mix. Delta™ refers to the shift in melting temperature of recombinant 15-PGDH in the presence of drug (with cofactor NADH also present). Concentration of Full Cell Line Reporter Induction refers to the concentration of drug that needs to be added to reporter cell line to achieve maximal induction of the 15-PGDH-luciferase gene fusion reporter cassette, as measured by luciferase assays. Hepatocyte stability refers to the half-life of compound in the presence of hepatocytes in culture. Toxicity refers to the concentration of compound needed to decrease cell numbers in a cell culture assay.

FIGS. 32(A-C) show titration of induction by SW033291 of the 15-PGDH-luciferase gene fusion reporter in three different cell line backgrounds. In general between 80-160 nM SW033291 exposure for 24 hours is needed to induce maximal reporter induction.

FIGS. 33(A-C) show titration of induction by SW206980 of the 15-PGDH-luciferase gene fusion reporter in three different cell line backgrounds. In general ≥300 nM SW206980 exposure for 24 hours is needed to induce maximal reporter induction.

FIGS. 34(A-C) show titration of induction by SW206992 of the 15-PGDH-luciferase gene fusion reporter in three different cell line backgrounds. In general ≥1000 nM SW206992 exposure for 24 hours is needed to induce maximal reporter induction.

FIGS. 35(A-C) show the shift in the melt curve of recombinant 15-PGDH protein (10 uM) by 20 uM SW033291, SW206980, and SW206992 in the presence of the cofactor NAD (+)(100 uM). Control melting temperature is 49 degrees centigrade. SW033291 shifts the melting temperature to 63 degrees. SW206980 shifts the melting temperature to 61 degrees. SW206992 shifts the melting temperature to 59 degrees. Thus all three compounds directly bind to 15-PGDH and markedly increase the melting temperature of the protein, with the order of the temperature shifts being SW033291>SW206980>SW206992.

FIGS. 36(A-B) show the shift in the melt curve of recombinant 15-PGDH protein (10 uM) by 20 uM SW033291, SW206980, and SW206992 in the presence of the cofactor NADH (100 uM). Control melting temperature is 55 degrees centigrade. SW033291 shifts the melting temperature to 74 degrees. SW206980 shifts the melting temperature to 70.5 degrees. SW206992 shifts the melting temperature to 68.5 degrees. Thus all three compounds directly bind to 15-PGDH and markedly increase the melting temperature of the protein, with the order of the temperature shifts being SW033291>SW206980>SW206992.

FIGS. 37(A-C) show a titration curve of 15-PGDH inhibitor compounds in an assay measuring effect on PGE2 levels in the medium of A549 cells that have been stimulated with IL1-beta. Highest PGE2 levels, 3000 pg/ml, are achieved with SW033291, with maximal effect attained at 2.5 uM compound. Next highest PGE2 level, 2500 pg/ml are achieved with SW206980, with maximal effect attained at 7.5 uM compound. Lowest induction, to 2100 pg/ml PGE2 is achieved with SW206992, with maximal effect attained at 2.5 uM. In these reactions, A549 cells were maintained in F12K medium supplemented with 10% fetal calf serum (FBS) and 50 gentamicin in a humidified atmosphere containing 5% $CO_2$ at 37° C. Cells were plated in 24-well plates (0.5 mL per well) at about 100,000 cells per well in duplicate and grown for 24 h before stimulation with IL-1β (1 ng/mL) overnight (16 h) to generate PGE2. SW033291 and its analogs were added at the indicated concentrations, and the incubation continued for 8 h. Medium was collected, and the level of PGE2 was analyzed by enzyme immunoassay. Data were analyzed from results of three independent experiments.

FIGS. 38(A-C) show assays of cellular toxicity on A549 cells at 24 hours of 15-PGDH inhibitors as assayed by CellTiter-Glo measurement. No effect on CellTitre-Glo levels is seen by concentrations of up to 10 uM of SW033291, SW206980, and SW2206992.

FIG. 39 shows structures of 7 SW033291 analogues, SW208064, SW208065, SW208066, SW208067, SW208068, SW208069, SW208070.

Table 4 provides tabular summary of the properties of 4 analogues, SW208064, SW208065, SW208066, SW208067, and in particular lists the IC50 for each of these 4 compounds against 2.5 nM recombinant 15-PGDH.

Time to inhibition refers to the time needed to inhibit the generation of NADH by 15-PGDH from the moment with drug is added into the reaction mix. Delta™ refers to the shift in melting temperature of recombinant 15-PGDH in the presence of drug (with cofactor NADH also present). Concentration of Full Cell Line Reporter Induction refers to the concentration of drug that needs to be added to reporter cell line to achieve maximal induction of the 15-PGDH-luciferase gene fusion reporter cassette, as measured by luciferase assays. Hepatocyte stability refers to the half-life of compound in the presence of hepatocytes in culture. Toxicity refers to the concentration of compound needed to decrease cell numbers in a cell culture assay.

Figure 40:
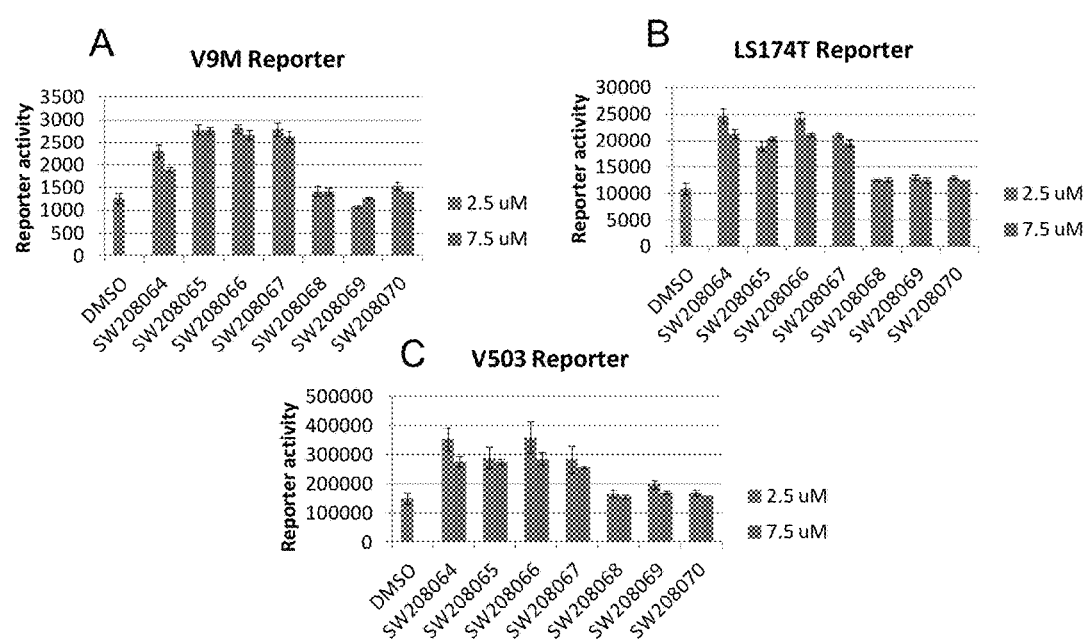
FIGS. 40(A-C) illustrate graphs showing luciferase activity of colon cancer cell lines V9M, LS174T, and V503 treated with 2.5 µM and 7.5 µM the compounds of FIG. 39.

FIG. 40 provides graphical summary showing the activity of each of the compounds in inducing a 15-PGDH-luciferase fusion gene reporter introduced into three different colon cancer cell lines, V9m, LS174T, and V503. Results are measured by assay of luciferase activity after exposure of cells to compound at either 2.5 uM or 7.5 uM compounds concentration.

Figure 41:
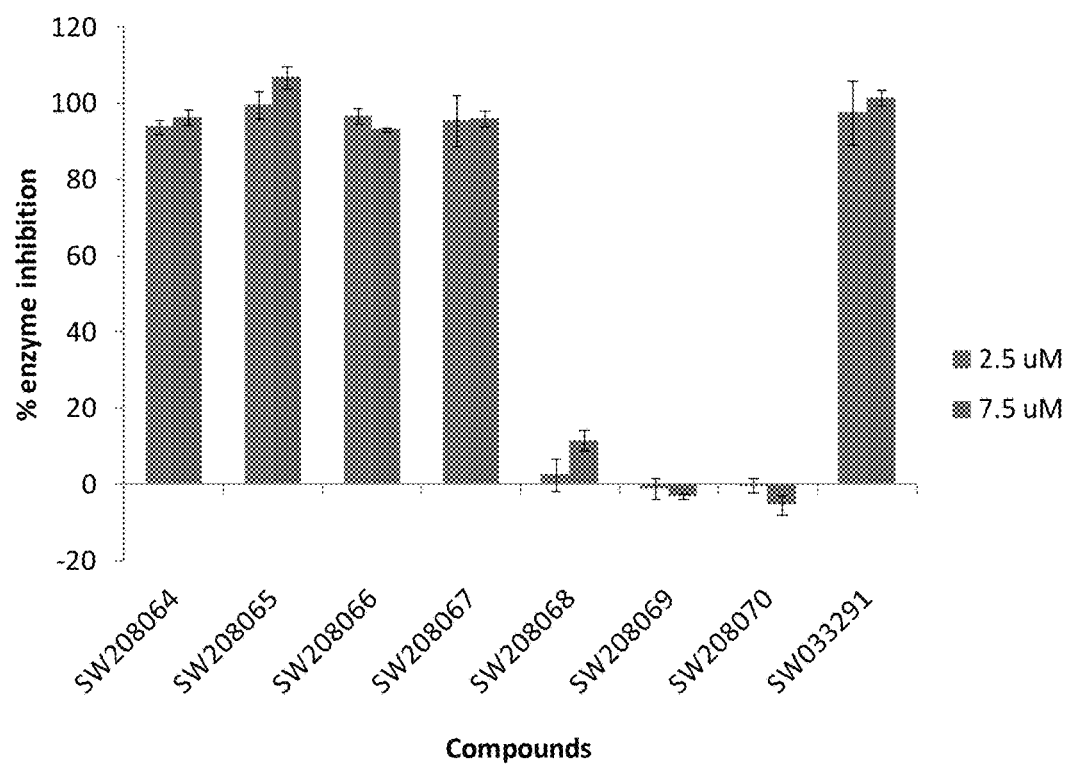
FIG. 41 illustrates a graph showing percent inhibition of 15-PGDH activity by the compounds of FIG. 40.

FIG. 41 provides graphical summary showing the activity of each of the compounds in inhibiting the enzymatic activity of recombinant 15-PGDH enzyme when compound is added at 2.5 uM and at 7.5 uM. 100% inhibition corresponds to complete inhibition of the enzyme.

Figure 42:
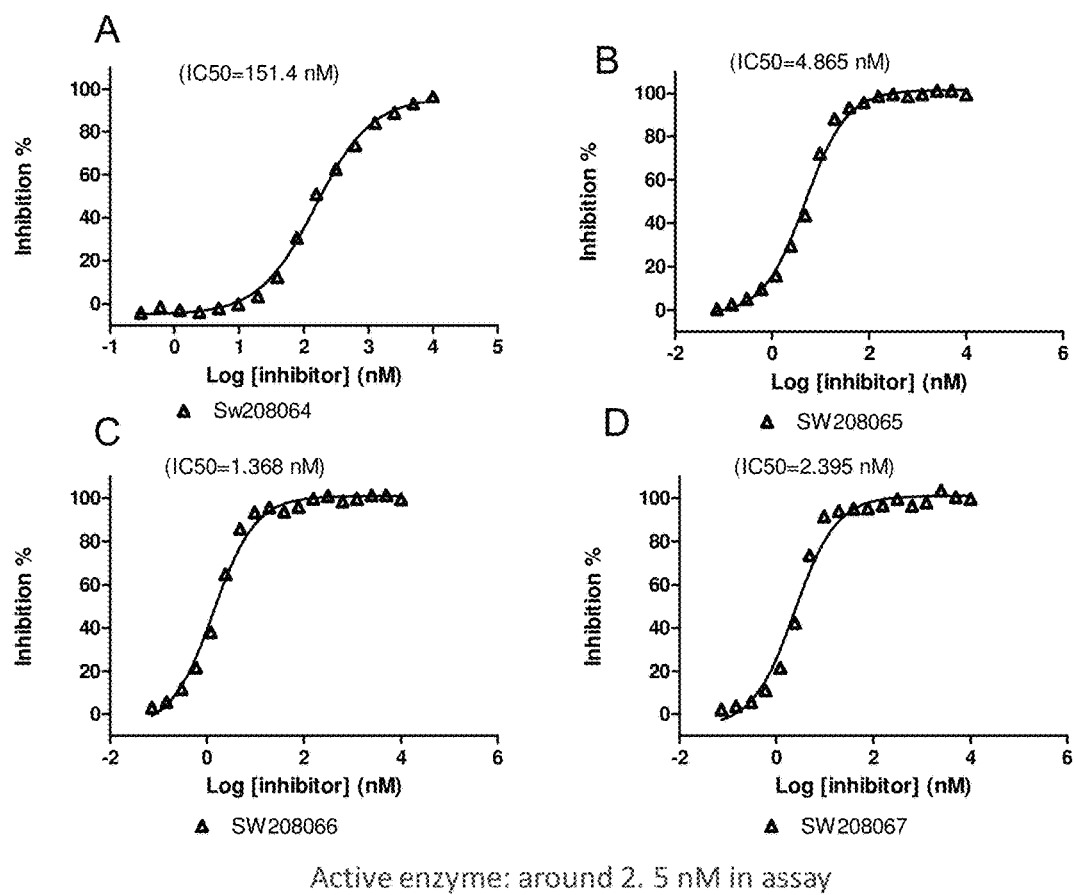
FIGS. 42(A-D) illustrate a graph showing percent inhibition of 15-PGDH activity by the compounds of FIG. 40.

FIG. 42 shows measurement of IC for inhibiting 2.5 nM of recombinant 15-PGDH when incubated across a range of concentrations of SW208064, SW208065, SW208066, and SW208067. Y-axis of each graph records percent inhibition of the 15-PGDH enzymatic activity. 100% Inhibition corresponds to complete inhibition of the enzyme. X-axis of each graph records the log of the inhibitor concentration expressed in nM.

Example 5

Analysis of Toxicity of SW033291

Table 5 shows a summary of a group of 8-12 week old male FVB mice in control or SW033291 treatment arms assessed for toxicity of SW033291, with 6 mice in each arm of the study.

TABLE 5

| Baseline Characteristics FVB male mice- 8-12 weeks old | | | |
|---|---|---|---|
| Toxicity Study | WT-Control | WT-Treatment | p-value |
| Number | 6 | 6 | |
| Sex | M | M | |

TABLE 4

| Summary of four SW033291 analogs from UTSW set 8 | | | | | |
|---|---|---|---|---|---|
| | SW033291 | SW2068064 | SW208065 | SW208066 | SW208067 |
| $IC_{50}$ | 1.23 nM | 151.4 nM | 4.865 nM | 1.368 nM | 2.395 nM |
| Time to inhibition (10 nM) | ~5 mins | | | | |
| Δ Tm (NADH) | 19° C. | 5° C. | 13° C. | 16.5° C. | 16.5° C. |
| Concentration for Full Cell Line Reporter Induction | ~100 nM | ~600 nM | ~100 nM | ~100 nM | ~500 nM |
| Hepatocyte stability | Stable > couple hrs | | | | |
| Toxicity | >10 μM | | | | |

TABLE 5-continued

Baseline Characteristics FVB male mice- 8-12 weeks old

| Toxicity Study | WT-Control | WT-Treatment | p-value |
|---|---|---|---|
| Age (Days) | 73.7.1 ± 4.7 | 73.2 ± 5.0 | 0.465 |
| Weight (gm) | 27.5 ± 2.4 | 26.8 ± 3.1 | 0.412 |

Figure 43:
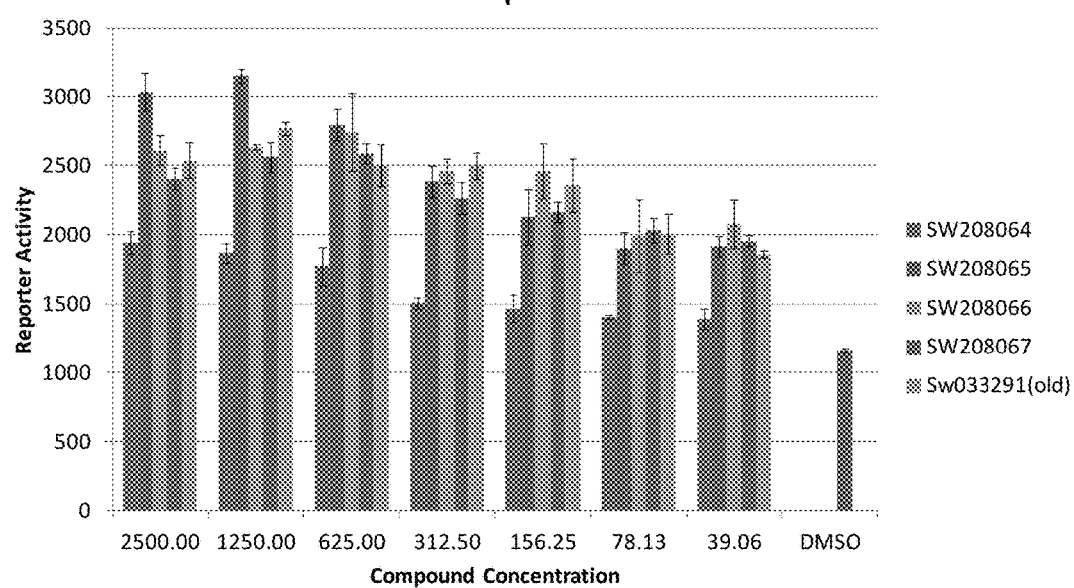
FIG. 43 shows the dose response curve for induction of a 15-PGDH-luciferase fusion gene reporter in the V9m cell line background of SW033291, SW208064, SW208065, SW208066, and SW208067.

FIG. 43 shows the dose response curve for induction of a 15-PGDH-luciferase fusion gene reporter in the V9m cell line background of SW033291, SW208064, SW208065, SW208066, and SW208067.

Figure 44:
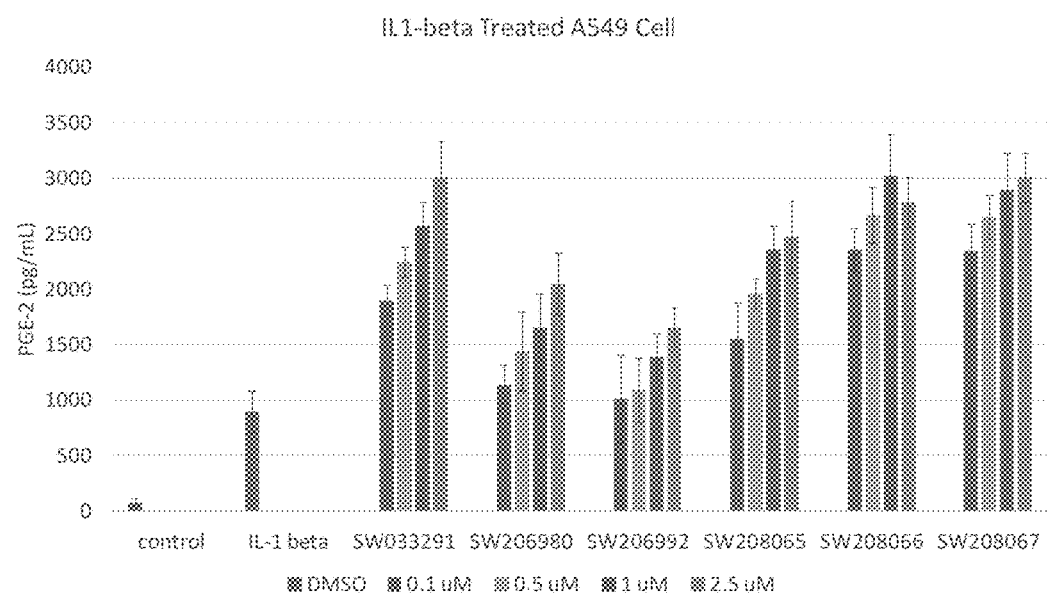
FIG. 44 illustrates titration curves of 15-PGDH inhibitor compounds in an assay measuring effects on PGE2 levels in the medium of A549 cells that have been stimulated with IL1-beta.

FIG. 44 Shows titration curves of 15-PGDH inhibitor compounds in an assay measuring effects on PGE2 levels in the medium of A549 cells that have been stimulated with IL1-beta in the same experimental design described for FIG. 37. At 100 nM concentration of drug, the highest levels of PGE2 in the medium are achieved by treating cells with SW208066 or with SW208067, after which the next highest level of PGE2 in the medium is achieved by treating cells with SW033291.

Figure 45:
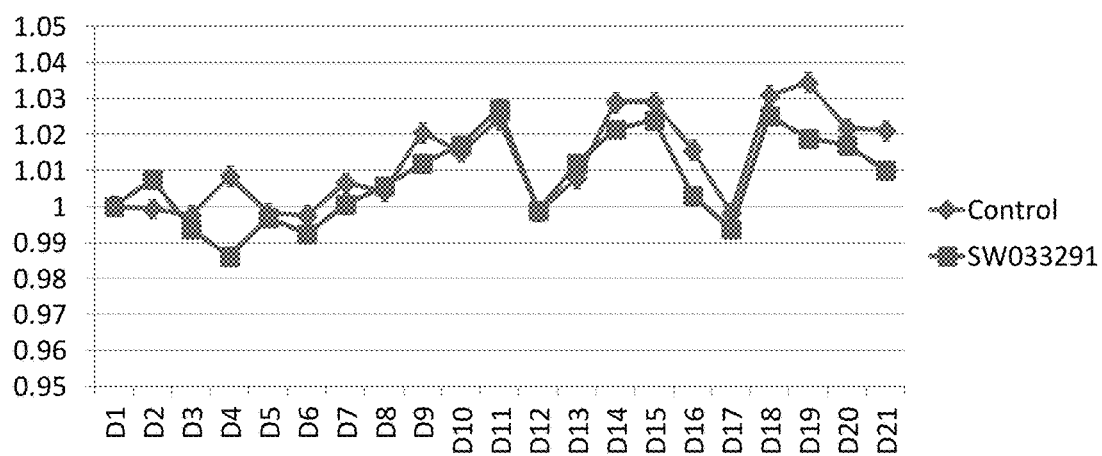
FIG. 45 is a plot showing weight change of FVB mice treated with SW033291.

FIG. 45 shows the daily weights of a group of 8-12 week old FVB mice treated with vehicle or with SW033291 IP at 5 mg/kg twice daily for 21 days. SW033291 was administered in a vehicle of 10% Ethanol, 5% Cremophor EL, 85% D5W at a concentration of 125 ug/200 ul. As shown, both vehicle and drug treated mice show equal weight gain during the 21 day period, with no evidence for SW033291 reducing mouse weight. N=6 mice in both the SW033291 treated and the vehicle treated arms.

Example 6

Analysis of Effect of SW033291 on Bone Marrow Function

This Example shows effects of SW033291 on bone marrow function.

FIGS. 46(A-C) show analysis of bone marrow of wild-type mice versus mice that are homozygous genetic knockouts for 15-PGDH (PGDH−/− mice). Total bone marrow cellularity and percent of Sca1+/c-Kit+ cells in lineage negative (SKL) cells are the same in both sets of mice. However, bone marrow from 15-PGDH−/− mice shows an approximately 50% increase in numbers of hematopoietic colonies generated when marrow is plated into methylcelluose. Experimental conditions are noted on the figure. 15-PGDH knockout mice are denoted by label PGDH−/− and by label 15-PGDH.

Figure 47:
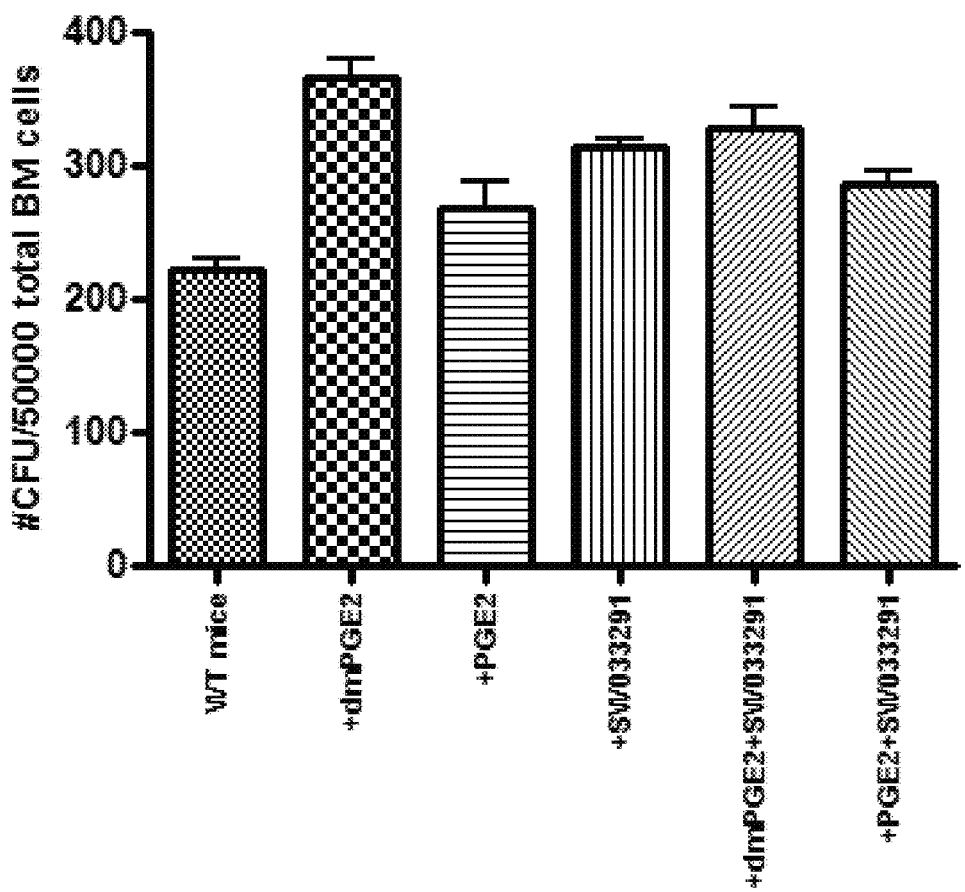
FIG. 47 illustrates a graph showing CFU counts in wild type bone marrow treated with SW033291 and PGE-2.

FIG. 47 shows assay in which bone marrow is harvested from a wild-type mouse, and incubated ex vivo on ice for 2 hours with either SW033291 (0.5 uM), or 1 uM PGE2 or 1 uM 16,16-dimethyl PGE2 (dmPGE2). Treated marrow is again then plated into methylcellulose for counting of hematopoietic colonies. SW033291 treated marrow again shows an approximately 50% increase in the number of bone marrow derived colonies generated. Under these conditions, a lesser increase is seen in marrow treated with PGE2, and a slightly greater increase is seen in marrow treated with dmPGE2.

Figure 48:
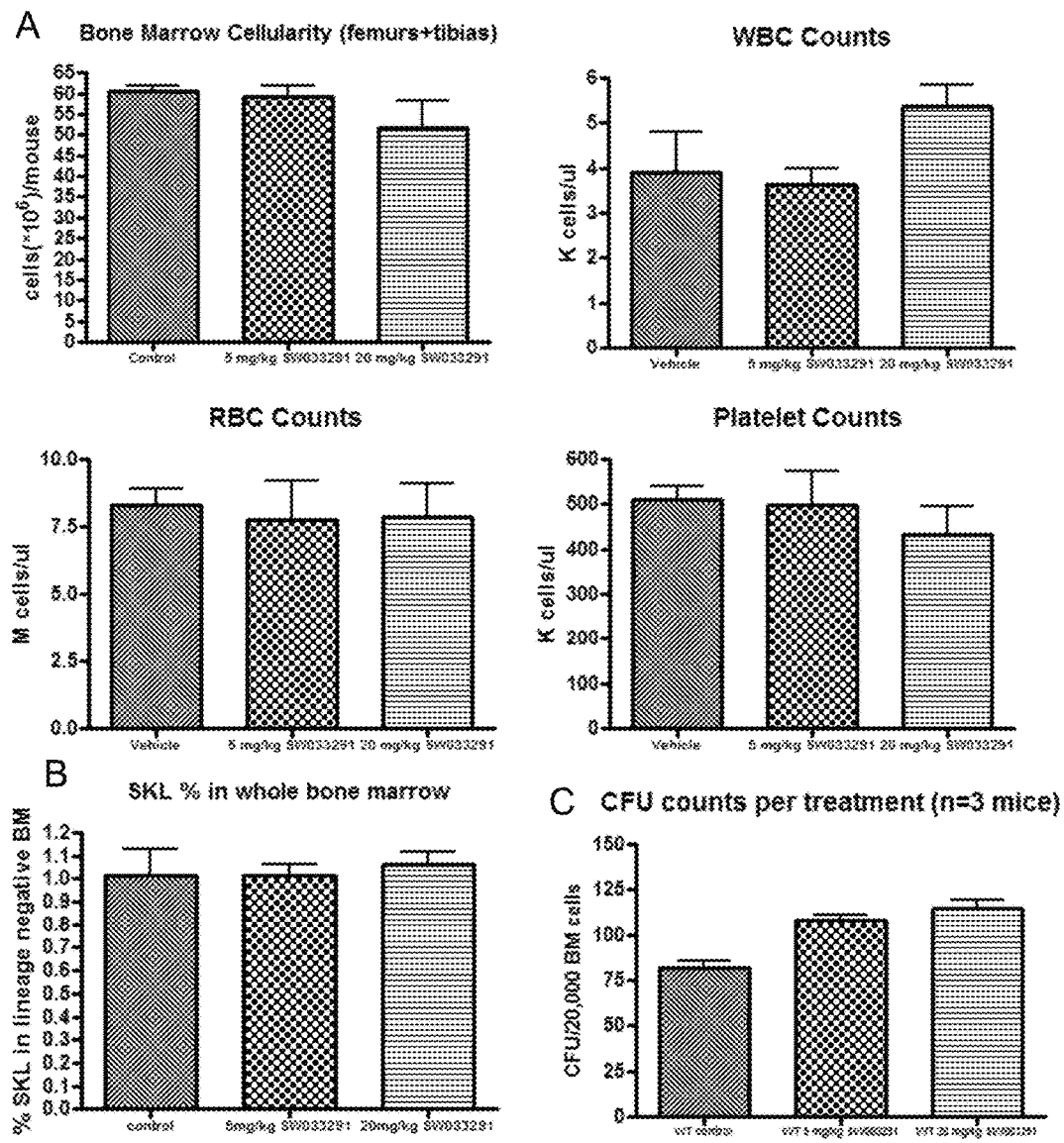
FIGS. 48(A-C) illustrate graphs showing: (A) bone marrow cellularity of mice treated with SW033291; (B) SKL % in whole bone marrow of mice treated with SW033291; and (C) CFU counts in mice treated SW033291.

FIGS. 48(A-C) show a study of C57BL/6J mice treated with IP SW033291 administered in a vehicle of 10% Ethanol, 5% Cremophor EL, 85% D5W at a dose of 5 mg/kg or 20 mg/kg. Panel A shows mouse bone marrow cellularity, white blood count (wbc), red blood count (rbc) and platelets counts. Panel B shows percent of Sca1+/c-Kit+ cells in lineage negative (SKL) cells are unchanged in SW033291 treated mice. Panel C shows that marrow from SW033291 treated mice gives rise to approximately 30% increase in numbers of hematopoietic colonies generated when marrow is plated into methylcelluose. Experimental conditions are noted on the figure.

FIGS. 49(A-B) show analysis of marrow from CD45.2 antigen marked C57BL/6J mice that were treated with SW033291 5 mg/kg IP daily for 3 doses in a vehicle of 10% Ethanol, 5% Cremophor EL, 85% D5W or that were treated with vehicle alone. On day 3 mice were sacrificed, marrow flushed and mixed at a 1:1 ratio with vehicle treated CD45.1 marrow. 2 million whole BM cells were injected into the tail vein of lethally irradiated CD45.1 mice and percent chimerism measured via flow cytometry at weeks 8, 12, 16. As shown, at weeks 12 and 16 the percent blood chimerism of CD45.2 marked cells was significantly increased in recipient mice whose CD45.2 marked marrow was harvested from SW033291 treated donor mice, as opposed to vehicle control treated donor mice. In other words, marrow from SW033291 treated mice demonstrated long term increased fitness in competition with control marrow. In particular, at week 16 CD45.2 harvested from SW033291 treated mice show a significant increase in contribution to B and T cell populations, suggesting marrow from SW033291 treated mice promotes earlier reconstitution of lymphoid populations and earlier return to immune competence.

Figure 50:
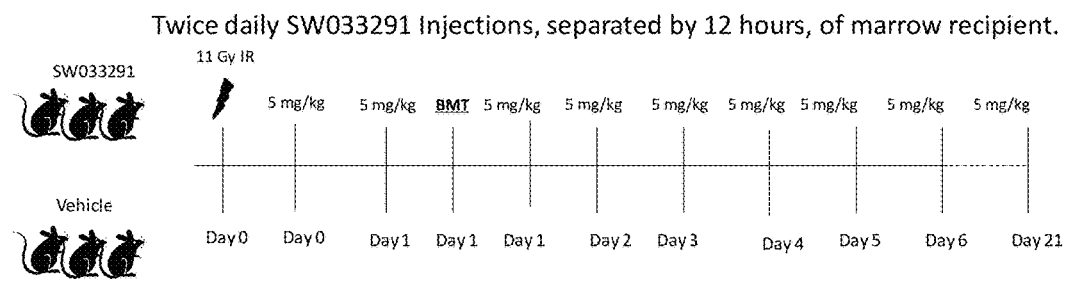
FIG. 50 illustrates a schematic diagram showing schema of a study in which C57BL/61 mice are irradiated with 11 GY on day 0 and followed by treatment with SW033291.

In an additional study, C57BL/6J mice are irradiated with 11 Gy on day 0, followed by treatment with SW033291 5 mg/kg IP twice daily (bid) in a vehicle of 10% Ethanol, 5% Cremophor EL, 85% D5W, or with vehicle only for 21 days. Mice treated with vehicle or with SW033291 all receive an allograft of marrow from a donor C57BL/6J mouse at a dose of either 100,000 cells, 200,000 cells, 500,000 cells. 3 control and 3 SW033291 mice are assessed under each condition. The experimental design is depicted in FIG. 50.

Table 6 shows the number of surviving mice in each cohort over the first 19 days of study. Under the conditions of the mouse colony during this study, control mice receiving 100,000-500,000 cells are all dead between days 4-13 of study. In contrast, two SW033291 treated mice receiving 500,000 cells remain alive on day 19 of the study and are presumed to have full hematopoietic reconstitution. Thus treatment with the 15-PGDH inhibitor SW033291 promoted survival of mice receiving a bone marrow transplant, an observation consistent with SW033291 enabling more rapid and complete hematopoietic reconstitution in the transplanted mice. Other 15-PGDH inhibitors with activity similar to SW033291 would be predicted to have similar activity in supporting hematopoietic reconstitution. Treatment with SW033291 also enabled mice to be successfully transplanted with a smaller inoculum of donor bone marrow than the 1,000,000 cells that are standardly needed. These observations suggest SW033291, as well as other similar 15-PGDH inhibitors, is able to support successful transplantation with smaller numbers of donor stem cells. Such activity would be of particular utility in settings, such as transplantation with umbilical cord stem cells, in which donor cell numbers are limited. Improved survival of transplanted mice treated with SW033291 suggests efficacy of SW033291, and of similar 15-PGDH inhibitors, as replacements for, or in enabling decreased use of, other treatments or growth factors commonly employed in support of patients receiving bone marrow, hematopoietic stem cell, and cord blood stem cell transplants. Improved survival of transplanted mice treated with SW033291 is consistent with SW033291, and by extension other similar 15-PGDH inhibitors, having activity in reducing infections in the transplanted mice, and/or in promoting recovery of mice intestines from damage by radiation, and/or in reducing pulmonary toxicity from radiation.

TABLE 6

| | | Mouse survival | | | | | | | | | | | | | | |
|---|---|---|---|---|---|---|---|---|---|---|---|---|---|---|---|---|
| Treatment | Cell number | 13-Mar Day 0 | 14-Mar Day 1 | 15-Mar Day 2 | 16-Mar Day 3 | 17-Mar Day 4 | 18-Mar Day 5 | 19-Mar Day 6 | 20-Mar Day 7 | 21-Mar Day 8 | 22-Mar Day 9 | 23-Mar Day 10 | 24-Mar Day 11 | 25-Mar Day 12 | 26-Mar Day 13 | ... 1-Apr Day 19 |
| Control | $1 \times 10^5$ | 3 | 3 | 3 | 2 | 0 | | | | | | | | | | |
| Control | $2 \times 10^5$ | 3 | 3 | 3 | 3 | 3 | 2 | 1 | 0 | | | | | | | |
| Control | $5 \times 10^5$ | 3 | 3 | 3 | 3 | 3 | 3 | 2 | 1 | 1 | 1 | 1 | 1 | 1 | 0 | |
| SW033291 | $1 \times 10^5$ | 3 | 3 | 3 | 3 | 2 | 1 | 0 | | | | | | | | |
| SW033291 | $2 \times 10^5$ | 3 | 3 | 3 | 3 | 3 | 3 | 2 | 2 | 2 | 2 | 2 | 2 | 1 | 0 | |
| SW033291 | $5 \times 10^5$ | 3 | 3 | 3 | 3 | 3 | 3 | 3 | 3 | 2 | 2 | 2 | 2 | 2 | 2 | ... 2 |

Example 7

Analysis of Effect of SW033291 on Radiation Survival

This Example shows studies of the effect of SW033291 in mice receiving whole body irradiation.

Table 7 shows the results of a study of 15 week old C57BL/6J female mice irradiated with 7 Gy, 9 Gy, or 11 Gy, and receiving daily SW033291 5 mg/kg IP in a vehicle of 10% Ethanol, 5% Cremophor EL, 85% D5W for 7 doses, or receiving vehicle alone. The table shows the number of mice surviving on sequential days of the study. Under the conditions of the mouse colony during this experiment, mice receiving a lethal dose of 11 Gy lived 48 hours longer if treated with SW033291 than if receiving vehicle control, with control mice all dead on day 8; whereas SW033219 treated mice were all dead on day 10.

TABLE 7

| Radiation Dose | Treatment Arm | 10/2 Day 0 | 10/3 Day 5 | 10/4 Day 6 | 10/5 Day 7 | 10/6 Day 8 | 10/7 Day 9 | 10/8 Day 10 | 10/9 Day 11 | 10/10 Day 12 | 10/11 Day 13 | 10/12 Day 14 | 10/13 Day 15 | Day 16 | 10/23 Day 25 |
|---|---|---|---|---|---|---|---|---|---|---|---|---|---|---|---|
| 7 Gy | Saline | 3 | 3 | 3 | 3 | 3 | 3 | 3 | 3 | 3 | 3 | 3 | 3 | | Looks Healthy |
| | SW033291 | 3 | 3 | 3 | 3 | 3 | 3 | 3 | 3 | 3 | 3 | 3 | 3 | | Looks Healthy |
| 9 Gy | Saline | 3 | 3 | 3 | 3 | 3 | 3 | 3 | 3 | 2 | 1 | 1 | 0 | | |
| | SW033291 | 3 | 3 | 3 | 3 | 3 | 3 | 3 | 3 | 2 | 2 | 1 | 0 | | |
| 11 Gy | Saline | 3 | 3 | 3 | 2 | 0 | | | | | | | | | |
| | SW033291 | 3 | 3 | 3 | 3 | 3 | 2 | 0 | | | | | | | |

Table 8 shows the number of mice surviving on sequential days of a study of mice treated at 11 Gy treated with either vehicle control or with SW033291 IP, in a vehicle of 10% Ethanol, 5% Cremophor EL, 85% D5W, with SW033291 administered either at 5 mg/kg daily for 7 days, 5 mg/kg daily throughout the study, or at 5 mg/kg twice daily for 7 days. Again mice treated with SW033291 on any of these dosing schedules live on average 1-2 days longer than mice receiving vehicle control. The activity of SW033291 in promoting resistance to toxic effects of radiation may extend to SW033291 and other similar 15-PGDH inhibitors in promoting resistance to other similar toxic insults including but not limited to Cytoxan, fludarabine, chemotherapy and immunosuppressive therapy.

TABLE 8

| Treatment Conditions | Friday 12-Oct Day 0 | Wed. 17-Oct Day 5 | Thurs. 18-Oct Day 6 | Friday 19-Oct Day 7 | Saturday 20-Oct Day 8 | Sunday 21-Oct Day 9 | Monday 22-Oct Day 10 |
|---|---|---|---|---|---|---|---|
| 11 Gy Saline (7 days, 1 does daily) | 2 | 2 | 2 | 2 | 0 | | |
| 11 Gy SW033291 (1 does/daily) for 7 days | 3 | 3 | 3 | 3 | 2 | 1 | 0 |
| 11 Gy SW033291 (1 does/daily, continuous every day) | 3 | 3 | 3 | 3 | 3 | 2 | 0 |

TABLE 8-continued

| Treatment Conditions | Friday 12-Oct Day 0 | Wed. 17-Oct Day 5 | Thurs. 18-Oct Day 6 | Friday 19-Oct Day 7 | Saturday 20-Oct Day 8 | Sunday 21-Oct Day 9 | Monday 22-Oct Day 10 |
|---|---|---|---|---|---|---|---|
| 11 Saline (7 Gy days, 2 does/daily | 3 | 3 | 3 | 2 | 1 | 0 | 0 |
| 11 SW033291 Gy (7 days, 2 dose daily) | 3 | 3 | 3 | 3 | 3 | 2 | 0 |

Example 8

Analysis of Effect of SW033291 on Liver Regeneration Post Partial Hepatectomy

This Example shows studies assessing the effect of SW033291 on liver regeneration in mice following partial hepatectomy.

Figure 51:
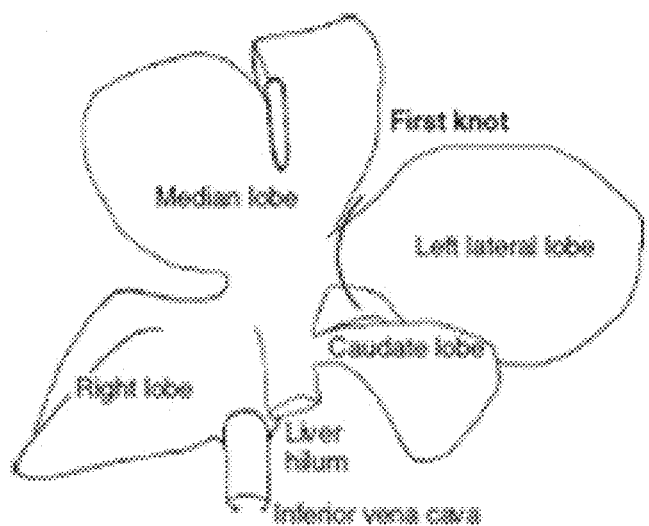
FIG. 51 illustrates a schematic diagram of a partial hepatectomy.

FIG. 51 shows a drawing of the anatomy of the mouse liver and of the partial hepatectomy procedure described in Mitchell et al., Nature Protocols, 3, 1167-1170 (2008), in which the median and left lateral lobes are resected, and then liver regeneration is observed via hypertrophy of the remaining right and caudate lobes. The total resection is of approximately 70% of the mouse liver mass. In these studies mice were euthanized using carbon dioxide inhalation. The mouse body was weighed in its entirety. The liver was removed from the mouse; the necrotic remnant from the surgical resection was trimmed; and the regenerated liver was weighed.

FIG. 52(A-D) show an anatomical view of the mouse liver. Pictures at left are pre-operative views, and those at right are post-resection views. The upper two pictures show anterior view of liver and at left display the median lobe and a part of the Lateral lobe. The lower two pictures show Inferior view of liver and at left display the Lateral lobe. In the partial hepatectomy procedure, the median and lateral lobes are resected as shown at right.

FIG. 53(A-D) at left reiterates photographs of the immediate post-hepatectomy views of the mouse liver, with anterior view at top and inferior view at bottom. Figure at top right shows the in situ view of the regenerated liver on post operative day (POD) 10, showing hypertrophy of the remnant right and caudate lobes. Photograph at lower right shows the anterior view of the regenerated liver after removal from the mouse body. Whitish region at the upper right liver edge is the necrotic stump from the resection, and is trimmed prior to weighing.

The first study was performed in 10 week old male C57BL/6.1 mice, receiving daily SW033291 5 mg/kg IP in a vehicle of 10% Ethanol, 5% Cremophor EL, 85% D5W, versus vehicle alone, and assessed daily for liver regeneration with 5 control and 5 SW033291 recipient mice sacrificed on each time point. In this study, ketamine anesthesia was employed.

FIG. 54(A-B) show micrograph of the hematoxylin and eosin stained liver on post-operative day 3 (POD 3) in the SW033291 treated mouse versus the control mouse, with mitotic figures marked by yellow arrows in the SW033291 treated mouse liver at left and by green arrows in the control mouse liver at right.

FIG. 55 shows a graph of the number of mitosis per high powered field in livers of SW033291 treated versus control mice on post-operative days two through five (2D-5D). Mitotic figures were counted in 10 high powered fields (40×) from each of 5 livers per SW033291 or control mice per day. SW033291 treated mice demonstrated significantly increased hepatic mitosis versus controls on days 3 and 4.

Table 9 shows the numbers of mitosis per random high powered field counted in livers of control versus SW033291 treated mice on post operative days 2 through 5 (2D-5D). SW033291 treated mice show significantly increased numbers of mitotic liver cells on post-operative days 3 and 4.

TABLE 9

| Mitotic index (40x) mean + SD | Control | SW033291 | p-value |
|---|---|---|---|
| 2D | 0.7000 ± 0.1933 | 1.240 ± 0.2330 | 0.0915 |
| 3D | 2.000 ± 0.4364 | 6.160 ± 0.3250 | <0.0001 |
| 4D | 2.560 ± 0.2242 | 4.560 ± 0.7190 | 0.0107 |
| 5D | 0.2000 ± 0.1069 | 0.2400 ± 0.08718 | ns |

Figure 56:
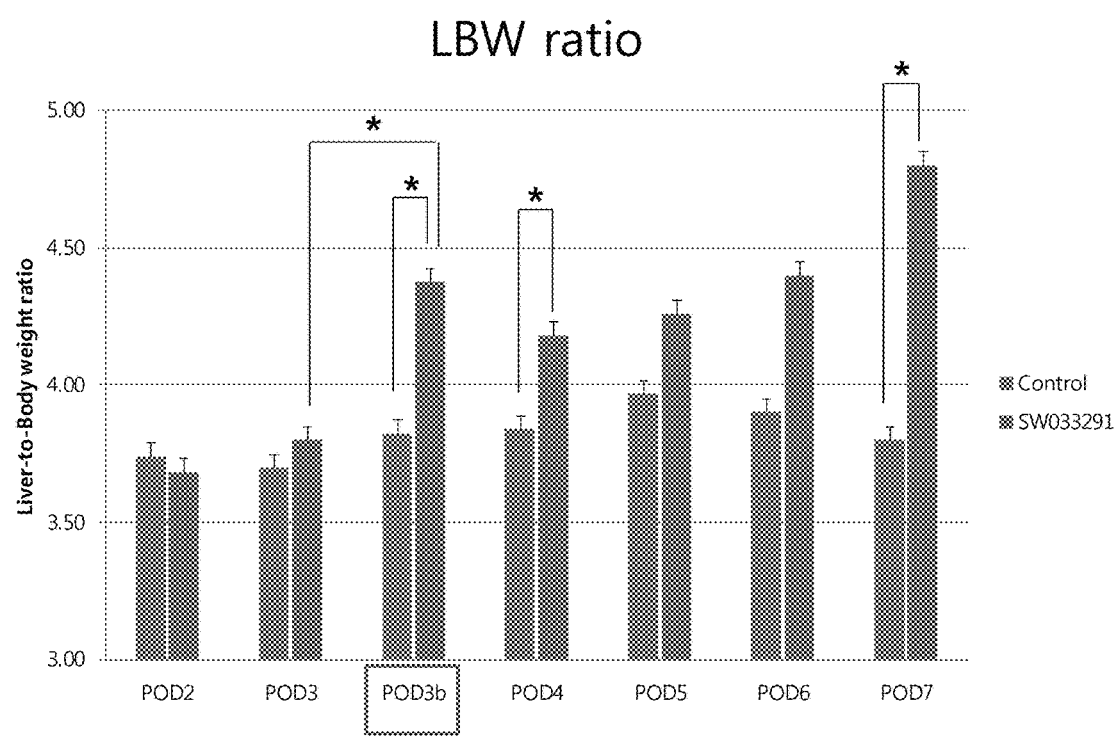
FIG. 56 illustrates a graph showing the liver to body weight ratios attained following partial hepatectomy in control versus SW033291 treated C57Bl/6J mice.

FIG. 56 shows the liver to body weight ratios attained following partial hepatectomy in control versus SW033291 treated C57Bl/6j mice injected at 5 mg/kg SW033291 IP daily (qd) starting on post operative day 0 and continuing throughout. Graph displays values from post-operative days 2-7 (POD 2-7). The SW033291 qd injection group of mice attain a higher liver to body weight ratio from post-operative days 4-7, with the increase being statistically significant on postoperative day 4 and day 7.

An additional group of mice received SW033291 5 mg/kg twice daily (bid) and were analyzed on post-operative day 3, with the data graphed as POD3b. This group of mice also showed a statistically significant increase in liver to body weight ratio compared to control mice.

Another study was performed testing the effects of SW033291 given 5 mg/kg IP twice daily (bid) on liver regeneration in C57BL/6.1 mice. 10 mice were used in the control and 10 mice in the drug treated arm for analysis of each time point of the study. The study again employed 10 week old male mice receiving daily SW033291 5 mg/kg IP in a vehicle of 10% Ethanol, 5% Cremophor EL, 85% D5W, versus vehicle alone, with 10 drug treated and 10 control mice sacrificed daily for comparison. In this study ketamine anesthesia was employed.

Figure 57:
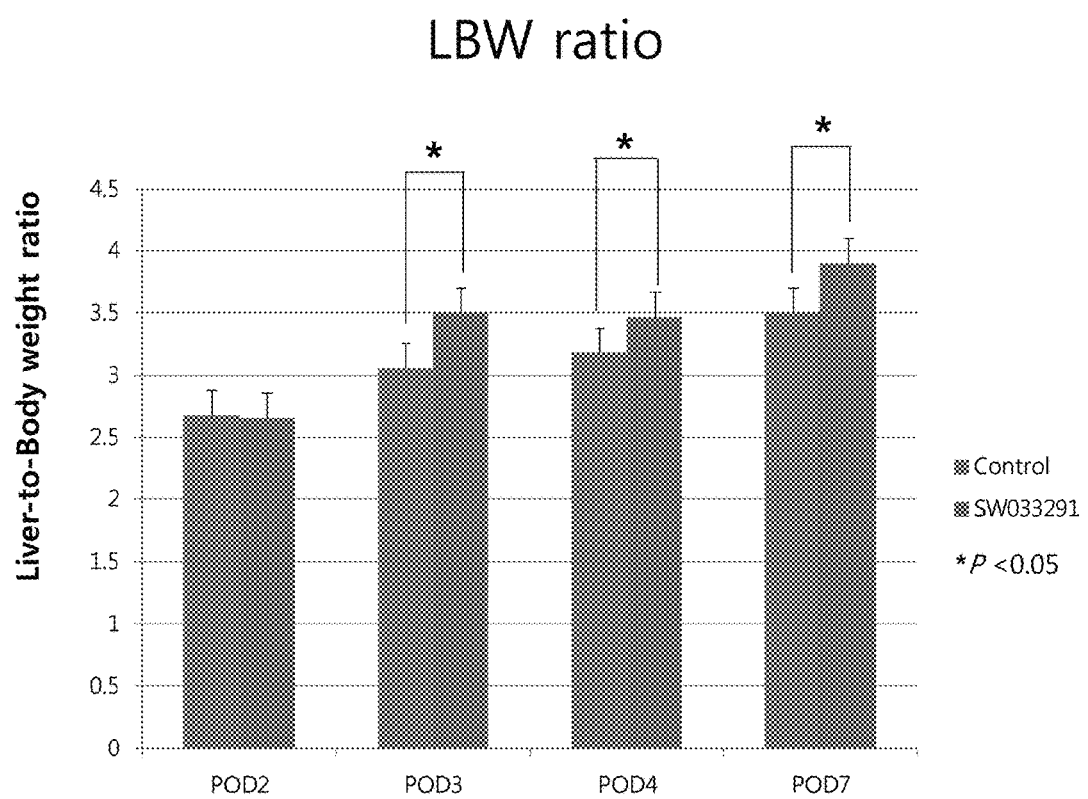
FIG. 57 illustrates a graph showing the liver to body weight ratios attained following partial hepatectomy in control versus SW033291 twice daily treated C57Bl/6J mice.

FIG. 57 shows graph of the liver to body weight ratio attained following partial hepatectomy in control versus SW033291 treated C57BL/6.1 mice injected at 5 mg/kg SW033291 IP twice daily (bid) starting at 1 hour post-surgery and continued throughout. Graph displays values from post-operative days 2-7 (POD 2-7). The SW033291 bid injected group of mice show a statistically significant higher liver to body weight ratio versus control mice on post-operative days 3, 4, and 7.

Figure 58:
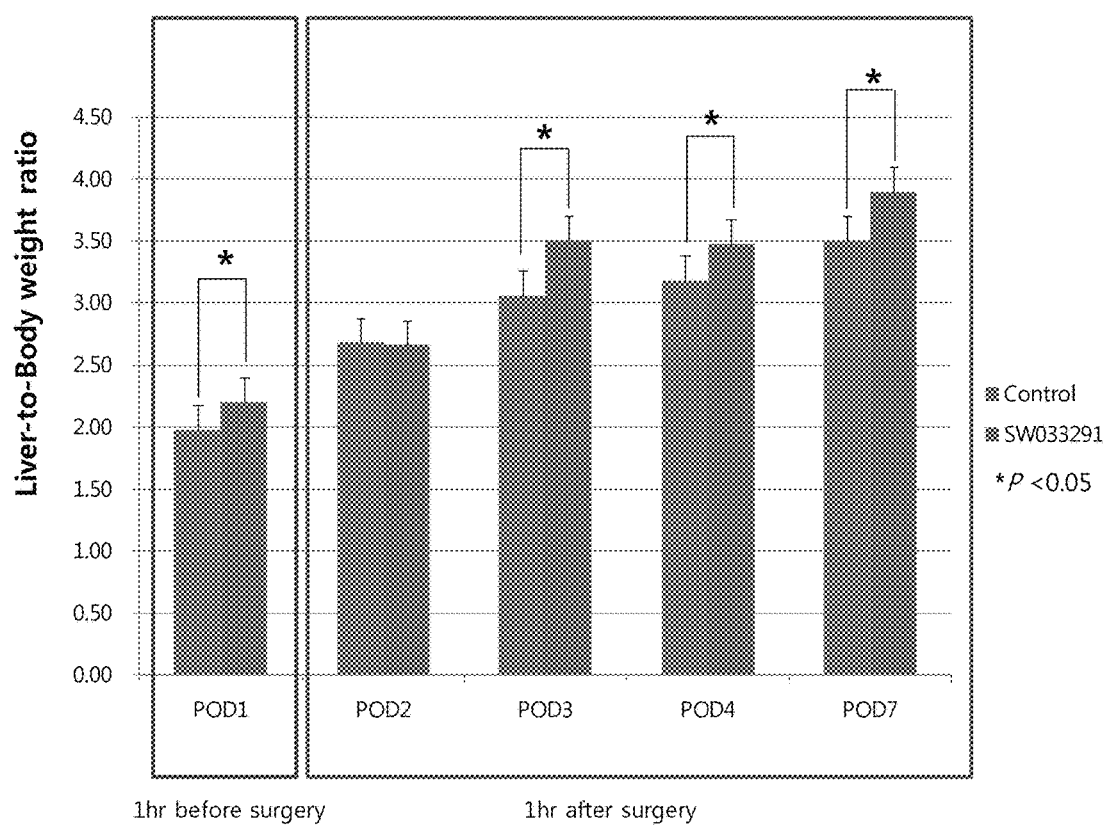
FIG. 58 illustrates a graph reprising the liver to body weight ratios attained following partial hepatectomy in control versus SW033291 treated C57Bl/6J mice.

FIG. 58 reprises the graph of the liver to body weight ratio attained following partial hepatectomy in control mice versus in mice treated with sw033291 5 mg/kg IP twice daily. In data enclosed within the blue box, drug was started 1 hour following surgery, and significant increases in liver to body weight ratio are seen in drug treated mice from post-operative day (POD) 3 onward. In data enclosed within the red box, the first dose of sw033291 is delivered commencing 1 hour before surgery, and significant increase in liver to body weight ratio is seen as early as post-operative day 1, the day following the surgery.

Figure 59:
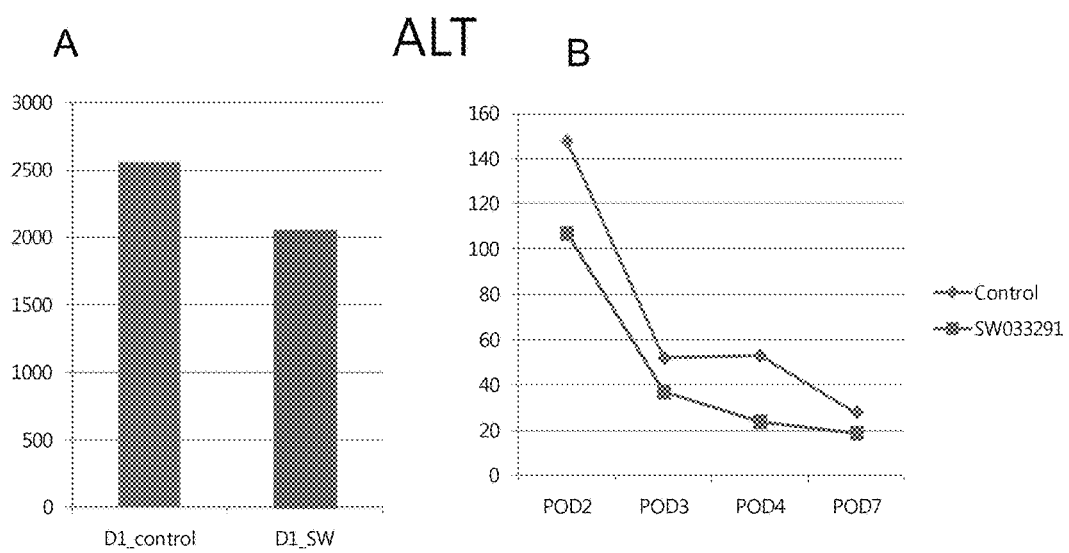
FIGS. 59(A-B) illustrate a graph and plot showing ALT levels following partial hepatectomy in one mouse control versus one mouse treated with SW033291.

FIGS. 59(A-B) show graphs of the serum ALT levels following partial hepatectomy in one control mouse versus one mouse treated with sw033291 at 5 mg/kg IP twice daily (bid). Post-operative day 1 values are compared at left, and post-operative day 2-7 values are compared at right. ALT values are lower in the drug treated mouse.

Figure 60:
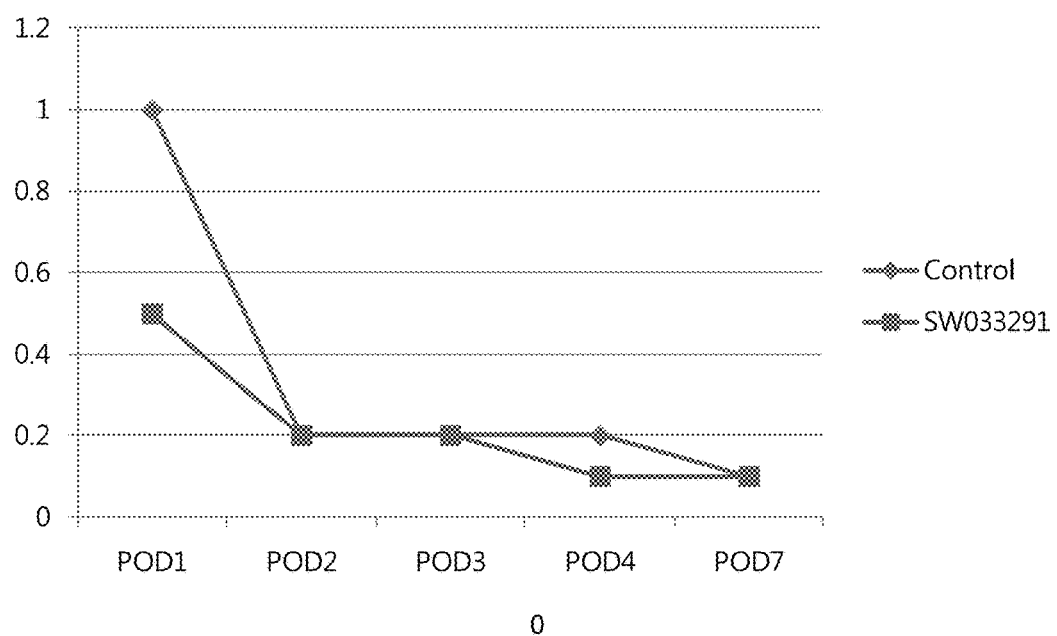
FIG. 60 illustrates a graph showing serum bilirubin levels following partial hepatectomy in a control mouse and a mouse treated with SW033291.

FIG. 60 shows graph of serum bilirubin levels following partial hepatectomy in one control mouse versus one mouse treated with SW033291 at 5 mg/kg IP twice daily (bid) from post-operative days (POD) 1-7.

In another study, SW033291 was tested in the partial hepatectomy model using the FVB strain of mice administered SW033291 5 mg/kg IP twice daily (bid), administered in a vehicle of 10% Ethanol, 5% Cremophor EL, 85% D5W, using 5 treated mice versus 5 control mice treated with vehicle alone for analysis at each time point from post operative day (POD) 1-7. In this study ketamine anesthesia was employed.

Figure 61:
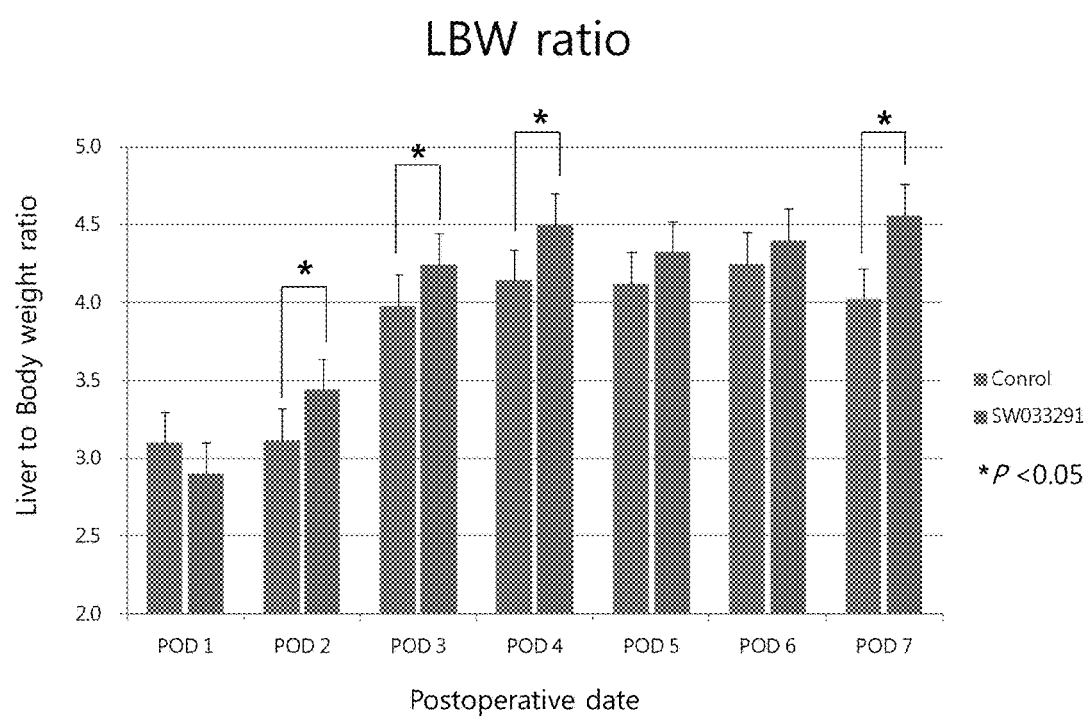
FIG. 61 illustrates a graph showing the liver to body weight ratios attained following partial hepatectomy in control versus SW033291 treated FVB mice.

FIG. 61 shows a graph of the liver to body weight ratio of attained following partial hepatectomy in FVB mice treated with 5 mg/kg IP SW033291 versus control mice treated with vehicle alone. SW033291 treated mice show increased liver to body weight ratio from post-operative days 2-7, with the increase being statistically significant on POD, 2, 3, 4 and 7.

In another study, SW033291 was tested in a partial hepatectomy model using the FVB strain of mice administered SW033291 5 mg/kg IP twice daily (bid), starting 1 hour before surgery. 10 week old male mice were employed, with 10 treated mice and 10 control mice used for analysis at each time point from post operative day (POD) 1-7. In this study isoflurane anesthesia was employed. Vehicle treated 15-PGDH knockout (KO) mice were also used as an additional comparator.

Figure 62:
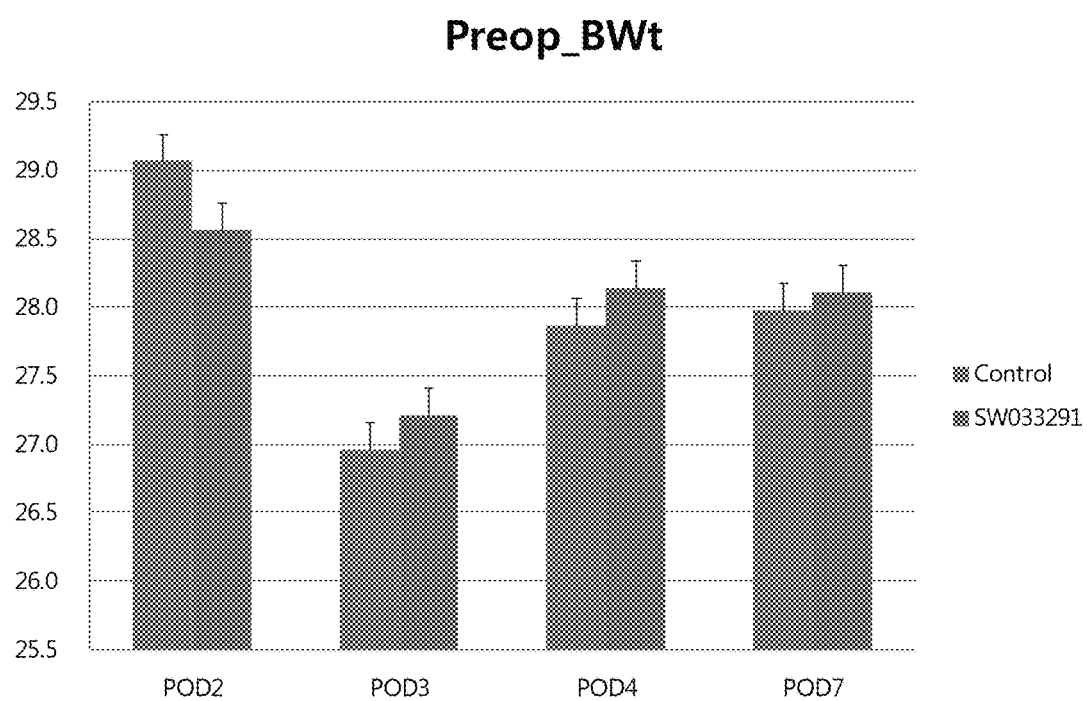
FIG. 62 illustrates a graph showing preoperative body weights in control versus SW033291 treated FVB mice.

FIG. 62 shows a graph depicting the pre-operative body weights of the FVB mice used for analysis of liver regeneration on post-operative days 2, 3, 4 and 7. SW033291 and control treated mice used on each day are well matched.

Figure 63:
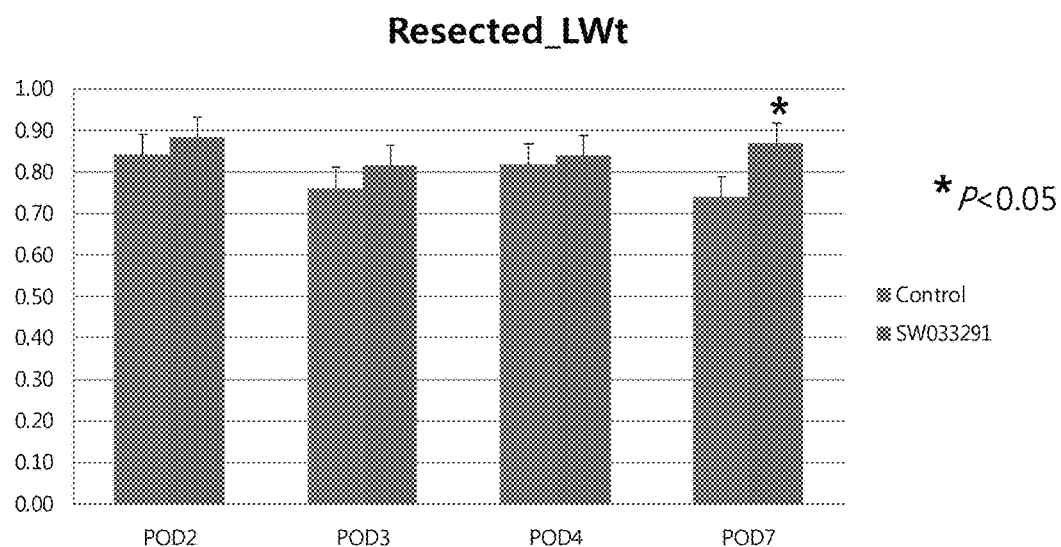
FIG. 63 illustrates a graph showing the weight of the resected liver segment from mice treated with either SW033291 or vehicle control and assayed for liver regeneration.

FIG. 63 shows a graph depicting the weight of the resected liver segment (resected LWt) from mice treated with either SW033291 or vehicle control and assayed for liver regeneration on post-operative days (POD) 2, 3, 4, and 7. Weight of the resected livers is well matched between control and drug treated mice on each day, except on day 7, when the weight of the resected liver was greater in the SW033291 treated than in the control mice.

Figure 64:
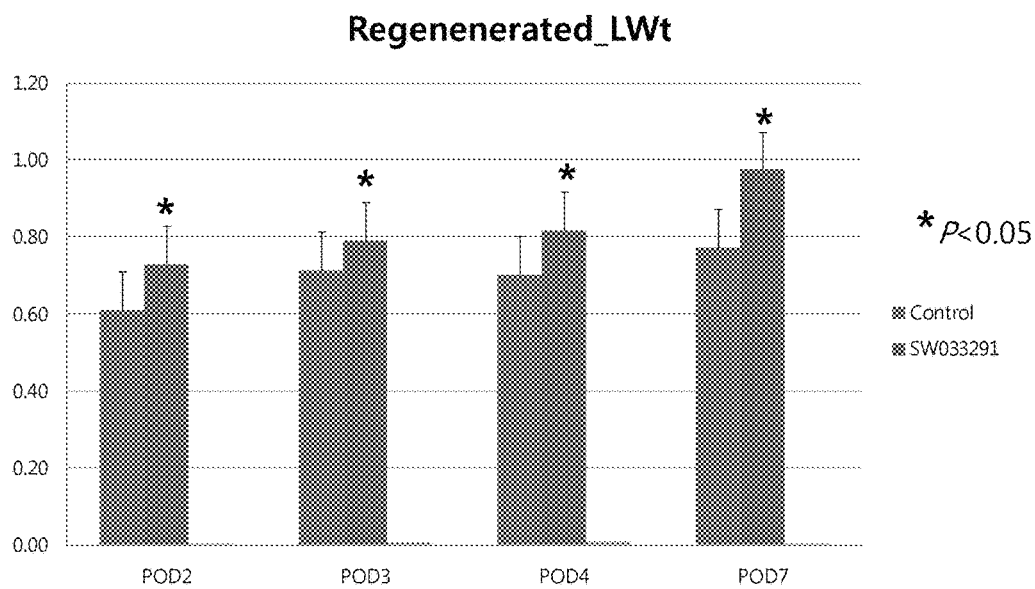
FIG. 64 illustrates a graph showing liver weights attained post partial heptatectomy in SW033291 and control mice.

FIG. 64 shows a graph depicting the liver weights attained (Regenerated_LWt) post partial hepatectomy in SW033291 and control mice on post-operative days 2, 3, 4 and 7 (POD 2, 3, 4, 7). SW033291 treated mice show significantly greater liver weights versus control mice at all time points, with SW033291 treated mice having approximately 25% greater liver weight on post-operative day 7 than control mice.

Figure 65:
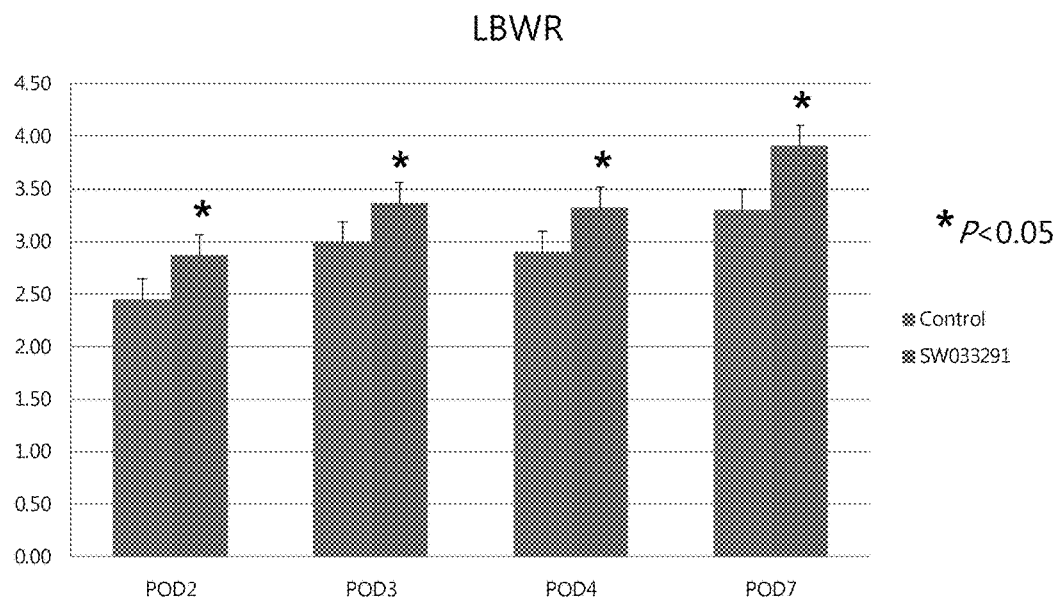
FIG. 65 illustrates a graph showing the liver to body weight ratios obtained post partial hepatectomy in SW033291 treated and control mice.

FIG. 65 shows a graph depicting the liver to body weight ratios attained (LBWR) post partial hepatectomy in SW033291 and control mice on post-operative days 2, 3, 4 and 7 (POD 2, 3, 4, 7). SW033291 treated mice show significantly greater liver to body weight ratios versus control mice at all time points, with SW033291 treated mice having approximately 20% greater liver to body weight ratio on post-operative day 7 than control mice.

Figure 66:
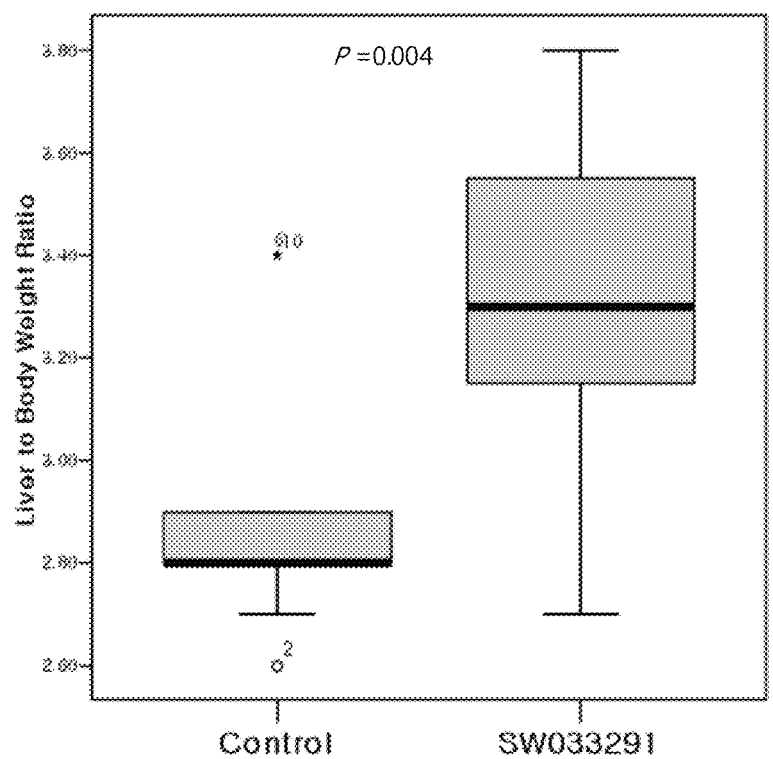
FIG. 66 illustrates a "box and whisker" plot comparing liver to body weight ratio following partial hepatectomy of SW033291 treated and control FVB mice at post-operative day 4.

FIG. 66 shows "box and whisker" plot comparing liver to body weight ratio's on post-operative day 4 following partial hepatectomy of FVB mice treated twice daily with SWO33291 5 mg/kg or with vehicle control, with 10 mice in each arm. Thick bars denote population median. Upper box margin denotes lower boundary of the highest quartile. Lower box margin denotes upper boundary of the lowest quartile. SW033291 treated mice show a significantly increased liver to body weight ratio at $P=0.004$.

Figure 67:
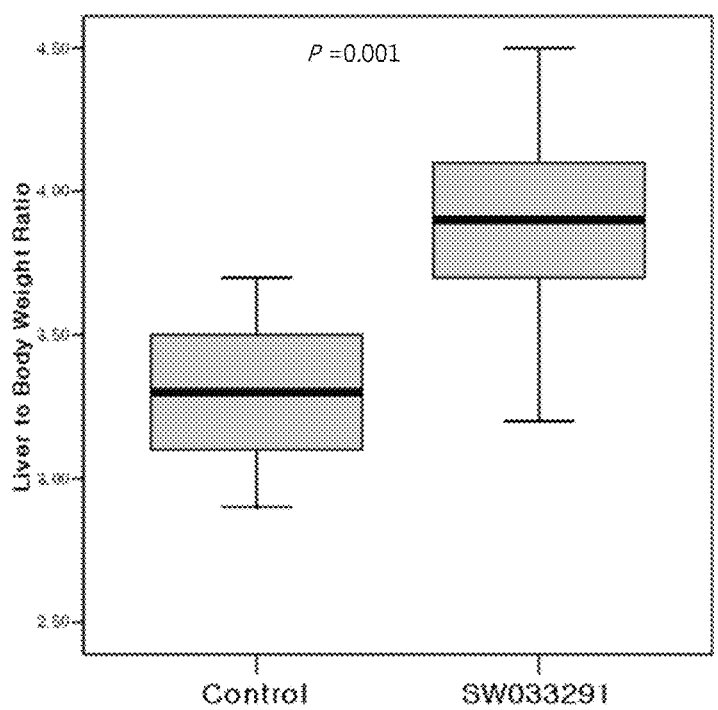
FIG. 67 illustrates a "box and whisker" plot comparing liver to body weight ratio following partial hepatectomy of SW033291 treated and control FVB mice at post-operative day 7.

FIG. 67 shows "box and whisker" plot comparing liver to body weight ratio's on post-operative day 7 following partial hepatectomy of FVB mice treated twice daily with SWO33291 5 mg/kg or with vehicle control, with 10 mice in each arm. Thick bars denote population median. Upper box margin denotes lower boundary of the highest quartile. Lower box margin denotes upper boundary of the lowest quartile. SW033291 treated mice show a significantly increased liver to body weight ratio at $P=0.001$.

Figure 68:
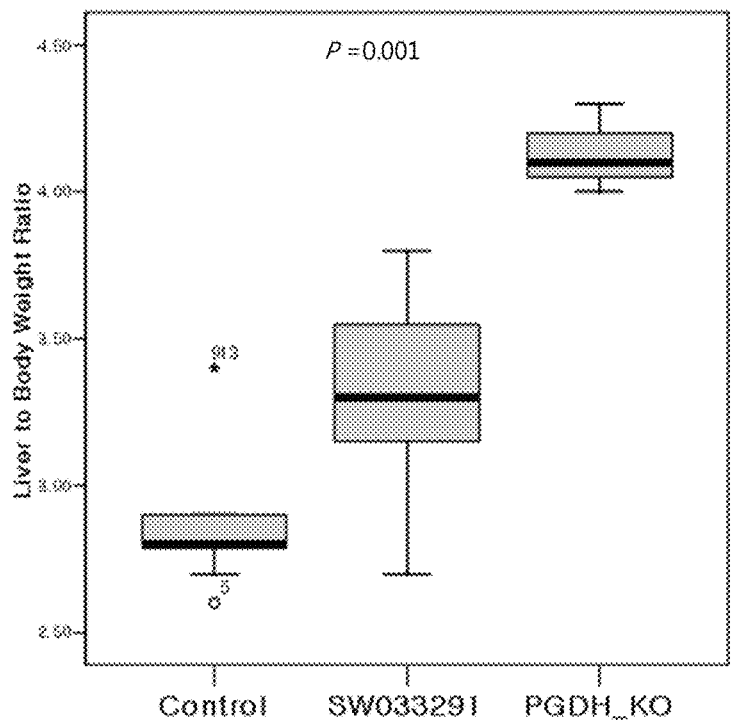
FIG. 68 illustrates a "box and whisker" plot comparing liver to body weight ratio following partial hepatectomy of SW033291 treated and control FVB mice at post-operative day 4.

FIG. 68 shows "box and whisker" plot comparing liver to body weight ratio's on post-operative day 4 following partial hepatectomy of FVB mice treated twice daily with SWO33291 5 mg/kg or with vehicle control, with 10 mice in each arm. Also shown is the liver to body weight ratio on post-operative day 4 of 15-PGDH knockout mice (PGDH-KO) treated with vehicle only. Thick bars denote population median. Upper box margin denotes lower boundary of the highest quartile. Lower box margin denotes upper boundary of the lowest quartile. SW033291 treated mice show a significantly increased liver to body weight ratio at $P=0.001$. 15-PGDH knockout mice also show greater a greater liver to body weight ratio than do vehicle treated 15-PGDH wild-type mice, supporting that the liver regeneration activity of SW033291 is mediated through inhibition of 15-PGDH. The larger effect of 15-PGDH gene knockout suggests further increase in effect of SW033291 may be attainable with additional modification of dosing schedule and delivery.

Figure 69:
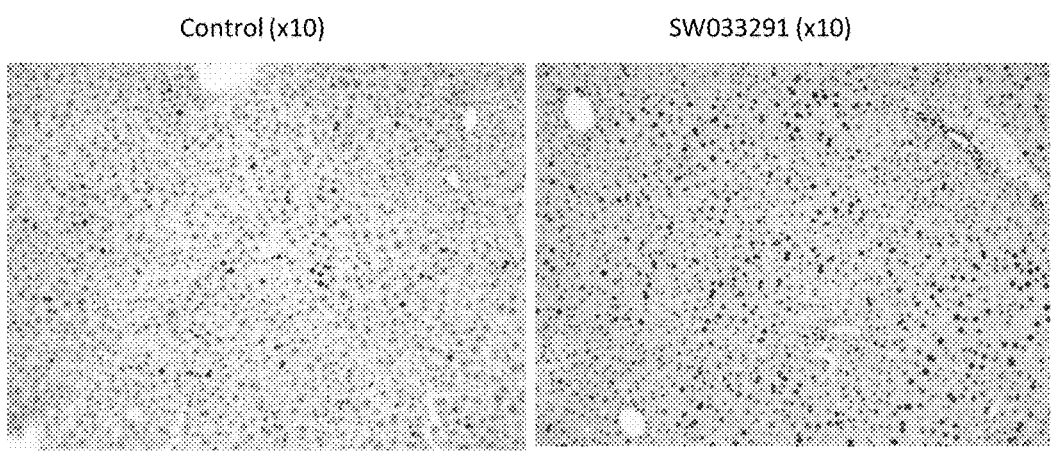
FIG. 69 illustrates photographs of S-phase cells following partial hepatectomy on post-operative day 2 in livers of SW033291 treated and vehicle treated control mice.

FIG. 69 shows visualization of S-phase cells following partial hepatectomy on post-operative day 2 in livers of SW033291 treated and vehicle treated control mice. Mice were injected with BrdU at 50 mg/kg IP 2 hours before sacrifice, and then S-phase cells were visualized by staining the livers with an antibody that detects BrdU that has been incorporated into DNA. Representative fields at 10× magnification show the clear increase in numbers of BrdU positive cells in the SW033291 treated liver.

Figure 70:
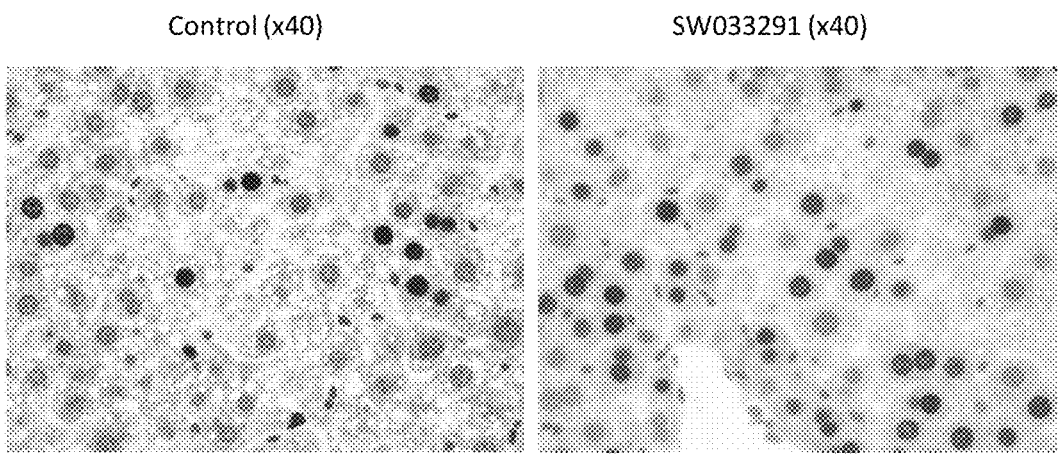
FIG. 70 illustrates a photograph showing high powered (40×) views of representative fields from the study of FIG. 69.

FIG. 70 shows high powered (40×) views of representative fields from the study of FIG. 69.

Figure 71:
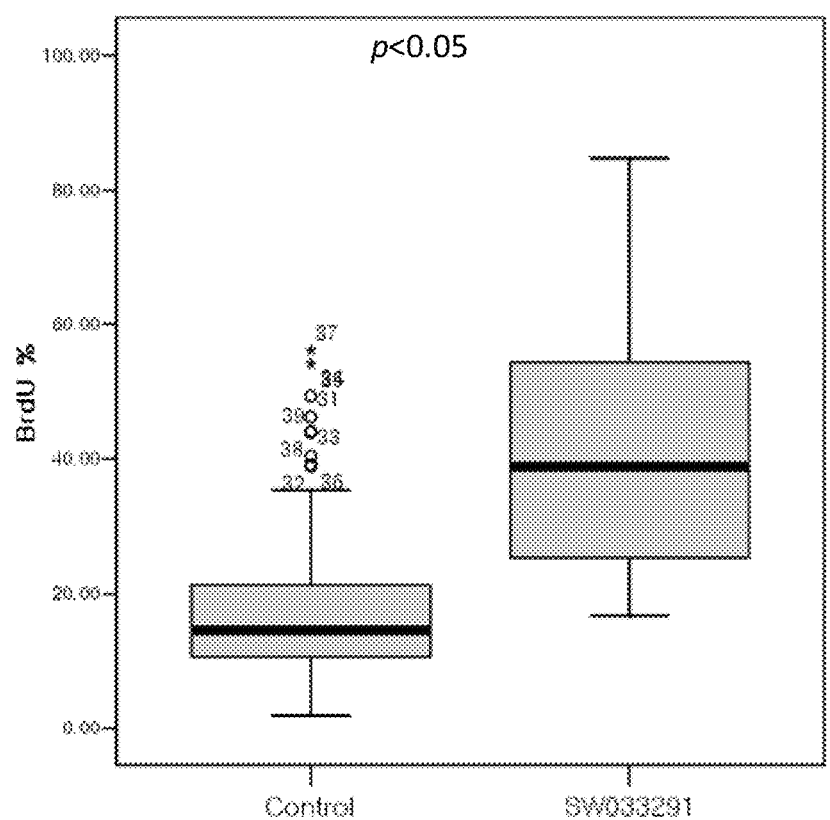
FIG. 71 illustrates a "box and whiskers" plot comparing percent of BrdU positive cells in livers of SW033291 treated versus vehicle control treated mice on post-operative day 2 following partial hepatectomy.

FIG. 71 shows "box and whiskers" plot comparing percent of BrdU positive cells in livers of SW033291 treated versus vehicle control treated mice on post-operative day 2 following partial hepatectomy. Plotted in each group are the percent BrdU positive cells from 100 random high powered fields (40× magnification) counted as 10 fields from each of 10 drug treated and each of 10 control vehicle treated mice. Heavy black bars show median values of each distribution. Upper box margin denotes lower boundary of the highest quartile. Lower box margin denotes upper boundary of the lowest quartile. SW033291 show a greater than 2-fold increase in median S-phase cells on post-operative day 2 ($P<0.05$).

Example 9

Analysis of Effect of SW033291 on Survival Following Acetaminophen (Tylenol) Overdose This Example provides data showing effects of SW033291 in mediating resistance to lethal doses of the liver toxin acetaminophen (Tylenol).

In the study, 11 week old female C57BL/6J mice are injected IP with a suspension of acetaminophen in phosphate buffered saline administered at the LD50 dose of 600 mg/kg.

Table 10 provides a tabular summary of the number of mice surviving out of an initial cohort of 6 mice that are all treated with acetaminophen (Tylenol) in phosphate buffered saline administered IP at the LD50 dose of 600 mg/kg.

TABLE 10

| Treatment | 0 hrs | 16 hr | 24 hrs | 40 hrs | 48 hrs | 64 hrs | 72 hrs | 88 hr | 96 hr | 112 hr | 120 hr |
|---|---|---|---|---|---|---|---|---|---|---|---|
| 1 does/daily, First dose immediately after Tylenol injection ||||||||||||
| Saline | 6 | 6 | 5 | 4 | 3 | 3 | 3 | 3 | 3 | 3 | 3 |
| 5 mg/kg SW033291 | 6 | 6 | 6 | 4 | 4 | 4 | 4 | 4 | 4 | 4 | 4 |
| 2 dose/daily, First dose immediately after Tylenol injection ||||||||||||
| Saline | 6 | 6 | 6 | 4 | 3 | 3 | 3 | 3 | 3 | 3 | 3 |
| 5 mg/kg SW033291 | 6 | 6 | 6 | 4 | 3 | 3 | 3 | 3 | 3 | 3 | 3 |

Test mice are additionally treated with SW033291 5 mg/kg IP in a vehicle of 10% Ethanol, 5% Cremophor EL, 85% D5W beginning immediately following acetaminophen and continued once daily, or twice daily. Control mice are additionally treated with vehicle alone once daily or twice daily. Survival is recorded from the 0 time point of administration of acetaminophen through 120 hours following. No difference is noted between survival of SW033291 treated and control mice.

Table 11 shows a summary of the number of mice surviving out of an initial cohort of 12 eleven week old C57BL/6J female mice that are all treated with acetaminophen (Tylenol) in phosphate buffered saline administered IP at the LD50 dose of 600 mg/kg, Mice are additionally treated with either SW033291 or vehicle control.

TABLE 11

| Survival | 0 hrs | 16 hr | 24 hrs | 40 hrs | 48 hrs | 64 hrs | 72 hrs | 88 hr | 96 hr | 112 hr | 120 hr |
|---|---|---|---|---|---|---|---|---|---|---|---|
| 5 mg/kg SW033291 | 12 | 12 | 12 | 11 | 10 | 10 | 10 | 10 | 10 | 10 | 10 |
| Saline | 12 | 12 | 12 | 6 | 5 | 5 | 5 | 5 | 5 | 5 | 5 |

SW033291 5 mg/kg was administered IP in a vehicle of 10% Ethanol, 5% Cremophor EL, 85% D5W twice daily (bid) beginning 48 hours prior to acetaminophen injection and continuing for 48 hours following acetaminophen injection for 9 doses total. At 120 hours post acetaminophen injection, 10 of 12 mice have survived in the SW033291 treated cohort versus 5 of 12 mice in the vehicle control treated cohort, P=0.045 in a one-tailed Fisher's exact test. Thus pre-administration of SW033291 protects from the lethal hepatotoxicity of acetaminophen.

Table 12 shows a summary of the number of mice surviving out of an initial cohort of 6 eleven week old C57BL/6J female mice that are treated with acetaminophen (Tylenol) in phosphate buffered saline administered IP at the LD50 dose of 600 mg/kg.

TABLE 12

| Survival | 0 hrs | 16 hr | 24 hrs | 40 hrs | 48 hrs | 64 hrs | 72 hrs | 88 hr | 96 hr | 112 hr | 120 hr |
|---|---|---|---|---|---|---|---|---|---|---|---|
| 5 mg/kg SW033291 | 6 | 6 | 5 | 4 | 3 | 3 | 3 | 3 | 3 | 3 | 3 |
| Saline | 6 | 6 | 5 | 3 | 2 | 2 | 2 | 2 | 2 | 2 | 2 |

Mice are additionally treated with either SW033291 or vehicle control. SW033291 5 mg/kg was administered IP in a vehicle of 10% Ethanol, 5% Cremophor EL, 85% D5W twice daily (bid) beginning 3 hours prior to acetaminophen injection and continuing at time 0 through 48 hours following acetaminophen injection for 6 total doses. At 120 hours post acetaminophen injection 3 of 6 mice have survived in the SW033291 treated cohort versus 2 of 6 mice in the vehicle control treated cohort.

Table 13 shows a summary of the number of mice surviving out of an initial cohort of 7 C57BL/6J 25 week old female 15-PGDH wild-type (WT) or 7 C57BL/6J 25 week old female 15-PGDH knockout (KO) mice treated with acetaminophen (Tylenol) in phosphate buffered saline administered IP at the LD50 dose of 600 mg/kg.

TABLE 13

| Survival | 0 hrs | 16 hr | 24 hrs | 40 hrs | 48 hrs | 64 hrs | 72 hrs | 88 hr | 96 hr | 112 hr | 120 hr |
|---|---|---|---|---|---|---|---|---|---|---|---|
| WT | 7 | 7 | 7 | 5 | 4 | 3 | 3 | 3 | 3 | 3 | 3 |
| KO | 7 | 7 | 7 | 6 | 6 | 6 | 6 | 6 | 6 | 6 | 6 |

At 120 hours post acetaminophen injection, 6 of 7 knockout mice survive versus 3 of 7 wild-type mice. Increased survival of 15-PGDH knockout mice is consistent with the survival benefit of SW033291 being mediated through inhibition of 15-PGDH.

Example 10

Analysis of Effect of SW033291 on Dextan Sodium Sulfate (DSS) Induced Colitis

This Example provides data from studies of the effect of SW033291 on prevention of induction of colitis in the dextran sodium sulfate (DSS) treated mouse. In the study, 8-12 week old FVB male mice are fed with 2% DSS in drinking water for days 1-7, and then switched to normal drinking water beginning on day 8, and continued through day 22. Mice are treated with twice daily SW033291 5 mg/kg IP in a vehicle of 10% Ethanol, 5% Cremophor EL, 85% D5W, at 125 ug/200 ul, versus with vehicle alone. Clinical scoring (body weight, rectal bleeding, stool consistency) is recorded daily, endoscopic scoring (ulcer number, mucosal thickening, and vascular pattern) is assessed on days 8, 11, 15. Mice are sacrificed on days 1, 8, 15 and 22 for assessment of colon length, colon weight, ulcer number, ulcer area, and crypt damage.

Table 14 shows summary of the baseline properties of age and weight of the 24 SW033291 treated mice and the 24 control group mice used in the study. Also provided is baseline characteristics of 4 FVB male 15-PGDH knockout (KO) mice that are used as a comparator group.

TABLE 14

| FVB PGDH WT/KO male mice 8-12 weeks old | | | | |
|---|---|---|---|---|
| DSS Study | WT-Control | WT-Treatment | KO | p-value |
| Number | 24 | 24 | 4 | |
| Sex | M | M | M | |
| Age (Days) | 74.1 ± 3.7 | 74.2 ± 4.0 | 73.9 ± 3.4 | 0.655 |
| Weight (gm) | 26.3 ± 1.19 | 26.8 ± 1.78 | 27.4 ± 1.4 | 0.391 |

Figure 72:
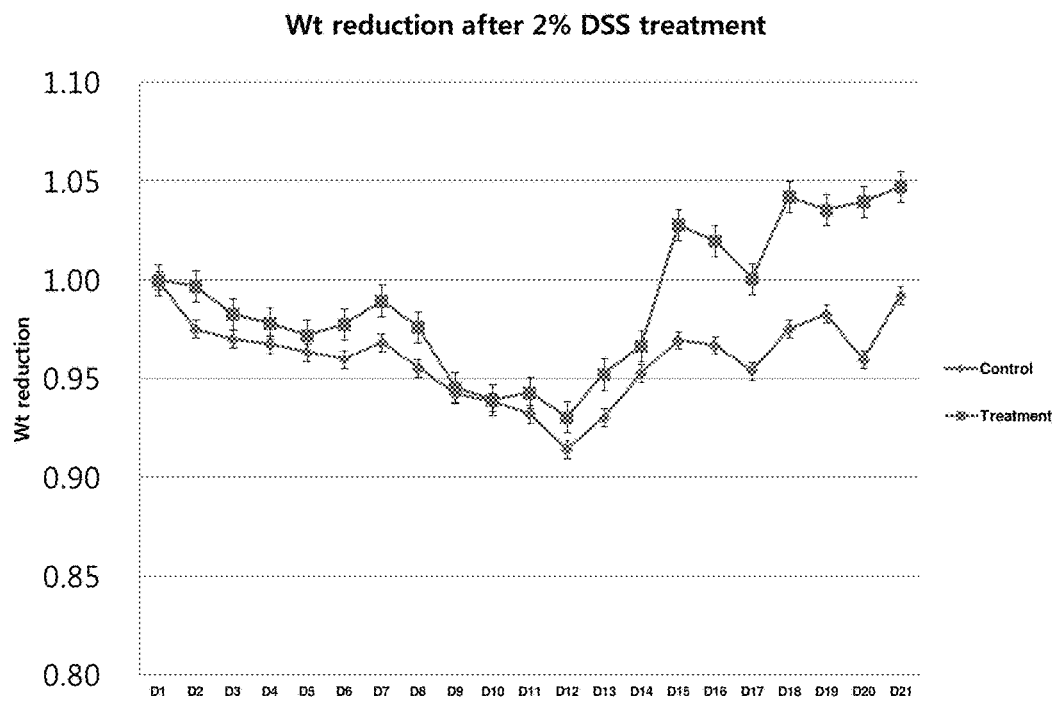
FIG. 72 illustrates a graph showing the average changes from baseline weight of the cohort of control versus SW033291 treated mice all treated with 2% dextran sulfate sodium (DSS) in the drinking water.

FIG. 72 shows a graph of the average changes from baseline weight of the cohort of control versus SW033291 treated mice across the 22 days of the study. SW033291 treated mice show greater weight at all time points, and in particular, show faster weight gain after washout of DSS then do the control mice, P=0.001.

Figure 73:
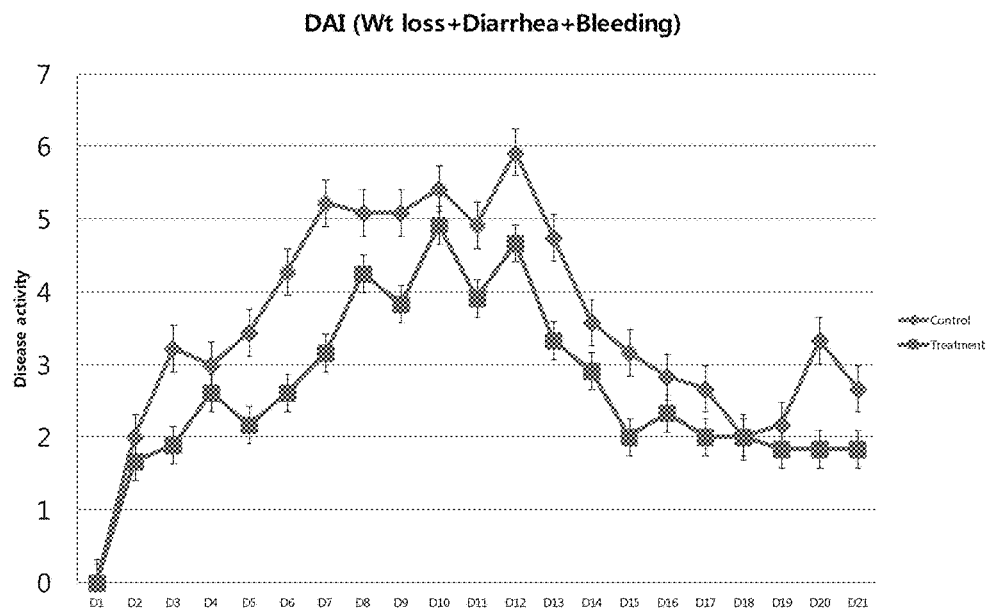
FIG. 73 illustrates a graph of the daily disease activity index of the cohort of control versus SW033291 treated mice all treated with 2% DSS in the drinking water.

FIG. 73 shows a graph of the daily Disease Activity Index (DAI) of the cohort of control versus SW033291 treated mice across the 22 days of the study. The Disease Activity Index is calculated as an equally weighted average of the change from baseline weight, the consistency of stool, and the presence of rectal bleeding, with each component normalized to span an identical numerical range. SW033291 treated mice show a lower Disease Activity Index than do control on each day of the study, P<0.001.

Figure 74:
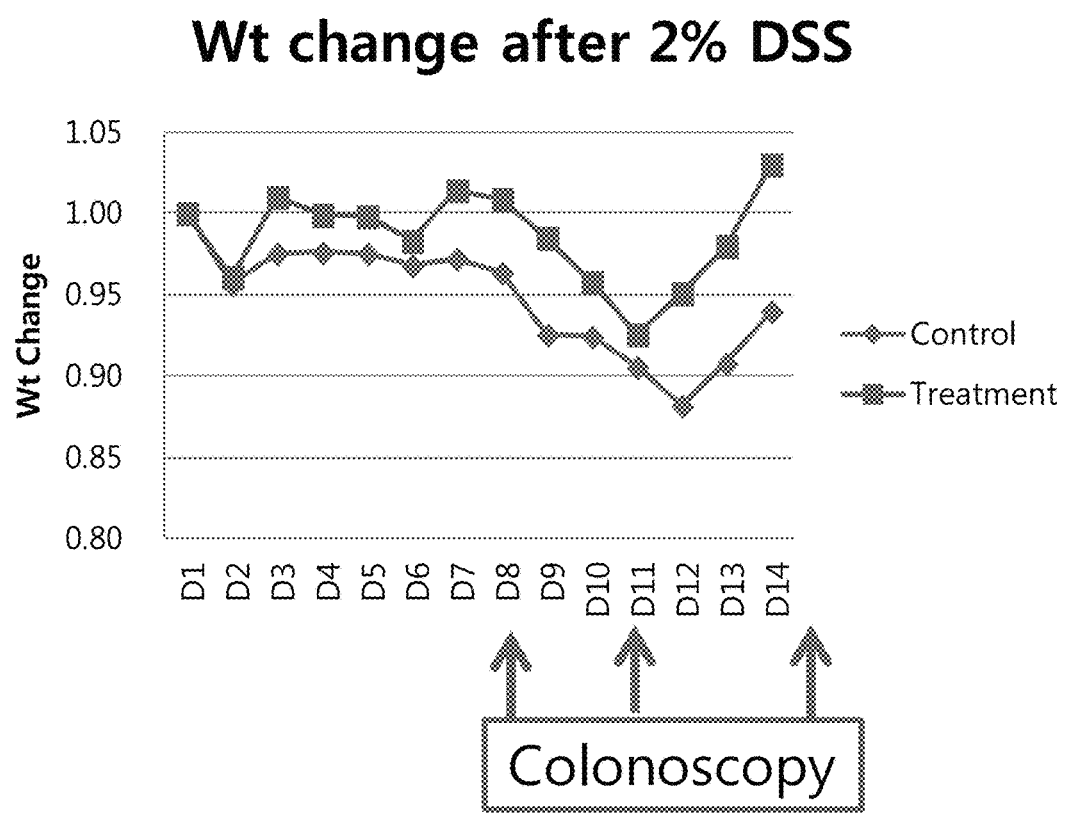
FIG. 74 illustrates a graph showing the average changes from baseline weight of the cohort of DSS treated mice receiving a control vehicle versus SW033291.

FIG. 74 shows the design of the study in which colonoscopic examination of the left colon, up to the splenic flexure, was performed on live mice on days 8, 11 and 15, under isoflurane anesthesia. In addition, post-mortem colonoscopy of the full colon was performed on two SW033291 treated and two control treated mice on day 15, with findings confirming that DSS induced ulcerations are largely confined to the descending colon distal to the splenic flexure.

Figure 75:
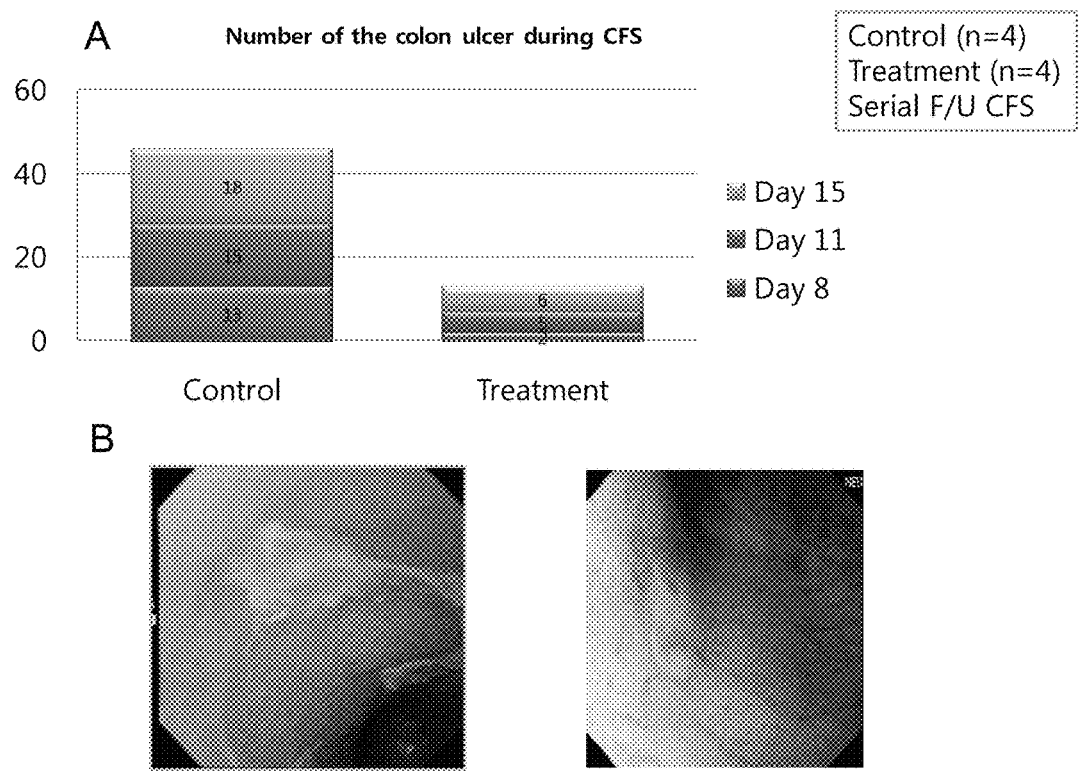
FIGS. 75(A-B) illustrates: (A) a graph showing the number of ulcers in a colon of DSS treated mice receiving a control vehicle versus SW033291; and (B) photographs showing ulcers of DSS treated mice receiving control (left) or SW033291 (right).

FIGS. 75(A-B) show at bottom left the colon as visualized during colonoscopy of a DSS treated control mouse that shows loss of the mucosal vascular pattern and a gross ulceration. At bottom right is shown the colonoscopic findings of a DSS treated mouse receiving SW033291, with only a small ulcer and with maintenance of the normal mucosal vascular pattern otherwise. Graph at top shows numbers of ulcers present on days 8, 11, and 15 in the control versus SW033291 treated mice. SW033291 treatment prevents two-thirds of ulcer formation. Additional studies of 15-PGDH knockout mice show that 15-PGDH gene knockout prevents 95% of colon ulcer formation. These findings support that the colitis prevention activity of SW033291 is mediated through its activity as a 15-PGDH inhibitor, and suggest further modifications of drug dosing and delivery may provide added colitis prevention.

Figure 76:
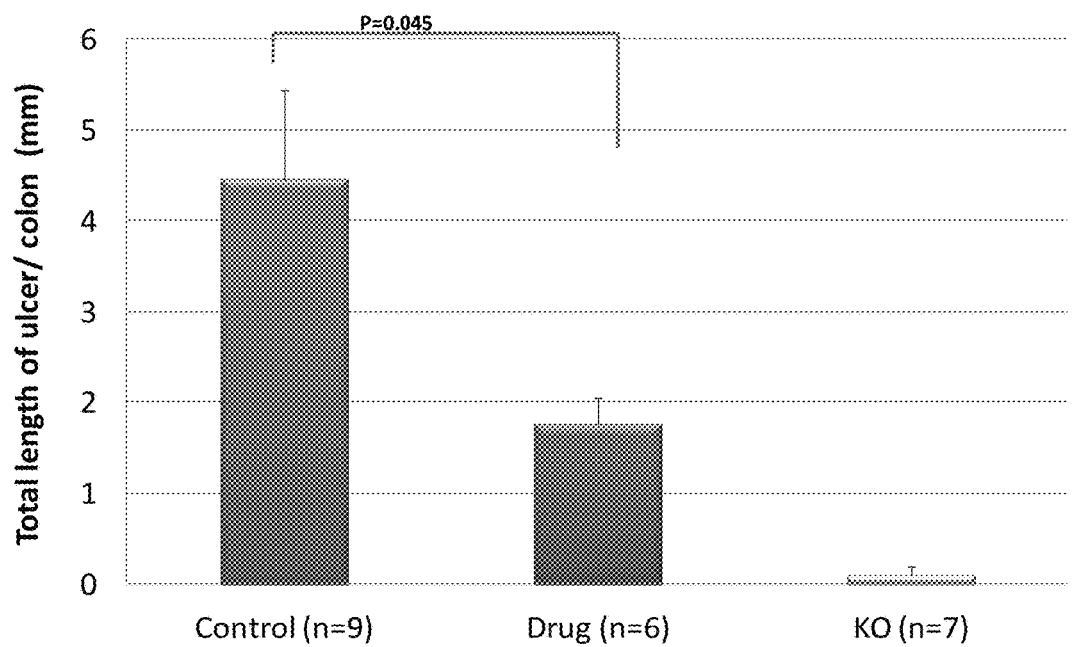
FIG. 76 illustrates a graph showing quantitation of ulcer burden on day 15 of DSS treated mice.

FIG. 76 shows quantitation of ulcer burden on day 15 of DSS treated mice as determined by embedding the full length of the formalin fixed colons of mice in paraffin blocks, and then microscopic inspection of a random 5 μm section along the full colon length for visualization and measurement of ulcerated mucosa. The graph shows that the average length of ulcerated mucosa is 4.48 mm per colon section in control mice (N=9 mice) and is reduced by 61% to a length of 1.74 mm per colon section in SW033291 (drug) treated mice (N=6 mice), P=0.045. Again, 15-PGDH gene knockout (KO) is highly effective in preventing colon ulceration, supporting that the therapeutic effect of SW033291 is mediated through inhibition of 15-PGDH.

FIGS. 77(A-B) shows examples of scoring murine colonic mucosa according to the Murine Endoscopic Index of Colitis Severity (MEICS) (Becker C. et al. Gut 2005; 54: 950-954). At top (A) is shown the colonoscopic findings and MEICS scoring for a DSS treated mouse receiving SW033291. At bottom (B) is shown the colonoscopic findings and MEICS scoring of a DSS treated mouse receiving vehicle only.

Figure 78:
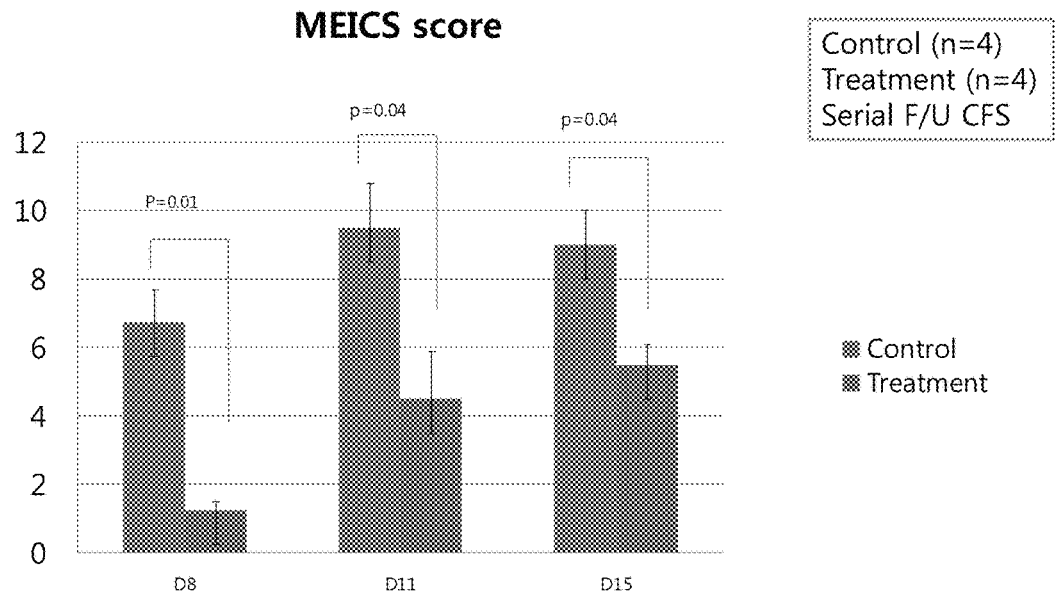
FIG. 78 illustrates a graph showing MEICS score of DSS treated mice receiving a control vehicle or SW033291.

FIG. 78 shows graphs of the MEICS scores for DSS treated mice receiving SW033291 (treatment) versus vehicle (control). MEICS scores show significantly less colitis activity in SW033291 treated mice on days 8, 11 and 15 of the study.

In addition to the gross visual inspection and scoring of colitis activity by the MEICS index, full length colons of mice were formalin fixed and paraffin embedded, and microscopic scoring of crypt damage was performed using the 0-4 severity scale of Cooper H S. Et al., Lab Invest. 1993; 69:238-249. For this analysis, the colons were divided into 3 segments of proximal, middle, and distal colon, each approximately 1.6 cm in length, with each segment was further subdivided into 4 sections each approximately 4 mm in length. For each section the crypt damage severity score was multiplied by the length in mm of the damaged area, creating a 0-16 cryptitis severity index. An average cryptitis severity index was calculated for each segment (proximal, middle, and distal colon), and the summed whole colon cryptitis severity index was determined on a scale of 0-48 for each mouse colon. In parallel with the visual MEICS score, the microscopic cryptitis severity index on day 8 of the DSS protocol was significantly greater in control mice (value of 9.49) than in the SW033291 treated mice (value of 3.16), P<0.05 (data described but not shown in the figure).

Figure 79:
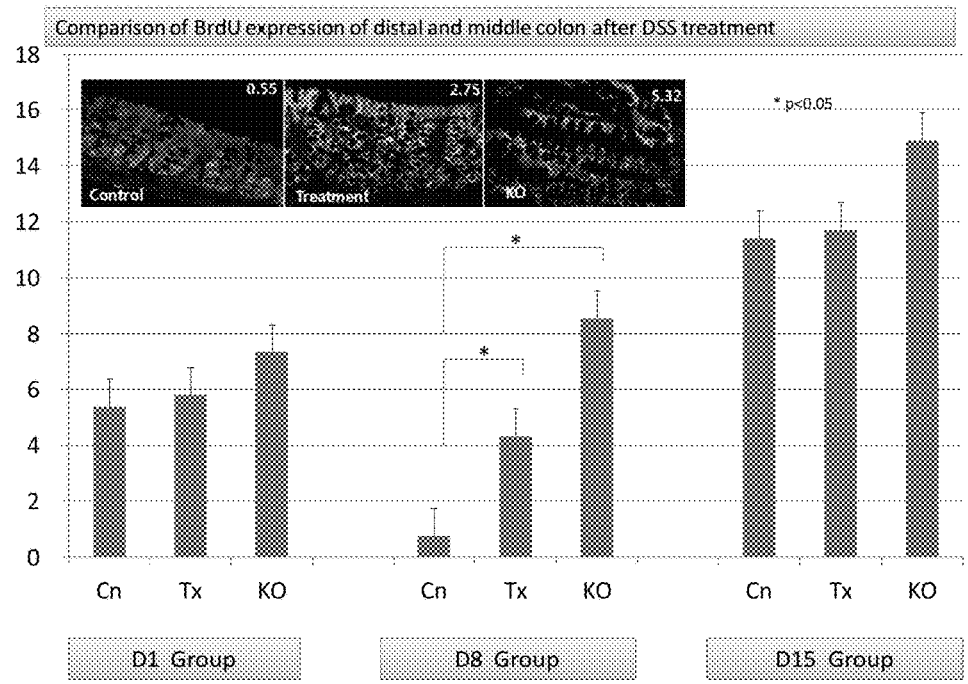
FIG. 79 illustrates photomicrographs of high powered fields from the mid-colon on day 8 of the DSS protocol from control mice, SW033291 treated mice (treatment) and 15-PGDH knockout mice (KO) and a graph depicting sum of the average number of BrdU positive cells per crypt in the distal plus middle colons of control (Cn), SW033219 treated mice (Tx), and 15-PGDH knockout mice (KO) on day 1, day 8, and day 15 of the DSS treatment protocol.

FIG. 79 shows assessment of the effect of SW033291 on maintaining DNA synthesis in the colonic mucosa of DSS treated mice. Mice were injected with BrdU at 100 mg/kg IP 3 hours before sacrifice and then full length colons were formalin fixed and embedded in paraffin. S-phase cells, that have incorporated BrdU into DNA, were visualized by immuno-fluorescent staining of 5 um thick sections with an antibody that detects the BrdU. Colonic crypts were visualized by immuno-fluorescent staining with an antibody to the epithelial marker E-Cadherin. Photographic insets show photomicrographs of high powered fields taken from the mid-colon on day 8 of the DSS protocol from control mice, SW033291 treated mice (treatment) and 15-PGDH knockout mice (KO). Red immune-fluorescence identifies BrdU positive nuclei, and green immune-fluorescence identifies E-Cadherin positive colonocytes. The number of BrdU positive cell per crypt is determined by counting the number of dual labeled red and green cells per average crypt. Green only cells that are not in S-phase are not counted, and red only cells, that are likely stromal cells outside of crypts, are also not counted. On the photomicrograph shown crypts are displayed as vertically oriented in control and SW033291 treated mice, and crypts are displayed as horizontally oriented in the 15-PGDH knockout mice. In the photographs the numbers of S-phase cells are fewest in the control mice and are increased in the SW033291 treated mice, and increased further in the knockout mice. In the particular photographs shown, the crypts from control mice both lack S-phase cells and are also visually decreased in height; whereas, crypt height is increased in the crypts shown from SW033291 treated mice, and crypt heights is increased further in the crypts shown from 15-PGDH knockout mice. The graph depicts the sum of the average number of BrdU positive cells per crypt in the distal colon plus the average number of BrdU positive cells per crypt middle colons of control (Cn), SW033219 treated (Tx), and 15-PGDH knockout mice (KO) on day 1, day 8, and day 15 of the DSS treatment protocol. On day 8, SW033291 treated mice demonstrate 5.7-fold greater numbers of BrdU positive cells than do control mice, which have lost 85% of the day 1 value of BrdU positive cells per crypt. 15-PGDH knockout mice show no loss of BrdU positive cells in the crypt on day 8, consistent with the protective effect of SW033291 being mediated by inhibition of 15-PGDH.

Table 15 shows a summary of colon length (in cm) in DSS treated mice sacrificed on days 8, 15 and 22, in SW033291 treated mice, versus vehicle treated control mice, versus 15-PGDH knockout (KO) mice, where shortening of the colon is a measure of disease activity.

TABLE 15

Colon length shortening may be correlated to severity of the colon ulceration

| Time Point | Control | SW033291 | KO | P-value |
|---|---|---|---|---|
| Baseline | 8.3 + 0.2 | 8.4 + 0.2 | | 0.71 |
| Day 8 | 6.6 + 0.4 | 6.6 + 0.1 | | 1.0 |
| Day 15 | 7.1 + 0.1 | 7.5 + 0.1 | 8.5 + 0.1 | 0.001 |
| Day 22 | 7.4 + 0.2 | 8.6 + 0.3 | | 0.012 |

Figure 80:
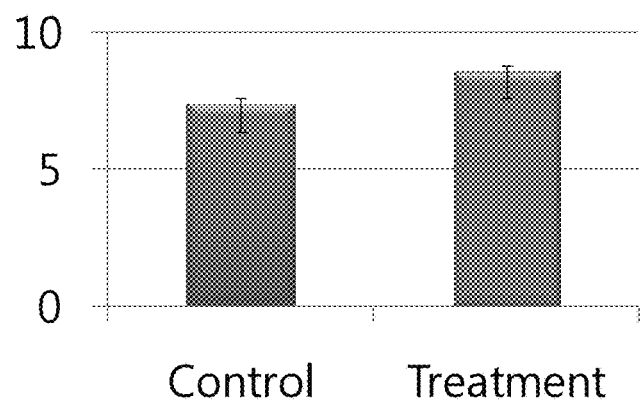
FIG. 80 illustrates a graph showing colon length at day 22 of DSS treated mice receiving a control vehicle or SW033291.

Vehicle treated control mice show significantly greater colon shortening at day 22 versus SW033291 treated mice, P=0.012. This comparison is also shown graphically in FIG. 80.

Table 16 shows a summary on day of sacrifice of mouse weights (gms) and colon lengths (cm) for DSS treated mice receiving SW033291 or vehicle control.

TABLE 16

| | Vehicle | SW033291 | KO |
|---|---|---|---|
| Wt @ sacrifice-gm Time Point | | | |
| Baseline | 26.3 + 0.7 | 25.9 + 0.7 | 29.2 + 1.3 |
| Day 8 | 25.4 + 0.7 | 26.4 + 0.5 | |
| Day 15 | 24.4 + 0.5 | 25.2 + 0.9 | |
| Day 22 * | 26.3 + 0.7 | 28.2 + 0.5 | |
| Colon length-cm Time Point | | | |
| Baseline | 8.3 + 0.2 | 8.4 + 0.2 | 8.5 + 0.1 |
| Day 8 | 6.6 + 0.4 | 6.6 + 0.1 | |
| Day 15 | 7.1 + 0.1 | 7.5 + 0.1 | |
| Day 22 * | 7.4 + 0.2 | 8.6 + 0.3 | |

On day 22 SW033291 treated mice show greater body weight and greater colon lengths, indicative of therapeutic effect of SW033291 in protecting against DSS induced colitis.

Example 11: Analysis of Analogues of Lead Compound SW054384, a 15-PGDH Activator This Example provides data on a group of structural analogues of SW054384. Data on Table 17 characterize analogues obtained by Case Western Reserve University from a chemical library shared with the University of Cincinnati. Data on Table 18 are analogues ordered from commercial sources. Data on Table 19 are analogues held in chemical libraries or synthesized by members of the inventors group at University of Texas Southwestern.

TABLE 17

| Structures | Name | V9M reporter activity (2.5 µM) | V9M reporter activity (7.5 µM) | LS174T reporter activity (2.5 µM) | 1S174T reporter activity (7.5 µM) | V503 reporter activity (2.5 µM) | V503 reporter activity (7.5 µM) |
|---|---|---|---|---|---|---|---|
| 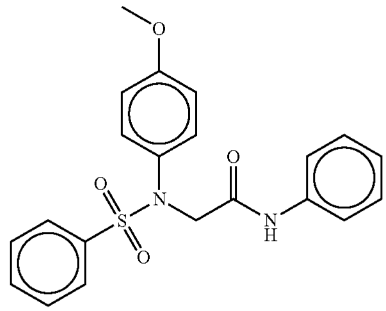 | 292301 | 12.92 | 23.57 | 12.07 | −3.67 | −0.91 | −3.60 |
| 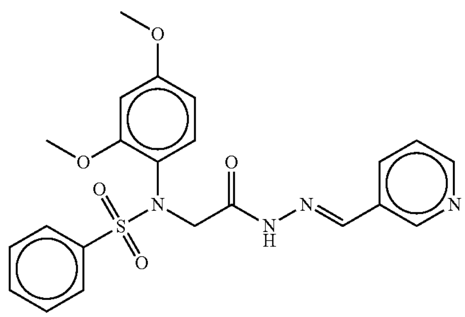 | 396087 | −8.51 | 10.08 | 4.37 | 10.18 | 17.23 | 30.79 |
| 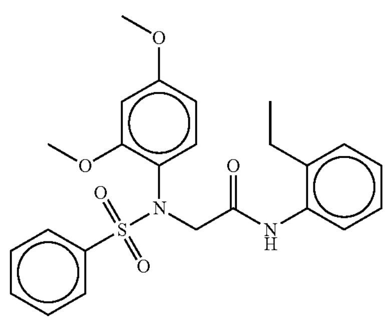 | 407572 | −8.45 | −6.12 | 2.22 | 6.94 | 17.22 | 35.88 |
| 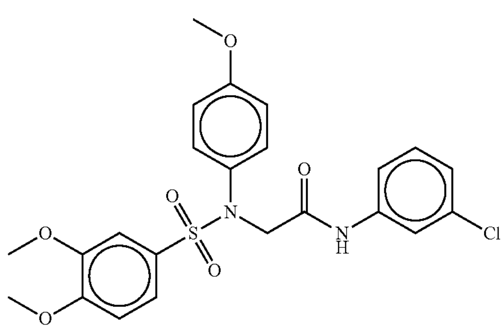 | 408961 | −12.39 | 0.56 | 2.46 | −4.51 | 11.71 | 17.61 |

TABLE 17-continued
| Structures | Name | V9M reporter activity (2.5 μM) | V9M reporter activity (7.5 μM) | LS174T reporter activity (2.5 μM) | 1S174T reporter activity (7.5 μM) | V503 reporter activity (2.5 μM) | V503 reporter activity (7.5 μM) |
|---|---|---|---|---|---|---|---|
| 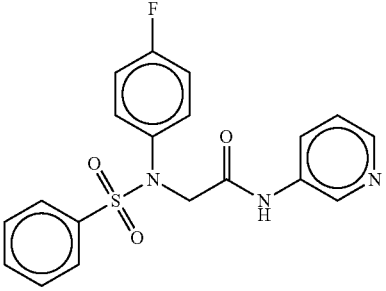 | 414177 | 10.61 | 7.72 | 9.51 | −0.62 | −2.80 | −5.73 |
| 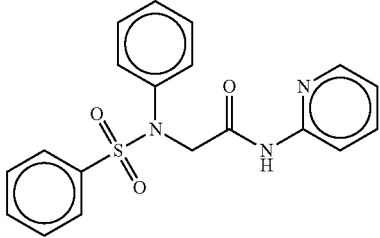 | 414183 | −9.15 | −3.89 | 5.35 | −4.77 | 11.49 | 37.17 |
| 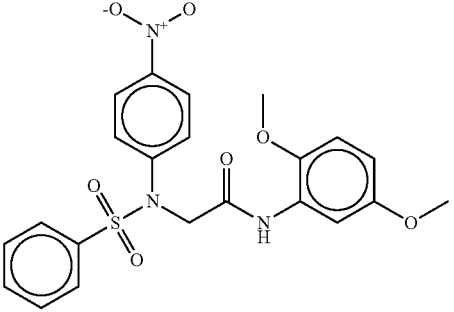 | 414195 | −13.95 | −16.76 | −1.15 | 2.34 | 13.14 | 19.47 |
| 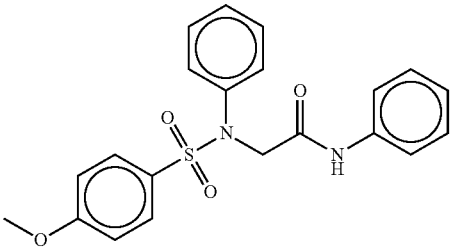 | 474738 | −7.27 | 3.48 | −0.36 | 3.50 | 17.03 | 24.59 |
| 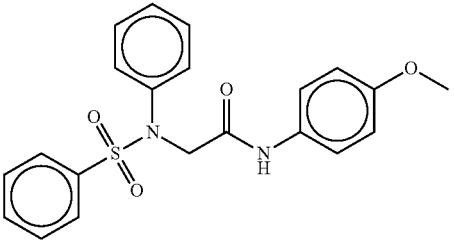 | 474759 | 2.58 | 6.40 | 5.54 | −0.03 | −5.04 | −12.72 |

TABLE 17-continued
| Structures | Name | V9M reporter activity (2.5 μM) | V9M reporter activity (7.5 μM) | LS174T reporter activity (2.5 μM) | lS174T reporter activity (7.5 μM) | V503 reporter activity (2.5 μM) | V503 reporter activity (7.5 μM) |
|---|---|---|---|---|---|---|---|
| 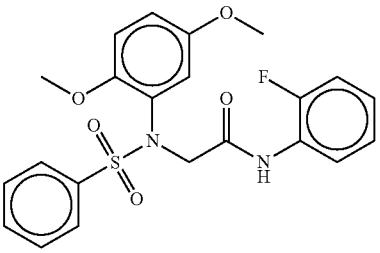 | 503270 | −4.47 | 24.06 | 12.29 | 32.82 | 29.88 | 42.14 |
| 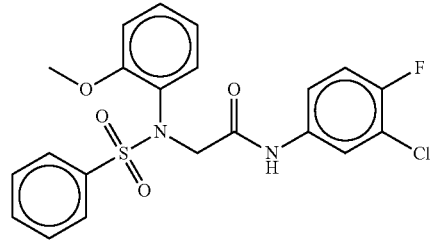 | 537833 | −7.54 | −7.44 | 4.94 | 9.04 | 42.31 | 73.22 |
| 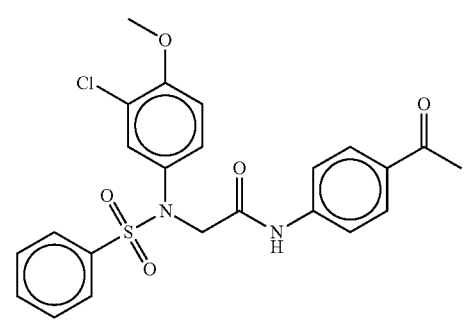 | 539430 | 21.27 | 21.35 | 5.62 | 10.45 | 38.75 | 103.04 |
| 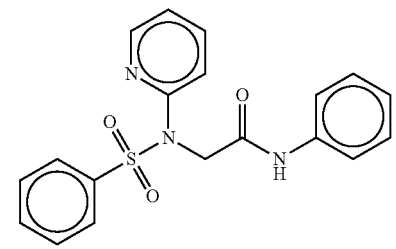 | 543512 | 36.82 | 79.64 | 18.05 | 8.33 | −4.56 | −4.26 |
| 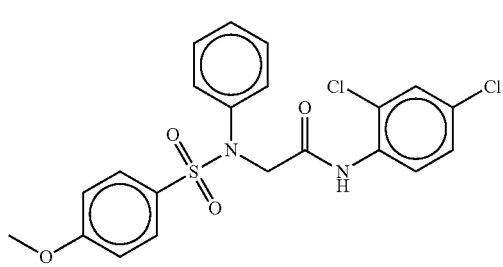 | 543716 | 4.20 | −0.14 | 3.26 | −2.08 | −8.04 | −8.60 |

TABLE 17-continued

| Structures | Name | V9M reporter activity (2.5 µM) | V9M reporter activity (7.5 µM) | LS174T reporter activity (2.5 µM) | 1S174T reporter activity (7.5 µM) | V503 reporter activity (2.5 µM) | V503 reporter activity (7.5 µM) |
|---|---|---|---|---|---|---|---|
| 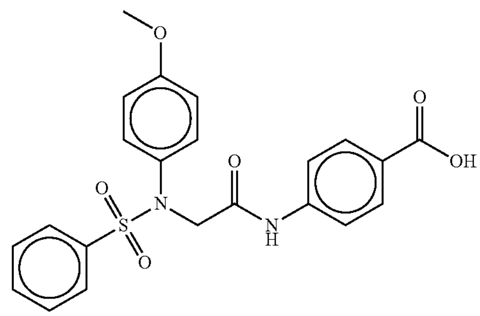 | 742790 | 13.79 | 23.09 | 12.77 | 17.32 | 5.94 | 34.38 |
| 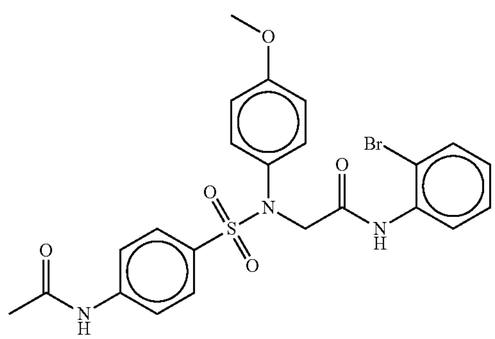 | 771064 | 43.32 | −19.19 | −2.11 | −29.63 | −13.75 | −24.80 |
| 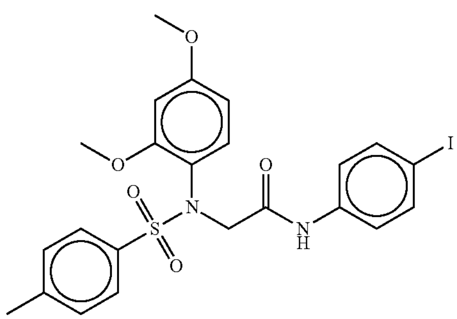 | 771069 | −22.56 | −54.66 | −29.88 | −82.88 | −62.71 | −90.88 |
| 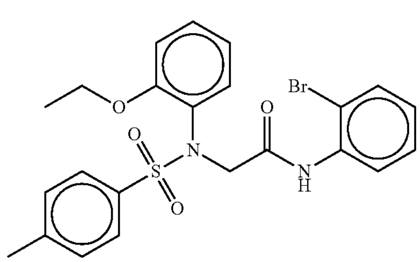 | 771074 | 13.50 | 24.69 | 20.67 | 20.60 | 22.96 | 39.52 |
| 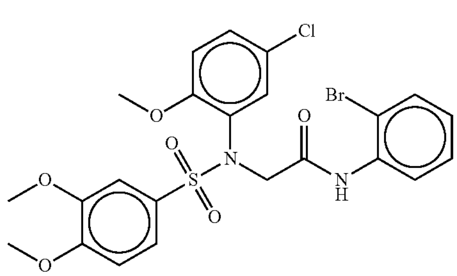 | 771081 | −14.22 | 7.58 | 5.74 | 15.38 | 31.87 | 51.68 |

TABLE 17-continued

| Structures | Name | V9M reporter activity (2.5 μM) | V9M reporter activity (7.5 μM) | LS174T reporter activity (2.5 μM) | 1S174T reporter activity (7.5 μM) | V503 reporter activity (2.5 μM) | V503 reporter activity (7.5 μM) |
|---|---|---|---|---|---|---|---|
| 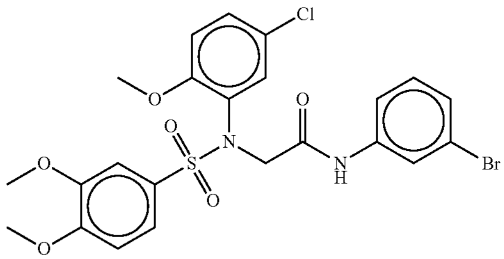 | 771130 | 8.67 | 5.84 | 8.66 | −0.48 | −10.19 | −3.48 |
| 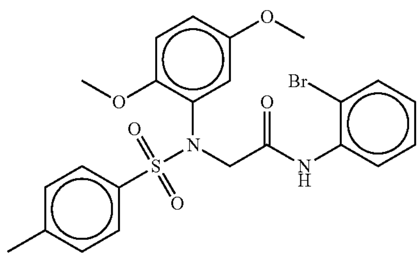 | 771132 | −2.26 | 12.24 | 13.98 | 13.54 | 24.75 | 40.76 |
| 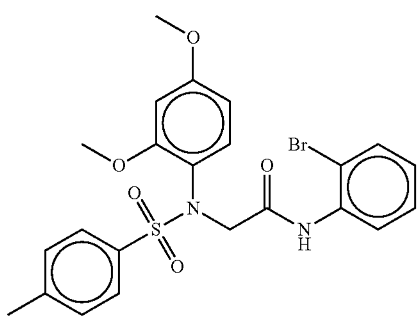 | 771138 | −4.36 | 6.75 | 13.64 | 9.23 | 34.44 | 72.58 |
| 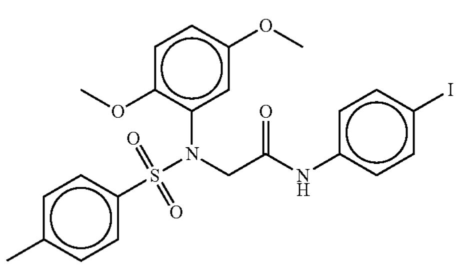 | 771146 | −38.07 | −78.30 | −31.58 | −68.78 | −49.73 | −86.60 |
| 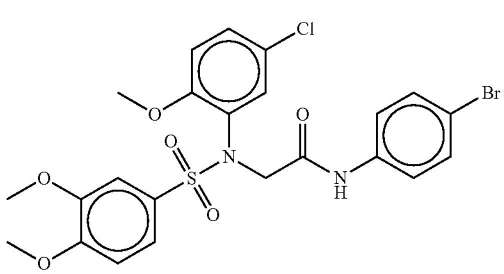 | 771432 | −7.11 | −3.13 | 3.86 | 4.24 | 33.72 | 42.82 |

TABLE 17-continued

| Structures | Name | V9M reporter activity (2.5 μM) | V9M reporter activity (7.5 μM) | LS174T reporter activity (2.5 μM) | 1S174T reporter activity (7.5 μM) | V503 reporter activity (2.5 μM) | V503 reporter activity (7.5 μM) |
|---|---|---|---|---|---|---|---|
| 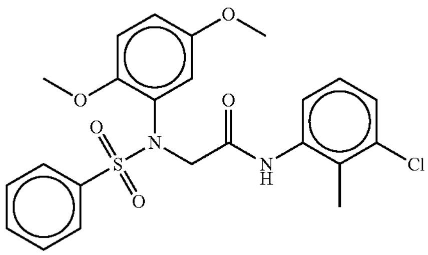 | 785160 | −15.99 | 21.00 | 5.93 | 48.64 | 33.85 | 44.75 |
| 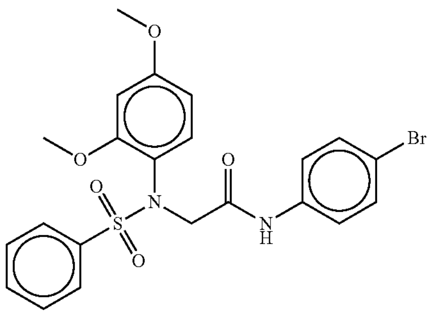 | 785161 | 0.54 | 3.48 | 10.68 | −41.92 | 56.72 | −52.51 |
| 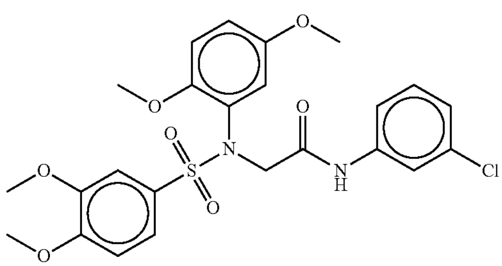 | 785254 | −16.05 | −8.48 | 2.93 | 4.29 | 16.14 | 28.28 |
| 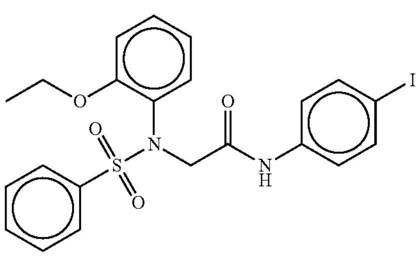 | 918280 | −16.26 | −77.26 | −21.21 | −72.09 | −35.68 | −74.96 |
| 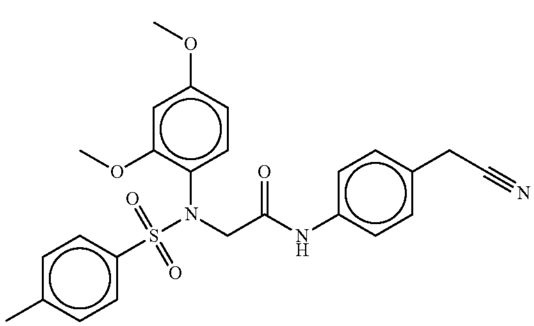 | 919570 | 87.71 | 127.26 | 78.80 | 102.68 | 80.94 | 104.40 |

TABLE 17-continued

| Structures | Name | V9M reporter activity (2.5 μM) | V9M reporter activity (7.5 μM) | LS174T reporter activity (2.5 μM) | lS174T reporter activity (7.5 μM) | V503 reporter activity (2.5 μM) | V503 reporter activity (7.5 μM) |
|---|---|---|---|---|---|---|---|
| 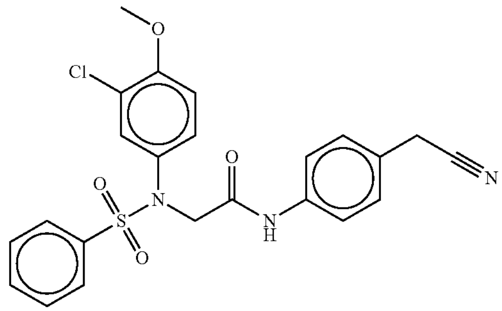 | 919576 | 49.89 | 63.03 | 17.49 | 30.74 | 49.20 | 73.74 |
| 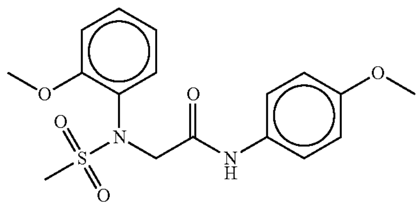 | 920847 | 9.26 | 17.73 | 6.18 | 2.97 | -4.47 | -10.57 |
| 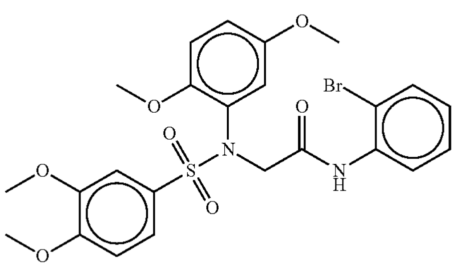 | 924740 | -0.54 | 6.33 | 7.69 | 16.73 | 20.16 | 52.17 |
| 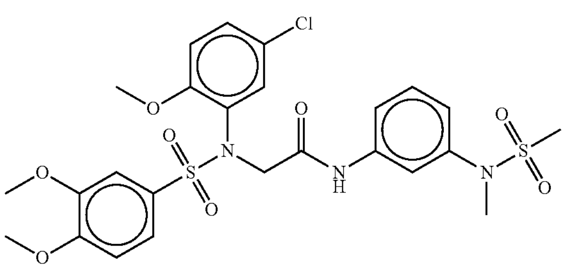 | 924787 | -1.45 | 18.08 | 4.32 | 13.10 | 21.87 | 47.97 |
| 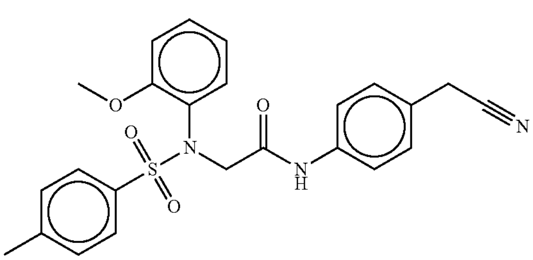 | 928861 | 64.65 | 134.49 | 74.89 | 124.37 | 73.17 | 138.59 |

TABLE 17-continued

| Structures | Name | V9M reporter activity (2.5 μM) | V9M reporter activity (7.5 μM) | LS174T reporter activity (2.5 μM) | 1S174T reporter activity (7.5 μM) | V503 reporter activity (2.5 μM) | V503 reporter activity (7.5 μM) |
|---|---|---|---|---|---|---|---|
| 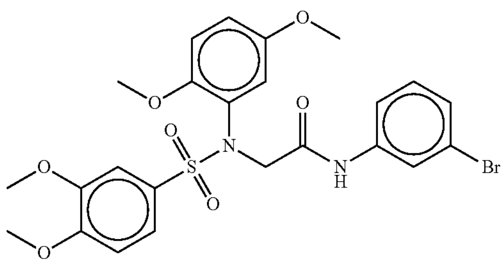 | 939417 | −11.15 | −9.81 | 6.50 | −1.64 | 12.58 | 16.25 |
| 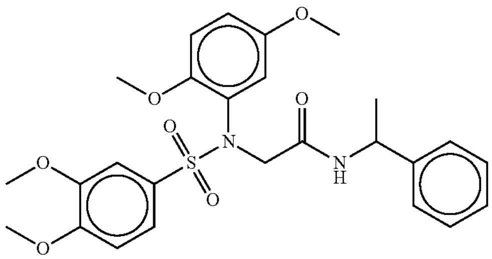 | 967134 | −10.12 | −2.64 | 5.11 | 5.73 | 18.43 | 36.12 |
| 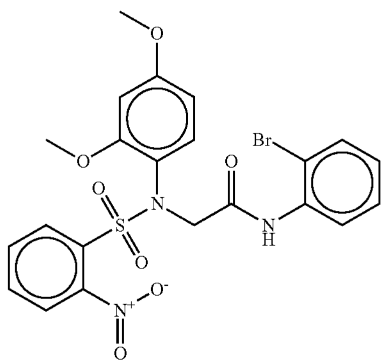 | 1002065 | 7.38 | 18.64 | 9.90 | 15.22 | 38.12 | 52.53 |
| 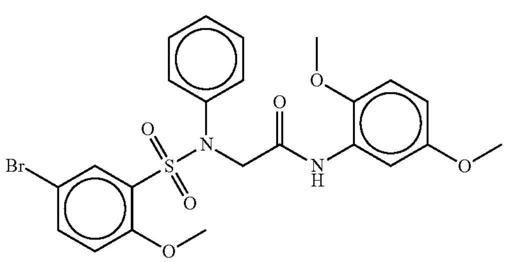 | 1002654 | −2.58 | −3.96 | 5.51 | −1.24 | 0.78 | 19.23 |
| 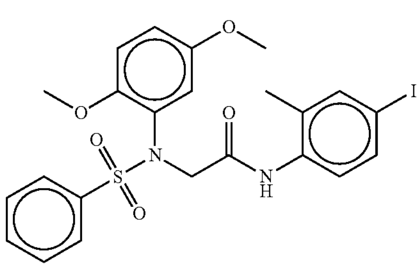 | 1003012 | −10.45 | −0.90 | 5.54 | 19.77 | 34.43 | 58.54 |

TABLE 17-continued
| Structures | Name | V9M reporter activity (2.5 µM) | V9M reporter activity (7.5 µM) | LS174T reporter activity (2.5 µM) | 1S174T reporter activity (7.5 µM) | V503 reporter activity (2.5 µM) | V503 reporter activity (7.5 µM) |
|---|---|---|---|---|---|---|---|
| 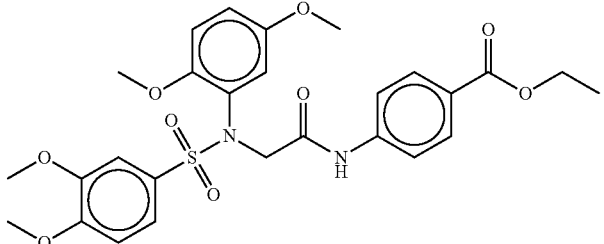 | 1003132 | −5.60 | −0.21 | 5.16 | 1.73 | 15.40 | 16.05 |
| 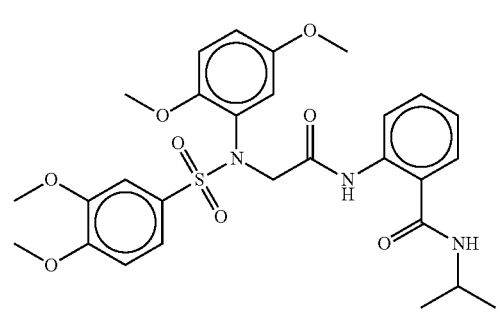 | 1003378 | −4.42 | −3.27 | 7.30 | 1.27 | 7.23 | 16.73 |
| 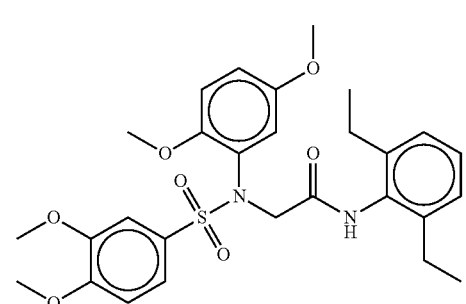 | 1003429 | 12.60 | 4.17 | 8.82 | −6.88 | −7.46 | −19.23 |
| 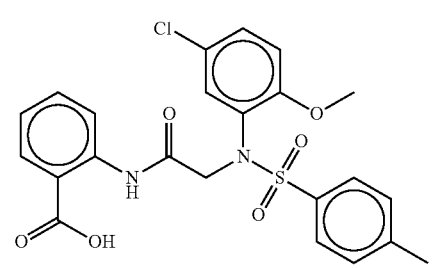 | 1003669 | 6.30 | 7.58 | 5.98 | −1.93 | 1.22 | 27.08 |
| 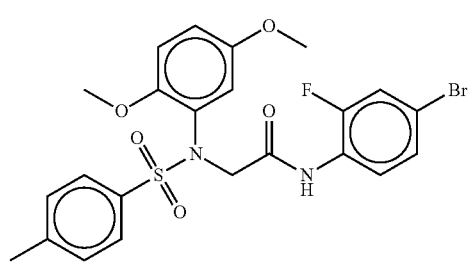 | 1004292 | 0.88 | −0.21 | 20.34 | 0.14 | 23.50 | 21.16 |

TABLE 17-continued

| Structures | Name | V9M reporter activity (2.5 μM) | V9M reporter activity (7.5 μM) | LS174T reporter activity (2.5 μM) | 1S174T reporter activity (7.5 μM) | V503 reporter activity (2.5 μM) | V503 reporter activity (7.5 μM) |
|---|---|---|---|---|---|---|---|
| 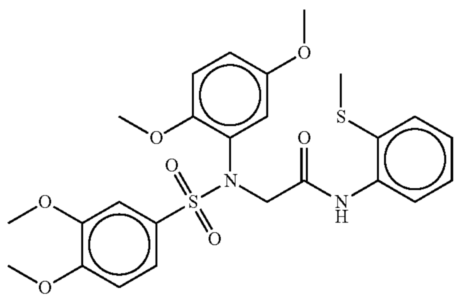 | 1004571 | −6.09 | 10.99 | 12.35 | 29.28 | 29.09 | 85.80 |
| 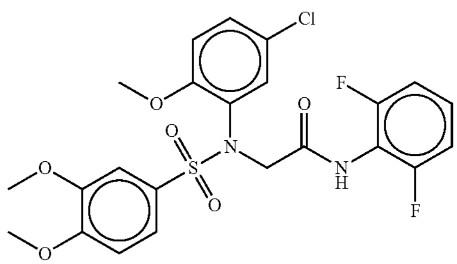 | 1004631 | −3.66 | 12.03 | 4.51 | 45.32 | 52.12 | 87.08 |

TABLE 18

| Structure | CAS # | V9M-SC3 Reporter activity (2.5 μM) (%) | V9M-SC3 Reporter activity % (7.5 μM) | Ls174T-SC1 reporter activity, % (2.5μM) | Ls174T-SC1 reporter activity, % (7.5 μM) | V503-3H9-7 reporter activity, % (2.5 μM) | V503-3H9-7 reporter activity, % (7.5 μM) | Enzyme inhibition % (2.5 μM) | Enzyme inhibition % (7.5 μM) |
|---|---|---|---|---|---|---|---|---|---|
| 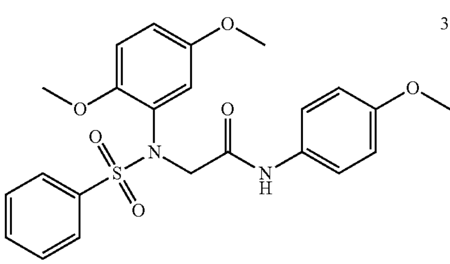 [SMILES: COc1ccc(NC(=O)CN(c2cc(OC)ccc2OC)S(=O)(=O)c2ccccc2)cc1] | 333447-10-2 | −0.5 | 10 | 7.54 | 14.44 | 76.87 | 158.91 | 27.01 | 46.46 |
| 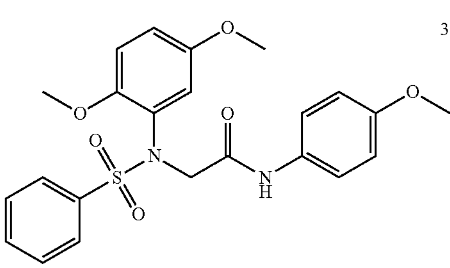 [SMILES: COc1ccc(NC(=O)CN(c2cc(OC)ccc2OC)S(=O)(=O)c2ccccc2)cc1] | 332419-63-3 | 2.5 | 2 | 12.44 | 9.81 | 1.65 | 46.28 | 36.59 | 47.22 |

TABLE 18-continued

| Structure | CAS # | V9M-SC3 Reporter activity (2.5 μM) (%) | V9M-SC3 Reporter activity % (7.5 μM) | Ls174T-SC1 reporter activity, % (2.5μM) | Ls174T-SC1 reporter activity, % (7.5 μM) | V503-3H9-7 reporter activity, % (2.5 μM) | V503-3H9-7 reporter activity, % (7.5 μM) | Enzyme inhibition % (2.5 μM) | Enzyme inhibition % (7.5 μM) |
|---|---|---|---|---|---|---|---|---|---|
| 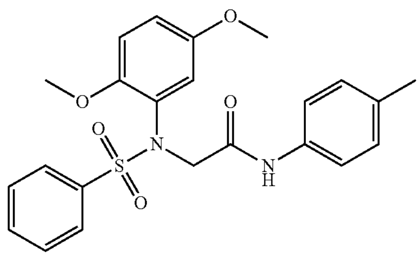 [SMILES: COc1ccc(OC)c(N(CC(=O)Nc2ccc(C)cc2)S(=O)(=O)c2ccccc2)c1] | 311333-86-5 | 53 | 117.25 | 29.97 | 53.41 | 102.18 | 131.25 | 33.99 | 34.01 |
| 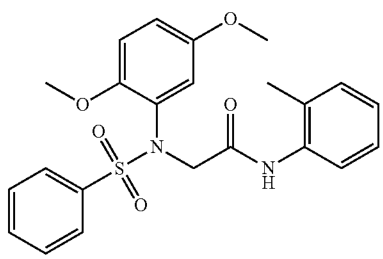 [SMILES: COc1ccc(OC)c(N(CC(=O)Nc2ccccc2C)S(=O)(=O)c2ccccc2)c1] | 428460-22-4 | 1.5 | 15.25 | −7.63 | −1.99 | 1.39 | 47.04 | 15.05 | 19.30 |
| 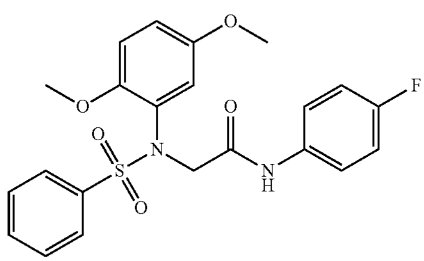 [SMILES: COc1ccc(OC)c(N(CC(=O)Nc2ccc(F)cc2)S(=O)(=O)c2ccccc2)c1] | 426231-26-7 | 10 | 2.5 | 16.17 | 22.07 | 64.02 | 113.49 | 39.81 | 56.40 |
| 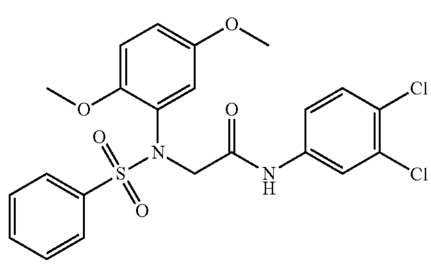 [SMILES: COc1ccc(OC)c(N(CC(=O)Nc2ccc(Cl)c(Cl)c2)S(=O)(=O)c2ccccc2)c1] | 339589-55-8 | −7 | 8 | −5.54 | 8.81 | 63.97 | 52.49 | 19.14 | 21.99 |
| 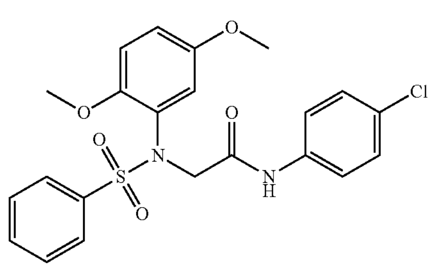 [SMILES: COc1ccc(OC)c(N(CC(=O)Nc2ccc(Cl)cc2)S(=O)(=O)c2ccccc2)c1] | 339589-53-6 | −1 | 4.25 | 51.18 | 89.74 | 199.56 | 105.28 | 35.46 | 37.35 |

TABLE 18-continued

| Structure | CAS # | V9M-SC3 Reporter activity (2.5 μM) (%) | V9M-SC3 Reporter activity % (7.5 μM) | Ls174T-SC1 reporter activity, % (2.5μM) | Ls174T-SC1 reporter activity, % (7.5 μM) | V503-3H9-7 reporter activity, % (2.5 μM) | V503-3H9-7 reporter activity, % (7.5 μM) | Enzyme inhibition % (2.5 μM) | Enzyme inhibition % (7.5 μM) |
|---|---|---|---|---|---|---|---|---|---|
| 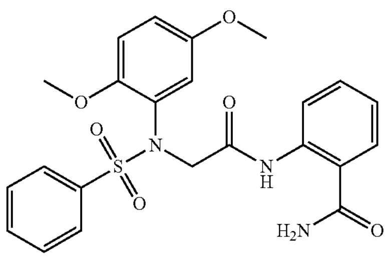 [SMILES: COc1ccc(OC)c(N(CC(=O)Nc2ccccc2C(N)=O)S(=O)(=O)c2ccccc2)c1] | 530107-57-4 | 59.5 | 116.5 | 5.45 | 8.27 | 52.62 | 84.39 | 21.74 | 9.25 |
| 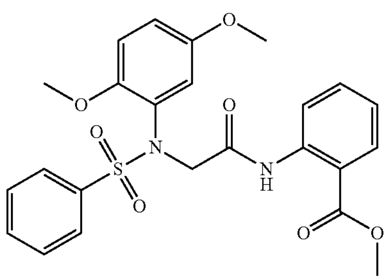 [SMILES: COC(=O)c1ccccc1NC(=O)CN(c1cc(OC)ccc1OC)S(=O)(=O)c1ccccc1] | 333449-58-4 | 6.5 | 71.25 | −5.90 | −3.99 | 50.08 | 20.72 | 9.72 | −3.12 |
| 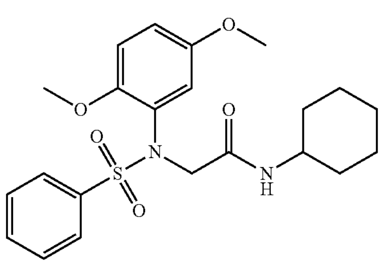 [SMILES: COc1ccc(OC)c(N(CC(=O)NC2CCCCC2)S(=O)(=O)c2ccccc2)c1] | 333446-93-8 | 16.5 | 44 | 12.90 | 13.53 | 53.78 | 44.10 | −5.31 | 5.85 |
| 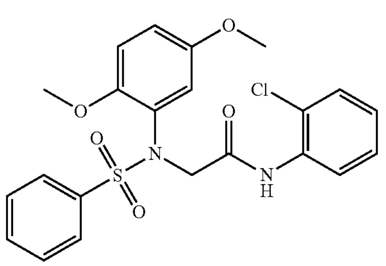 [SMILES: COc1ccc(OC)c(N(CC(=O)Nc2ccccc2Cl)S(=O)(=O)c2ccccc2)c1] | 333450-97-8 | | | | | | | | |
| 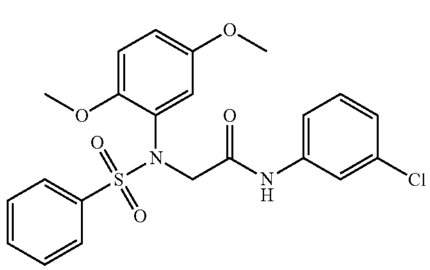 [SMILES: COc1ccc(OC)c(N(CC(=O)Nc2cccc(Cl)c2)S(=O)(=O)c2ccccc2)c1] | 311315-25-0 | | | 62.59 | 75.79 | | | 18.69 | 34.70 |

TABLE 18-continued

| Structure | CAS # | V9M-SC3 Reporter activity (2.5 μM) (%) | V9M-SC3 Reporter activity % (7.5 μM) | Ls174T-SC1 reporter activity, % (2.5μM) | Ls174T-SC1 reporter activity, % (7.5 μM) | V503-3H9-7 reporter activity, % (2.5 μM) | V503-3H9-7 reporter activity, % (7.5 μM) | Enzyme inhibition % (2.5 μM) | Enzyme inhibition % (7.5 μM) |
|---|---|---|---|---|---|---|---|---|---|
| 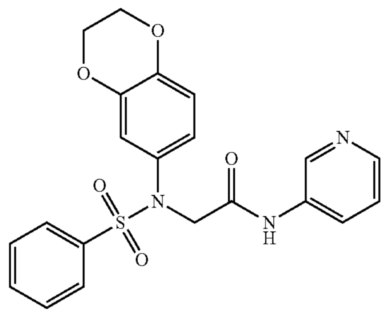 [SMILES: O=C(CN(c1ccc2c(c1)OCCO2)S(=O)(=O)c1ccccc1)Nc1cccnc1] | 701217-00-7 | −2.05 | 79.49 | −6.89 | −0.54 | 20.078 | 33.42 | 10.07 | 13.12 |
| 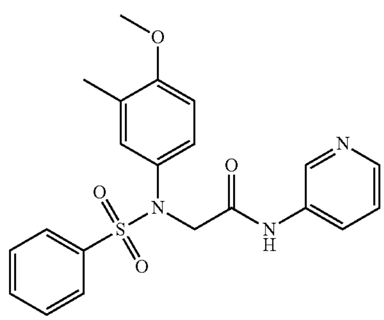 [SMILES: COc1ccc(N(CC(=O)Nc2cccnc2)S(=O)(=O)c2ccccc2)cc1C] | 592469-85-7 | −9.74 | 18.46 | 3.77 | 13.99 | 10.16 | 5.30 | 6.23 | 17.24 |
| 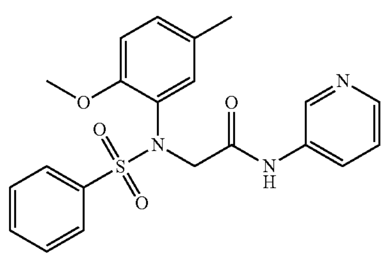 [SMILES: COc1ccc(C)cc1N(CC(=O)Nc1cccnc1)S(=O)(=O)c1ccccc1] | 526206-05-3 | 23.08 | 113.85 | 68.46 | 145.94 | 110.21 | 197.50 | 41.97 | 70.19 |
| 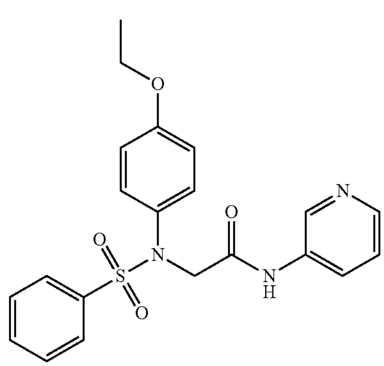 [SMILES: CCOc1ccc(N(CC(=O)Nc2cccnc2)S(=O)(=O)c2ccccc2)cc1] | 428473-22-7 | −17.95 | 2.051 | −15.50 | 10.58 | 19.09 | 19.81 | 3.76 | 8.67 |

TABLE 18-continued

| Structure | CAS # | V9M-SC3 Reporter activity (2.5 μM) (%) | V9M-SC3 Reporter activity % (7.5 μM) | Ls174T-SC1 reporter activity, % (2.5μM) | Ls174T-SC1 reporter activity, % (7.5 μM) | V503-3H9-7 reporter activity, % (2.5 μM) | V503-3H9-7 reporter activity, % (7.5 μM) | Enzyme inhibition % (2.5 μM) | Enzyme inhibition % (7.5 μM) |
|---|---|---|---|---|---|---|---|---|---|
| 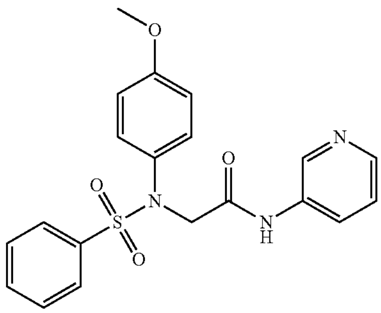 [SMILES: COc1ccc(N(CC(=O)Nc2cccnc2)S(=O)(=O)c2ccccc2)cc1] | 418783-65-0 | 0.51 | 67.18 | −12.59 | 5.81 | 11.63 | 6.68 | 10.85 | 12.12 |
| 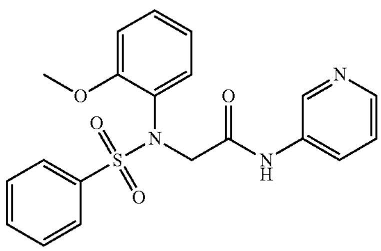 [SMILES: COc1ccccc1N(CC(=O)Nc1cccnc1)S(=O)(=O)c1ccccc1] | 367929-80-4 | −27.79 | −19 | 18.80 | −17.98 | −0.87 | −6.22 | 8.95 | 34.80 |
| 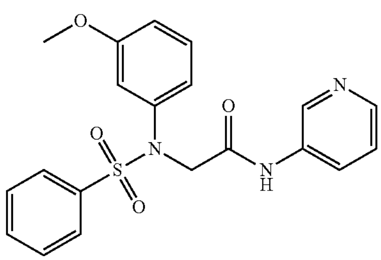 [SMILES: COc1cccc(N(CC(=O)Nc2cccnc2)S(=O)(=O)c2ccccc2)c1] | 335392-39-7 | −12.82 | 7.18 | −0.54 | 14.32 | 18.89 | 21.95 | 11.00 | 5.37 |
| 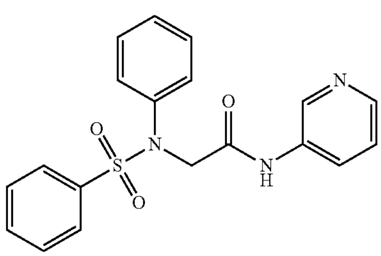 [SMILES: O=C(CN(c1ccccc1)S(=O)(=O)c1ccccc1)Nc1cccnc1] | 331727-07-2 | 28.21 | 120 | −7.53 | 9.47 | 8.13 | 1.14 | 9.65 | 17.53 |
| 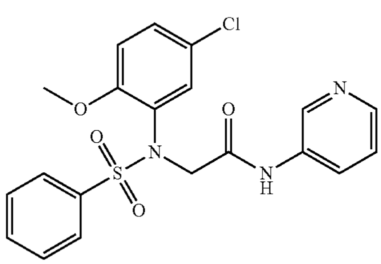 [SMILES: COc1ccc(Cl)cc1N(CC(=O)Nc1cccnc1)S(=O)(=O)c1ccccc1] | 328012-52-8 | −15.38 | 0.51 | 127.66 | 175.99 | 242.64 | −4.89 | 67.39 | 82.06 |

TABLE 18-continued

| Structure | CAS # | V9M-SC3 Reporter activity (2.5 μM) (%) | V9M-SC3 Reporter activity % (7.5 μM) | Ls174T-SC1 reporter activity, % (2.5μM) | Ls174T-SC1 reporter activity, % (7.5 μM) | V503-3H9-7 reporter activity, % (2.5 μM) | V503-3H9-7 reporter activity, % (7.5 μM) | Enzyme inhibition % (2.5 μM) | Enzyme inhibition % (7.5 μM) |
|---|---|---|---|---|---|---|---|---|---|
| 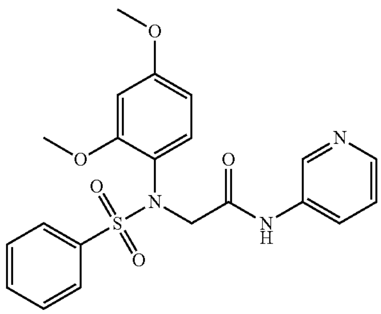 [SMILES: COc1ccc(N(CC(=O)Nc2cccnc2)S(=O)(=O)c2ccccc2)c(OC)c1] | 310875-38-8 | −8.72 | −16.41 | 27.66 | 101.94 | 64.11 | 147.62 | 23.51 | 33.40 |
| 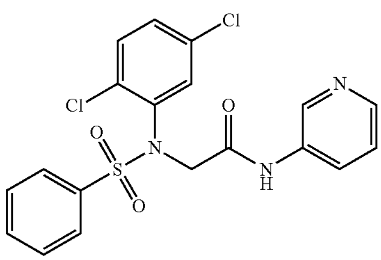 [SMILES: O=C(CN(c1cc(Cl)ccc1Cl)S(=O)(=O)c1ccccc1)Nc1cccnc1] | 833428-03-8 | −4.10 | 17.44 | 25.08 | 47.36 | 96.38 | 149.97 | 16.39 | 49.25 |
| 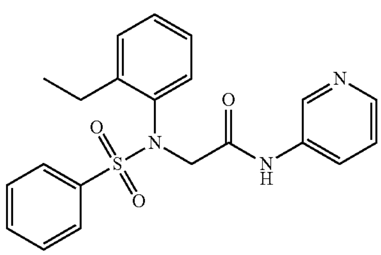 | 528580-69-0 | 4.71 | −0.5 | 11.49 | −4.81 | 66.03 | 110.41 | −8.22 | 10.23 |
| 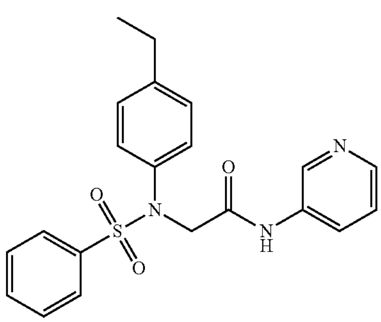 | 461439-84-9 | −30.29 | −41.75 | 4.83 | −34.97 | 1.57 | 5.41 | 9.28 | 3.35 |
| 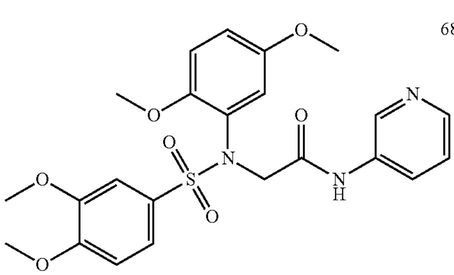 [SMILES: COc1ccc(OC)c(N(CC(=O)Nc2cccnc2)S(=O)(=O)c2ccc(OC)c(OC)c2)c1] | 680599-58-0 | −5.29 | −22.5 | 11.489 | −13.81 | 16.66 | 28.86 | 31.81 | 50.71 |

TABLE 18-continued

| Structure | CAS # | V9M-SC3 Reporter activity (2.5 μM) (%) | V9M-SC3 Reporter activity % (7.5 μM) | Ls174T-SC1 reporter activity, % (2.5μM) | Ls174T-SC1 reporter activity, % (7.5 μM) | V503-3H9-7 reporter activity, % (2.5 μM) | V503-3H9-7 reporter activity, % (7.5 μM) | Enzyme inhibition % (2.5 μM) | Enzyme inhibition % (7.5 μM) |
|---|---|---|---|---|---|---|---|---|---|
| 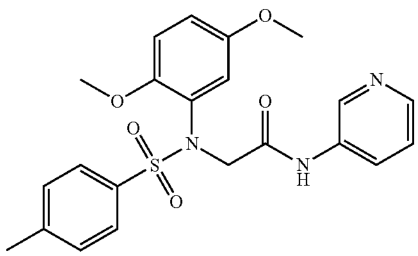 [SMILES: COc1ccc(OC)c(N(CC(=O)Nc2cccnc2)S(=O)(=O)c2ccc(C)cc2)c1] | 505072-23-1 | 94.71 | 71.5 | 100.91 | 109.26 | 242.42 | 238.88 | 67.44 | 84.57 |
| 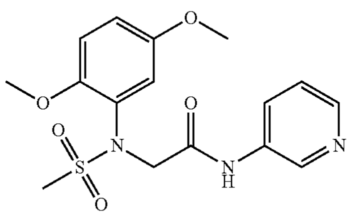 [SMILES: COc1ccc(OC)c(N(CC(=O)Nc2cccnc2)S(C)(=O)=O)c1] | 527699-66-7 | −31.03 | −37.25 | 7.31 | −29.61 | 38.78 | 70.92 | −20.58 | 27.93 |

TABLE 19

| Structure | UTSW ID | V9M-SC3 Reporter activity (2.5 μM) (%) | V9M-SC3 Reporter activity (7.5 μM), % | Ls174T-SC1 reporter activity, % (2.5 μM) | Ls174T-SC1 reporter activity, % (7.5 μM) | V503-3H9-7 reporter activity, % (2.5 μM) | V503-3H9-7 reporter activity, % (7.5 μM) | Enzyme inhibition % (2.5 μM) | Enzyme inhibition % (7.5 μM) | Enzyme inhibition (IC50) | Decrease PGE-2 (IL-1beta-A549, %) | Decrease Cell viability in A549 cell (%) | Decrease of coloning formation % |
|---|---|---|---|---|---|---|---|---|---|---|---|---|---|
| (2,5-dimethoxyphenyl, phenylsulfonyl, pyridin-3-yl amide) | SW054384 | 116.34 | 147.89 | 129.91 | 155.75 | 148.89 | 157.49 | 20.17 | 58.20 | | 41.96 | | |
| (2,5-dimethoxyphenyl, 4-methylphenylsulfonyl, pyridin-3-yl amide) | SW202939 | 75.34 | 127.84 | 75.46 | 166.46 | 26.60 | 27.30 | 53.54 | 78.32 | | | | |
| (2,5-dimethoxyphenyl, 4-chlorophenylsulfonyl, pyridin-3-yl amide) | SW202942 | 52.69 | 104.86 | 53.59 | 122.86 | 37.26 | 86.87 | 48.39 | 64.86 | | | | |

TABLE 19-continued

| Structure | UTSW ID | V9M-SC3 Reporter activity (2.5 µM) (%) | V9M-SC3 Reporter activity (7.5 µM), % | Ls174T-SC1 reporter activity, % (2.5 µM) | Ls174T-SC1 reporter activity, % (7.5 µM) | V503-3H9-7 reporter activity, % (2.5 µM) | V503-3H9-7 reporter activity, % (7.5 µM) | Enzyme inhibition % (2.5 µM) | Enzyme inhibition % (7.5 µM) | Enzyme inhibition (IC50) | Decrease PGE-2 (IL-1beta-A549, %) | Decrease Cell viability in A549 cell (%) | Decrease of coloning formation % |
|---|---|---|---|---|---|---|---|---|---|---|---|---|---|
| [structure] | SW202945 | 28.49 | 89.98 | 45.67 | 134.54 | 33.99 | 127.43 | 8.83 | 11.07 | | | | |
| [structure] | SW202949 | 5.76 | −5.69 | −1.58 | −5.87 | −12.46 | 5.32 | 12.52 | 34.37 | | | | |
| [structure] | SW202950 | 12.59 | 23.87 | −2.70 | 10.69 | −6.56 | 12.95 | 46.26 | 56.39 | | | | |

TABLE 19-continued

| UTSW ID | V9M-SC3 Reporter activity (2.5 μM) (%) | V9M-SC3 Reporter activity (7.5 μM), % | Ls174T-SC1 reporter activity, % (2.5 μM) | Ls174T-SC1 reporter activity, % (7.5 μM) | V503-3H9-7 reporter activity, % (2.5 μM) | V503-3H9-7 reporter activity, % (7.5 μM) | Enzyme inhibition % (2.5 μM) | Enzyme inhibition % (7.5 μM) | Enzyme inhibition (IC50) | Decrease PGE-2 (IL-1beta-A549, %) | Decrease Cell viability in A549 cell (%) | Decrease of coloning formation % |
|---|---|---|---|---|---|---|---|---|---|---|---|---|
| SW202953 | 12.97 | 34.79 | 20.69 | 30.69 | 31.98 | 50.93 | 8.81 | 15.06 | | | | |
| SW202954 | 2.70 | 4.80 | −4.59 | −6.99 | −8.94 | 2.39 | 6.02 | 9.88 | | | | |
| SW202944 | −0.95 | −3.73 | 32.47 | 15.76 | 130.94 | 94.57 | 28.28 | 57.78 | | | | |

TABLE 19-continued

| UTSW ID | Structure | V9M-SC3 Reporter activity (2.5 µM) (%) | V9M-SC3 Reporter activity (7.5 µM), % | Ls174T-SC1 reporter activity, % (2.5 µM) | Ls174T-SC1 reporter activity, % (7.5 µM) | V503-3H9-7 reporter activity, % (2.5 µM) | V503-3H9-7 reporter activity, % (7.5 µM) | Enzyme inhibition % (2.5 µM) | Enzyme inhibition % (7.5 µM) | Enzyme inhibition (IC50) | Decrease PGE-2 (IL-1beta-A549, %) | Decrease Cell viability in A549 cell (%) | Decrease of coloning formation % |
|---|---|---|---|---|---|---|---|---|---|---|---|---|---|
| SW202948 | 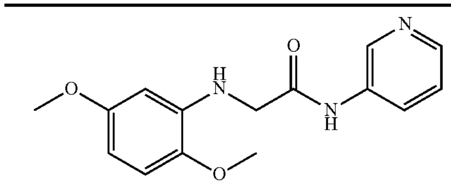 | −21.99 | −23.05 | −6.73 | 8.36 | 16.44 | 7.54 | 28.27 | 56.73 | | | | |
| SW202947 | 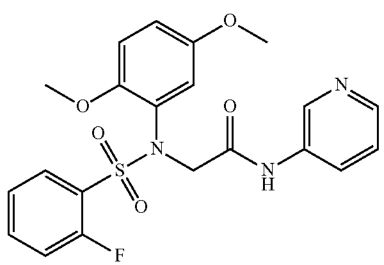 [SMILES: COc1ccc(OC)c(N(CC(=O)Nc2cccnc2)S(=O)(=O)c2ccccc2F)c1] | 21.89 | 2.57 | 52.05 | 21.22 | 142.96 | 97.85 | 28.80 | 59.19 | | | | |
| SW202952 | 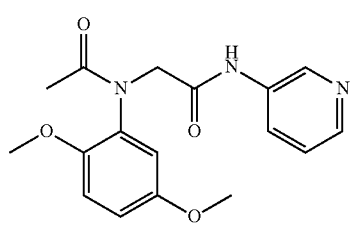 [SMILES: COc1ccc(OC)c(N(CC(=O)Nc2cccnc2)C(C)=O)c1] | −20.74 | −19.53 | −10.30 | 10.58 | 26.18 | 7.16 | 29.01 | 57.03 | | | | |
| SW202940 | 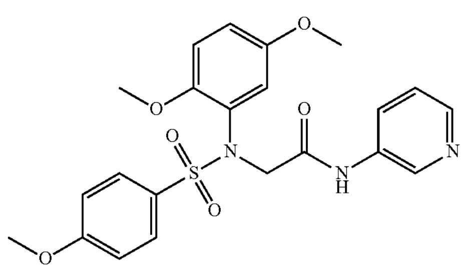 [SMILES: COc1ccc(S(=O)(=O)N(CC(=O)Nc2cccnc2)c2cc(OC)ccc2OC)cc1] | 146.58 | 181.17 | 147.86 | 210.71 | 180.73 | 182.58 | 24.30 | 63.29 | ~5 µM | 80.46 | 45.18 | |

TABLE 19-continued

| Structure | UTSW ID | V9M-SC3 Reporter activity (2.5 μM) (%) | V9M-SC3 Reporter activity (7.5 μM), % | Ls174T-SC1 reporter activity, % (2.5 μM) | Ls174T-SC1 reporter activity, % (7.5 μM) | V503-3H9-7 reporter activity, % (2.5 μM) | V503-3H9-7 reporter activity, % (7.5 μM) | Enzyme inhibition % (2.5 μM) | Enzyme inhibition % (7.5 μM) | Enzyme inhibition (IC50) | Decrease PGE-2 (IL-1beta-A549, %) | Decrease Cell viability in A549 cell (%) | Decrease of coloning formation % |
|---|---|---|---|---|---|---|---|---|---|---|---|---|---|
| 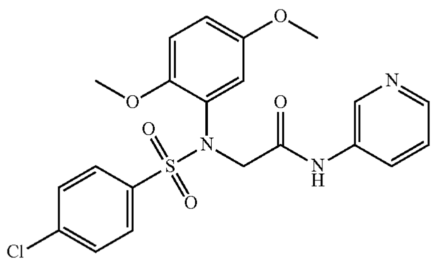 [SMILES: COc1ccc(OC)c(N(CC(=O)Nc2cccnc2)S(=O)(=O)c2ccc(Cl)cc2)c1] | SW202942 | 1.00 | 32.05 | 46.96 | 86.98 | 95.39 | 129.34 | −3.72 | 28.87 | | | | |
| 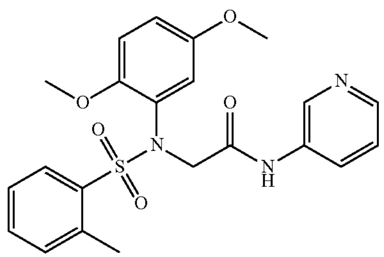 [SMILES: COc1ccc(OC)c(N(CC(=O)Nc2cccnc2)S(=O)(=O)c2ccccc2C)c1] | SW202943 | 7.12 | 17.84 | 33.07 | 55.73 | 72.27 | 146.87 | −7.42 | 21.84 | | | | |
| 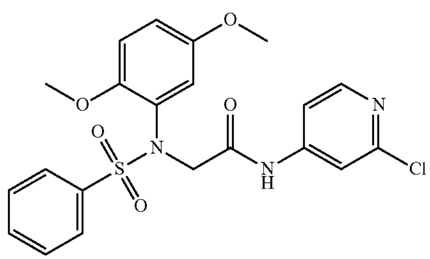 | SW202946 | 64.59 | −41.52 | 105.33 | −23.62 | 136.73 | 34.27 | 81.60 | 89.84 | | | | |

TABLE 19-continued

| UTSW ID | V9M-SC3 Reporter activity (2.5 μM) (%) | V9M-SC3 Reporter activity (7.5 μM), % | Ls174T-SC1 reporter activity, % (2.5 μM) | Ls174T-SC1 reporter activity, % (7.5 μM) | V503-3H9-7 reporter activity, % (2.5 μM) | V503-3H9-7 reporter activity, % (7.5 μM) | Enzyme inhibition % (2.5 μM) | Enzyme inhibition % (7.5 μM) | Enzyme inhibition (IC50) | Decrease PGE-2 (IL-1beta-A549, %) | Decrease Cell viability in A549 cell (%) | Decrease of coloning formation % |
|---|---|---|---|---|---|---|---|---|---|---|---|---|
| SW202951 | 4.56 | 17.661 | 34.26 | 47.64 | 97.53 | 131.49 | −15.43 | −8.59 | | −1.01 | | |
| SW122063 | 1.67 | 4.80 | 22.56 | 19.86 | 42.51 | 44.12 | −12.23 | −10.49 | | | | |
| SW202938 | 154.92 | 230.12 | 216.99 | 240.95 | 309.09 | 300.99 | 52.66 | 75.64 | 2.67 μM | −47.55 | | |

TABLE 19-continued

| Structure | UTSW ID | V9M-SC3 Reporter activity (2.5 µM) (%) | V9M-SC3 Reporter activity (7.5 µM), % | Ls174T-SC1 reporter activity, % (2.5 µM) | Ls174T-SC1 reporter activity, % (7.5 µM) | V503-3H9-7 reporter activity, % (2.5 µM) | V503-3H9-7 reporter activity, % (7.5 µM) | Enzyme inhibition % (2.5 µM) | Enzyme inhibition % (7.5 µM) | Enzyme inhibition (IC50) | Decrease PGE-2 (IL-1beta-A549, %) | Decrease Cell viability in A549 cell (%) | Decrease of coloning formation % |
|---|---|---|---|---|---|---|---|---|---|---|---|---|---|
| 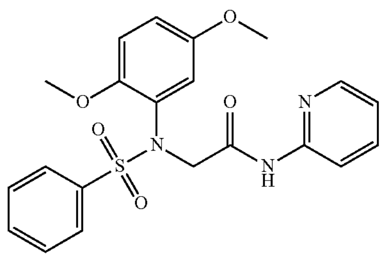 [SMILES: COc1ccc(OC)c(N(CC(=O)Nc2ccccn2)S(=O)(=O)c2ccccc2)c1] | SW202941 | −10.89 | 2.57 | −23.79 | −43.20 | 75.94 | 83.54 | 10.86 | 35.61 | | | | |
| 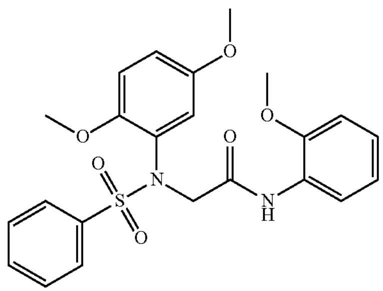 [SMILES: COc1ccc(OC)c(N(CC(=O)Nc2ccccc2OC)S(=O)(=O)c2ccccc2)c1] | SW202965 | −30.92 | −25.80 | −23.51 | 3.52 | 23.76 | 98.06 | 11.26 | 33.13 | | | | |
| 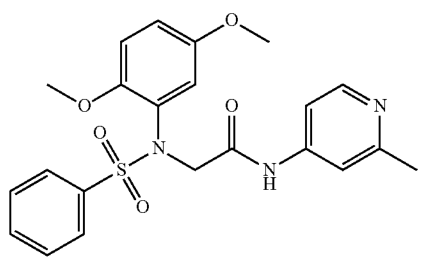 [SMILES: COc1ccc(OC)c(N(CC(=O)Nc2ccnc(C)c2)S(=O)(=O)c2ccccc2)c1] | SW202966 | −0.84 | 67.67 | 1.82 | 78.15 | 115.05 | 248.97 | 44.66 | 61.39 | | | | |

TABLE 19-continued

| Structure | UTSW ID | V9M-SC3 Reporter activity (2.5 μM) (%) | V9M-SC3 Reporter activity (7.5 μM), % | Ls174T-SC1 reporter activity, % (2.5 μM) | Ls174T-SC1 reporter activity, % (7.5 μM) | V503-3H9-7 reporter activity, % (2.5 μM) | V503-3H9-7 reporter activity, % (7.5 μM) | Enzyme inhibition % (2.5 μM) | Enzyme inhibition % (7.5 μM) | Enzyme inhibition (IC50) | Decrease PGE-2 (IL-1beta-A549, %) | Decrease Cell viability in A549 cell (%) | Decrease of coloning formation % |
|---|---|---|---|---|---|---|---|---|---|---|---|---|---|
| 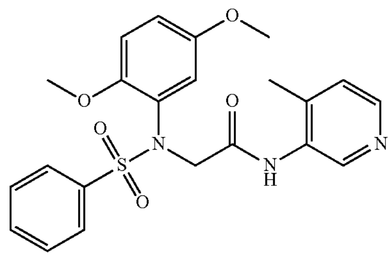 [SMILES: COc1ccc(OC)c(N(CC(=O)Nc2cnccc2C)S(=O)(=O)c2ccccc2)c1] | SW202967 | −15.98 | 0 | −11.69 | 9.37 | 34.05 | 69.62 | −11.56 | 0.94 |  |  |  |  |
| 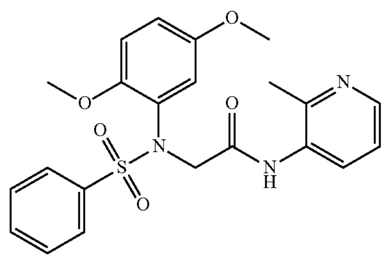 | SW202968 | −21.10 | −7.36 | −17.50 | 6.08 | 35.18 | 53.87 | −7.09 | 0.78 |  |  |  |  |
| 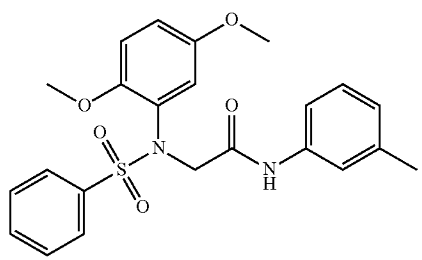 | SW202969 | −20.96 | −14.30 | −15.87 | 17.90 | 62.42 | 126.16 | 0.91 | 9.43 |  |  |  |  |

TABLE 19-continued

| Structure | UTSW ID | V9M-SC3 Reporter activity (2.5 μM) (%) | V9M-SC3 Reporter activity (7.5 μM), % | Ls174T-SC1 reporter activity, % (2.5 μM) | Ls174T-SC1 reporter activity, % (7.5 μM) | V503-3H9-7 reporter activity, % (2.5 μM) | V503-3H9-7 reporter activity, % (7.5 μM) | Enzyme inhibition % (2.5 μM) | Enzyme inhibition % (7.5 μM) | Enzyme inhibition (IC50) | Decrease PGE-2 (IL-1beta-A549, %) | Decrease Cell viability in A549 cell (%) | Decrease of coloning formation % |
|---|---|---|---|---|---|---|---|---|---|---|---|---|---|
| 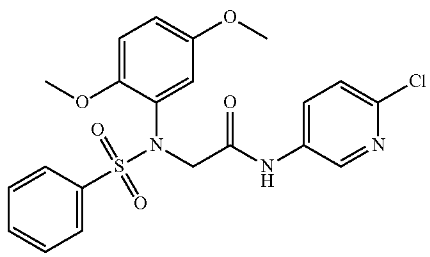 [SMILES: COc1ccc(OC)c(N(CC(=O)Nc2ccc(Cl)nc2)S(=O)(=O)c2ccccc2)c1] | SW202970 | 32.74 | 17.81 | 47.94 | 55.89 | 179.12 | 121.93 | 17.46 | 48.04 | | | | |
| 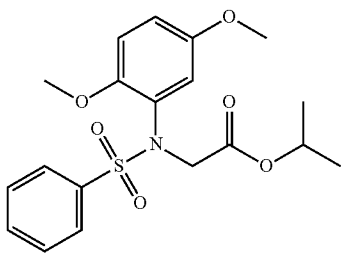 [SMILES: COc1ccc(OC)c(N(CC(=O)OC(C)C)S(=O)(=O)c2ccccc2)c1] | SW202971 | −14.51 | 9.67 | −7.91 | 34.55 | 85.50 | 169.04 | −0.72 | −13.18 | | | | |
| 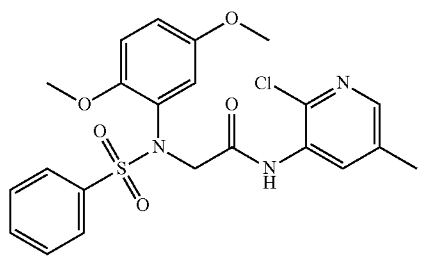 [SMILES: COc1ccc(OC)c(N(CC(=O)Nc2cc(C)cnc2Cl)S(=O)(=O)c2ccccc2)c1] | SW202972 | −15.42 | 0.14 | −17.45 | 16.64 | 39.42 | 100.21 | −6.29 | −2.94 | | | | |

TABLE 19-continued

| Structure | UTSW ID | V9M-SC3 Reporter activity (2.5 μM) (%) | V9M-SC3 Reporter activity (7.5 μM), % | Ls174T-SC1 reporter activity, % (2.5 μM) | Ls174T-SC1 reporter activity, % (7.5 μM) | V503-3H9-7 reporter activity, % (2.5 μM) | V503-3H9-7 reporter activity, % (7.5 μM) | Enzyme inhibition % (2.5 μM) | Enzyme inhibition % (7.5 μM) | Enzyme inhibition (IC50) | Decrease PGE-2 (IL-1beta-A549, %) | Decrease Cell viability in A549 cell (%) | Decrease of colining formation % |
|---|---|---|---|---|---|---|---|---|---|---|---|---|---|
| 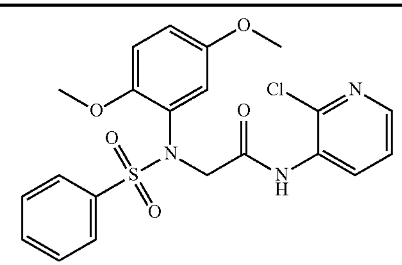 | SW202973 | −15.63 | 5.61 | −16.38 | 19.29 | 41.53 | 106.91 | 3.3 | 13.55 | | | | |
| 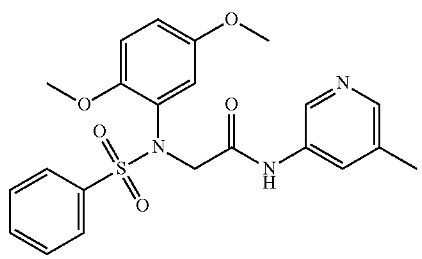 [SMILES: COc1ccc(OC)c(N(CC(=O)Nc2cncc(C)c2)S(=O)(=O)c2ccccc2)c1] | SW202974 | −9.04 | 35.90 | −8.77 | 34.79 | 59.88 | 179.28 | −4.42 | 24.85 | | | | |
| 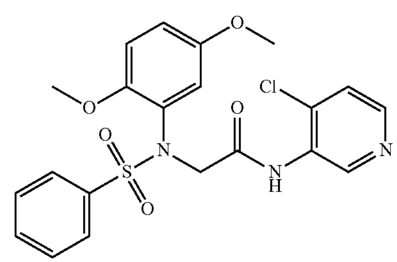 | SW202977 | −8.69 | 26.22 | −16.61 | 15.09 | 16.92 | 85.24 | −14.95 | −8.63 | | | | |

TABLE 19-continued

| Structure | UTSW ID | V9M-SC3 Reporter activity (2.5 µM) (%) | V9M-SC3 Reporter activity (7.5 µM), % | Ls174T-SC1 reporter activity, % (2.5 µM) | Ls174T-SC1 reporter activity, % (7.5 µM) | V503-3H9-7 reporter activity, % (2.5 µM) | V503-3H9-7 reporter activity, % (7.5 µM) | Enzyme inhibition % (2.5 µM) | Enzyme inhibition % (7.5 µM) | Enzyme inhibition (IC50) | Decrease PGE-2 (IL-1beta-A549, %) | Decrease Cell viability in A549 cell (%) | Decrease of coloning formation % |
|---|---|---|---|---|---|---|---|---|---|---|---|---|---|
| [structure] | SW202978 | −13.81 | −0.07 | −10.05 | 20.43 | 46.77 | 116.46 | 4.14 | 3.12 | | | | |
| [structure] | SW202979 | −14.44 | 10.79 | −8.92 | 17.83 | 41.64 | 133.05 | 3.92 | 6.24 | | | | |
| [structure] | SW202980 | −27.55 | −13.39 | −7.34 | 5.17 | 11.41 | 50.62 | −4.19 | 1.44 | | | | |

TABLE 19-continued

| Structure | UTSW ID | V9M-SC3 Reporter activity (2.5 μM) (%) | V9M-SC3 Reporter activity (7.5 μM), % | Ls174T-SC1 reporter activity, % (2.5 μM) | Ls174T-SC1 reporter activity, % (7.5 μM) | V503-3H9-7 reporter activity, % (2.5 μM) | V503-3H9-7 reporter activity, % (7.5 μM) | Enzyme inhibition % (2.5 μM) | Enzyme inhibition % (7.5 μM) | Enzyme inhibition (IC50) | Decrease PGE-2 (IL-1beta-A549, %) | Decrease Cell viability in A549 cell (%) | Decrease of coloning formation % |
|---|---|---|---|---|---|---|---|---|---|---|---|---|---|
| 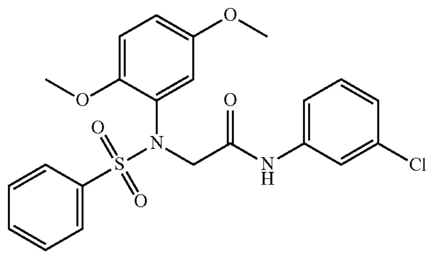 [SMILES: COc1ccc(OC)c(N(CC(=O)Nc2cccc(Cl)c2)S(=O)(=O)c2ccccc2)c1] | SW202985 | −27.34 | −21.87 | −4.89 | 26.32 | 79.56 | 149.89 | 13.79 | 30.87 | | | | |
| 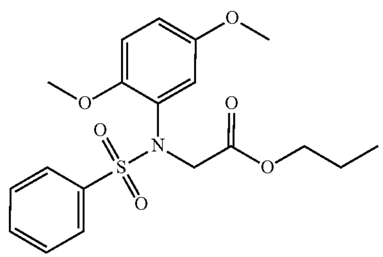 [SMILES: CCCOC(=O)CN(c1cc(OC)ccc1OC)[S@SP3](=O)(=O)c1ccccc1] | SW202986 | −22.86 | −9.60 | 0.21 | 33.80 | 60.17 | 175.41 | −2.22 | 2.58 | | | | |
| 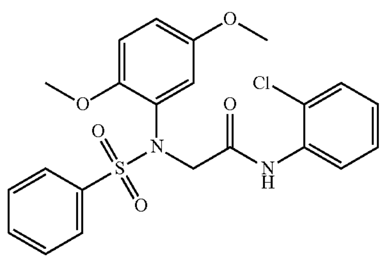 [SMILES: COc1ccc(OC)c(N(CC(=O)Nc2ccccc2Cl)S(=O)(=O)c2ccccc2)c1] | SW202987 | −22.01 | −21.03 | −8.30 | 20.65 | 70.129 | 145.13 | 4.61 | 6.13 | | | | |

TABLE 19-continued

| Structure | UTSW ID | V9M-SC3 Reporter activity (2.5 μM) (%) | V9M-SC3 Reporter activity (7.5 μM), % | Ls174T-SC1 reporter activity, % (2.5 μM) | Ls174T-SC1 reporter activity, % (7.5 μM) | V503-3H9-7 reporter activity, % (2.5 μM) | V503-3H9-7 reporter activity, % (7.5 μM) | Enzyme inhibition % (2.5 μM) | Enzyme inhibition % (7.5 μM) | Enzyme inhibition (IC50) | Decrease PGE-2 (IL-1beta-A549, %) | Decrease Cell viability in A549 cell (%) | Decrease of coloning formation % |
|---|---|---|---|---|---|---|---|---|---|---|---|---|---|
| 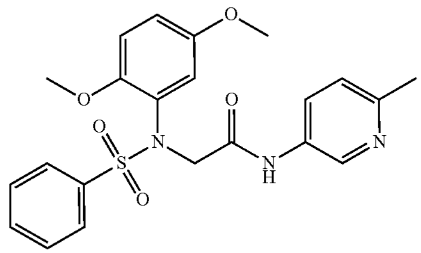 [SMILES: COc1ccc(OC)c(N(CC(=O)Nc2ccc(C)nc2)[S@SP3](=O)(=O)c2ccccc2)c1] | SW202988 | 7.36 | 54.41 | 40.50 | 125.44 | 125.39 | 258.27 | 10.27 | 33.70 | ~10 μM | -16.79 | | |
| 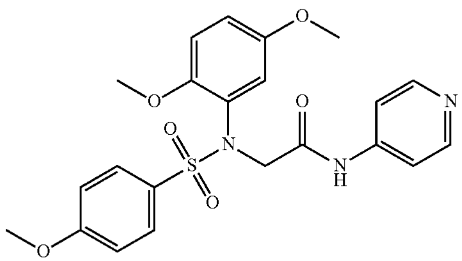 [SMILES: COc1ccc(S(=O)(=O)N(CC(=O)Nc2ccncc2)c2cc(OC)ccc2OC)cc1] | SW202989 | 187.65 | 183.80 | 158.81 | 171.45 | 207.62 | 213.94 | 81.32 | 89.86 | 427 nM | 69.40 | 30.59 | |
| 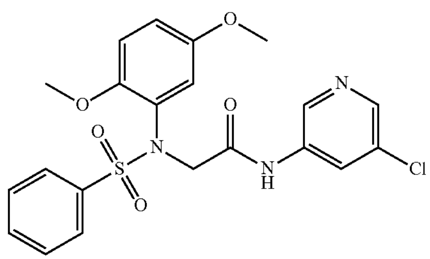 [SMILES: COc1ccc(OC)c(N(CC(=O)Nc2cncc(Cl)c2)S(=O)(=O)c2ccccc2)c1] | SW202990 | 3.57 | 23.49 | 32.01 | 106.56 | 172.00 | 214.22 | 22.88 | 47.16 | | | | |

TABLE 19-continued

| Structure | UTSW ID | V9M-SC3 Reporter activity (2.5 µM) (%) | V9M-SC3 Reporter activity (7.5 µM), % | Ls174T-SC1 reporter activity, % (2.5 µM) | Ls174T-SC1 reporter activity, % (7.5 µM) | V503-3H9-7 reporter activity, % (2.5 µM) | V503-3H9-7 reporter activity, % (7.5 µM) | Enzyme inhibition % (2.5 µM) | Enzyme inhibition % (7.5 µM) | Enzyme inhibition (IC50) | Decrease PGE-2 (IL-1beta-A549, %) | Decrease Cell viability in A549 cell (%) | Decrease of coloning formation % |
|---|---|---|---|---|---|---|---|---|---|---|---|---|---|
| 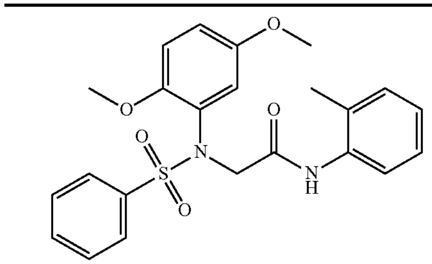 | SW202975 | −26.64 | −8.97 | −7.32 | 17.21 | 47.35 | 116.21 | −14.82 | 4.53 | | | | |
| 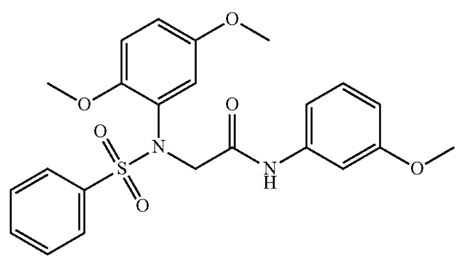 [SMILES: COc1cccc(NC(=O)CN(c2cc(OC)ccc2OC)S(=O)(=O)c2ccccc2)c1] | SW202976 | −18.51 | 9.60 | −9.97 | 30.14 | 36.75 | 138.31 | 7.87 | 29.78 | | | | |
| 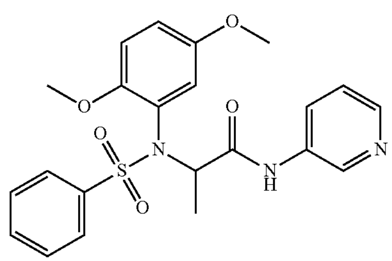 [SMILES: COc1ccc(OC)c(N(C(C)C(=O)Nc2cccnc2)S(=O)(=O)c2ccccc2)c1] | SW202991 | −25.03 | −7.50 | −15.58 | 2.09 | −6.08 | 8.90 | −14.71 | −6 | | | | |

TABLE 19-continued

| Structure | UTSW ID | V9M-SC3 Reporter activity (2.5 μM) (%) | V9M-SC3 Reporter activity (7.5 μM), % | Ls174T-SC1 reporter activity, % (2.5 μM) | Ls174T-SC1 reporter activity, % (7.5 μM) | V503-3H9-7 reporter activity, % (2.5 μM) | V503-3H9-7 reporter activity, % (7.5 μM) | Enzyme inhibition % (2.5 μM) | Enzyme inhibition % (7.5 μM) | Enzyme inhibition (IC50) | Decrease PGE-2 (IL-1beta-A549, %) | Decrease Cell viability in A549 cell (%) | Decrease of coloning formation % |
|---|---|---|---|---|---|---|---|---|---|---|---|---|---|
| 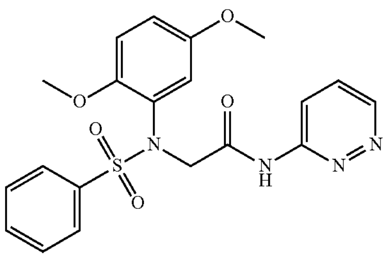 | SW203680 | 13.98 | 25.21 | 11.73 | 45.97 | 10.43 | 32.98 | 34.82 | 62.10 | | | | |
| 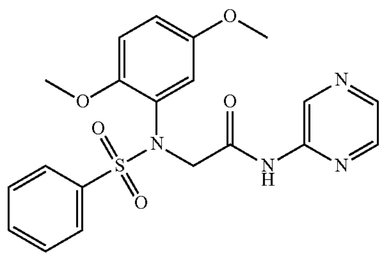 [SMILES: COc1ccc(OC)c(N(CC(=O)Nc2cnccn2)S(=O)(=O)c2ccccc2)c1] | SW203681 | 17.99 | 121.71 | 120.56 | 151.88 | 90.42 | 72.37 | 36.77 | 64.87 | | | | |
| 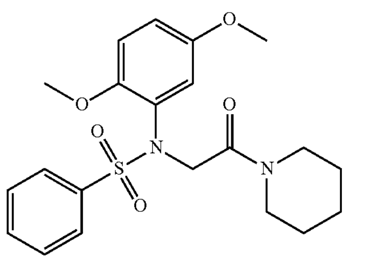 [SMILES: COc1ccc(OC)c(N(CC(=O)N2CCCCC2)S(=O)(=O)c2ccccc2)c1] | SW131633 | 77.21 | 140.98 | 8.42 | 149.84 | 103.52 | −40.56 | 23.13 | 35.21 | | | | |

TABLE 19-continued

| UTSW ID | V9M-SC3 Reporter activity (2.5 μM) (%) | V9M-SC3 Reporter activity (7.5 μM), % | Ls174T-SC1 reporter activity, % (2.5 μM) | Ls174T-SC1 reporter activity, % (7.5 μM) | V503-3H9-7 reporter activity, % (2.5 μM) | V503-3H9-7 reporter activity, % (7.5 μM) | Enzyme inhibition % (2.5 μM) | Enzyme inhibition % (7.5 μM) | Enzyme inhibition (IC50) | Decrease PGE-2 (IL-1beta-A549, %) | Decrease Cell viability in A549 cell (%) | Decrease of coloning formation % |
|---|---|---|---|---|---|---|---|---|---|---|---|---|
| SW203682 | 15.31 | 22.45 | 187.26 | 13.76 | -32.19 | 79.19 | 15.73 | 36.23 | | | | |
| SW203683 | 137.32 | 190.83 | 3.76 | 209.77 | 103.81 | -41.03 | 23.41 | 57.09 | ~7 μM | -3.41 | | |
| SW131635 | 11.39 | 15.05 | 110.93 | 14.07 | -37.66 | 14.39 | 11.80 | 35.44 | | | | |

TABLE 19-continued

| Structure | UTSW ID | V9M-SC3 Reporter activity (2.5 μM) (%) | V9M-SC3 Reporter activity (7.5 μM), % | Ls174T-SC1 reporter activity, % (2.5 μM) | Ls174T-SC1 reporter activity, % (7.5 μM) | V503-3H9-7 reporter activity, % (2.5 μM) | V503-3H9-7 reporter activity, % (7.5 μM) | Enzyme inhibition % (2.5 μM) | Enzyme inhibition % (7.5 μM) | Enzyme inhibition (IC50) | Decrease PGE-2 (IL-1beta-A549, %) | Decrease Cell viability in A549 cell (%) | Decrease of colinimg formation % |
|---|---|---|---|---|---|---|---|---|---|---|---|---|---|
| 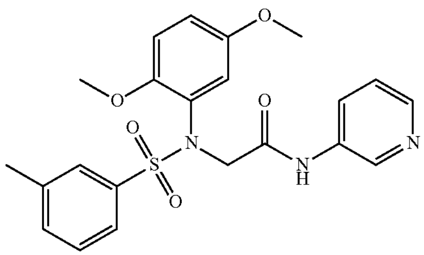 [SMILES: COc1ccc(OC)c(N(CC(=O)Nc2cccnc2)S(=O)(=O)c2cccc(C)c2)c1] | SW203684 | 50.72 | 74.89 | 170.37 | 119.07 | 81.19 | 52.46 | 36.35 | 64.72 | | | | |
| 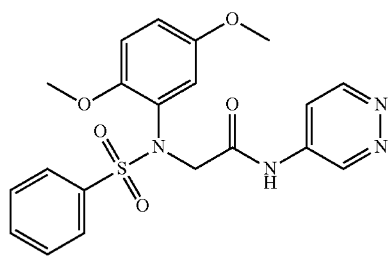 [SMILES: COc1ccc(OC)c(N(CC(=O)Nc2ccnnc2)S(=O)(=O)c2ccccc2)c1] | SW203685 | 99.95 | 204.48 | 22.34 | 253.97 | 121.53 | −33.18 | 44.34 | 73.30 | 5 μM | 17.84 | | |
| 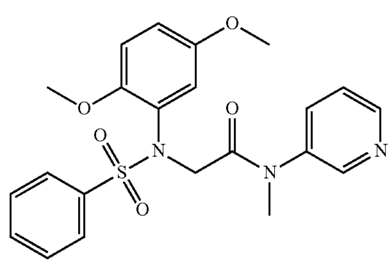 [SMILES: COc1ccc(OC)c(N(CC(=O)N(C)c2cccnc2)S(=O)(=O)c2ccccc2)c1] | SW203686 | 15.05 | 30.30 | 116.07 | 28.49 | −11.03 | 65.60 | 14.86 | 34.24 | | | | |

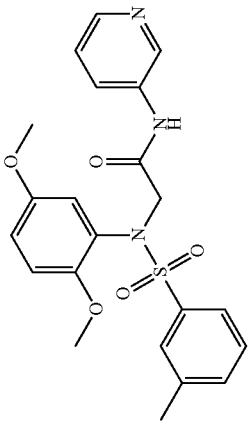

TABLE 19-continued

| Structure | UTSW ID | V9M-SC3 Reporter activity (2.5 µM) (%) | V9M-SC3 Reporter activity (7.5 µM), % | Ls174T-SC1 reporter activity, % (2.5 µM) | Ls174T-SC1 reporter activity, % (7.5 µM) | V503-3H9-7 reporter activity, % (2.5 µM) | V503-3H9-7 reporter activity, % (7.5 µM) | Enzyme inhibition % (2.5 µM) | Enzyme inhibition % (7.5 µM) | Enzyme inhibition (IC50) | Decrease PGE-2 (IL-1beta-A549, %) | Decrease Cell viability in A549 cell (%) | Decrease of coloning formation % |
|---|---|---|---|---|---|---|---|---|---|---|---|---|---|
| 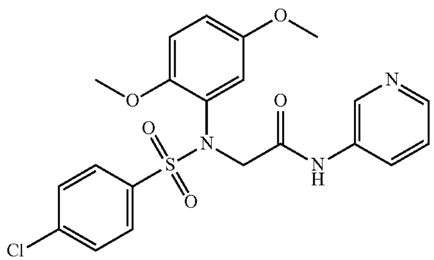 [SMILES: COc1ccc(OC)c(N(CC(=O)Nc2cccnc2)S(=O)(=O)c2ccc(Cl)cc2)c1] | SW202942 | 85.24 | 132.15 | 30.25 | 143.05 | 69.32 | 3.29 | 36.78 | 53.24 | | | | |
| 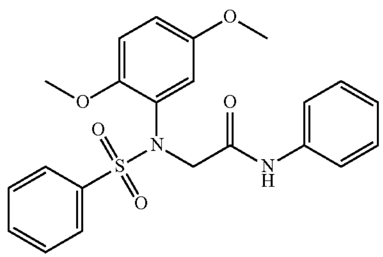 [SMILES: COc1ccc(OC)c(N(CC(=O)Nc2ccccc2)S(=O)(=O)c2ccccc2)c1] | SW203687 | 28.25 | 47.51 | 1.75 | 56.00 | 45.74 | −41.65 | 15.07 | 33.55 | | | | |
| 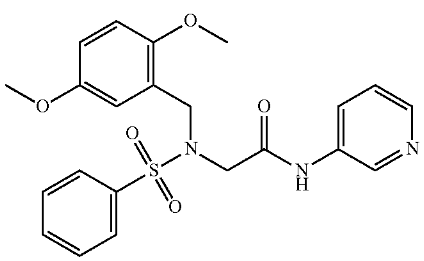 [SMILES: COc1ccc(OC)c(CN(CC(=O)Nc2cccnc2)S(=O)(=O)c2ccccc2)c1] | SW203688 | 12.10 | 6.04 | 12.59 | 14.75 | −28.10 | −99.52 | 13.13 | 39.96 | | | | |

TABLE 19-continued

| Structure | UTSW ID | V9M-SC3 Reporter activity (2.5 µM) (%) | V9M-SC3 Reporter activity (7.5 µM), % | Ls174T-SC1 reporter activity, % (2.5 µM) | Ls174T-SC1 reporter activity, % (7.5 µM) | V503-3H9-7 reporter activity, % (2.5 µM) | V503-3H9-7 reporter activity, % (7.5 µM) | Enzyme inhibition % (2.5 µM) | Enzyme inhibition % (7.5 µM) | Enzyme inhibition (IC50) | Decrease PGE-2 (IL-1beta-A549, %) | Decrease Cell viability in A549 cell (%) | Decrease of coloning formation % |
|---|---|---|---|---|---|---|---|---|---|---|---|---|---|
| 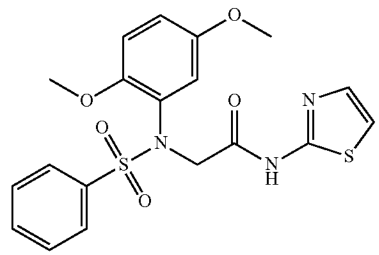 [SMILES: COc1ccc(OC)c(N(CC(=O)Nc2nccs2)S(=O)(=O)c2ccccc2)c1] | SW203691 | 7.78 | 19.82 | 5.47 | 22.03 | 47.07 | 90.04 | 2.62 | 3.12 | | 36.76 | 0.00 | |
| 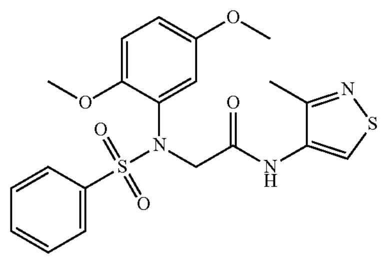 [SMILES: COc1ccc(OC)c(N(CC(=O)Nc2csnc2C)S(=O)(=O)c2ccccc2)c1] | SW203703 | 108.15 | 105.91 | 85.80 | 80.20 | 142.81 | 77.97 | 26.50 | 58.88 | | 31.90 | −1.97 | |
| 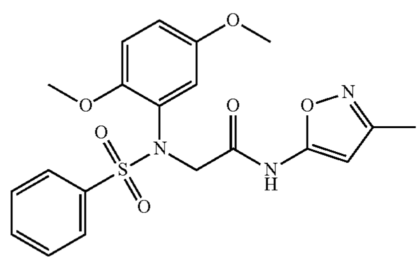 [SMILES: COc1ccc(OC)c(N(CC(=O)Nc2cc(C)no2)S(=O)(=O)c2ccccc2)c1] | SW203704 | 8.71 | 8.04 | 8.64 | 12.47 | 52.84 | 37.84 | 4.19 | 7.26 | | 22.33 | −2.70 | |

TABLE 19-continued

| Structure | UTSW ID | V9M-SC3 Reporter activity (2.5 μM) (%) | V9M-SC3 Reporter activity (7.5 μM), % | Ls174T-SC1 reporter activity, % (2.5 μM) | Ls174T-SC1 reporter activity, % (7.5 μM) | V503-3H9-7 reporter activity, % (2.5 μM) | V503-3H9-7 reporter activity, % (7.5 μM) | Enzyme inhibition % (2.5 μM) | Enzyme inhibition % (7.5 μM) | Enzyme inhibition (IC50) | Decrease PGE-2 (IL-1beta-A549, %) | Decrease Cell viability in A549 cell (%) | Decrease of coloning formation % |
|---|---|---|---|---|---|---|---|---|---|---|---|---|---|
| [structure] | SW125991 | 77.40 | 74.63 | 67.28 | 83.33 | 160.61 | 148.71 | 11.61 | 31.62 | | 31.33 | −2.13 | |
| [structure] | SW203736 | 132.36 | 145.08 | 126.75 | 155.67 | 244.43 | 203.63 | 1.70 | 24.86 | | 31.86 | −3.06 | 2.5 μM (3.12%), 7.5 μM (5.18%) |
| [structure] | SW203737 | 93.37 | 103.47 | 76.65 | 85.09 | 175.94 | 153.58 | 23.81 | 42.45 | | 47.78 | −2.56 | 2.5 μM (10.25%), 7.5 μM (82.15%) |

TABLE 19-continued

| UTSW ID | V9M-SC3 Reporter activity (2.5 μM) (%) | V9M-SC3 Reporter activity (7.5 μM), % | Ls174T-SC1 reporter activity, % (2.5 μM) | Ls174T-SC1 reporter activity, % (7.5 μM) | V503-3H9-7 reporter activity, % (2.5 μM) | V503-3H9-7 reporter activity, % (7.5 μM) | Enzyme inhibition % (2.5 μM) | Enzyme inhibition % (7.5 μM) | Enzyme inhibition (IC50) | Decrease PGE-2 (IL-1beta-A549, %) | Decrease Cell viability in A549 cell (%) | Decrease of coloning formation % |
|---|---|---|---|---|---|---|---|---|---|---|---|---|
| SW208001 | 19.59 | 23.31 | −0.61 | 1.87 | −4.07 | 6.68 | 21.79 | 27.74 | | | | |
| SW208002 | −12.39 | −21.84 | −14.51 | −14.57 | −15.65 | −16.54 | 34.73 | 59.23 | | | | |
| SW208003 | 13.32 | −11.46 | 37.00 | 45.62 | 117.02 | 75.883 | 15.19 | 20.91 | | | | |

TABLE 19-continued

| Structure | UTSW ID | V9M-SC3 Reporter activity (2.5 μM) (%) | V9M-SC3 Reporter activity (7.5 μM), % | Ls174T-SC1 reporter activity, % (2.5 μM) | Ls174T-SC1 reporter activity, % (7.5 μM) | V503-3H9-7 reporter activity, % (2.5 μM) | V503-3H9-7 reporter activity, % (7.5 μM) | Enzyme inhibition % (2.5 μM) | Enzyme inhibition % (7.5 μM) | Enzyme inhibition (IC50) | Decrease PGE-2 (IL-1beta-A549, %) | Decrease Cell viability in A549 cell (%) | Decrease of coloning formation % |
|---|---|---|---|---|---|---|---|---|---|---|---|---|---|
| (structure) | SW208004 | 43.68 | 76.14 | 62.19 | 118.21 | 146.61 | 176.82 | 52.33 | 57.00 | | | | |
| (structure) | SW208005 | 42.44 | 19.75 | 63.86 | 53.93 | 102.72 | 61.24 | 44.10 | 52.02 | | | | |
| (structure) | SW208006 | 34.85 | 0.15 | 38.20 | 42.18 | 89.69 | 43.90 | 15.71 | 24.78 | | | | |

TABLE 19-continued

| Structure | UTSW ID | V9M-SC3 Reporter activity (2.5 μM) (%) | V9M-SC3 Reporter activity (7.5 μM), % | Ls174T-SC1 reporter activity, % (2.5 μM) | Ls174T-SC1 reporter activity, % (7.5 μM) | V503-3H9-7 reporter activity, % (2.5 μM) | V503-3H9-7 reporter activity, % (7.5 μM) | Enzyme inhibition % (2.5 μM) | Enzyme inhibition % (7.5 μM) | Enzyme inhibition (IC50) | Decrease PGE-2 (IL-1beta-A549, %) | Decrease Cell viability in A549 cell (%) | Decrease of colening formation % |
|---|---|---|---|---|---|---|---|---|---|---|---|---|---|
| 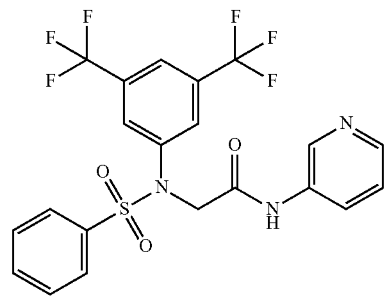 [SMILES: O=C(CN(c1cc(C(F)(F)F)cc(C(F)(F)F)c1)S(=O)(=O)c1ccccc1)Nc1cccnc1] | SW208007 | −25.48 | −26.41 | −9.01 | −5.15 | −3.17 | −2.10 | 48.27 | 38.41 | | | | |
| 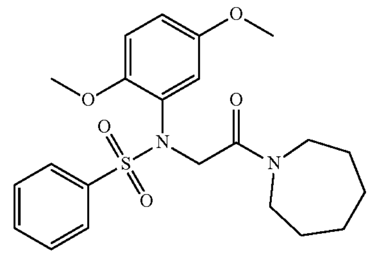 [SMILES: COc1ccc(OC)c(N(CC(=O)N2CCCCCC2)S(=O)(=O)c2ccccc2)c1] | SW208000 | 33.54 | 36.63 | 41.98 | 70.53 | 121.50 | 138.25 | 5.82 | 12.47 | | | | |
| 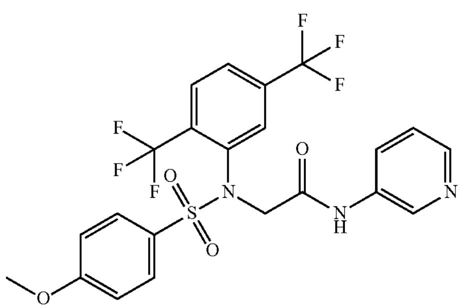 [SMILES: COc1ccc(S(=O)(=O)N(CC(=O)Nc2cccnc2)c2cc(C(F)(F)F)ccc2C(F)(F)F)cc1] | SW208008 | −5.96 | −0.92 | −2.16 | 10.01 | 31.93 | 39.63 | 58.70 | 70.90 | | | | |

TABLE 19-continued

| Structure | UTSW ID | V9M-SC3 Reporter activity (2.5 μM) (%) | V9M-SC3 Reporter activity (7.5 μM), % | Ls174T-SC1 reporter activity, % (2.5 μM) | Ls174T-SC1 reporter activity, % (7.5 μM) | V503-3H9-7 reporter activity, % (2.5 μM) | V503-3H9-7 reporter activity, % (7.5 μM) | Enzyme inhibition % (2.5 μM) | Enzyme inhibition % (7.5 μM) | Enzyme inhibition (IC50) | Decrease PGE-2 (IL-1beta-A549, %) | Decrease Cell viability in A549 cell (%) | Decrease of coloning formation % |
|---|---|---|---|---|---|---|---|---|---|---|---|---|---|
| 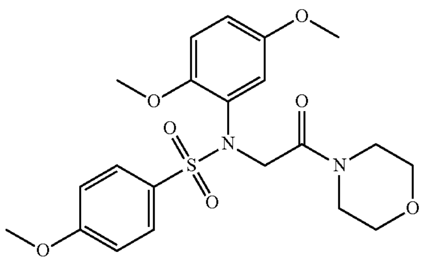 [SMILES: COc1ccc(S(=O)(=O)N(CC(=O)N2CCOCC2)c2cc(OC)ccc2OC)cc1] | SW207997 | 59.48 | 71.03 | 87.60 | 94.08 | 148.77 | 156.90 | −7.08 | −0.86 | | | | |
| 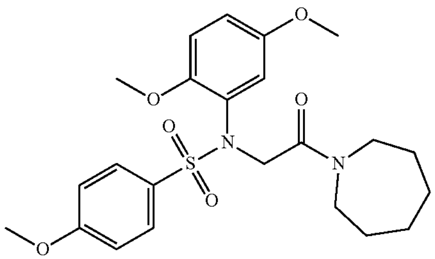 [SMILES: COc1ccc(S(=O)(=O)N(CC(=O)N2CCCCCC2)c2cc(OC)ccc2OC)cc1] | SW207998 | 53.36 | 58.94 | 65.15 | 76.99 | 143.67 | 147.18 | 8.09 | 14.38 | | | | |
| 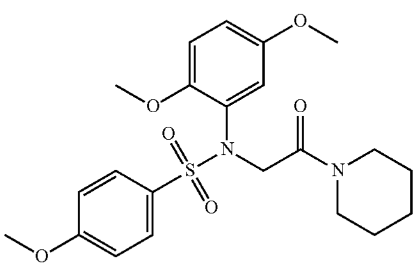 [SMILES: COc1ccc(S(=O)(=O)N(CC(=O)N2CCCCC2)c2cc(OC)ccc2OC)cc1] | SW207999 | 128.11 | 124.32 | 98.00 | 122.98 | 123.99 | 110.28 | −0.86 | 3.34 | | | | |

Data provided include level of induction of a 15-PGDH-luciferase fusion gene reporter, recorded as % induction of luciferase activity over basal level, in three colon cancer cell lines, V9m, V503, and LS174T, engineered to contain the reporter, and treated with either 2.5 uM or 7.5 uM compound. Also recorded for some compounds is the inhibition of enzyme activity of recombinant 15-PGDH protein treated with 2.5 µM or 7.5 µM compound. Also recorded for some compounds is the $IC_{50}$ of each compound for inhibiting enzymatic activity of recombinant 15-PGDH in an in vitro assay. Additionally, for selected compounds is recorded the decrease in PGE2 levels in the media of compound treated A549 cells that have been stimulated with IL-1 beta. Additionally recorded for selected compounds is the effect on A549 cell viability as measured by a CellTiter-Glo assay, and the effect of compounds on A549 cell colony formation.

We first note that the amino group participating in the peptide bond in SW054384 can be modified as shown in compound MCD-03-025, and that the derived compound retains the ability to activate expression of the 15-PGDH-luciferase reporter in reporter cell lines, and indeed shows lesser inhibition of recombinant 15-PGDH at 2 µM in the test tube than does parent compound SW054384.

We also note that addition to the phenyl ring of SW054384 of fluorine (SW203736) or bromine (SW203737), is well tolerated, and yields a compound that is active in inducing 15-PGDH-luciferase reporter activity in cell lines, is similar or improved compared to parental SW054383 in minimally inhibiting recombinant 15-PGDH at 2.5 uM, and is similar or improved versus parental SW054384 in decreasing PGE2 levels in the media of compound treated A549 cells that have been stimulated with IL-1 beta. The phenyl ring of SW054384 also tolerates addition of a methoxy group (SW202940), which yields a compound that is that is active in inducing 15-PGDH-luciferase reporter activity in cell lines, and is similar to parental SW054384 in not inhibiting recombinant 15-PGDH at 2.5 uM.

We also note the favorable properties of compound SW125591, also denoted SW125991, which converts the nitrogen in the SW054384 peptide bond from an (Aryl)-NH— group into a cyclic amine. This compound retains activity in induction of the 15-PGDH-luciferase reporter assay. It shows less inhibition of 15-PGDH at high compound concentration than does the lead enzyme activator SW054384. SW125991 shows similar activity to SW054384 in reducing PGE2 levels in IL1-beta stimulated A549 cells. SW125991 shows no toxicity as assessed by effect on CellTiter-Glo assays done at 24 hours. Moreover, SW125991 shows marked improvement in metabolic stability.

We also note the favorable properties of compounds SW207997, SW207998, and SW207998. These three compounds, like SW125991, have all converted the nitrogen in the SW054384 peptide bond from an (Aryl)-NH— group into a cyclic amine. In addition, SW207997, SW207998, and SW207998, have all added a methoxy group to the phenyl ring in SW054384. SW207997, SW207998, and SW207998 all show activity equal to, or in some assays greater than, SW054384 in inducing the 15-PGDH-luciferase gene fusion reporter construct, and all show much less inhibition of enzymatic activity of 15-PGDH at 2.5 µM and 7.5 µM than does SW054384.

Example 12

The following Example describes the synthesis of SW054384 and analogues thereof as well as provides mass spectrometry NMR confirmation of the structures.
General Procedure 1:

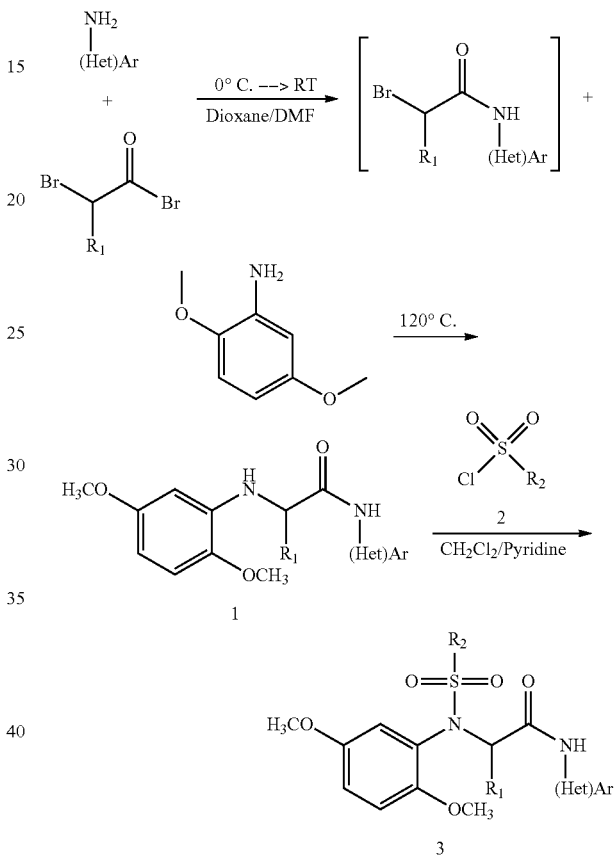

Procedure (Hetero)aryl amine was dissolved in 1:1 mixture of DMF/dioxane (1.215 M based on amine) and cooled to 0° C. Bromoacetyl bromide (1.26 equiv) added drop-wise and allowed to warm to room temperature overnight. Dioxane and excess acid bromide were removed under reduced pressure, and 2,5-dimethoxy aniline (3.5 equiv) was added. The crude material was heated to 120° C. for three hours. The reaction was cooled to room temperature, diluted with EtOAc, and filtered through celite. The filtrate was washed with water (3x), sodium bicarbonate, and brine. The organic phase was dried with MgSO4 and concentrated to give crude amide (1). The product was further purified by flash chromatography to afford pure N-aryl glycinamide 1.

N-Aryl glycinamide (1) was dissolved in $CH_2Cl_2$ (1M). Pyridine (4.9 equiv) and sulfonyl chloride (2) were added (1.3 equiv) and the reaction was stirred overnight. The solution was diluted with EtOAc, washed with water (3x) and brine, dried over MgSO4 and concentrated under reduced pressure to give crude sulfonamide 3. The product was purified by flash chromatography.

General Procedure 2:

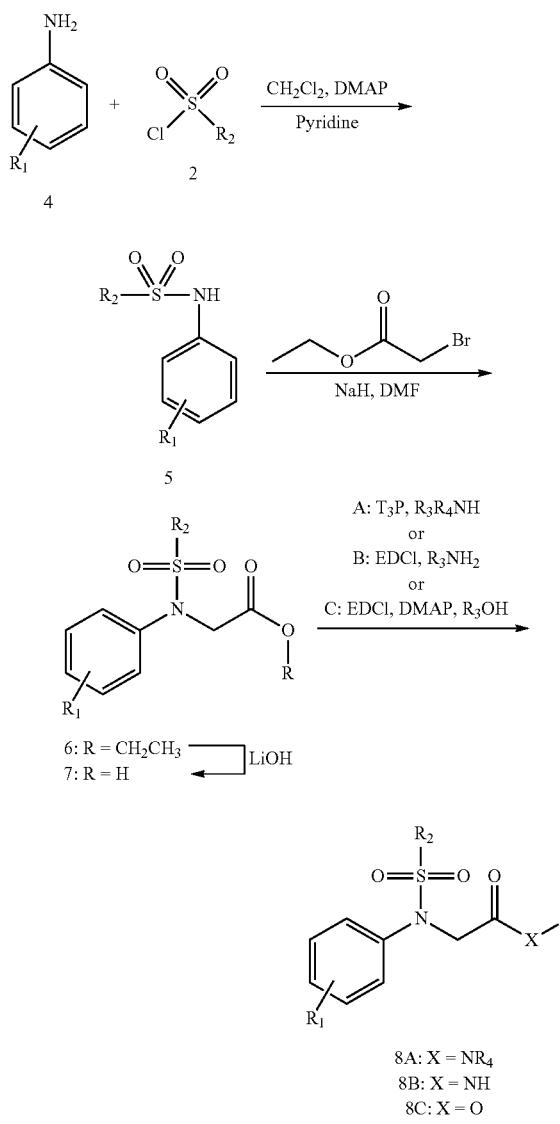

Procedure

Aniline 4 (1 equiv) was dissolved in CH$_2$Cl$_2$ (1 M based on 4). DMAP (0.3 equiv) and pyridine (4.9 equiv) were added followed by sulfonyl chloride 2 (1 equiv). The reaction was stirred for 36 hours, diluted with CH$_2$Cl$_2$ and washed with water, HCl (1 M), sodium bicarbonate, and brine. The organic layer was dried over MgSO4 and solvent was removed under reduced pressure to afford 5.

Without purification, secondary sulfonamide 5 (1 equiv) was dissolved in a solution of DMF (0.1 M) and ethyl bromo acetate (4 equiv). This solution was added drop-wise to sodium hydride at 0° C. After bubbling ceased, the reaction was warmed to room temperature and left stirring overnight. After 12-18 hours, water was added and the aqueous phase was extracted 3 times with CH$_2$Cl$_2$. The combined organic extracts were washed again with water followed by brine, dried with MgSO4, and concentrated under reduced pressure to provide an oil. Addition of hexanes resulted in precipitation of the crude product, which was isolated by filtration and used without purification.

Ester 6 was dissolved in 3:3:1 ratio of MeOH:THF:Water. Lithium hydroxide was added and the reaction was stirred until complete (1-3 hrs). The reaction was concentrated under reduced pressure and then diluted with CH$_2$Cl$_2$. The acid (7) was extracted into saturated sodium bicarbonate. The aqueous layer was neutralized with 1M HCl (pH~5) and extracted with CH$_2$Cl$_2$ to afford 7, which was used without purification.

General Procedure 2A

Acid 7 (1 equiv) was dissolved in EtOAc (2 vol). Pyridine (1 vol) and secondary amine (1.1 equiv) were added followed by T3P (2 equiv, 50% in EtOAc) and reaction was stirred overnight. The reaction was quenched with HCl (0.5 M, 3 vol), and the mixture was diluted with EtOAc, washed with water, bicarbonate, and brine, dried with sodium sulfate and concentrated. Compound 8A was purified by flash chromatography.

General Procedure 2B

Primary amine (1 equiv), DMAP (0.3 equiv) and EDCI (1.3 equiv) were added to a solution of acid 7 (1 equiv) in CH$_2$Cl$_2$ (0.5 M). The reaction vial was purged with nitrogen stirred for 12-24 h. The reaction mixture was diluted with CH$_2$Cl$_2$ and washed with brine, water, HCl (1 M), sodium bicarbonate and brine again. The organic layer was dried with sodium sulfate and concentrated to afford 8B. If needed, the compound was purified by flash chromatography.

General Procedure 2C:

Alcohol (4 equiv), DMAP (0.3 equiv) and EDCI (1.1 equiv) were added to a solution of acid 7 (1 equiv) in CH$_2$Cl$_2$ (0.5 M) at 0° C. After five minutes the reaction was allowed to warm to room temperature and was stirred until complete. The reaction mixture was diluted with CH$_2$Cl$_2$ and washed with brine, HCl (1 M), and water. The organic phase was dried with MgSO4 and concentrated to afford the pure ester 8C.

General Procedure 3

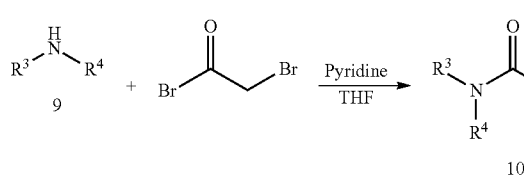 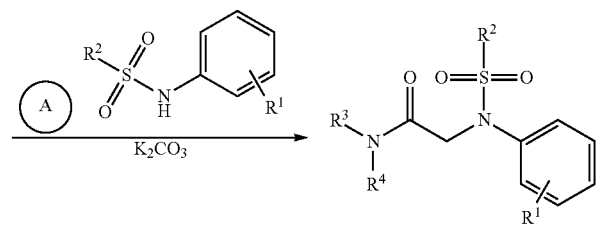

-continued

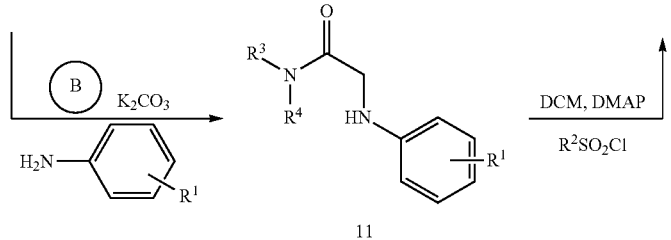

11

Procedure: Pyridine (1.1 equiv) was added to a solution of secondary amine 9 in THF (0.5M), and reaction mixture was cooled to 0° C. Bromoacetyl bromide (1 equiv) was then added drop-wise and reaction was warmed to room temperature. The reaction was stirred for two hours at this temperature and then diluted with EtOAc and washed with water. The organic layer was dried with sodium sulfate and concentrated to afford bromo acetamide 10, which was purified by flash chromatography on silica gel.

General Procedure 3A: A solution of amide 10 in DMF (0.0.075 M) was added to a solution of sulfonamide 12 (1.5 equiv; synthesis identical to sulfonamide 5 in Procedure 2), potassium carbonate (2 equiv), and DMF (0.075 M). The reaction was stirred overnight and then diluted with EtOAc and washed with water and brine. EtOAc was removed under reduced pressure to afford crude 12, which was purified by flash chromatography on silica gel.

General Procedure 3B: A solution of amide 10 in DMF (0.075 M) was added to a solution of aniline, potassium carbonate (2 equiv), and DMF (0.075 M). The reaction was stirred overnight and was then diluted with EtOAc and washed with water and brine to afford amide 11 crude, which was used without purification.

DMAP (0.3 equiv), pyridine (4.9 equiv) and then sulfonyl chloride (1 equiv) were added to a solution of amide 11 in CH$_2$Cl$_2$ (1 M). The reaction was stirred for 12-24 hours, diluted with CH$_2$Cl$_2$ and washed with water, HCl (1 M), sodium bicarbonate, and brine. The organic layer was dried over MgSO4 and compound concentrated under reduced pressure to afford sulfonamide 12, which was purified by flash chromatography.

Example 13: Properties of Selected Analogues of Lead Compound SW054384, a 15-PGDH Activator This Example provides data on properties of selected analogues of SW054384.

Figure 81:
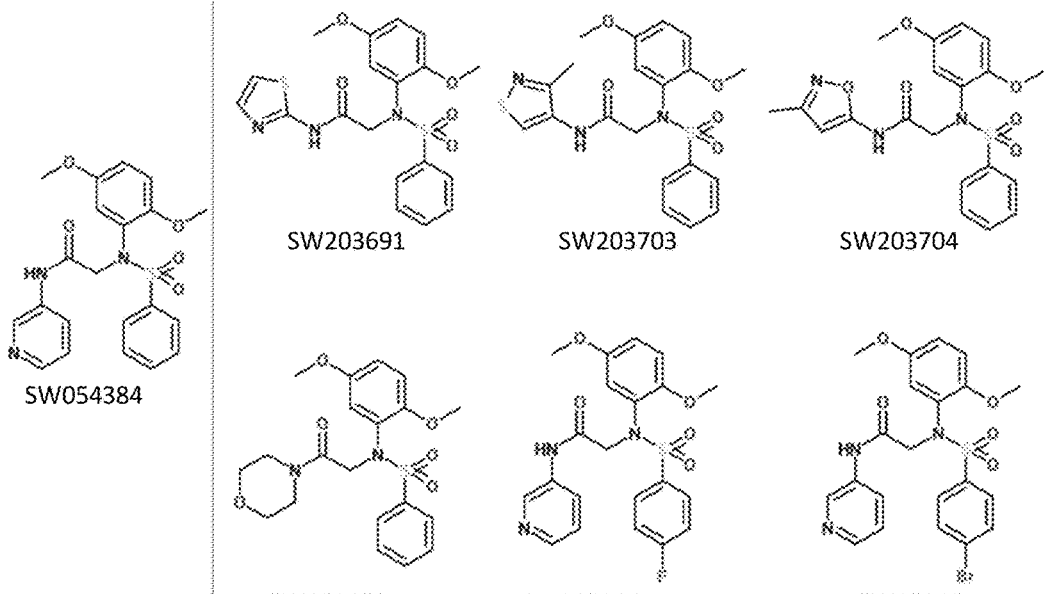
FIG. 81 illustrates a schematic diagram of analogues of SW054384.

FIG. 81 shows structures of selected analogues of SW054384.

Figure 82:
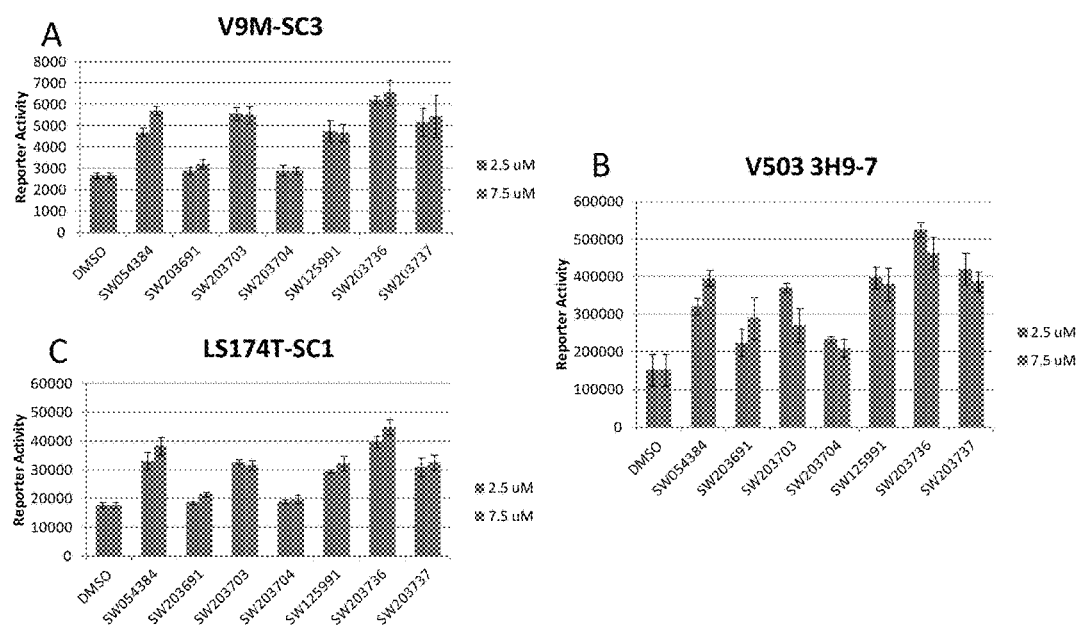
FIGS. 82(A-C) illustrate graphs showing luciferase activity of colon cancer cell lines V9M, LS174T, and V503 treated with 2.5 µM and 7.5 µM the compounds of FIG. 81.

FIGS. 82(A-C) show graphs that show the level of activity in inducing the 15-PGDH-luciferase fusion reporter in three different test cell line backgrounds, V9m, LS174T, and V503. Each compound was tested at two concentrations, 2.5 uM, and 7.5 uM. Y-axis is luciferase activity. Compounds active in inducing the 15-PGDH-luciferase reporter include SW20370, SW203704, SW125991, SW203736, SW203737.

Figure 83:
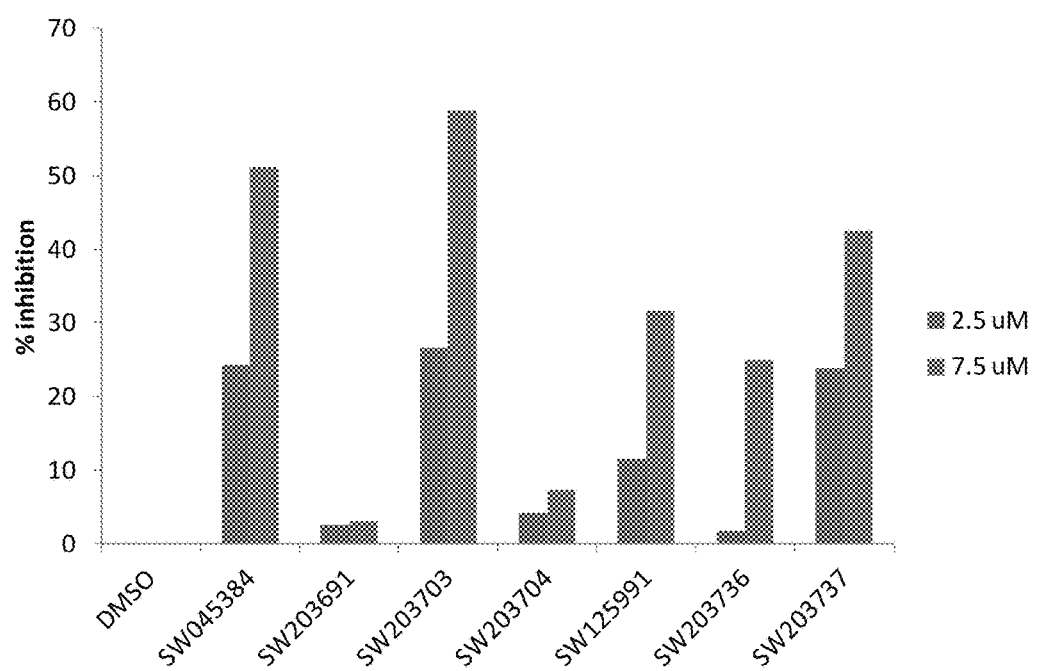
FIG. 83 illustrates a graph showing percent inhibition of 15-PGDH activity by the compounds of FIG. 74.

FIG. 83 shows activity of tested compounds in inhibiting enzymatic activity of recombinant 15-PGDH when tested at high concentrations of 2.5 uM and 7.5 uM. SW125991 and SW203736 show lesser inhibitory activity at high concentration than the lead 15-PGDH activator, SW054384. SW203737 at these concentrations shows inhibitory activity against recombinant 15-PGDH that is similar to SW054384.

Figure 84:
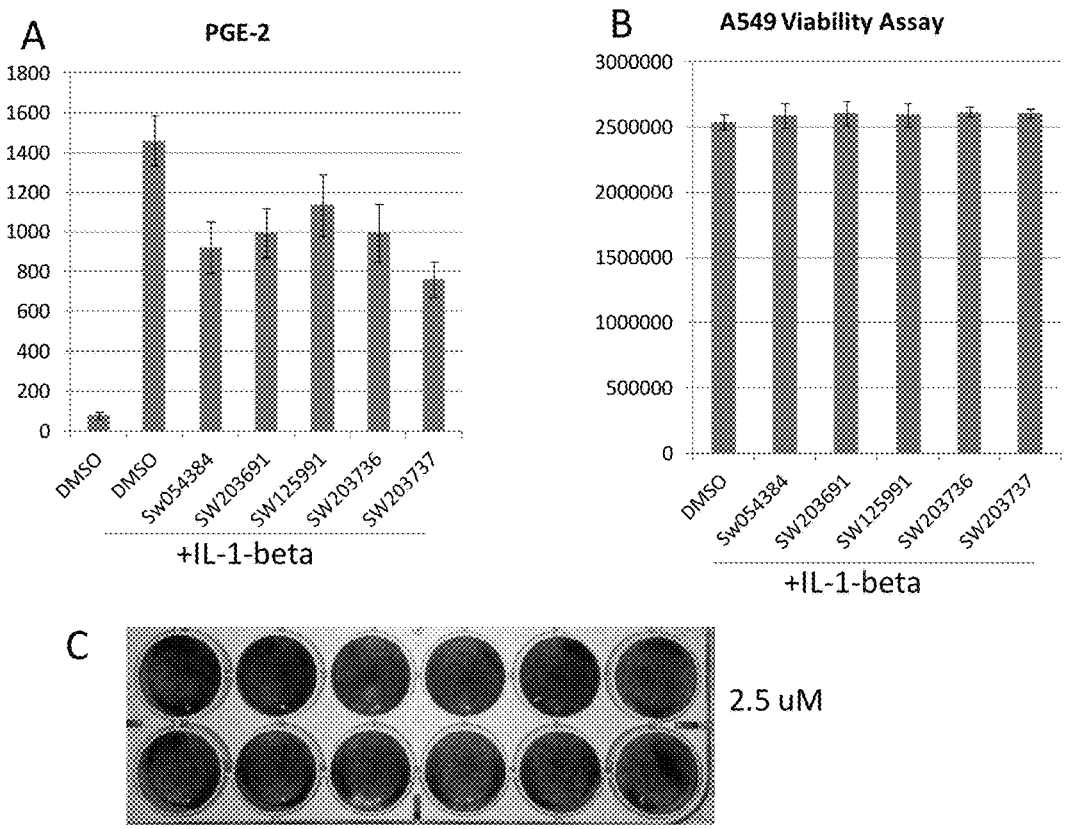
FIGS. 84(A-C) illustrate: (A) a graph showing activity in lowering PGE2 levels in media of A549 cells that are stimulated to produce PEG2 by treatment using IL1-beta using compounds of FIG. 81; (B) a graph showing toxicity of A549 cells administered the compounds of FIG. 81; and (C) photographs of A549 cells treated with compounds of FIG. 81.

FIGS. 84(A-C) show at left (84A) activity in lowering PGE2 levels in media of A549 cells that are stimulated to produce PGE2 by treatment with IL1-beta. All of the compounds tested, including SW054384, SW203703, SW125991, SW203736, and SW203737, show activity in lowering PGE2, consistent with their acting in vivo as inducers of 15-PGDH activity. FIG. 84B shows at right that none of the tested compounds demonstrate any toxicity against A549 cells as assessed by CellTitre-Glo assay levels at 24 hours of treatment. FIG. 84C shows at bottom photographs of A549 cells tested in the CellTitre-Glo assay ordered left to right in the same order as in the graphical display of CellTitre-Glo data at upper right.

Figure 85:
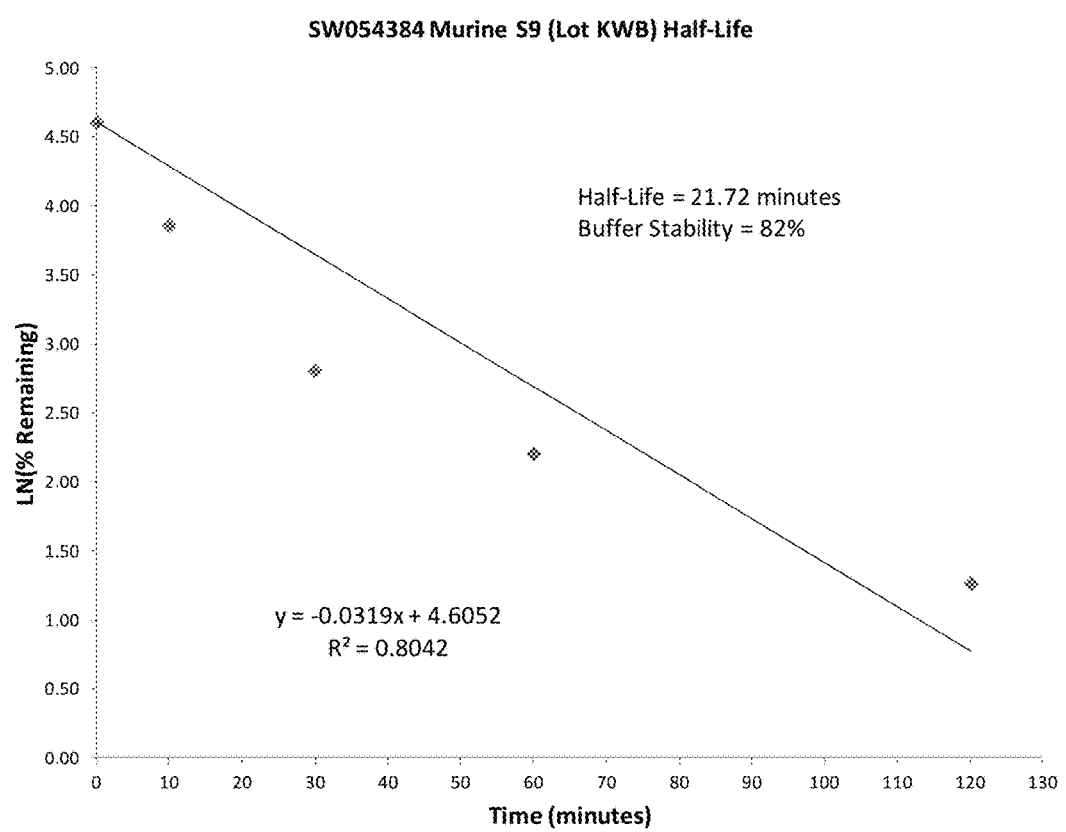
FIG. 85 illustrates a plot showing metabolic stability of SW054384 by incubation with murine liver S9 microsomes.
Figure 86:
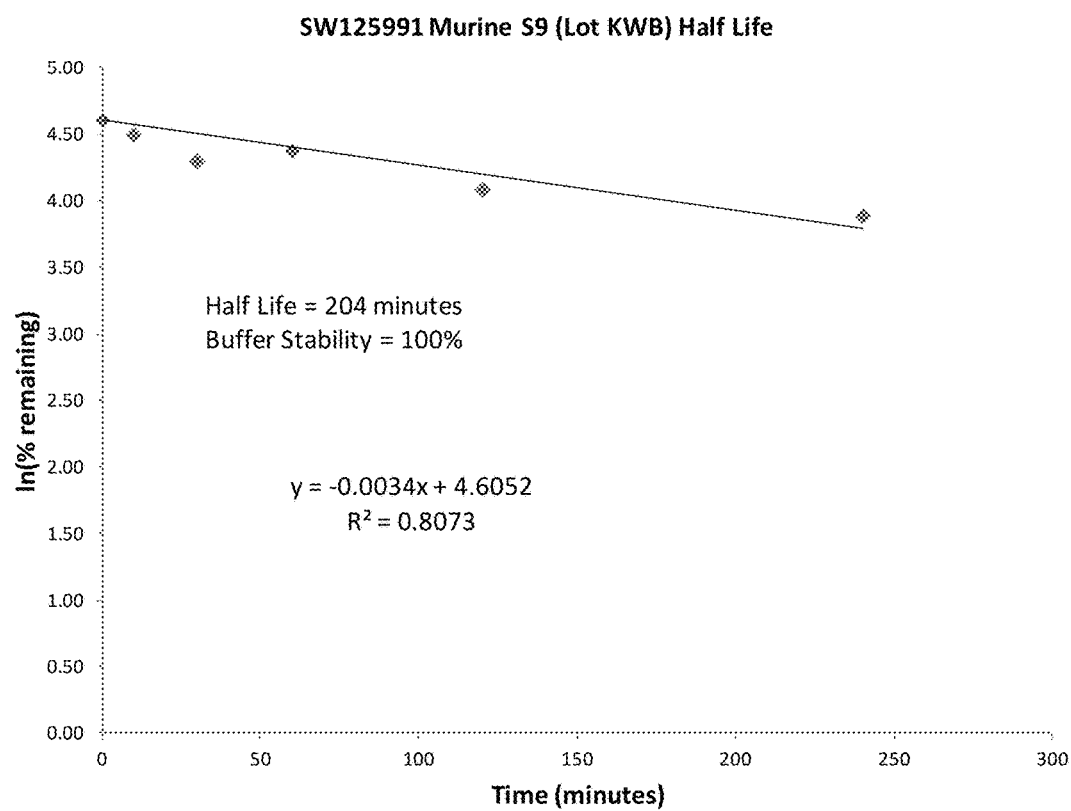
FIG. 86 illustrates a plot showing metabolic stability of SW0125991 by incubation with murine liver S9 microsomes

FIG. 85 shows measurement of metabolic stability of SW054384 by incubation with murine liver S9 microsomes. Measured half-life is 21.72 minutes. SW054384 (2 mM in DMSO) was incubated with Murine S9 (Lot KWB) fraction and Phase I (NADPH Regenerating System) cofactors for 0-240 minutes. Reactions were quenched with a 1 mL (1:1) of MeOH/(+)IS/0.2% Formic Acid, vortexed for 15 seconds, incubated at RT for 10 minutes and spun for 5 minutes at 2400 rpms. Supernatant (1 mL) was then transferred to an eppendorf tube and spun in a table top, chilled centrifuge for 5 minutes at 13.2K rpms. Supernatant (800 µL) was transferred to an HPLC vial (w/out insert) and analyzed by HPLC/MS. A: dH$_2$O+0.1% FA B: MeOH+0.1% FA FIG. 86 shows measurement of metabolic stability of SW125991 by incubation with murine liver S9 microsomes. Measured half-life is 204 minutes. SW125991 (2 mM in DMSO) was incubated with Murine S9 (Lot KWB) fraction and Phase I (NADPH Regenerating System) cofactors for 0-240 minutes. Reactions were quenched with 1 mL (1:1) of methanol containing 0.2% formic acid and 100 ng/ml IS (IS final conc.=50 ng/ml). Samples were vortexed for 15 seconds, incubated at RT for 10 minutes and spun for 5 minutes at 2400 rpm. Supernatant (1 mL) was then transferred to an eppendorf tube and spun in a table top, chilled centrifuge for 5 minutes at 13.2K rpm. Supernatant (800 µL) was transferred to an HPLC vial (w/out insert). Analyzed by Qtrap 3200 mass spectrometer.

Figure 87:
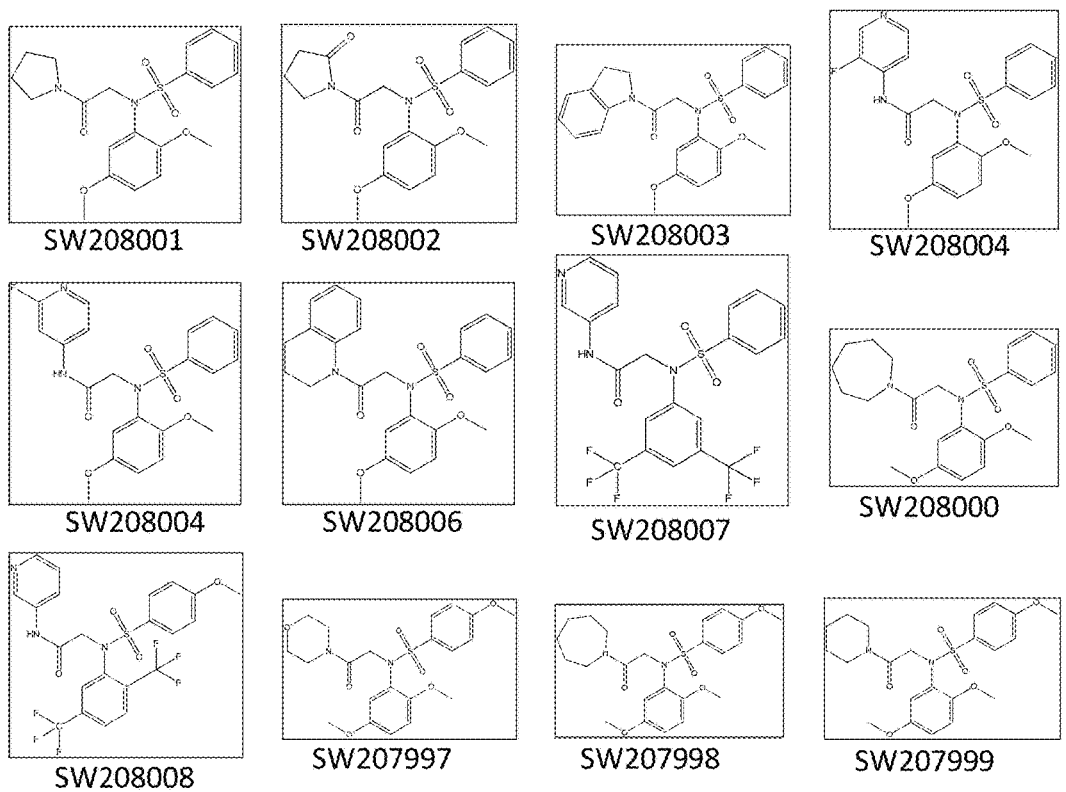
FIG. 87 illustrates a schematic diagram of analogues of SW054384.

FIG. 87 shows the structures of additional analogues of SW054384.

Figure 88:
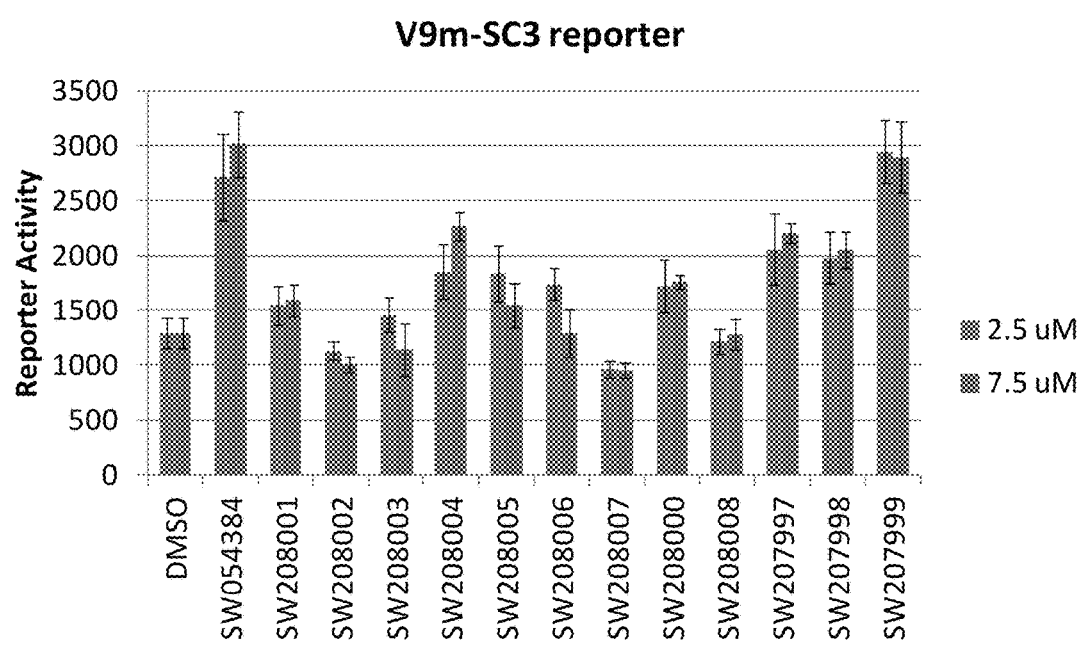
FIG. 88 illustrates a graph showing luciferase activity of colon cancer cell V9m treated with 2.5 µM and 7.5 µM the compounds of FIG. 87.
Figure 89:
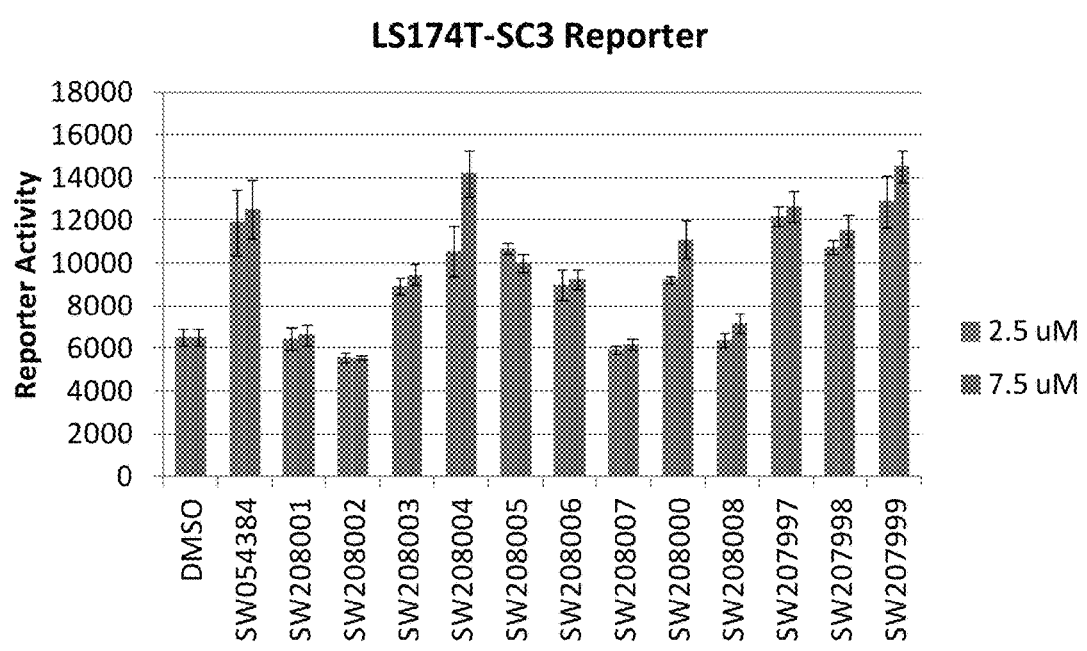
FIG. 89 illustrates a graph showing luciferase activity of colon cancer LS174T cells treated with 2.5 µM and 7.5 µM the compounds of FIG. 87.
Figure 90:
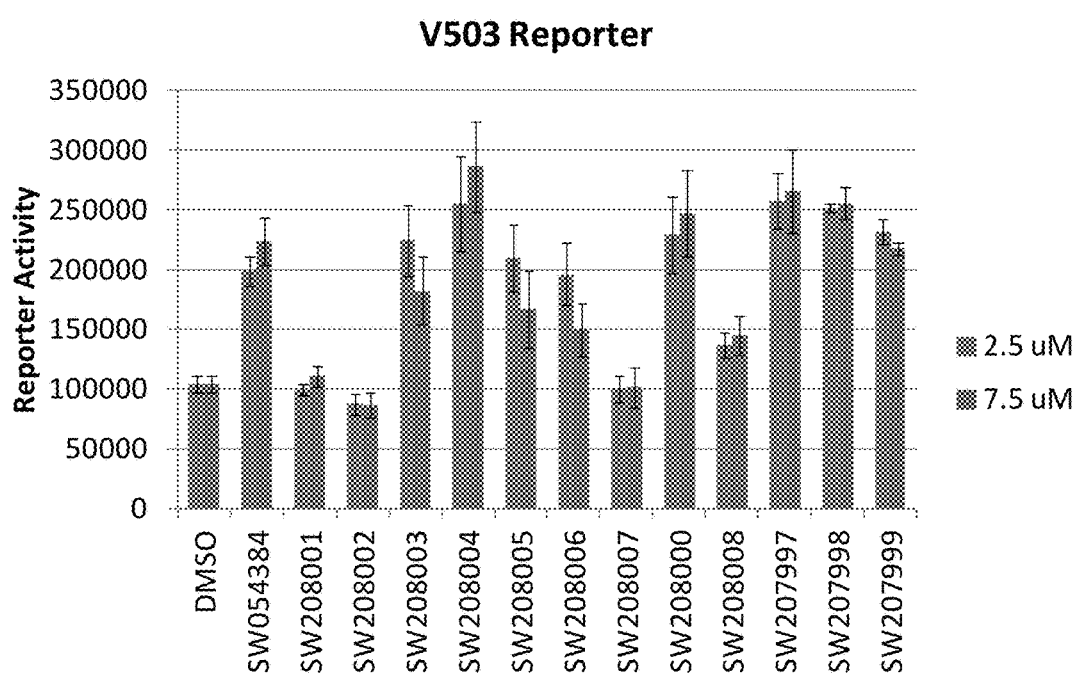
FIG. 90 illustrates a graph showing luciferase activity of colon cancer cell V503 treated with 2.5 µM and 7.5 µM the compounds of FIG. 87.

FIGS. 88-90 show graphs that show the level of activity in inducing the 15-PGDH-luciferase fusion reporter in three different test cell line backgrounds, V9m, LS174T, and V503. Each compound was tested at two concentrations, 2.5 uM, and 7.5 uM. Y-axis is luciferase activity. Compounds active in inducing the 15-PGDH-luciferase reporter include (but are not limited to): SW207997, SW207998, and SW207999.

Figure 91:
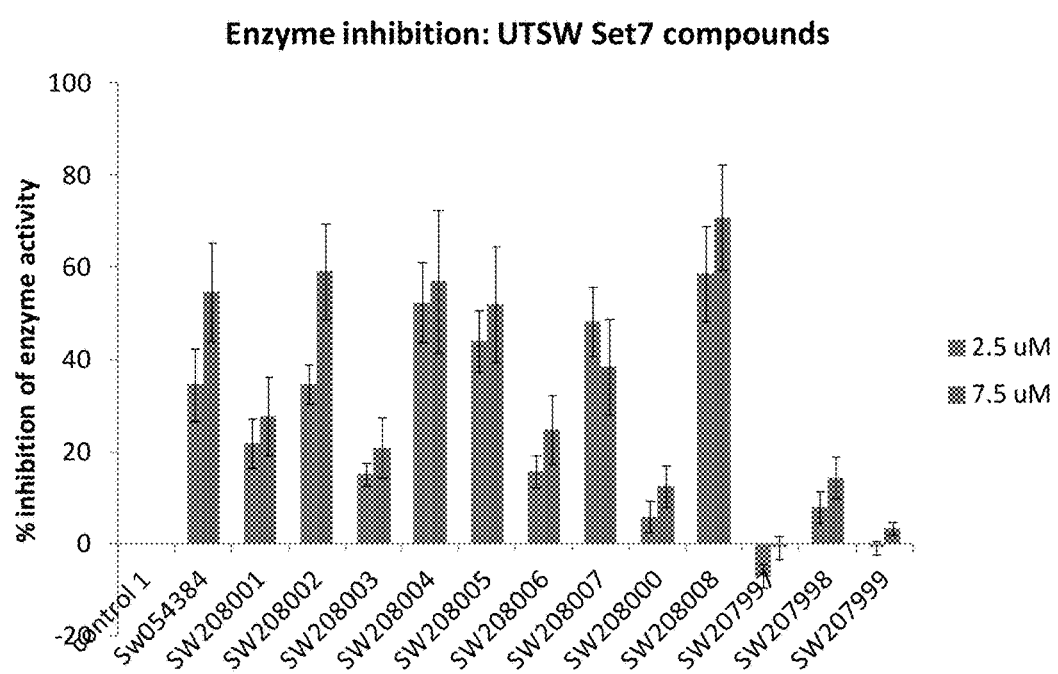
FIG. 91 illustrates a graph showing percent inhibition of 15-PGDH activity by the compounds of FIG. 87.

FIG. 91 shows activity of tested compounds in inhibiting enzymatic activity of 15-PGDH when tested at high concentrations of 2.5 uM and 7.5 uM. SW207997, SW207998, and SW207999 show lesser inhibitory activity at high concentration than the lead 15-PGDH activator, SW054384.

Figure 92:
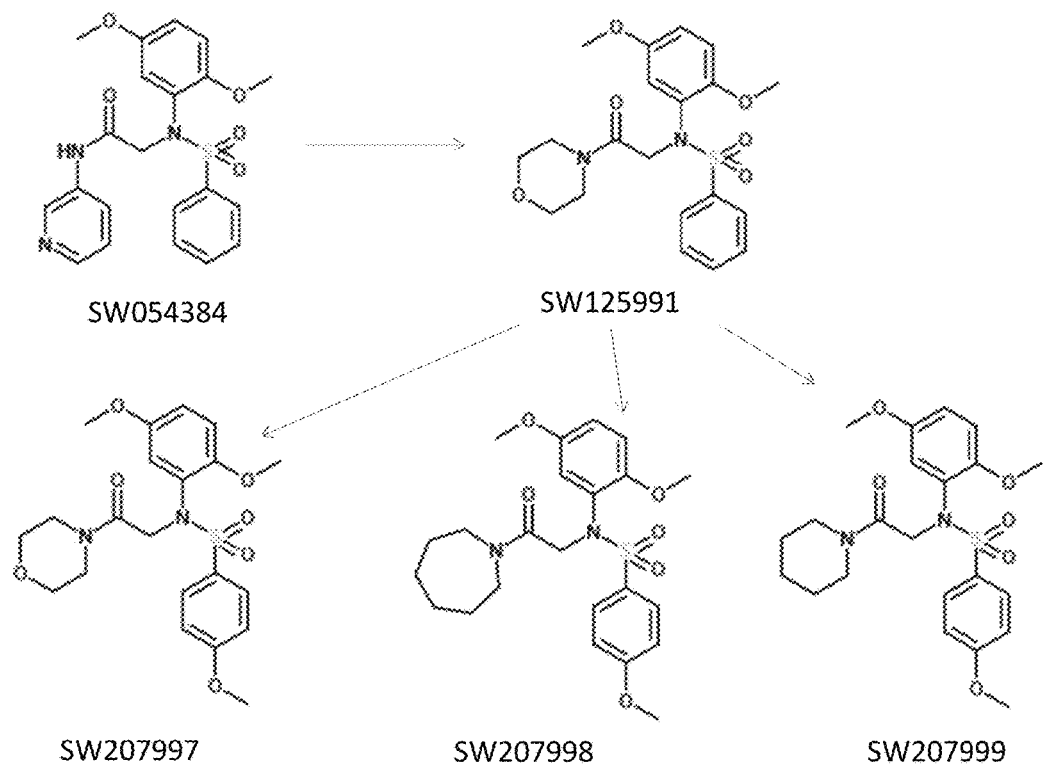
FIG. 92 is a schematic illustration showing the structures of 15-PGDH activators SW054384, SW125991, SW207997, SW207998, and SW207999.

FIG. 92 reprises structures of 15-PGDH activators SW054383, SW125991, SW207997, SW207998, SW207999.

Figure 93:
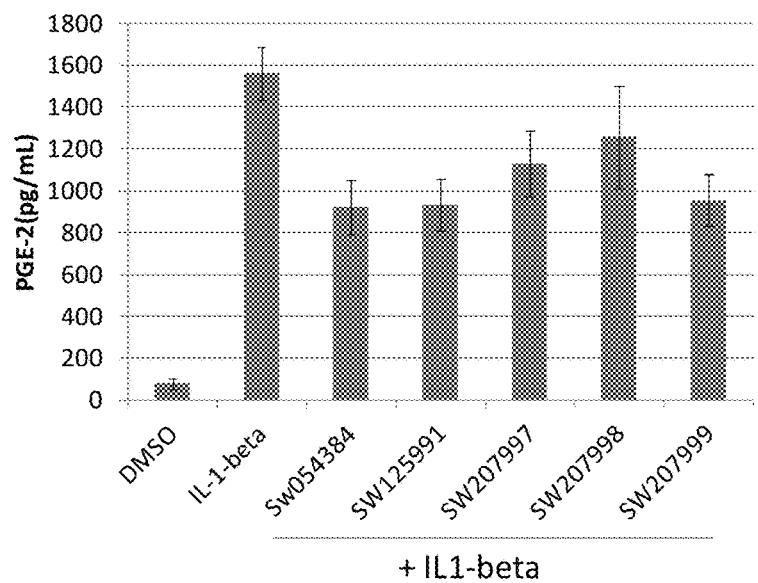
FIG. 93 illustrates a graph showing the activities of SW054384, SW125991, SW207997, SW207998, SW207999 in lowering PGE2 levels in medium of A549 cells that have been treated with 2.5 µM of each compound along with addition of 2.5 ng/ml IL1-beta.

FIG. 93 shows graphical display of the activities of SW054383, SW125991, SW207997, SW207998, SW207999 in lowering PGE2 levels in medium of A549 cells that have been treated with 2.5 µM of each compound for 24 hours, along with addition of 2.5 ng/ml IL1-beta for the last 16 hours of the incubation, and with then collection and assay of PGE2 concentration in the medium at the 24 hour time point. Activity of compounds in lowering 15-PGDH in the IL1-beta stimulated A549 cells is consistent with these compounds activating intracellular 15-PGDH.

Figure 94:
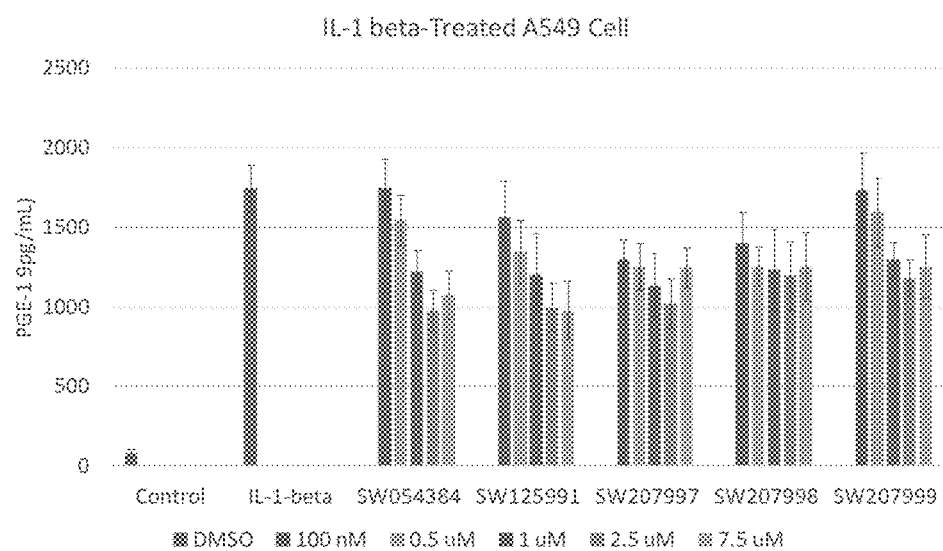
FIG. 94 illustrates titration curves of 15-PGDH activator compounds in an assay measuring effects on PGE2 levels in the medium of A549 cells that have been stimulated with IL1-beta.

FIG. 94 shows titration curves of 15-PGDH activator compounds in an assay measuring effects on PGE2 levels in the medium of A549 cells that have been stimulated with IL1-beta in the same experimental design described for FIG. 93. At 100 nM concentration of drug, the greatest reduction in levels of PGE2 in the medium are achieved by treating cells with SW207997 or with SW207998, followed by SW125991. SW054384 and SW207999 attain comparable levels of reduction of PGE2 in the medium at doses of between 0.5 µM-1.0 µM.

Figure 95:
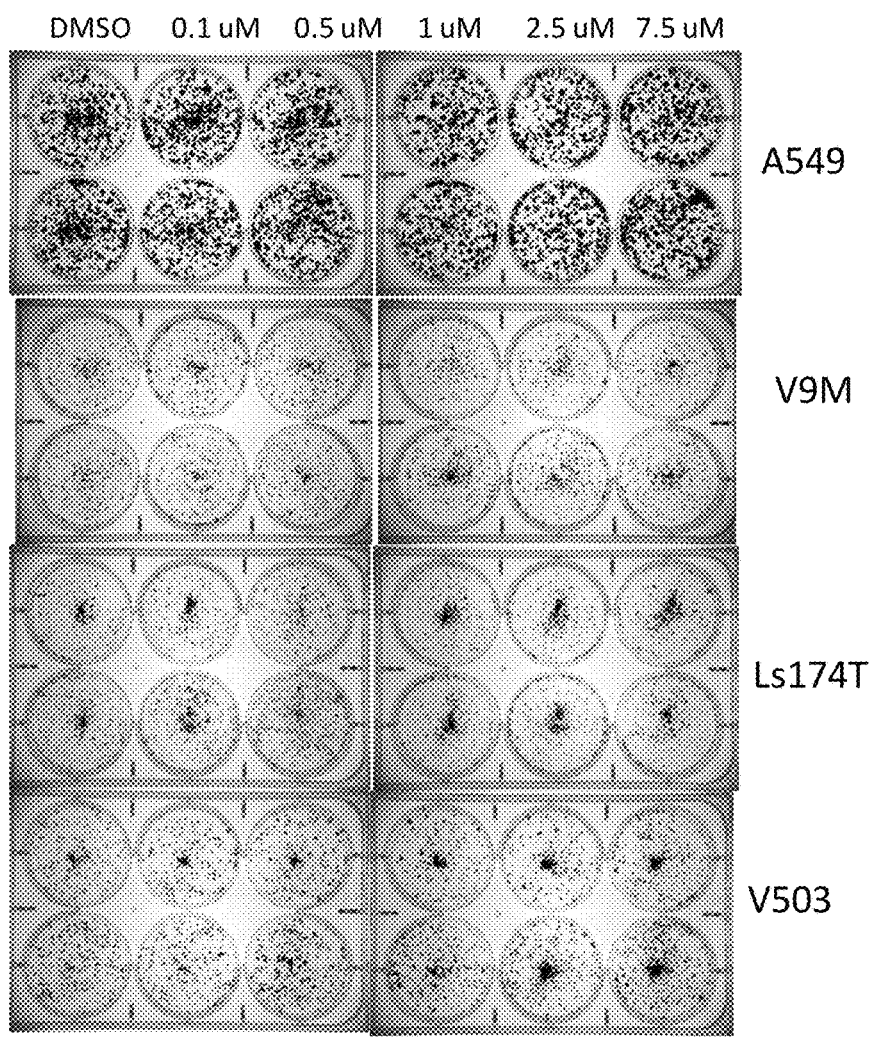
FIG. 95 illustrates a photograph showing assessment of toxicity of SW125991 by testing effect of increasing doses on colony formation of A549 cells, Vaco9M (V9m) cells, LS174T cells, and Vaco503 (V503) cells.

FIG. 95 shows assessment of toxicity of SW125991 by testing effect of increasing doses on colony formation of A549 cells, Vaco9M (V9m) cells, LS174T cells, and Vaco503 (V503) cells. No reduction of colony forming activity is seen at doses up to 7.5 µM compound.

Figure 96:
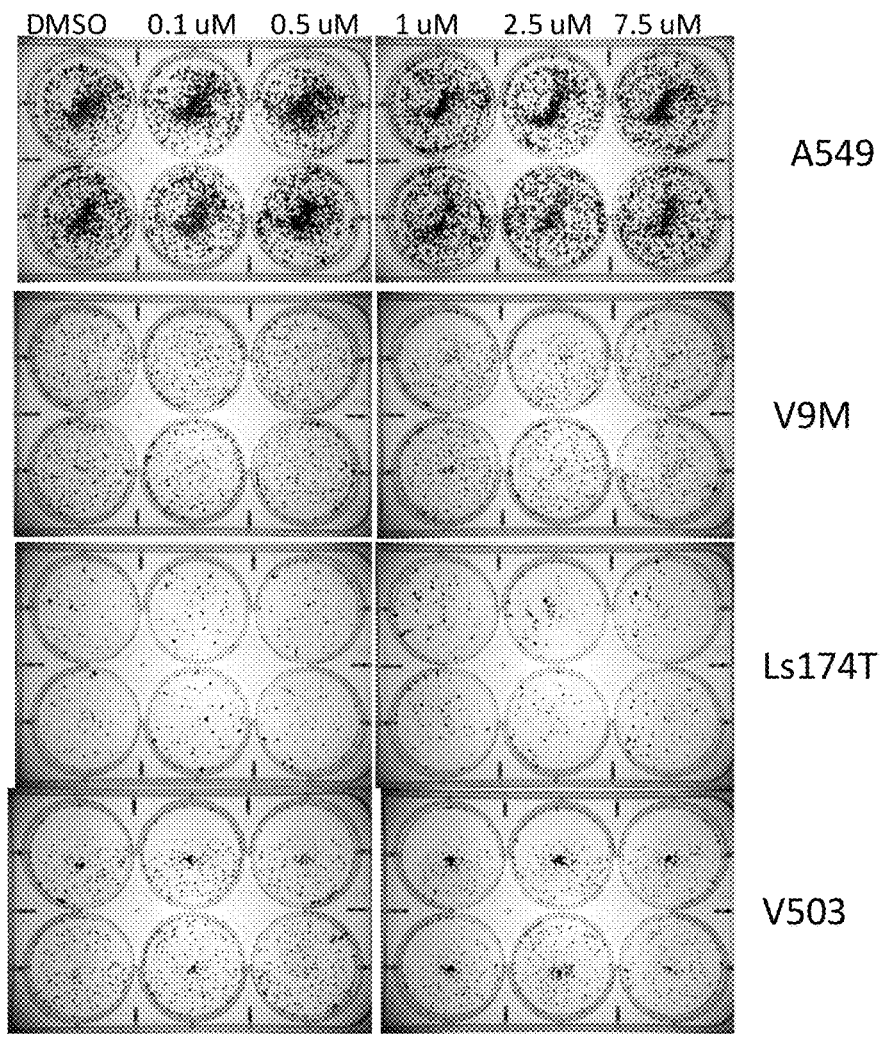
FIG. 96 illustrates a photograph showing assessment of toxicity of SW207997 by testing effect of increasing doses on colony formation of A549 cells, Vaco9M (V9m) cells, LS174T cells, and Vaco503 (V503) cells.

FIG. 96 shows assessment of toxicity of SW207997 by testing effect of increasing doses on colony formation of A549 cells, Vaco9M (V9m) cells, LS174T cells, and Vaco503 (V503) cells. No reduction of colony forming activity is seen at doses up to 7.5 µM compound.

Figure 97:
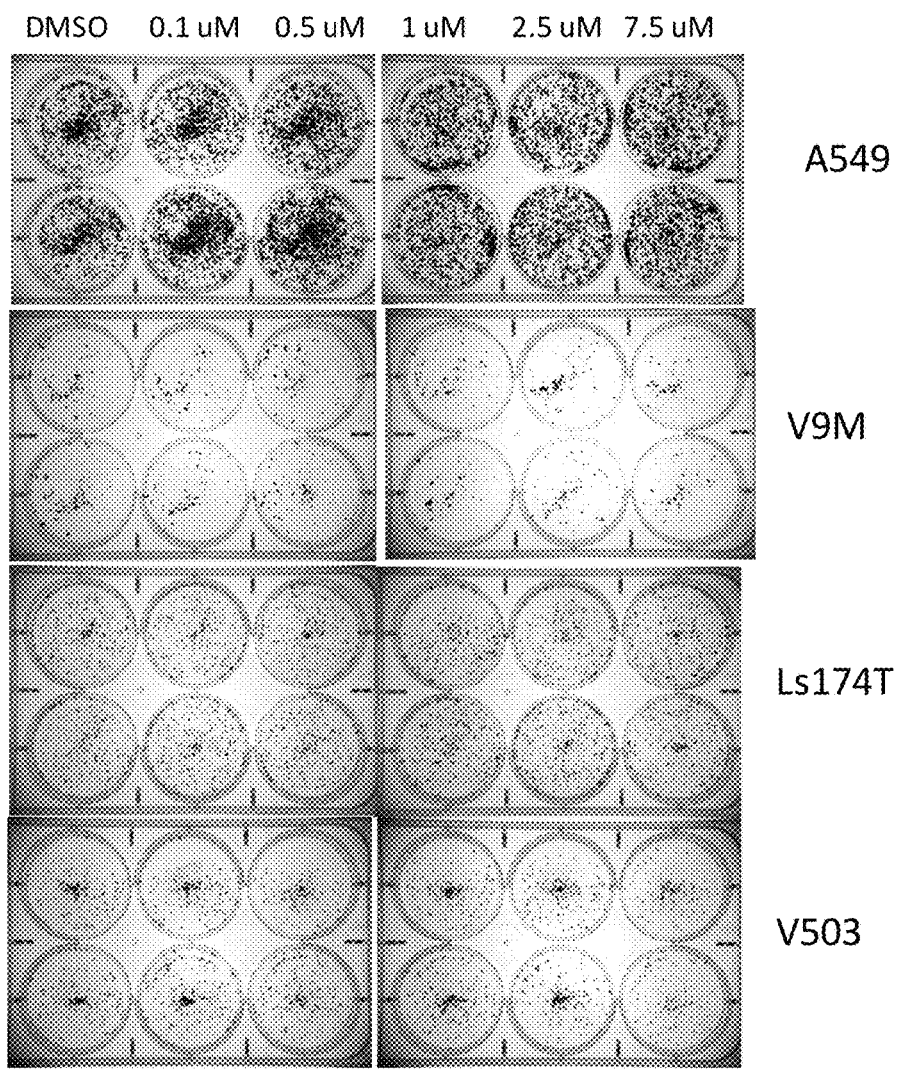
FIG. 97 illustrates a photograph showing assessment of toxicity of SW207998 by testing effect of increasing doses on colony formation of A549 cells, Vaco9M (V9m) cells, LS174T cells, and Vaco503 (V503) cells.

FIG. 97 shows assessment of toxicity of SW207998 by testing effect of increasing doses on colony formation of A549 cells, Vaco9M (V9m) cells, LS174T cells, and Vaco503 (V503) cells. No reduction of colony forming activity is seen at doses up to 7.5 µM compound.

Figure 98:
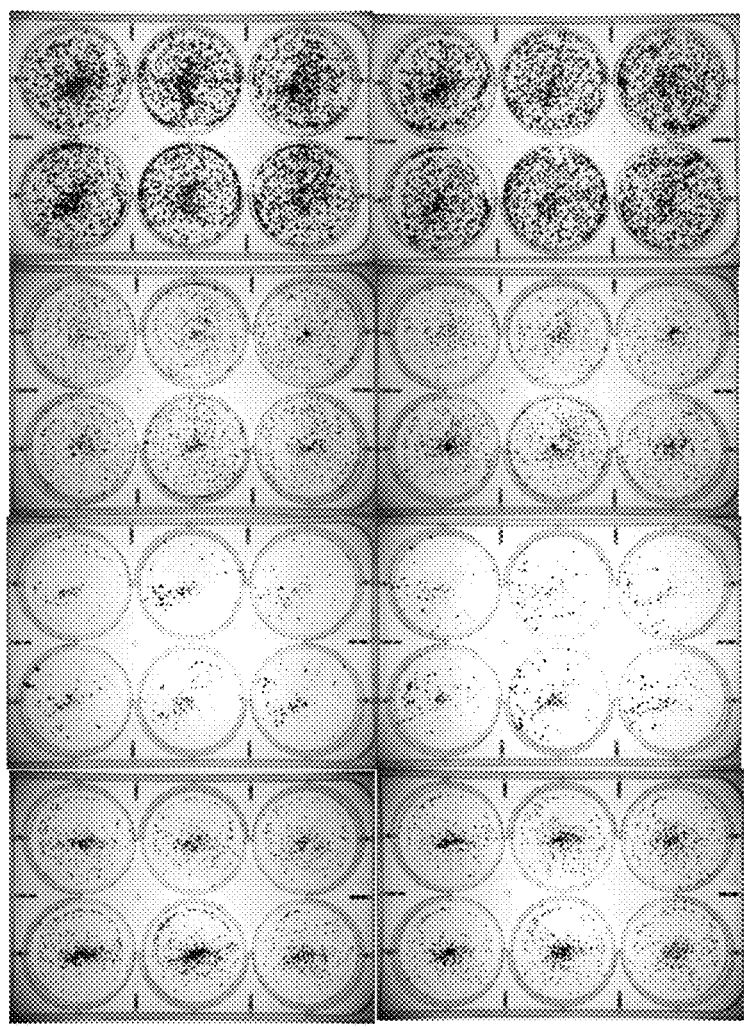
FIG. 98 illustrates a photograph showing assessment of toxicity of SW207999 by testing effect of increasing doses on colony formation of A549 cells, Vaco9M (V9m) cells, LS174T cells, and Vaco503 (V503) cells.

FIG. 98 shows assessment of toxicity of SW207999 by testing effect of increasing doses on colony formation of A549 cells, Vaco9M (V9m) cells, LS174T cells, and Vaco503 (V503) cells. No reduction of colony forming activity is seen at doses up to 7.5 µM compound.

While this invention has been particularly shown and described with references to preferred embodiments thereof, it will be understood by those skilled in the art that various changes in form and details may be made therein without departing from the scope of the invention encompassed by the appended claims. All patents, publications and references cited in the foregoing specification are herein incorporated by reference in their entirety.

The following is claimed:

1. A method of inhibiting the activity of 15-PGDH enzyme, the method comprising:
   administering to the enzyme a compound having the following formula (III):

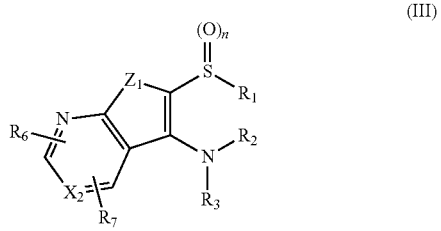

(III)

wherein n is 1 or 2;
$R_1$ is a $C_{1-8}$ alkyl, which is linear, branched, or cyclic and which is unsubstituted or substituted;
$R_2$ and $R_3$ are the same or different and are each selected from the group consisting of a H, a lower alkyl group, $(CH_2)_{n1}OR'$ (wherein n1=1, 2, or 3), $CF_3$, $CH_2—CH_2X$, $O—CH_2—CH_2X$, $CH_2—CH_2—CH_2X$, $O—CH_2—CH_2X$ (wherein X=F, Cl, Br, or I), CN, $(C=O)—R'$, $(C=O)N(R')_2$, $O(CO)R'$, $COOR'$ (wherein R' is H or a lower alkyl group);
$Z_1$ is S;
$X_2$ is N or C;
$R_6$ and $R_7$ are optional and if present are the same or different and are each selected from the group consisting of a H, F, Cl, Br, I, a lower alkyl group, $(CH_2)_{n1}OR'$ (wherein n1=1, 2, or 3), $CF_3$, $CH_2—CH_2X$, $O—CH_2—CH_2X$, $CH_2—CH_2—CH_2X$, $O—CH_2—CH_2X$ (wherein X=F, Cl, Br, or I), CN, $(C=O)—R'$, $N(R')_2$, $NO_2$, $(C=O)N(R')_2$, $O(CO)R'$, $OR'$, $SR'$, $COOR'$ (wherein R' is H or a lower alkyl group); substituted or unsubstituted aryl, a substituted or unsubstituted cycloalkyl, and a substituted or unsubstituted heterocyclyl; or a pharmaceutically acceptable salt thereof.

2. The method of claim 1, wherein the compound has a formula selected from the group consisting of:

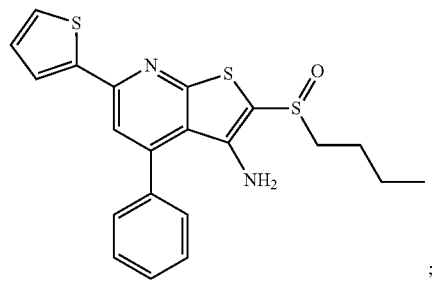

;

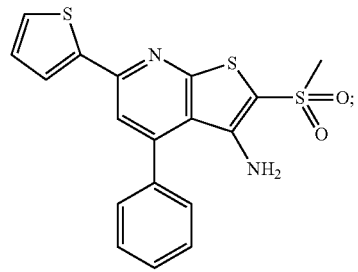

;

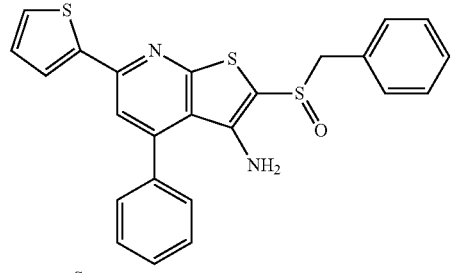

;

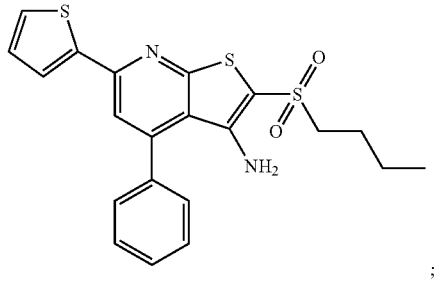

;

-continued
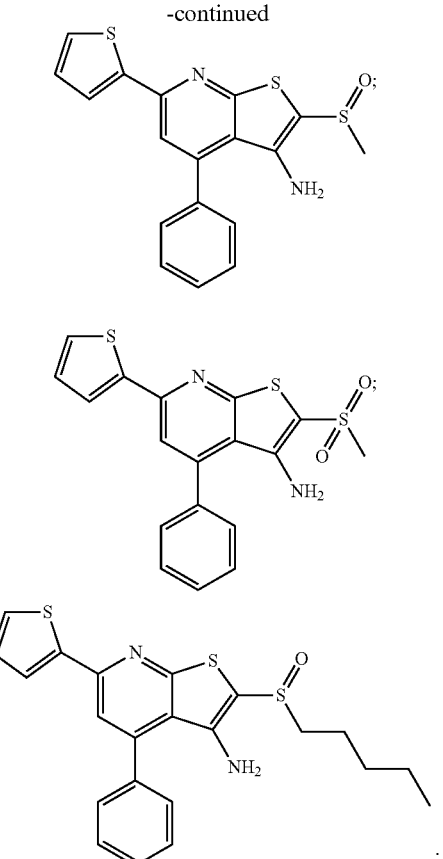
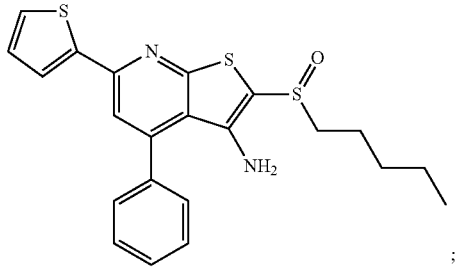
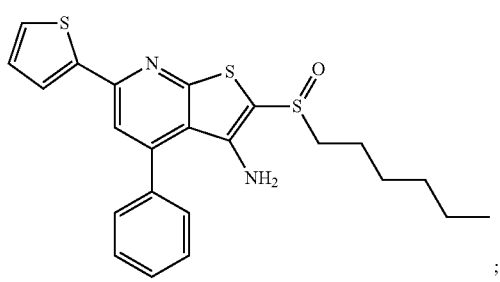
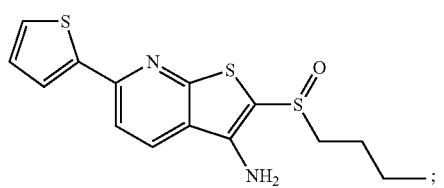
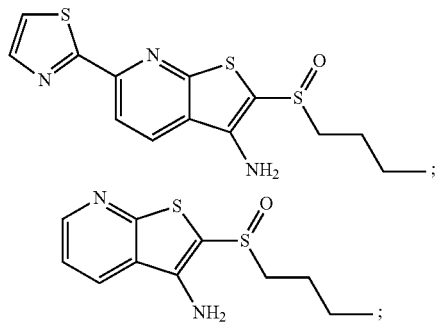
-continued
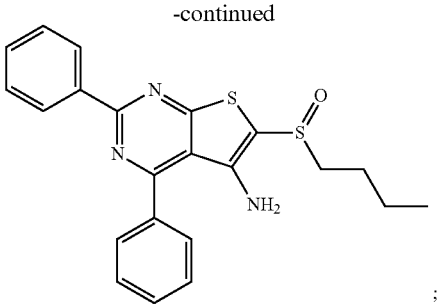
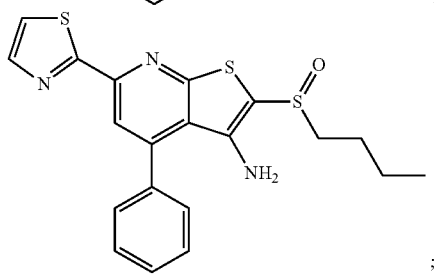
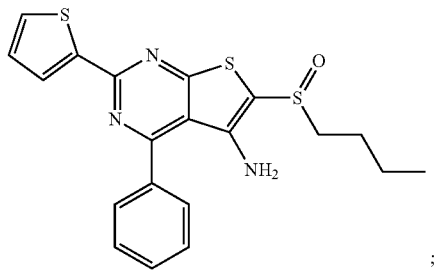 [SMILES: CCCCS(=O)c1sc2nc(-c3cccs3)nc(-c3ccccc3)c2c1N]
and pharmaceutically acceptable salts thereof.
3. The method of claim 1, wherein the compound has the formula:
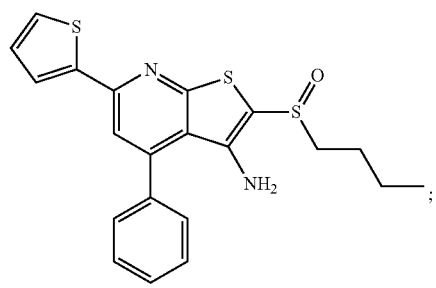 [SMILES: CCCCS(=O)c1sc2nc(-c3cccs3)cc(-c3ccccc3)c2c1N]
and pharmaceutically acceptable salts thereof.
4. The method of claim 1, wherein the compound has the formula:
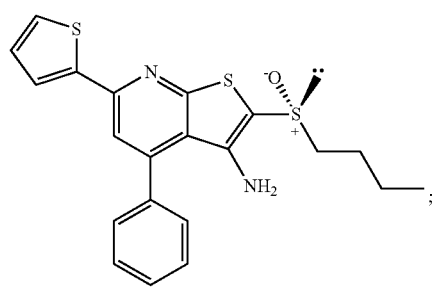
and pharmaceutically acceptable salts thereof.

5. The method of claim 1, wherein the compound has the formula:

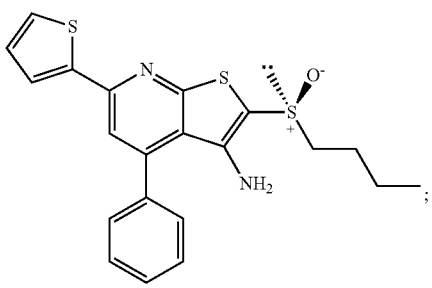

and pharmaceutically acceptable salts thereof.

6. The method of claim 1, wherein the 15-PGDH enzyme is in a tissue of a subject and the compound is administered to the tissue of the subject at an amount effective to increase prostaglandin levels in the tissue.

7. A method for mitigating rejection or enhancing engraftment of a bone marrow graft in a subject recipient of the bone marrow graft, comprising administering to the subject a compound having the following formula (III):

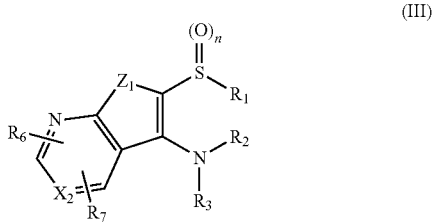

wherein n is 1 or 2;
$R_1$ is a $C_{1-8}$ alkyl, which is linear, branched, or cyclic and which is unsubstituted or substituted;
$R_2$ and $R_3$ are the same or different and are each selected from the group consisting of a H, a lower alkyl group, $(CH_2)_{n1}OR'$ (wherein n1=1, 2, or 3), $CF_3$, $CH_2$—$CH_2X$, $O$—$CH_2$—$CH_2X$, $CH_2$—$CH_2$—$CH_2X$, $O$—$CH_2$—$CH_2X$ (wherein X=F, Cl, Br, or I), CN, (C=O)—R', (C=O)N(R')$_2$, O(CO)R', COOR' (wherein R' is H or a lower alkyl group);
$Z_1$ is S;
$X_2$ is N or C;
$R_6$ and $R_7$ are optional and if present are the same or different and are each selected from the group consisting of a H, F, Cl, Br, I, a lower alkyl group, $(CH_2)_{n1}OR'$ (wherein n1=1, 2, or 3), $CF_3$, $CH_2$—$CH_2X$, $O$—$CH_2$—$CH_2X$, $CH_2$—$CH_2$—$CH_2X$, $O$—$CH_2$—$CH_2X$ (wherein X=F, Cl, Br, or I), CN, (C=O)—R', N(R')$_2$, $NO_2$, (C=O)N(R')$_2$, O(CO)R', OR', SR', COOR' (wherein R' is H or a lower alkyl group); substituted or unsubstituted aryl, a substituted or unsubstituted cycloalkyl, and a substituted or unsubstituted heterocyclyl; or a pharmaceutically acceptable salt thereof.

8. The method of claim 7, where the compound or pharmaceutically acceptable salt thereof is administered to the subject before receipt of the bone marrow graft.

9. The method of claim 7, where the compound or pharmaceutically acceptable salt thereof is administered to the subject during receipt of the bone marrow graft.

10. The method of claim 7, where the compound or pharmaceutically acceptable salt thereof is administered to the subject after receipt of the bone marrow graft.

11. The method of claim 7, wherein the administration occurs following treatment of the subject or the bone marrow of the subject with radiation therapy, chemotherapy, or immunosuppressive therapy.

12. A method for treating colitis in a subject, comprising administering to the subject a compound having the following formula (III):

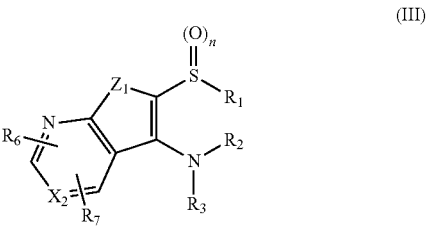

wherein n is 1 or 2;
$R_1$ is a $C_{1-8}$ alkyl, which is linear, branched, or cyclic and which is unsubstituted or substituted;
$R_2$ and $R_3$ are the same or different and are each selected from the group consisting of a H, a lower alkyl group, $(CH_2)_{n1}OR'$ (wherein n1=1, 2, or 3), $CF_3$, $CH_2$—$CH_2X$, $O$—$CH_2$—$CH_2X$, $CH_2$—$CH_2$—$CH_2X$, $O$—$CH_2$—$CH_2X$ (wherein X=F, Cl, Br, or I), CN, (C=O)—R', (C=O)N(R')$_2$, O(CO)R', COOR' (wherein R' is H or a lower alkyl group);
$Z_1$ is S;
$X_2$ is N or C;
$R_6$ and $R_7$ are optional and if present are the same or different and are each selected from the group consisting of a H, F, Cl, Br, I, a lower alkyl group, $(CH_2)_{n1}OR'$ (wherein n1=1, 2, or 3), $CF_3$, $CH_2$—$CH_2X$, $O$—$CH_2$—$CH_2X$, $CH_2$—$CH_2$—$CH_2X$, $O$—$CH_2$—$CH_2X$ (wherein X=F, Cl, Br, or I), CN, (C=O)—R', N(R')$_2$, $NO_2$, (C=O)N(R')$_2$, O(CO)R', OR', SR', COOR' (wherein R' is H or a lower alkyl group); substituted or unsubstituted aryl, a substituted or unsubstituted cycloalkyl, and a substituted or unsubstituted heterocyclyl; or a pharmaceutically acceptable salt thereof.

13. The method of claim 12, wherein the colitis is ulcerative colitis.

14. A method for promoting liver regeneration following liver surgery or injury in a subject, comprising administering to the subject a compound having the following formula (III):

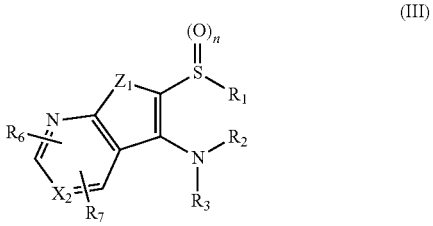

wherein n is 1 or 2;
$R_1$ is a $C_{1-8}$ alkyl, which is linear, branched, or cyclic and which is unsubstituted or substituted;

$R_2$ and $R_3$ are the same or different and are each selected from the group consisting of a H, a lower alkyl group, $(CH_2)_{n1}OR'$ (wherein n1=1, 2, or 3), $CF_3$, $CH_2$—$CH_2X$, O—$CH_2$—$CH_2X$, $CH_2$—$CH_2$—$CH_2X$, O—$CH_2$—$CH_2X$ (wherein X=F, Cl, Br, or I), CN, (C=O)—R', (C=O)N(R')$_2$, O(CO)R', COOR' (wherein R' is H or a lower alkyl group);

$Z_1$ is S;

$X_2$ is N or C;

$R_6$ and $R_7$ are optional and if present are the same or different and are each selected from the group consisting of a H, F, Cl, Br, I, a lower alkyl group, $(CH_2)_{n1}OR'$ (wherein n1=1, 2, or 3), $CF_3$, $CH_2$—$CH_2X$, O—$CH_2$—$CH_2X$, $CH_2$—$CH_2$—$CH_2X$, O—$CH_2$—$CH_2X$ (wherein X=F, Cl, Br, or I), CN, (C=O)—R', N(R')$_2$, NO$_2$, (C=O)N(R')$_2$, O(CO)R', OR', SR', COOR' (wherein R' is H or a lower alkyl group); substituted or unsubstituted aryl, a substituted or unsubstituted cycloalkyl, and a substituted or unsubstituted heterocyclyl; or a pharmaceutically acceptable salt thereof.

15. The method of claim 14, wherein the surgery is liver resection.

\* \* \* \* \*

UNITED STATES PATENT AND TRADEMARK OFFICE
CERTIFICATE OF CORRECTION

PATENT NO.         : 10,301,320 B2
APPLICATION NO.    : 15/359330
DATED              : November 22, 2016
INVENTOR(S)        : Sanford Markowitz et al.

Page 1 of 1

It is certified that error appears in the above-identified patent and that said Letters Patent is hereby corrected as shown below:

In the Specification

Please replace the paragraph starting at Line 12, Column 1:
--GOVERNMENT FUNDING
This invention was made with government support under Grant Nos. CA127306, CA150964, and CA095471 awarded by The National Institutes of Health. The government has certain rights in the invention.--

Signed and Sealed this
Eighteenth Day of May, 2021

Drew Hirshfeld
*Performing the Functions and Duties of the*
*Under Secretary of Commerce for Intellectual Property and*
*Director of the United States Patent and Trademark Office*